United States Patent
Cha et al.

(10) Patent No.: US 10,468,603 B2
(45) Date of Patent: *Nov. 5, 2019

(54) ORGANIC LIGHT-EMITTING DIODE HAVING LOW DRIVING VOLTAGE AND LONG LIFESPAN

(71) Applicant: SFC CO., LTD., Cheongju-si (KR)

(72) Inventors: Soon-Wook Cha, Goyang-si (KR); Seok-Bae Park, Geumsan-gun (KR); Sang-woo Park, Seoul (KR); Yoona Shin, Seoul (KR); Hee-Dae Kim, Miryang-si (KR)

(73) Assignee: SFC CO., LTD., Cheongju-si (KR)

( * ) Notice: Subject to any disclaimer, the term of this patent is extended or adjusted under 35 U.S.C. 154(b) by 197 days.

This patent is subject to a terminal disclaimer.

(21) Appl. No.: 15/545,700

(22) PCT Filed: Jan. 15, 2016

(86) PCT No.: PCT/KR2016/000473
§ 371 (c)(1),
(2) Date: Jul. 23, 2017

(87) PCT Pub. No.: WO2016/126022
PCT Pub. Date: Aug. 11, 2016

(65) Prior Publication Data
US 2018/0013071 A1    Jan. 11, 2018

(30) Foreign Application Priority Data
Feb. 4, 2015 (KR) .................. 10-2015-0017265

(51) Int. Cl.
*H01L 51/00*    (2006.01)
*C09K 11/06*    (2006.01)
(Continued)

(52) U.S. Cl.
CPC ........ *H01L 51/0061* (2013.01); *C07D 307/91* (2013.01); *C07D 307/94* (2013.01);
(Continued)

(58) Field of Classification Search
None
See application file for complete search history.

(56) References Cited

U.S. PATENT DOCUMENTS 10,014,479 B2 *    7/2018    Kim .................... H01L 51/0061
2007/0247059 A1 *   10/2007   Cho .................... C07D 221/20
                                                            313/499
(Continued)

FOREIGN PATENT DOCUMENTS

EP    2163550 A1    3/2010
EP    3309235 A1    4/2018
(Continued)

OTHER PUBLICATIONS

Office Action from Korean intellectual Property Office of 10-2015-0017265, dated Oct. 4, 2018.
(Continued)

*Primary Examiner* — Robert S Loewe
(74) *Attorney, Agent, or Firm* — STIP Law Group, LLC

(57) ABSTRACT

The present disclosure relates to an organic light-emitting diode having a low driving voltage and long lifespan and more particularly, to an organic light-emitting diode, comprising a first electrode, a second electrode facing the first electrode, and a light-emitting layer interposed therebetween, wherein the light-emitting layer contains at least one of the amine compounds represented by the following Chemical Formula A or Chemical Formula B, plus the compound represented by Chemical Formula D. The structures of Chemical Formulas A, B, and D are the same as in the specification.

16 Claims, 1 Drawing Sheet

US 10,468,603 B2
Page 2

(51) Int. Cl.
*H01L 51/50* (2006.01)
*C07D 307/91* (2006.01)
*C07D 307/94* (2006.01)
*C07D 493/10* (2006.01)
*C09K 11/02* (2006.01)

(52) U.S. Cl.
CPC .......... *C07D 493/10* (2013.01); *C09K 11/025* (2013.01); *C09K 11/06* (2013.01); *H01L 51/00* (2013.01); *H01L 51/006* (2013.01); *H01L 51/0073* (2013.01); *H01L 51/50* (2013.01); *C09K 2211/1007* (2013.01); *C09K 2211/1011* (2013.01); *C09K 2211/1014* (2013.01); *C09K 2211/1022* (2013.01); *H01L 51/0002* (2013.01); *H01L 51/5024* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | | |
|---|---|---|---|---|
| 2010/0045170 A1* | 2/2010 | Lee | ........... | C07C 13/547 313/507 |
| 2011/0068683 A1* | 3/2011 | Kawamura | ........... | C07C 13/465 313/504 |
| 2012/0056165 A1* | 3/2012 | Kawamura | ........... | C09K 11/06 257/40 |
| 2012/0112174 A1* | 5/2012 | Lee | ........... | C07D 307/93 257/40 |
| 2013/0313538 A1* | 11/2013 | Kawamura | ........... | C07D 307/79 257/40 |
| 2014/0054559 A1* | 2/2014 | Kim | ........... | H01L 51/0094 257/40 |
| 2014/0061622 A1* | 3/2014 | Ikeda | ........... | H01L 51/0073 257/40 |
| 2015/0144937 A1* | 5/2015 | Park | ........... | H01L 51/0067 257/40 |
| 2017/0062732 A1* | 3/2017 | Jatsch | ........... | C07D 401/04 |

FOREIGN PATENT DOCUMENTS

| | | | | |
|---|---|---|---|---|
| JP | 2012028548 A | * | 2/2012 | ............. H01L 51/50 |
| KR | 1020080015865 A | | 2/2008 | |
| KR | 10-2009-0086015 A | | 8/2009 | |
| KR | 10-2010-0093064 A | | 8/2010 | |
| KR | 10-2010-0108903 A | | 10/2010 | |
| KR | 1020120047706 A | | 5/2012 | |
| KR | 1020130121947 A | | 4/2015 | |

OTHER PUBLICATIONS

The Extended European Search Report, dated Jun. 6, 2018.
International Search Report of PCT/KR2016/000473, dated Apr. 21, 2016, English Translation.

* cited by examiner

| 80 |
|----|
| 70 |
| 60 |
| 50 |
| 40 |
| 30 |
| 20 |
| 10 |

ORGANIC LIGHT-EMITTING DIODE HAVING LOW DRIVING VOLTAGE AND LONG LIFESPAN

CROSS-REFERENCE TO RELATED APPLICATIONS

This application is the U.S. National Phase under 35 U.S.C. § 371 of International Application No. PCT/KR2016/000473 filed on Jan. 15, 2016, which in turn claims the benefit of Korean Application No. 10-2015-0017265, filed on Feb. 4, 2015, the disclosures of which are incorporated by reference into the present application.

TECHNICAL FIELD

The present disclosure relates to an organic light-emitting diode having a low driving voltage and long lifespan and more particularly, to an organic light-emitting diode containing host and dopant materials of certain structures in a light-emitting layer thereof.

BACKGROUND ART

Organic light-emitting diodes (OLEDs), based on self-luminescence, enjoy the advantage of having a wide viewing angle and being able to be made thinner and lighter than liquid crystal displays (LCDs). In addition, an OLED display exhibits a very fast response time. Accordingly, OLEDs find applications in the illumination field as well as the full-color display field.

Materials used as organic layers in OLEDs may be divided into luminescent materials and charge transport materials, for example, a hole injection material, a hole transport material, an electron injection material, and an electron transport material. As for the luminescent materials, there are two main families of OLED: those based on small molecules and those employing polymers. The light-emitting mechanism forms the basis for classification of the luminescent materials as fluorescent or phosphorescent materials, which use excitons in singlet and triplet states, respectively. Further, luminescent materials may be divided according to color into blue, green, and red light-emitting materials. Furthermore, yellow and reddish yellow light-emitting materials have been developed in order to achieve more natural colors.

Meanwhile, when a single material is employed as the luminescent material, intermolecular actions cause the wavelength of maximum luminescence to shift toward a longer wavelength, resulting in reduced color purity and light emission efficiency. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of dopant because the wavelength of the host moves to the wavelength range of the dopant.

With regard to related arts pertaining to dopant compounds in the light-emitting layer, reference may be made to Korean Patent Publication No. 10-2008-0015865 (Feb. 20, 2008), which describes an organic light-emitting diode using an arylamine-coupled indenofluorene derivative, and Korean Patent Publication No. 10-2012-0047706 (May 14, 2012), which describes an organic photoelectric device using a compound in which dibenzofuran or dibenzothiophene coexists with fluorene or carbazole.

Further, and Korean Patent Application No. 10-2013-0121947 (Oct. 14, 2013), pertaining to a related art of host compound in the light-emitting layer, discloses an organic light-emitting diode employing an anthracene derivative as a fluorescent host.

Despite enormous efforts including the documents describing the related art, there is still the continued need to develop organic light-emitting diodes that exhibit lower driving voltages and longer lifespan.

RELATED ART DOCUMENT

Korean Patent Publication No. 10-2008-0015865 (Feb. 20, 2008)

Korean Patent Publication No. 10-2012-0047706 (May 14, 2012)

Korean Patent Application No. 10-2013-0121947 (Oct. 14, 2013)

DETAILED DESCRIPTION OF THE INVENTION

Technical Problem

Accordingly, the purpose to be achieved by the present disclosure is to provide a novel organic light-emitting diode (OLED), characterized by low power and long lifespan, comprising a dopant and a host of specific structures.

Technical Solution

To accomplish the technical purpose, the present disclosure provides an organic light-emitting diode, comprising a first electrode, a second electrode facing the first electrode, and a light-emitting layer interposed therebetween, wherein the light-emitting layer contains at least one of the amine compounds represented by the following Chemical Formula A or Chemical Formula B, plus the compound represented by Chemical Formula D:

[Chemical Formula A]

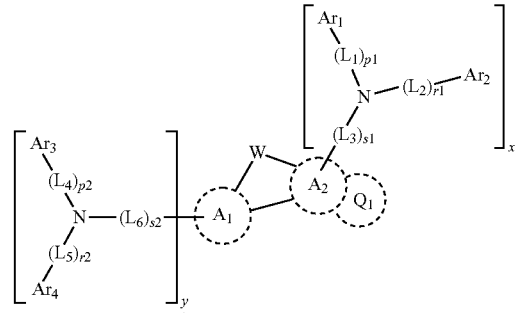

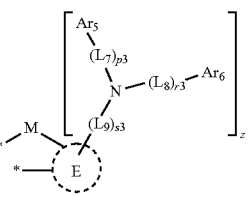

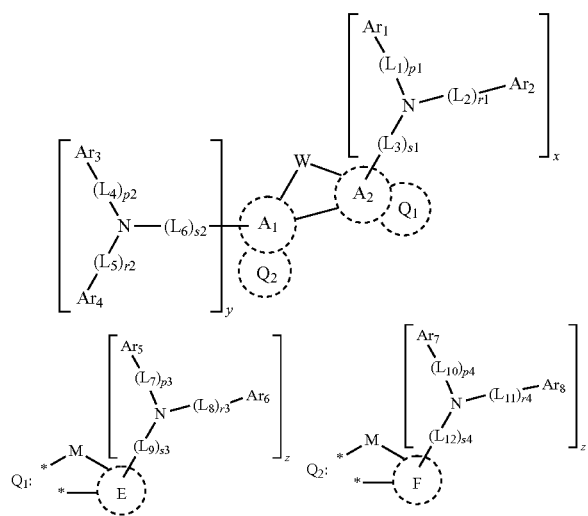

[Chemical Formula B]

wherein

A1, A2, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring A1 and two adjacent carbon atoms of the aromatic ring A2 form a 5-membered fused ring together with W;

linkers L1 to L12 may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

W is selected from among $CR_1R_2$, $SiR_1R_2$, $GeR_1R_2$, O, and S;

M is any one selected from among N—R3, CR4R5, SiR6R7, GeR8R9, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to carbon atoms, a substituted or unsubstituted alkylgermanium of 1 to 30 carbon atoms, a substituted or unsubstituted arylgermanium of 1 to 30 carbon atoms, a cyano, a nitro, and a halogen, with the proviso that $R_1$ and $R_2$ may be bonded to each other to form a mono- or polycyclic aliphatic or aromatic ring, which may be a heterocyclic ring containing a heteroatom selected from among N, O, P, Si, S, Ge, Se, and Te as a ring member;

p1 to p4, r1 to r4, and s1 to s4 are each independently an integer of 1 to 3, with the proviso that when any of them is 2 or greater, the corresponding linkers may be the same or different, x is an integer of 1 or 2, and y and z may be the same or different and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring,

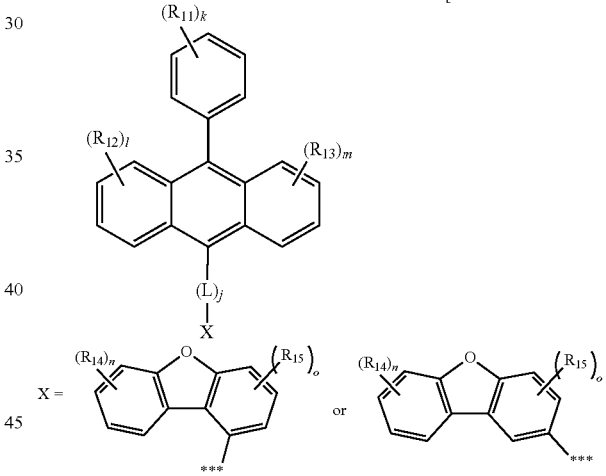

[Chemical Formula D]

wherein $R_{11}$ to $R_{15}$ may be the same or different and are each independently any one selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxyl of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N or S as a heteroatom, a cyano, a nitro, a halogen a substituted or unsubstituted silyl of 1 to 30 carbon atoms, a substituted or unsubstituted alkylgermanium of 1 to 30 carbon atoms, a substituted or unsubstituted alkyl boron of 1 to 30 carbon atoms, a substituted or unsubstituted alkyl aluminum of 1 to 30 carbon atoms, a carbonyl, a phosphoryl, an amino, a thiol, a hydroxyl, a selenium, a tellurium, an amide, an ether, and an ester, wherein each of unsubstituted carbon atoms of $R_{11}$ to $R_{15}$ is bound with a hydrogen atom or a deuterium atom;

linker L is a single bond, or a substituted or unsubstituted arylene of 6 to 60 carbon atoms;

j is an integer of 0 to 2, with the proviso that when j is 2 or greater, corresponding L's may be the same or different;

k is an integer of 1 to 5, l to n may be the same or different and are each independently an integer of 1 to 4, o is an integer of 1 to 3, with the proviso that when k to o are each an integer of 2 or greater, corresponding $R_{11}$'s to $R_{15}$'s may be individually the same or different, and "***" of X denotes a bonding site to be linked to linker L.

wherein the term 'substituted' in the expression 'substituted or unsubstituted' used in Chemical Formulas A, B and D means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

Advantageous Effects

The OLED according to the present disclosure has lower driving voltages and longer lifespan compared to conventional OLEDs.

BRIEF DESCRIPTION OF THE DRAWINGS

FIG. 1 is a schematic diagram of an OLED according to some embodiments of the present disclosure.

MODE FOR CARRYING OUT THE INVENTION

Below, a detailed description will be given of the present disclosure.

The present disclosure addresses an organic light-emitting diode, comprising a first electrode, a second electrode facing the first electrode, and a light-emitting layer interposed therebetween, wherein the light-emitting layer contains at least one of the amine compounds represented by Chemical Formula A or Chemical Formula B plus the compound represented by Chemical Formula D.

The expression for a number of carbon atoms, such as in "a substituted or unsubstituted alkyl of 1 to 30 carbon atoms", "a substituted or unsubstituted aryl of 6 to 50 carbon atoms", etc., in the amine compounds represented by Chemical Formula A or B and in the compounds represented by Chemical Formulas H1 to H7 means the total number of carbon atoms in, for example, the alkyl or aryl radical or moiety alone, exclusive of the number of carbon atoms of the substituent. For instance, a phenyl group with a butyl at the para position falls within the scope of an aryl of 6 carbon atoms, even if it is substituted with a butyl radical of 4 carbon atoms.

As used herein, the term "aryl" as a substituent used in the compounds of the present disclosure means an organic radical derived from an aromatic hydrocarbon by removing a hydrogen atom and may further include a fused ring that is formed by adjacent substituents on the organic radical.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino ($-NH_2$, $-NH(R)$, or $-N(R')(R'')$ wherein R' and R'' are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms containing one to three heteroatoms selected from among N, O, P, Si, S, Ge, Se, and Te. In the aromatic system, two or more rings may be fused. One or more hydrogen atoms on the heteroaryl may be substituted with the same substituents as on the aryl.

As used herein, the term "heteroaromatic ring" refers to an aromatic hydrocarbon ring containing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the substituent silyl useful in the present disclosure are trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl, and dimethylfurylsilyl. One or more hydrogen atoms of the silyl may be substituted by the same substituent as in the aryl.

The amine compound, useful in the OLED of the present invention, represented by Chemical Formula A or B has the structural feature that if Structural Formula $Q_1$ is connected to the $A_2$ ring in Chemical Formula A, the amine moiety containing $Ar_1$ and $Ar_2$ must be bonded to the $A_2$ ring and that if Structural Formula $Q_2$ and $Q_1$ are connected respectively to $A_1$ and $A_2$ rings in Chemical Formula B, the amine moiety containing $Ar_1$ and $Ar_2$ must be bonded to the $A_2$ ring.

In Chemical Formula D, linking occurs between the carbon atom at position 9 of the anthracene moiety and the carbon atom at position 1 or 2 of either phenyl ring of the substituted or unsubstituted dibenzofuran moiety, as shown in the following Diagram 1, through the linker L.

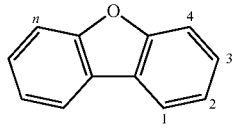

[Diagram 1]

The light-emitting layer of the OLED according to the present disclosure comprises a host and a dopant, wherein the dopant is selected from among the amine compounds represented by Chemical Formulas A and B and the host is the compound represented by Chemical Formula D, whereby the OLED can be operated at a lower voltage and exhibits longer lifespan compared to conventional OLEDs.

According to some embodiments of the present disclosure, $A_1$, $A_2$, E, and F in Chemical Formula A or B may be the same or different and are each independently substituted or unsubstituted aromatic hydrocarbon rings of 6 to 50 carbon atoms.

As stated above, when $A_1$, $A_2$, E and F in Chemical Formula A or B are each independently substituted or unsubstituted aromatic hydrocarbon rings of 6 to 50 carbon atoms, the substituted or unsubstituted aromatic hydrocarbon rings of 6 to 50 carbon atoms may be the same or different and are each independently selected from among compounds represented by Structural Formulas 10 to 21.

[Structural Formula 10]

[Structural Formula 11]

[Structural Formula 12]

[Structural Formula 13]

[Structural Formula 14]

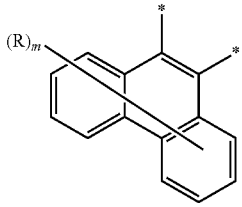

[Structural Formula 15]

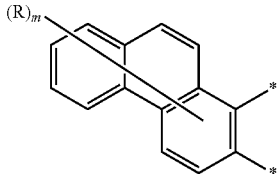

[Structural Formula 16]

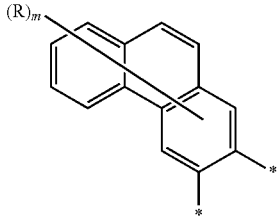

[Structural Formula 17]

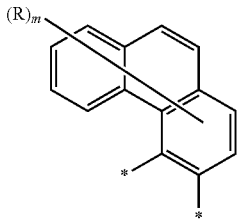

[Structural Formula 18]

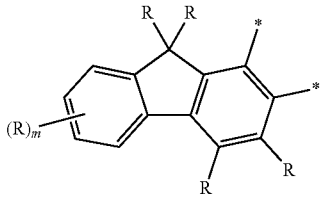

[Structural Formula 19]

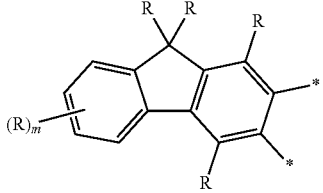

[Structural Formula 20]

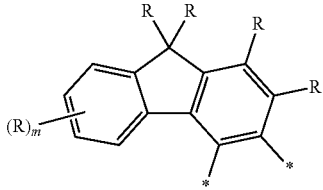

[Structural Formula 21]

wherein

"-*" denotes a bonding site for forming a 5-membered ring containing W or a bonding site for forming a 5-membered ring containing M of the structural Formula $Q_1$ and $Q_2$;

when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R's are the same as defined above for $R_1$ and $R_2$, and m is an integer of 1 to 8, with the proviso that when m is 2 or greater or when two or more R's exist, the corresponding R's may be the same or different.

In addition, the linker L in Chemical Formula D may each be a single bond or any one selected from among the following Structural Formulas 22 to 30:

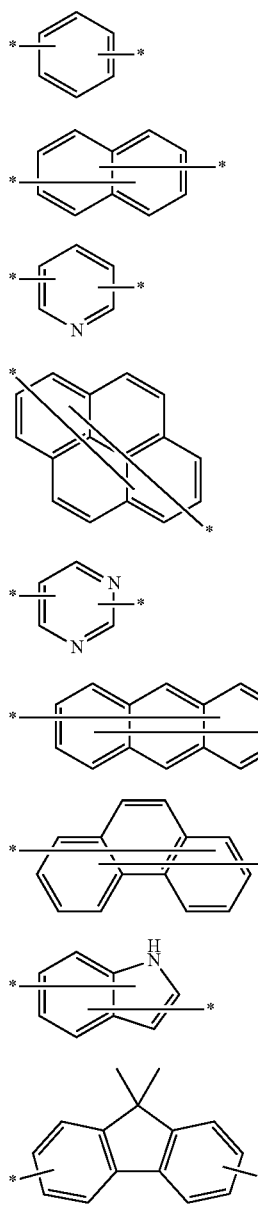

wherein each of the unsubstituted carbon atoms of the aromatic ring moiety in L may be bound with a hydrogen atom or a deuterium atom.

According to some embodiments of the present disclosure, the linkers $L_1$ to $L_{12}$ in Chemical Formulas A and B may be the same or different, and each may be a single bond or any one selected from among a substituted or unsubstituted arylene of 6 to 20 carbon atoms and a substituted or unsubstituted heteroarylene of 2 to 20 carbon atoms.

In this regard, the linkers $L_1$ to $L_{12}$ may each be a single bond or any one selected from among the following Structural Formulas 22 to 30:

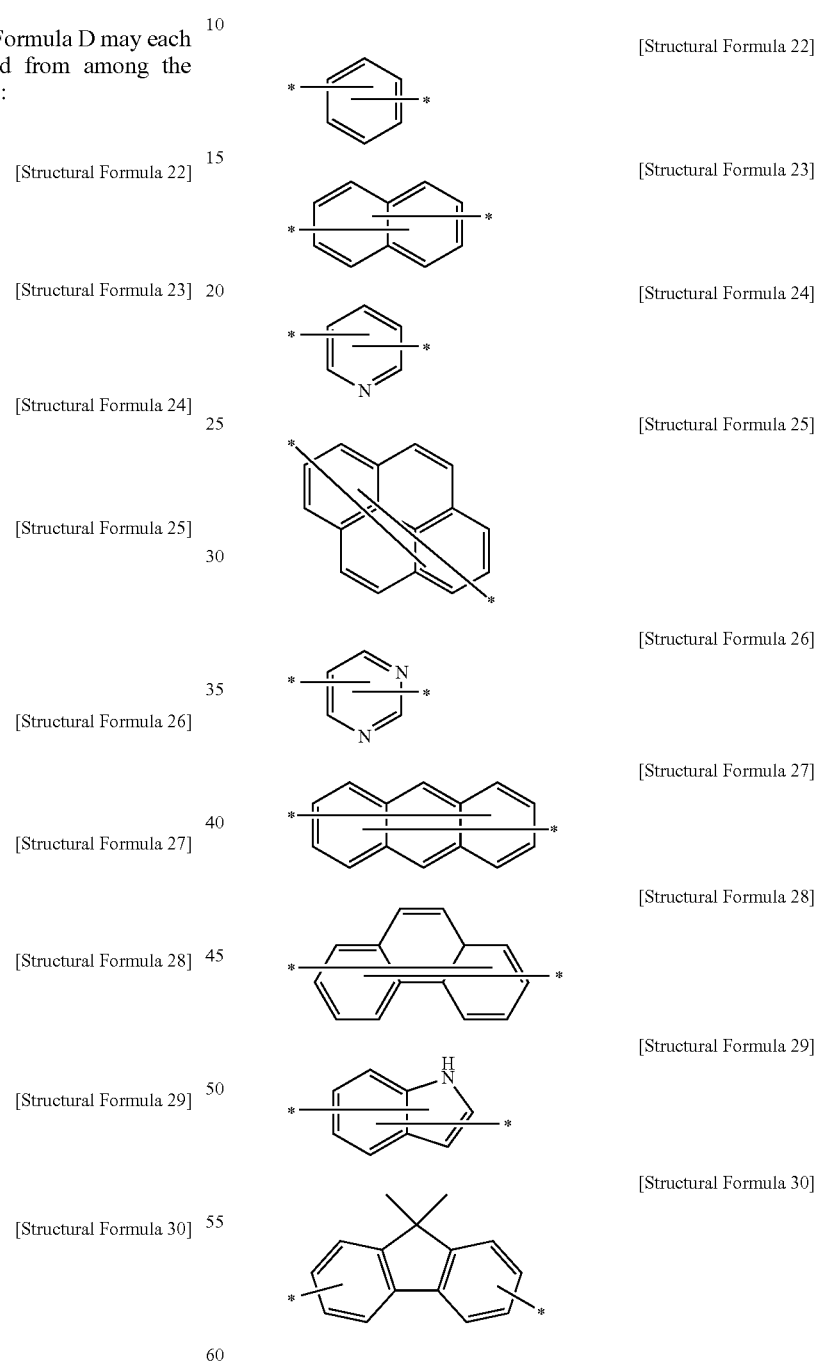

In the linkers L, each of the unsubstituted carbon atoms of the aromatic ring moiety is bound with a hydrogen atom or a deuterium atom.

For instance, the linker L, and $L_1$ to $L_{12}$ may each be independently a single bond or have one of the structures represented by the following [$L_{21}$] to [$L_{26}$].

$L_{21}$ 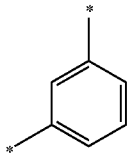

$L_{22}$ 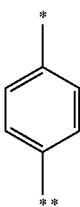

$L_{23}$ 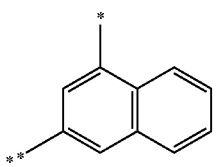

$L_{24}$ 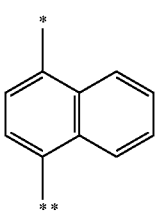

$L_{25}$ 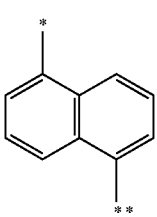

$L_{26}$ 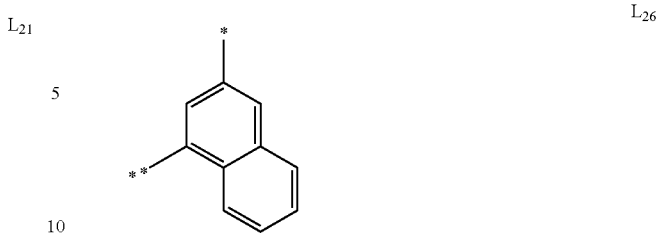

wherein '-*' denotes a bonding site to be linked to the anthracene moiety, and '-**' denotes a bonding site to linked to X.

In this case, particularly, y may be 1 and z may be 0.

In addition, at least one of the substituents $R_{11}$ to $R_{15}$ in Chemical Formula D may contain a deuterium.

In one embodiment, $R_{11}$ is a deuterium, and k is 5.

In another embodiment, $R_{12}$ and/or $R_{13}$ is a deuterium, and l is an integer of 2 or greater or m is an integer of 2 or greater.

In another embodiment, $R_{12}$ and $R_{13}$ are both a deuterium, and l and m are each an integer of 2 or greater.

In another embodiment, $R_{14}$ and/or $R_{15}$ is a deuterium, and n is an integer of 2 or greater or o is an integer of 2 or greater.

In another embodiment, $R_{14}$ and $R_{15}$ are both a deuterium, and n and o are each an integer of 2 or greater.

According to a specific embodiment of the present disclosure, $R_1$ to $R_9$, and $Ar_1$ to $Ar_8$ in the amine compound represented by Chemical Formula A or B may be the same or different and may each be independently any one selected from among a hydrogen, a deuterium, a substituted or unsubstituted aryl of 6 to 20 carbon atoms, a substituted or unsubstituted cycloalkyl of 3 to 30 carbon atoms, a substituted or unsubstituted heteroaryl of 2 to 20 carbon atoms bearing at least one heteroatom selected from among O, N, S, and Si, a cyano, and a halogen.

In the amine compound of Chemical Formula A or B according to some embodiments of the present disclosure, $A_1$, $A_2$, E, F, $Ar_1$ to $Ar_8$, $L_1$ to $L_{12}$, and $R_1$ to $R_9$ may have as a substituent any one selected from the group consisting of a cyano, a halogen, an alkyl of 1 to 6 carbon atoms, an aryl of 6 to 18 carbon atoms, an arylalkyl of 7 to 18 carbon atoms, a heteroaryl of 3 to 18 carbon atoms, an alkylsilyl of 1 to 12 carbon atoms, and an arylsilyl of 6 to 18 carbon atoms.

According to another embodiment, W in Chemical Formulas A and B may be $CR_1R_2$, or $SiR_1R_2$.

The compound represented by Chemical Formula A or B according to the present disclosure may be any one selected from among compounds represented by the following Chemical Formulas 1 to 239:

<Chemical Formula 1>
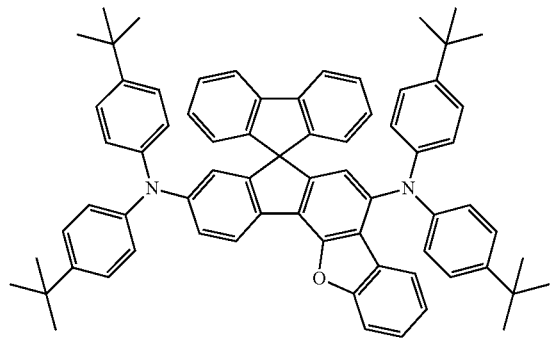
<Chemical Formula 2>
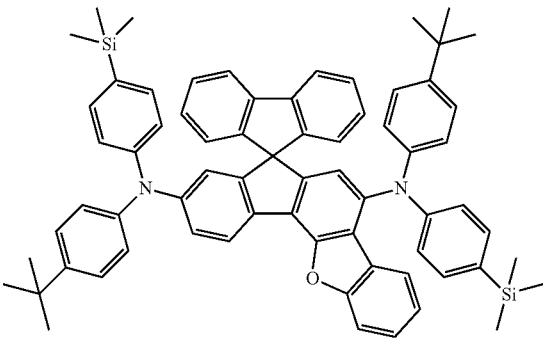
<Chemical Formula 3>
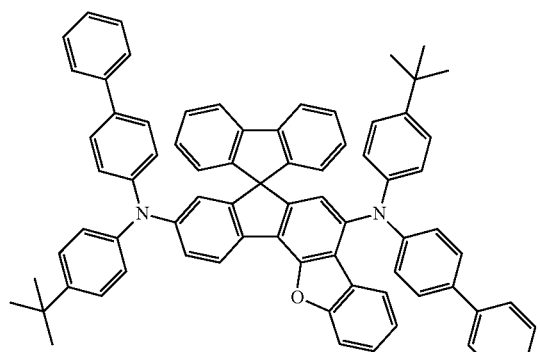
<Chemical Formula 4>
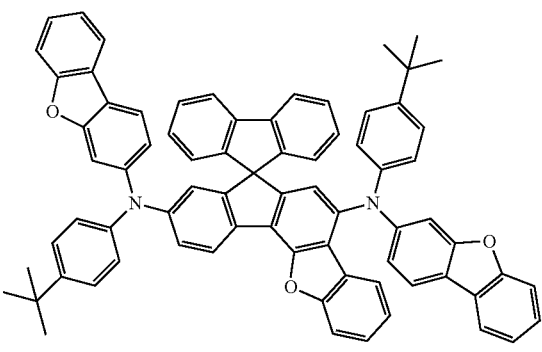
<Chemical Formula 5>
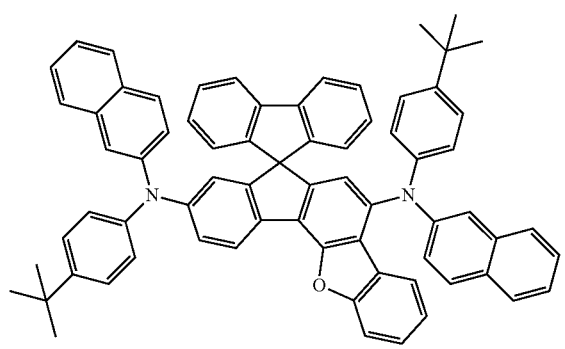
<Chemical Formula 6>
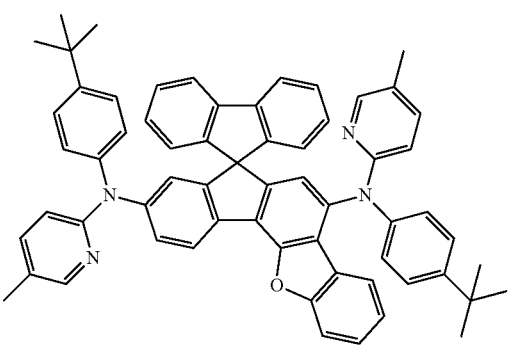
<Chemical Formula 7>
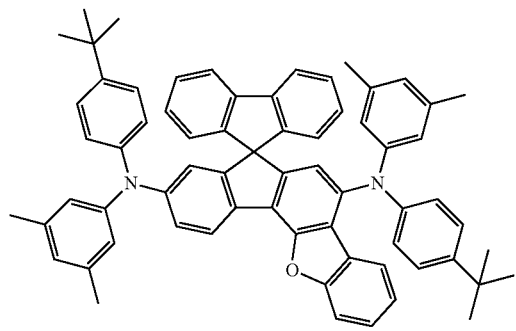
<Chemical Formula 8>
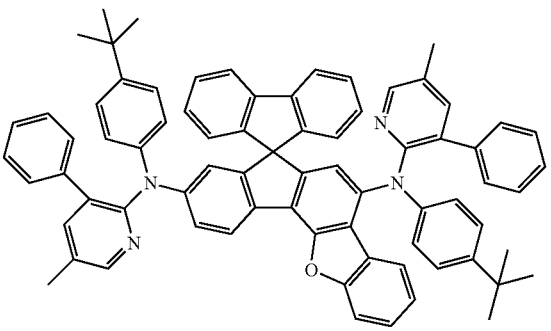

-continued
<Chemical Formula 9>
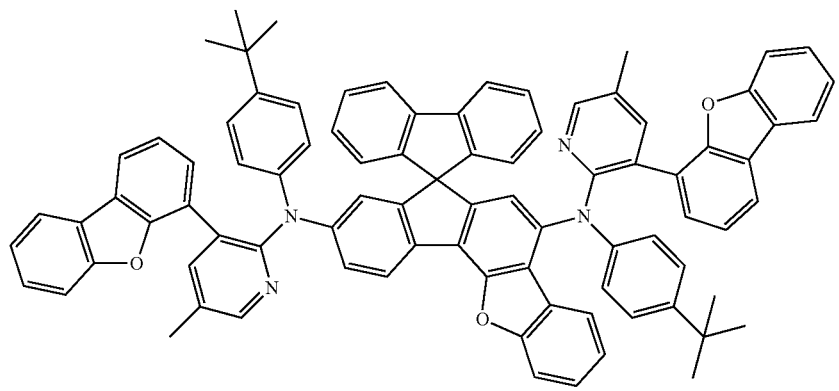
<Chemical Formula 10>
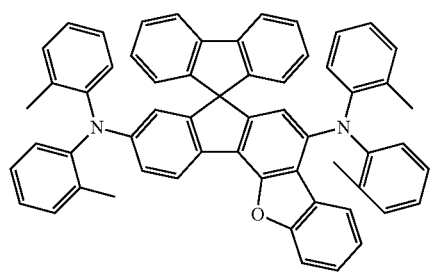
<Chemical Formula 11>
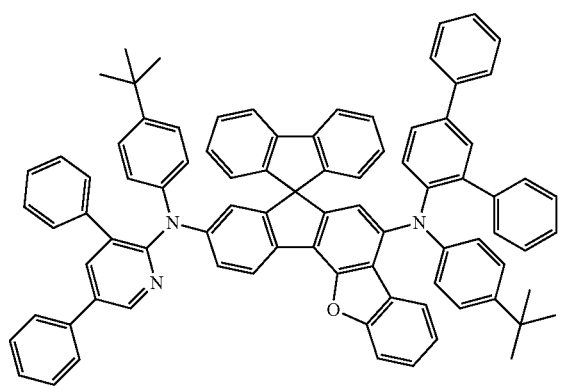
<Chemical Formula 12>
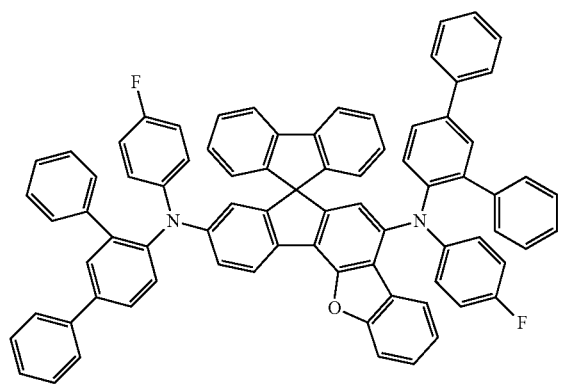
<Chemical Formula 13>
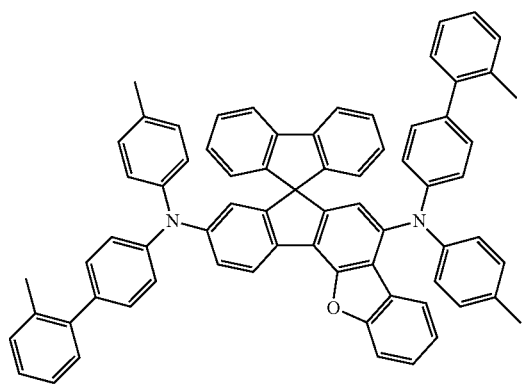

-continued
<Chemical Formula 14>
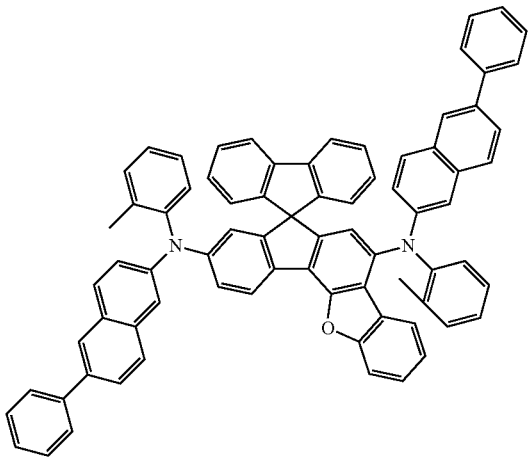
<Chemical Formula 15>
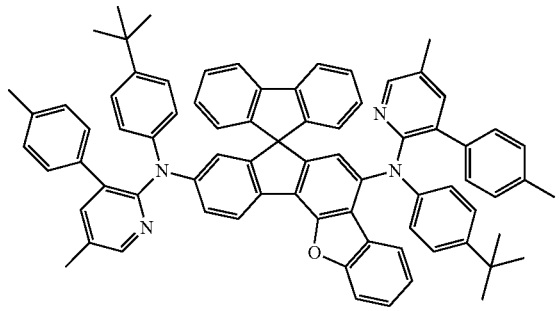
<Chemical Formula 16>
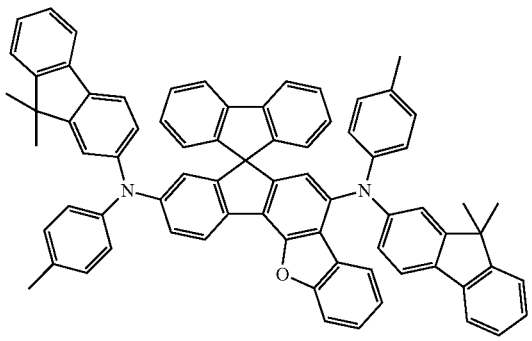
<Chemical Formula 17>
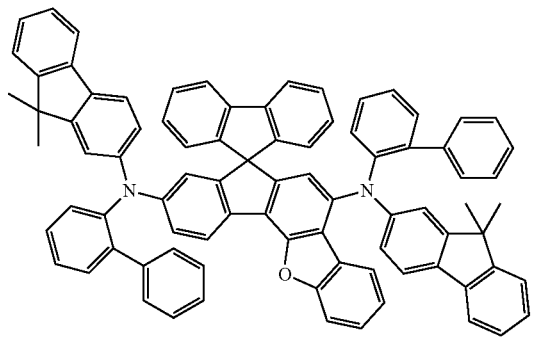
<Chemical Formula 18>
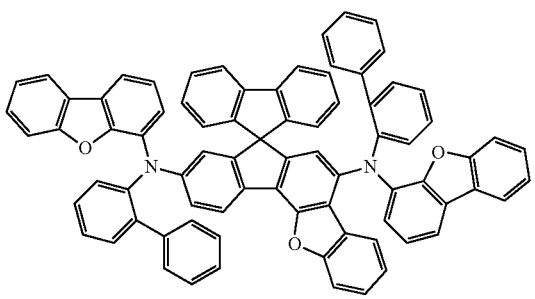
<Chemical Formula 19>
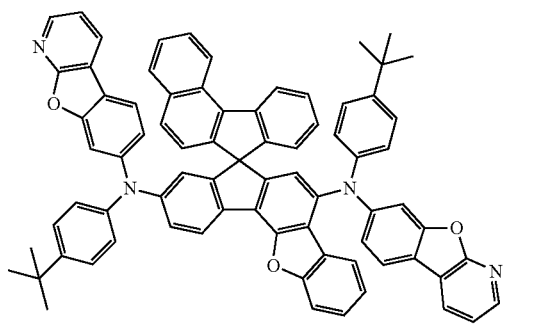
<Chemical Formula 20>
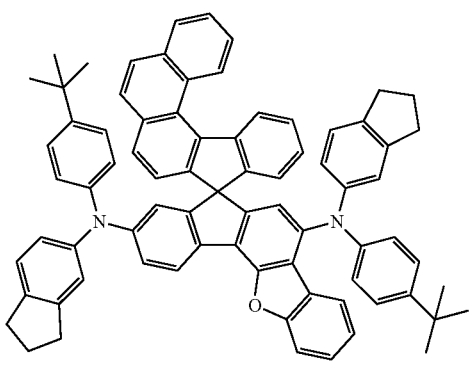
<Chemical Formula 21>
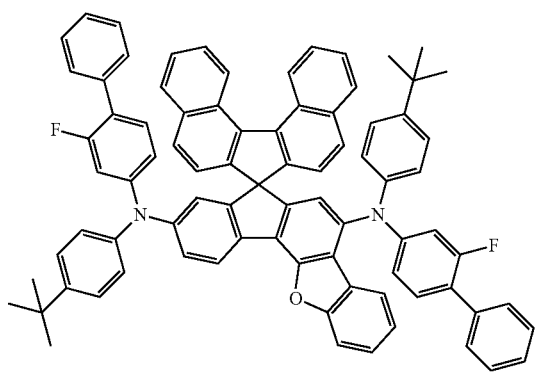

-continued
<Chemical Formula 22>
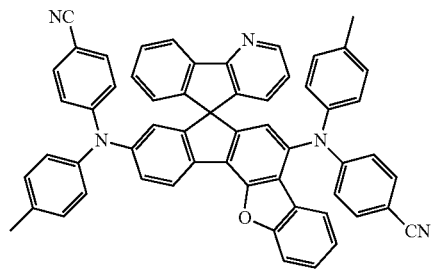
<Chemical Formula 23>
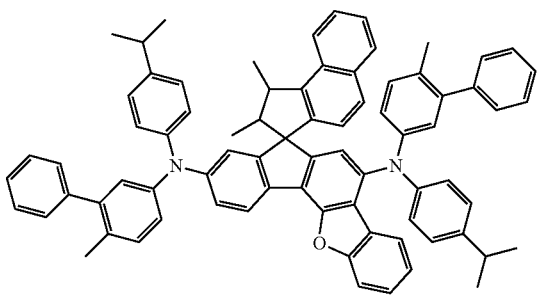
<Chemical Formula 24>
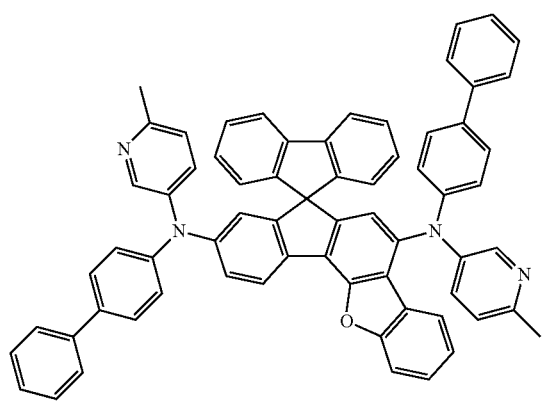
<Chemical Formula 25>
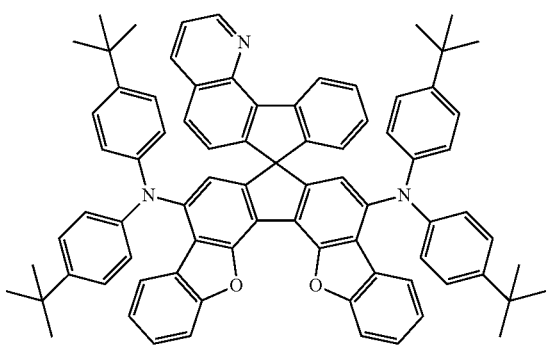
<Chemical Formula 26>
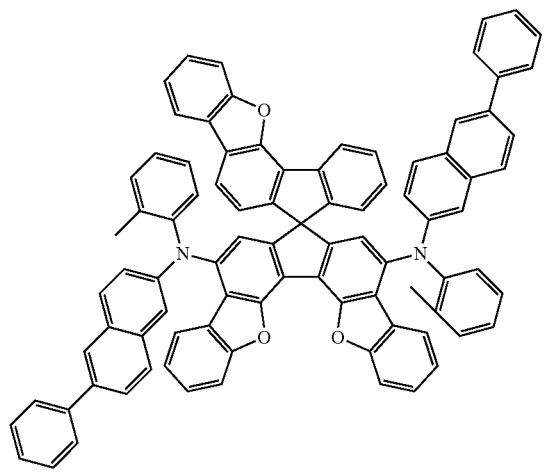
<Chemical Formula 27>
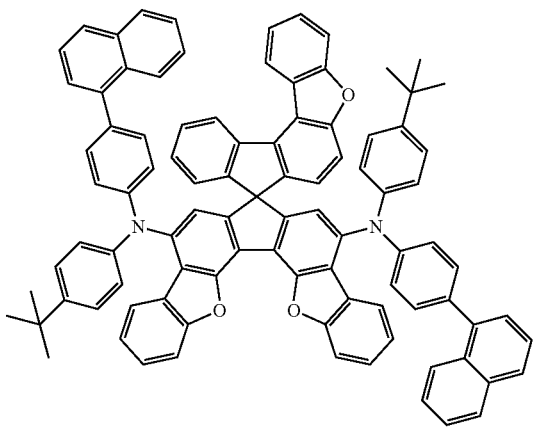
<Chemical Formula 28>
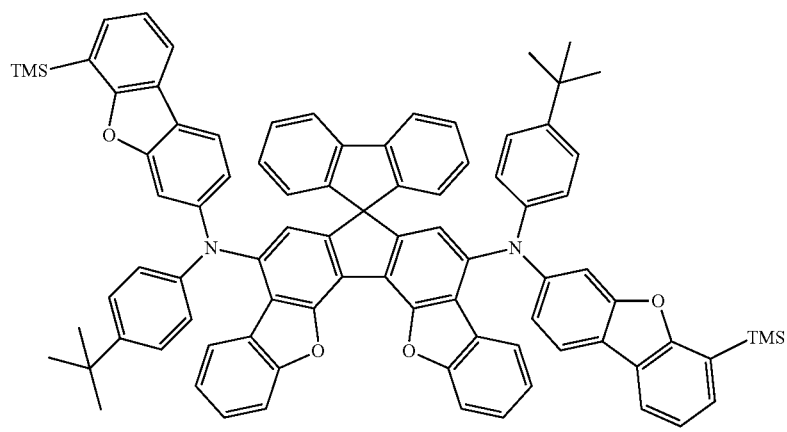

<Chemical Formula 29>
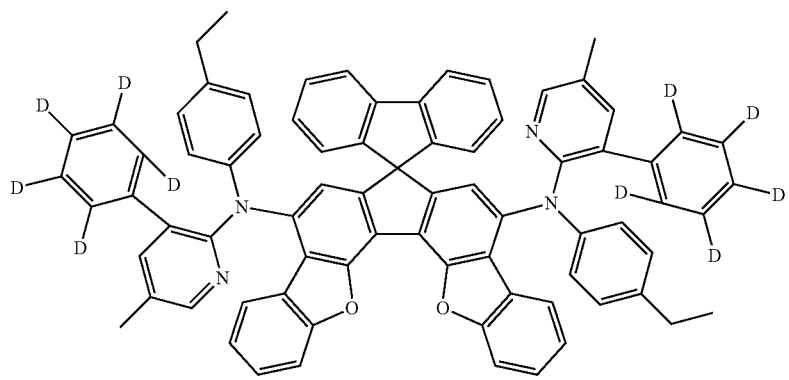
<Chemical Formula 30>
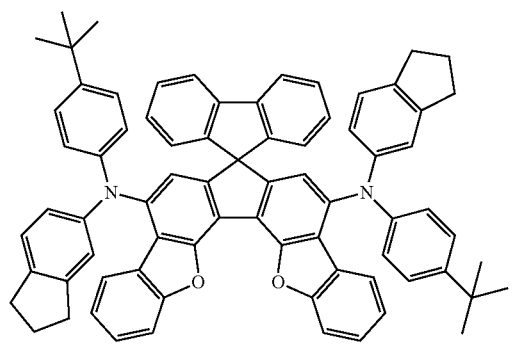
<Chemical Formula 31>
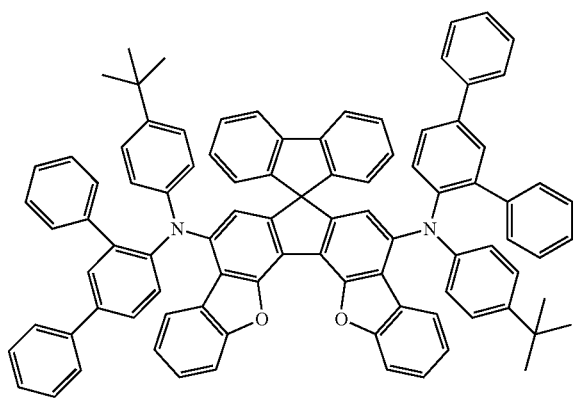
<Chemical Formula 32>
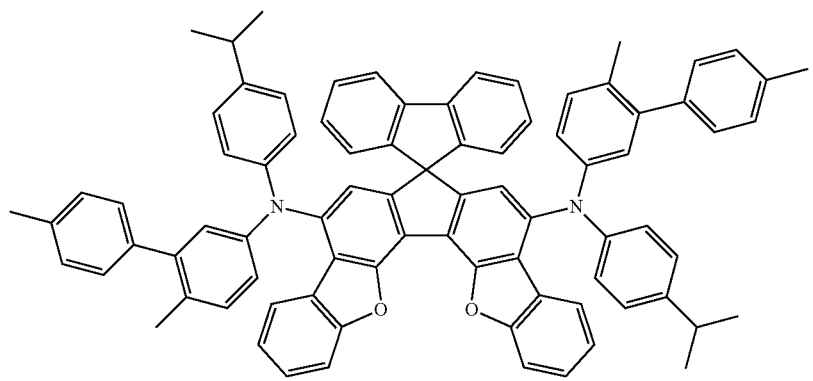
<Chemical Formula 33>
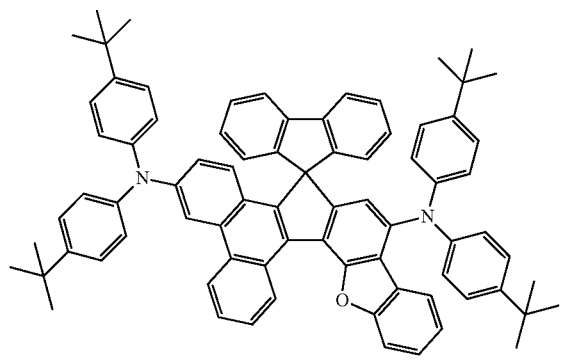
<Chemical Formula 34>
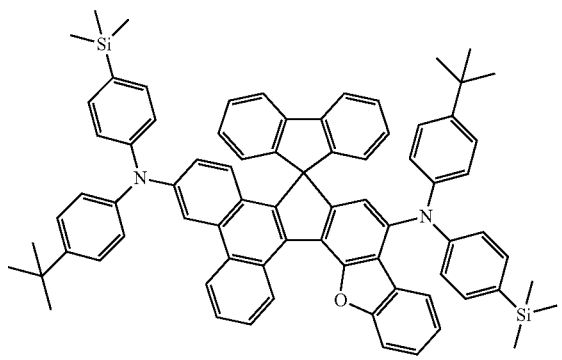

-continued
<Chemical Formula 35>
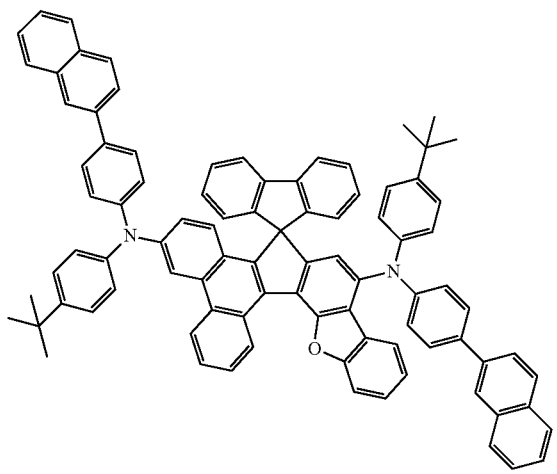
<Chemical Formula 36>
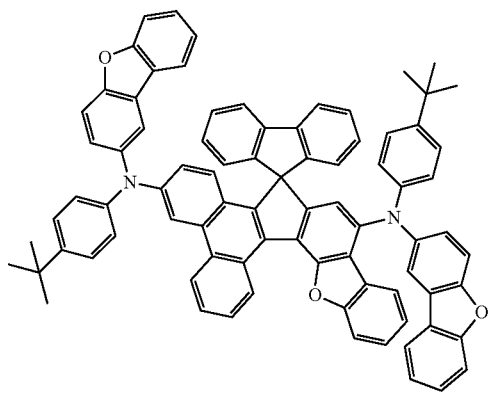
<Chemical Formula 37>
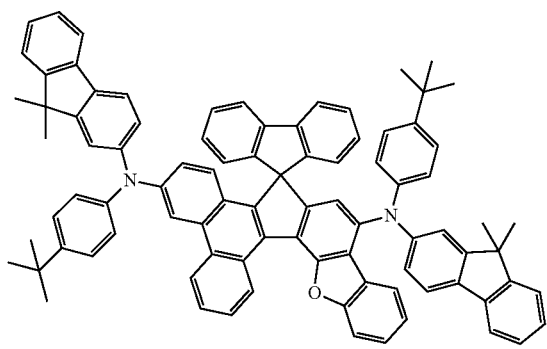
<Chemical Formula 38>
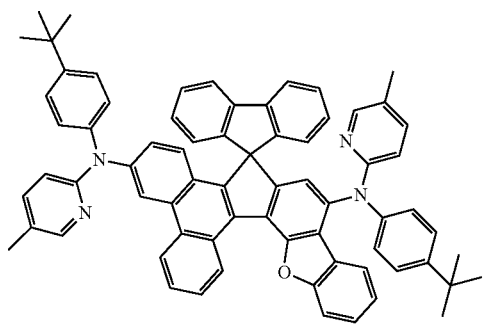
<Chemical Formula 39>
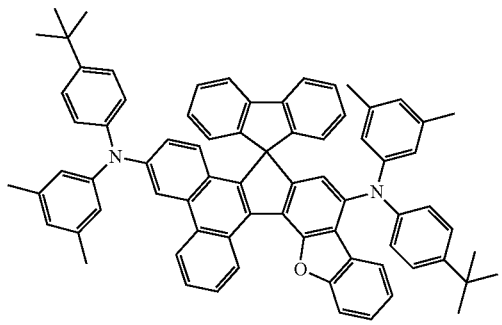
<Chemical Formula 40>
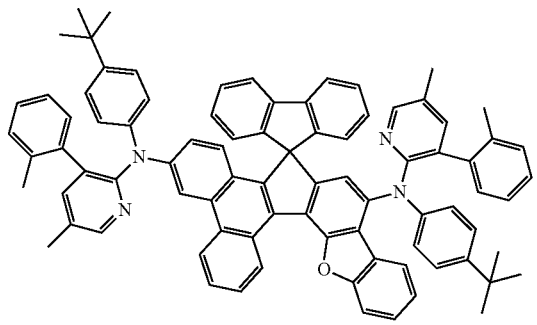
<Chemical Formula 41>
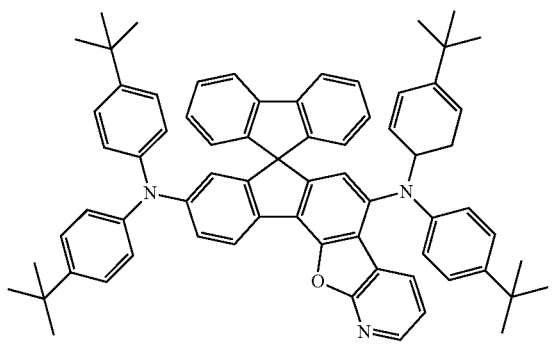
<Chemical Formula 42>
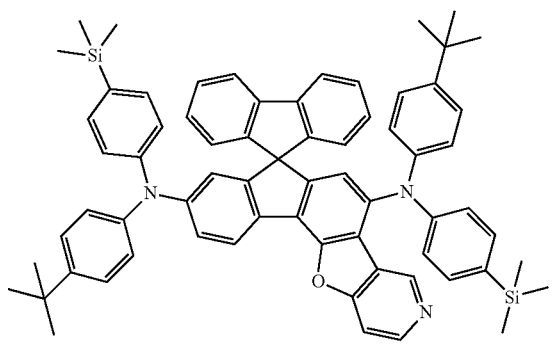

<Chemical Formula 43>
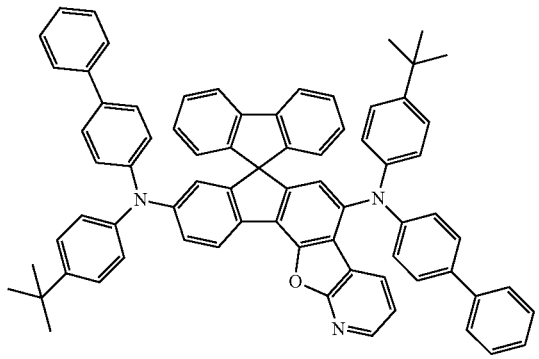
<Chemical Formula 44>
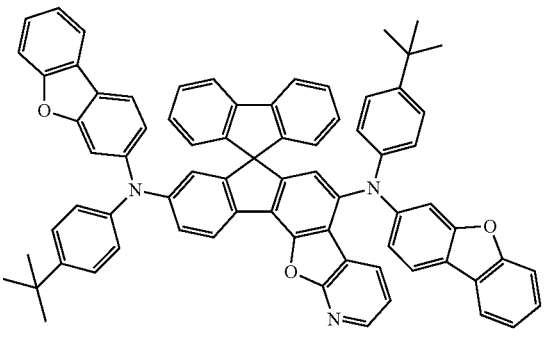
<Chemical Formula 45>
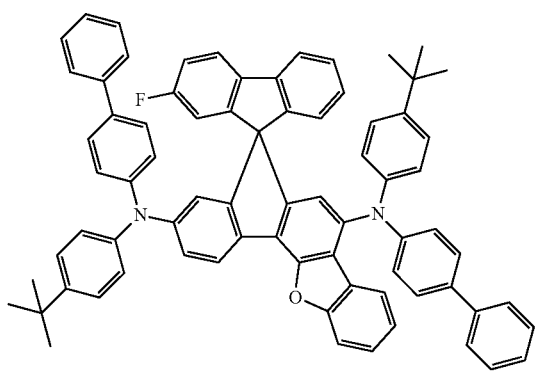
<Chemical Formula 46>
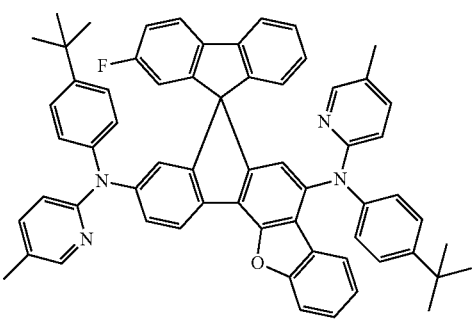
<Chemical Formula 47>
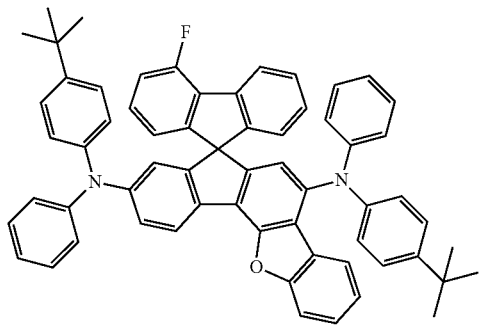
<Chemical Formula 48>
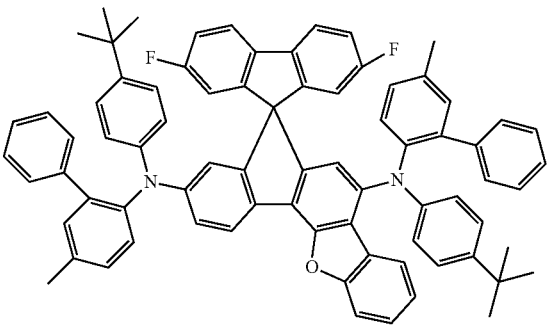
<Chemical Formula 49>
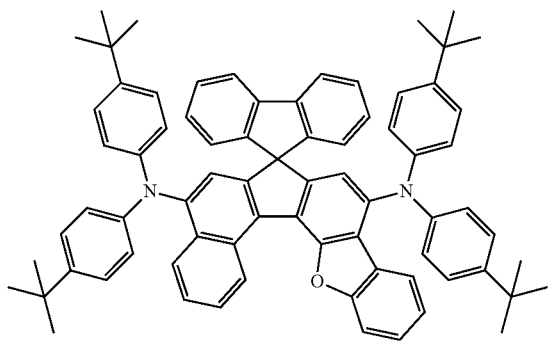
<Chemical Formula 50>
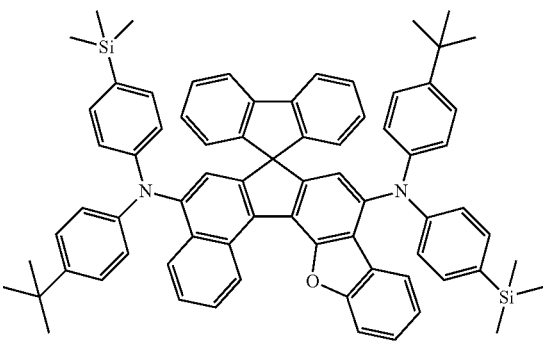

-continued
<Chemical Formula 51>
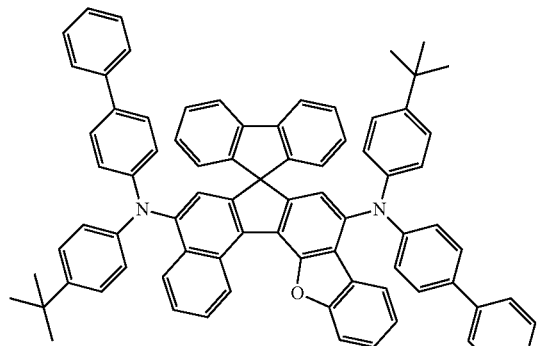
<Chemical Formula 52>
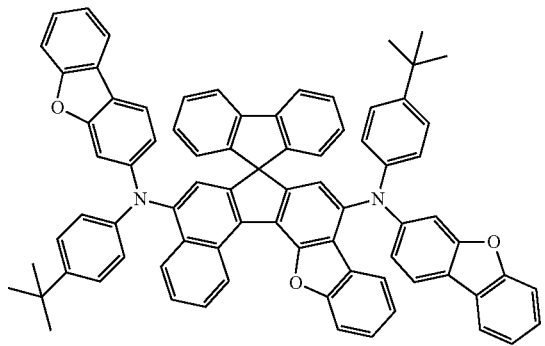
<Chemical Formula 53>
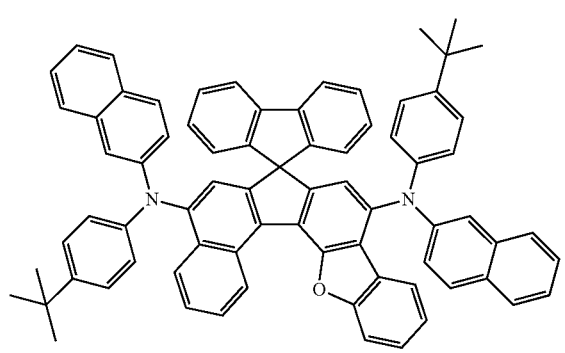
<Chemical Formula 54>
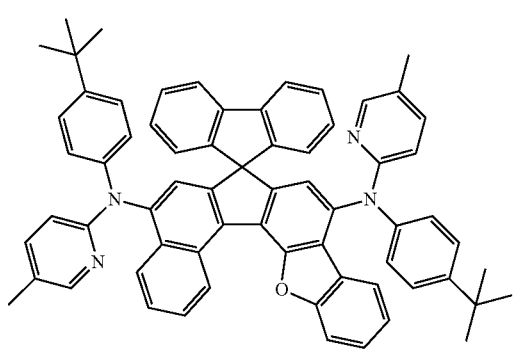
<Chemical Formula 55>
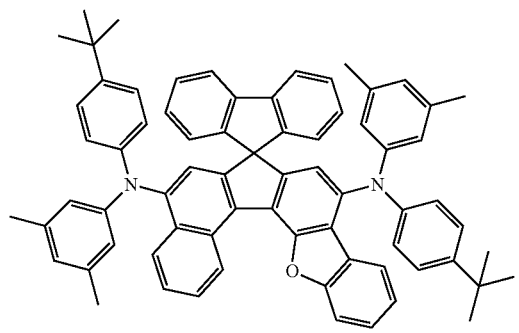
<Chemical Formula 56>
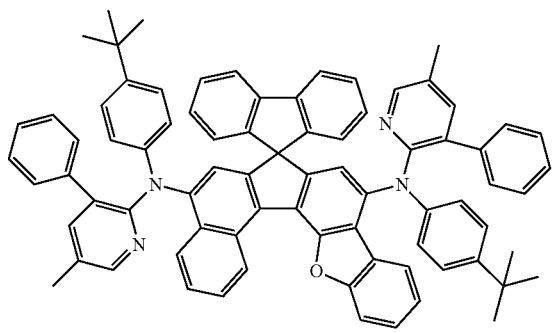
<Chemical Formula 57>
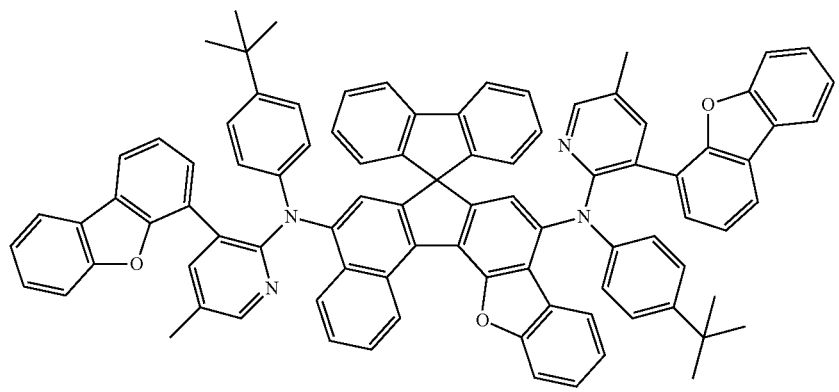

-continued
<Chemical Formula 58>
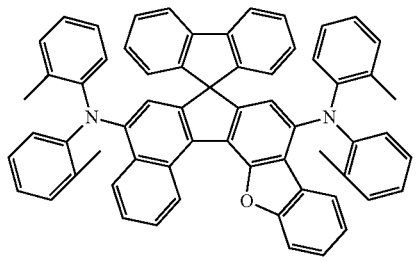
<Chemical Formula 59>
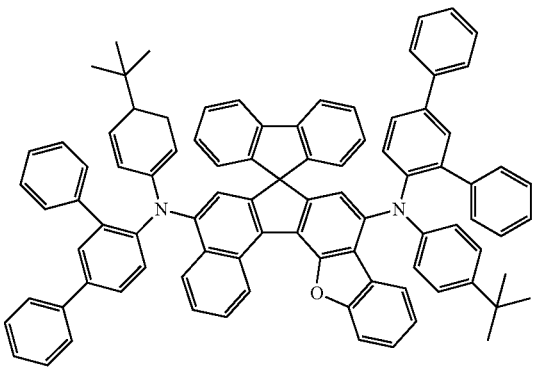
<Chemical Formula 60>
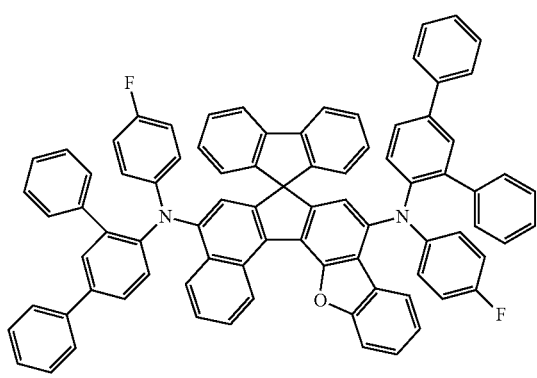
<Chemical Formula 61>
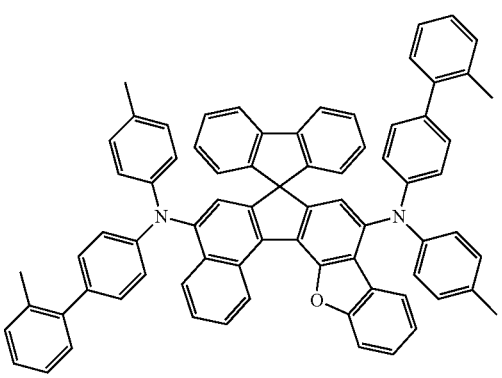
<Chemical Formula 62>
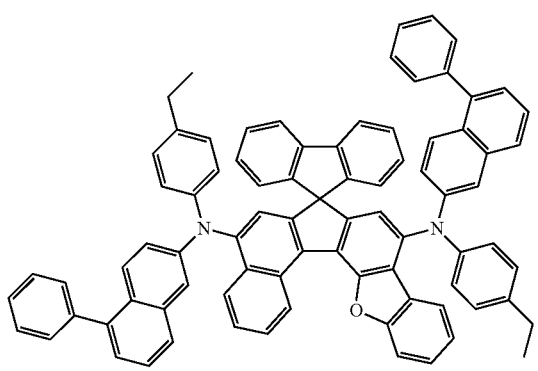
<Chemical Formula 63>
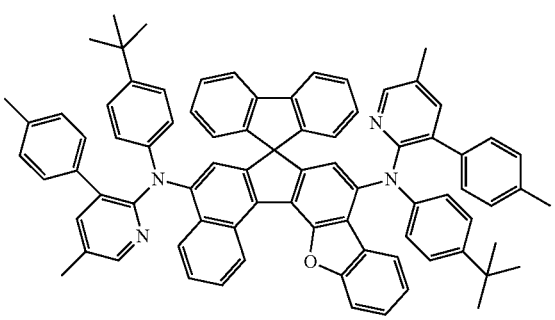
<Chemical Formula 64>
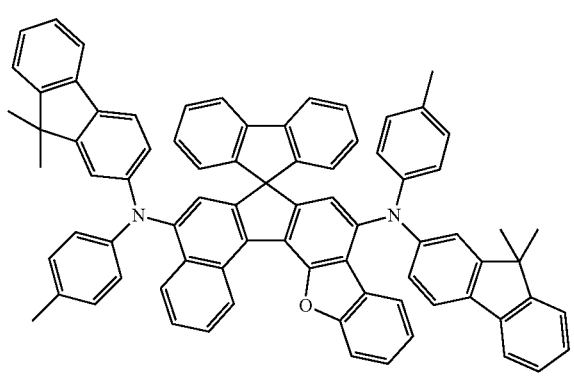

<Chemical Formula 65>
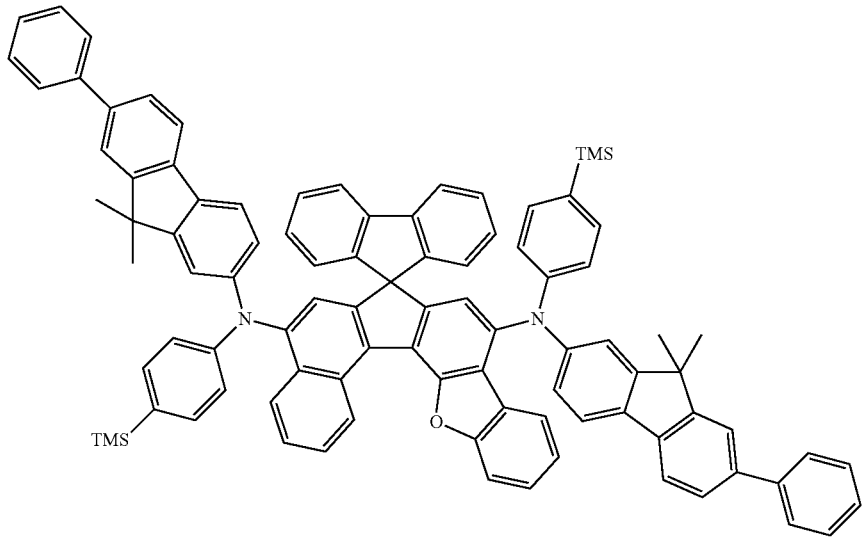
<Chemical Formua 66>
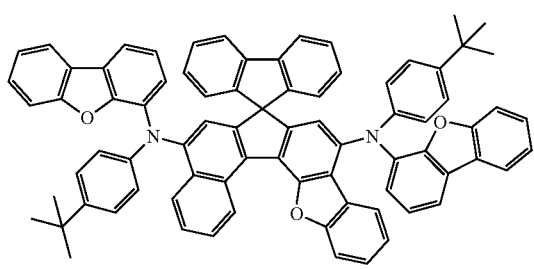
<Chemical Formula 67>
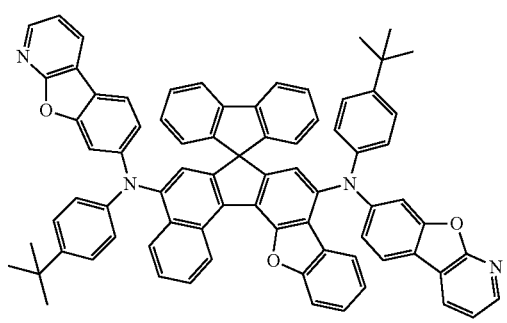
<Chemical Formula 68>
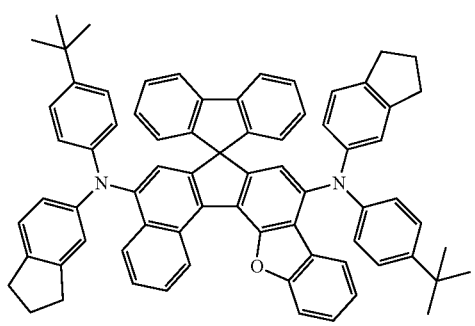
<Chemical Formula 69>
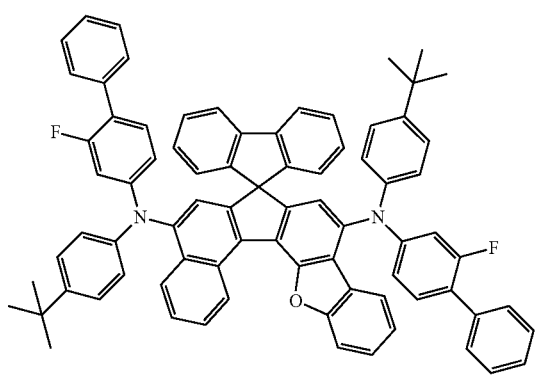
<Chemical Formula 70>
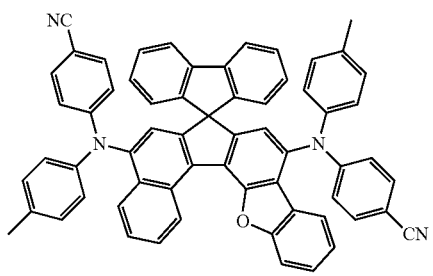
<Chemical Formula 71>
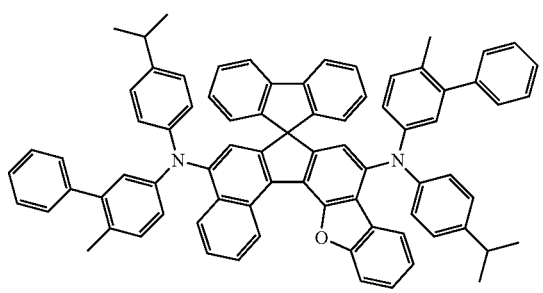

<Chemical Formula 72>
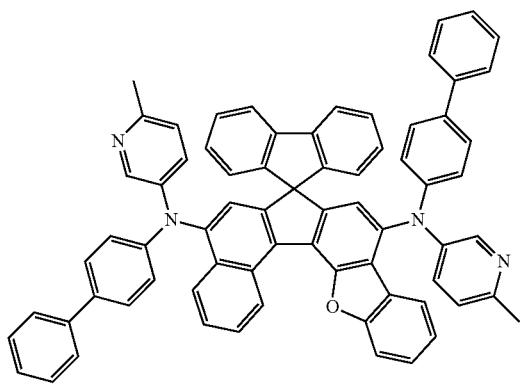
<Chemical Formula 73>
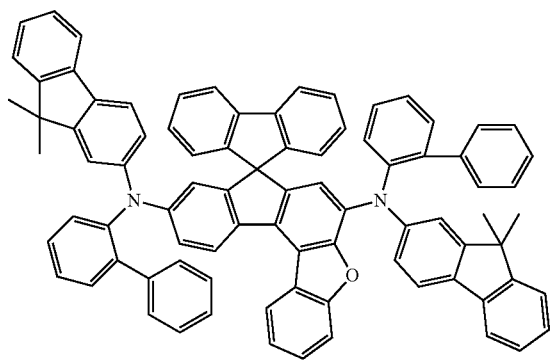
<Chemical Formula 74>
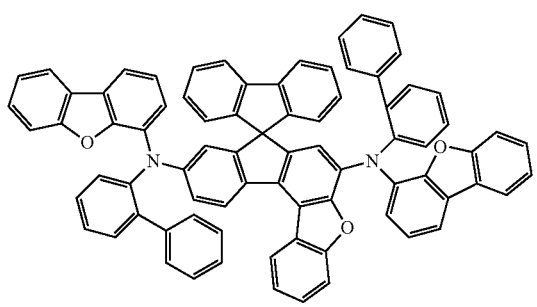
<Chemical Formula 75>
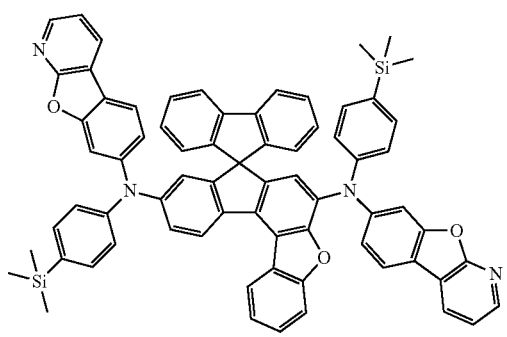
<Chemical Formula 76>
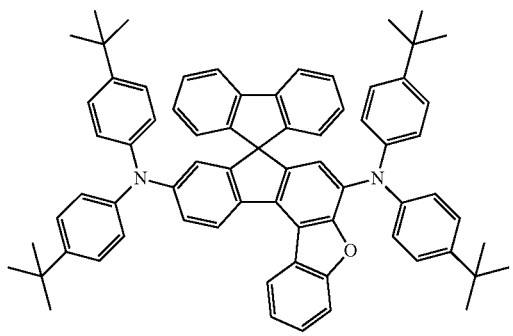
<Chemical Formula 77>
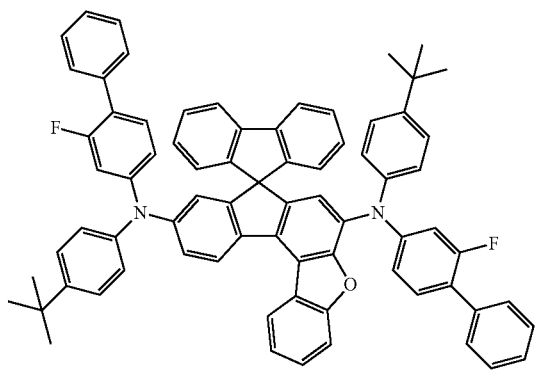
<Chemical Formula 78>
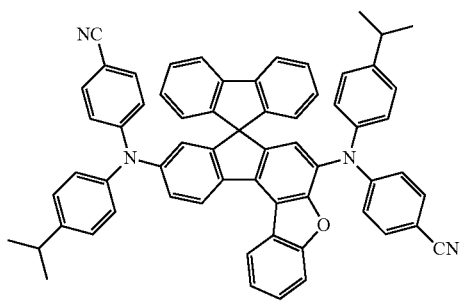
<Chemical Formula 79>
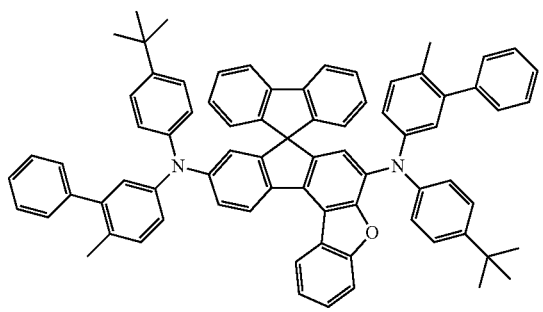

<Chemical Formula 80>
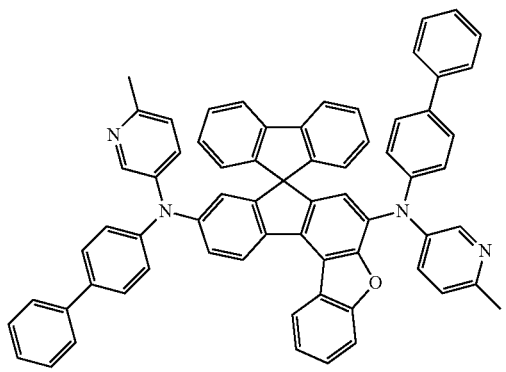
<Chemical Formula 81>
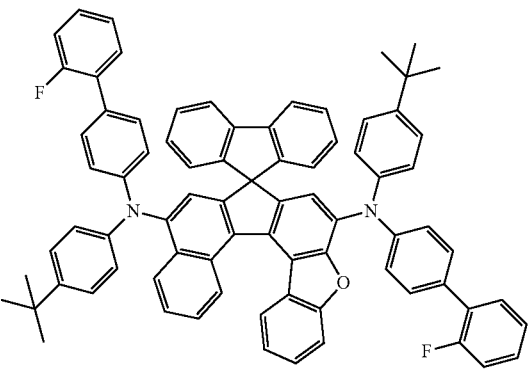
<Chemical Formula 82>
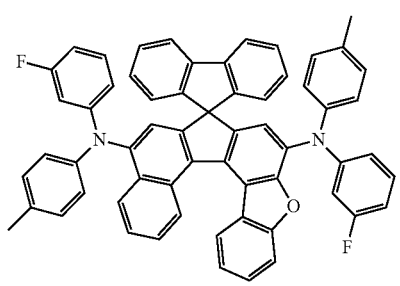
<Chemical Formula 83>
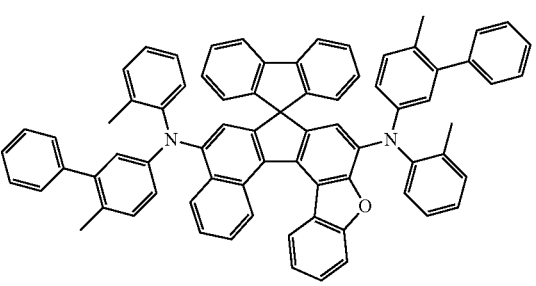
<Chemical Formula 84>
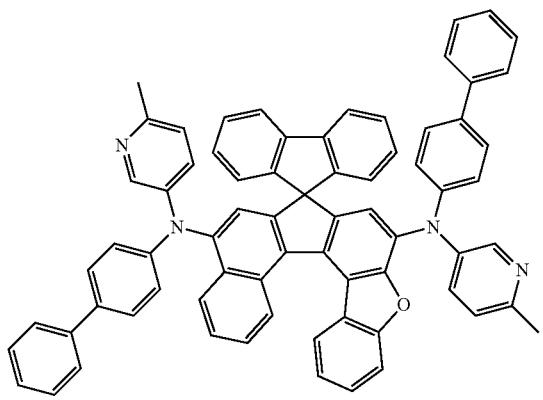
<Chemical Formula 85>
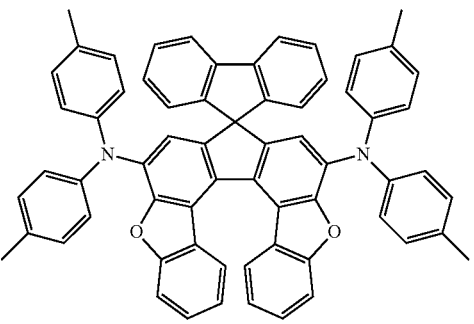
<Chemical Formula 86>
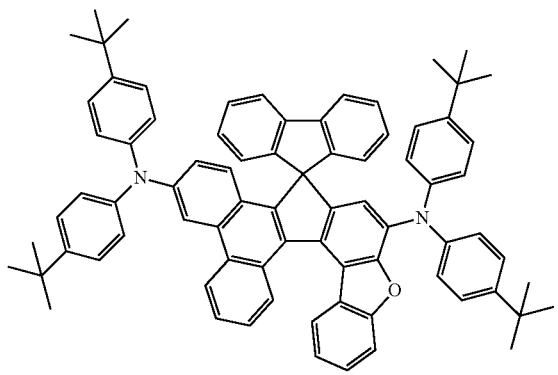
<Chemical Formula 87>
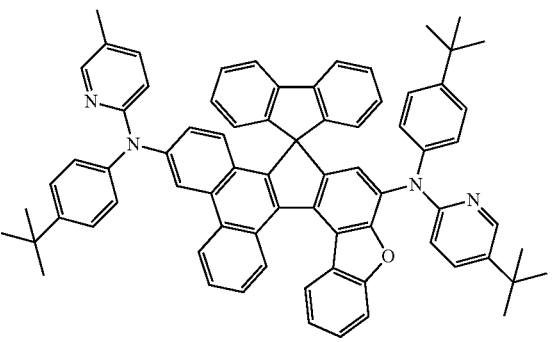

<Chemical Formula 88>
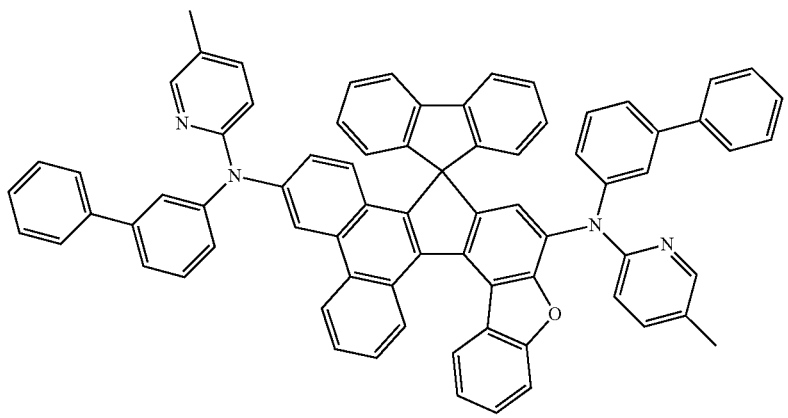
<Chemical Formula 89>
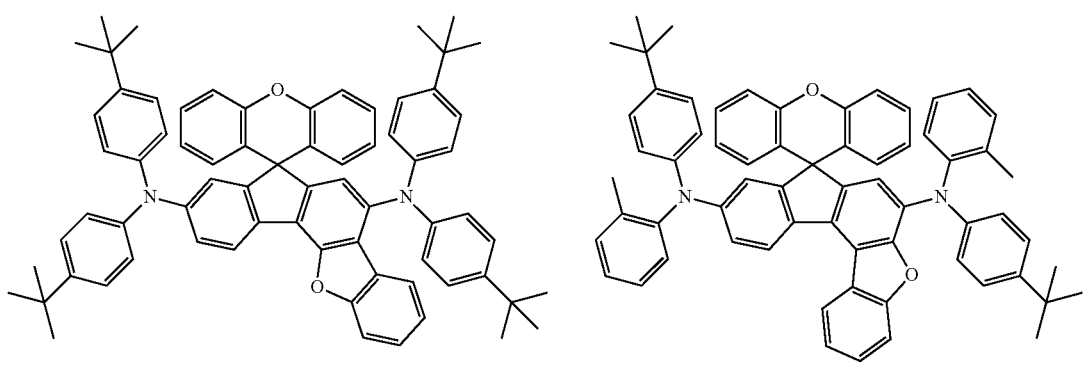
<Chemical Formula 90>
<Chemical Formula 91>
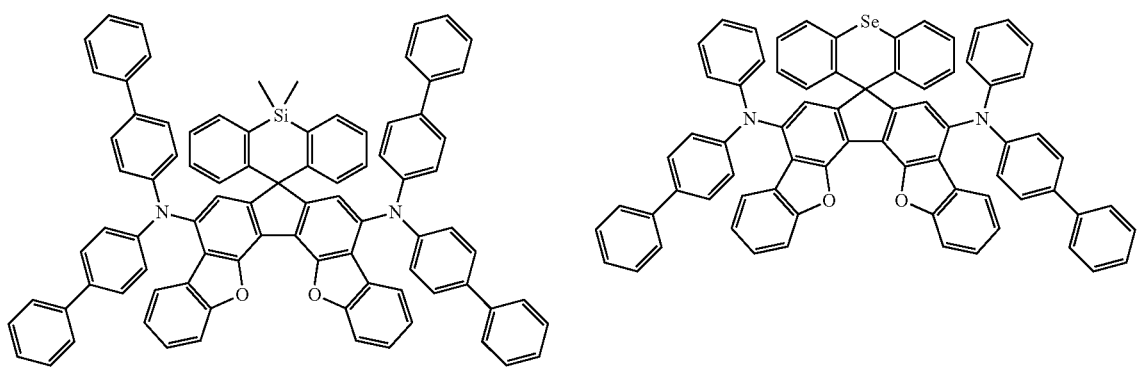
<Chemical Formula 92>
<Chemical Formula 93>
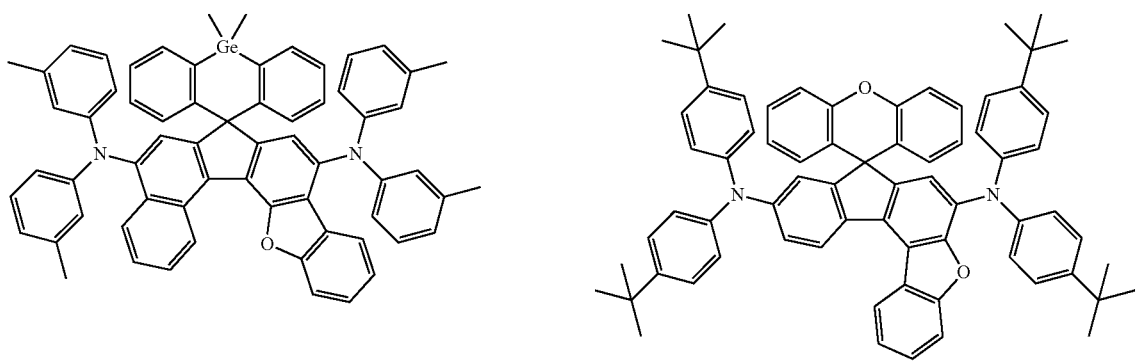
<Chemical Formula 94>

<Chemical Formula 95>
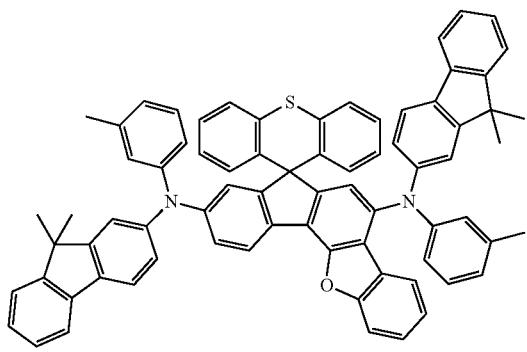
<Chemical Formula 96>
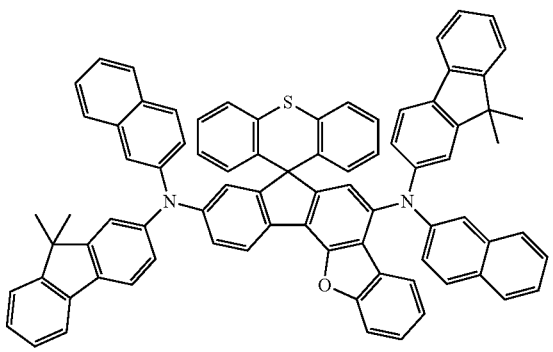
<Chemical Formula 97>
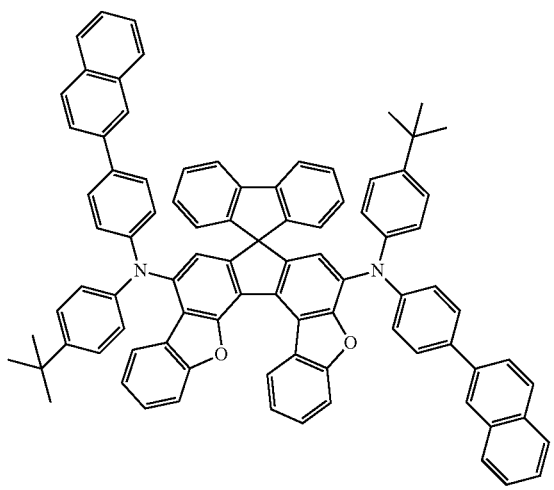
<Chemical Formula 98>
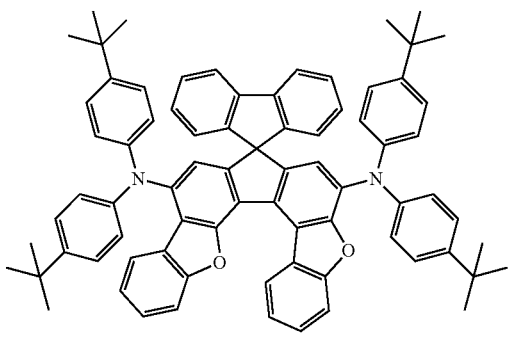
<Chemical Formula 99>
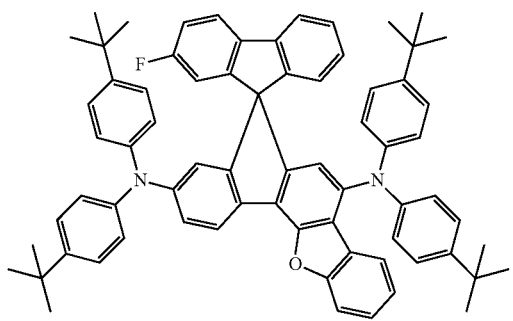
<Chemical Formula 100>
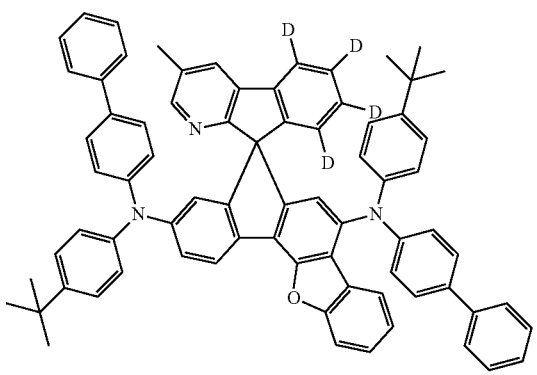

-continued
<Chemical Formula 101>
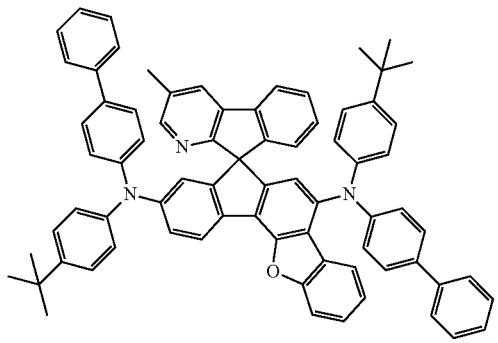
<Chemical Formula 102>
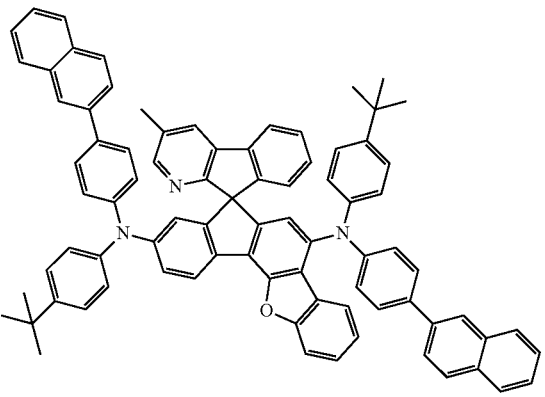
<Chemical Formula 103>
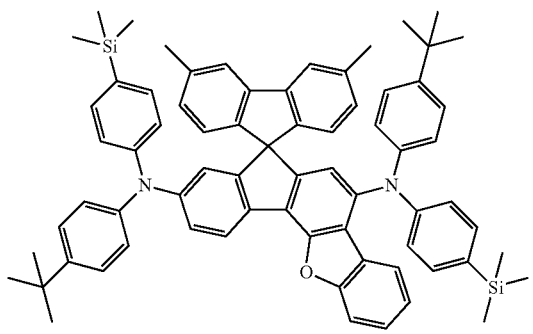
<Chemical Formula 104>
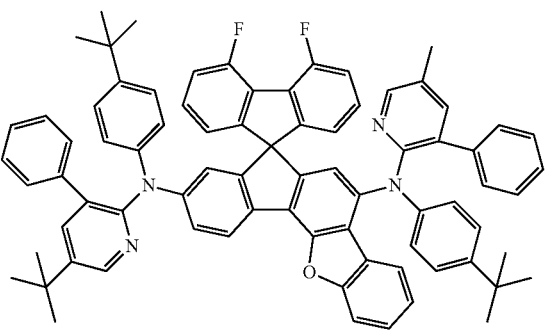
<Chemical Formula 105>
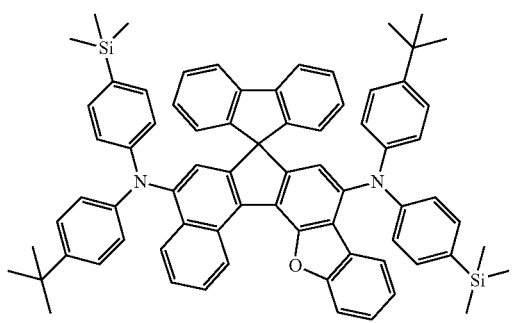
<Chemical Formula 106>
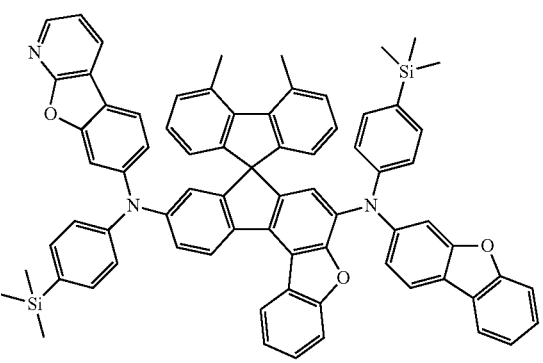
<Chemical Formula 107>
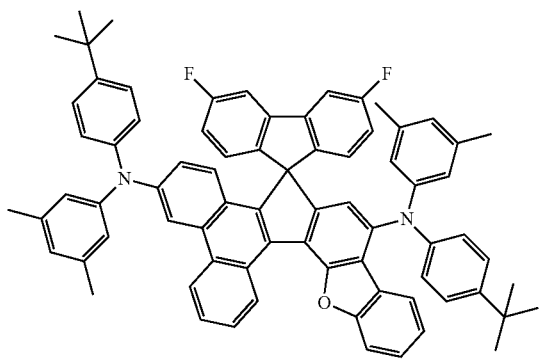
<Chemical Formula 108>

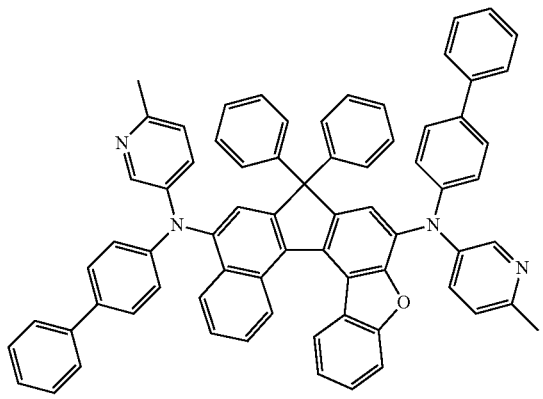
<Chemical Formula 109>
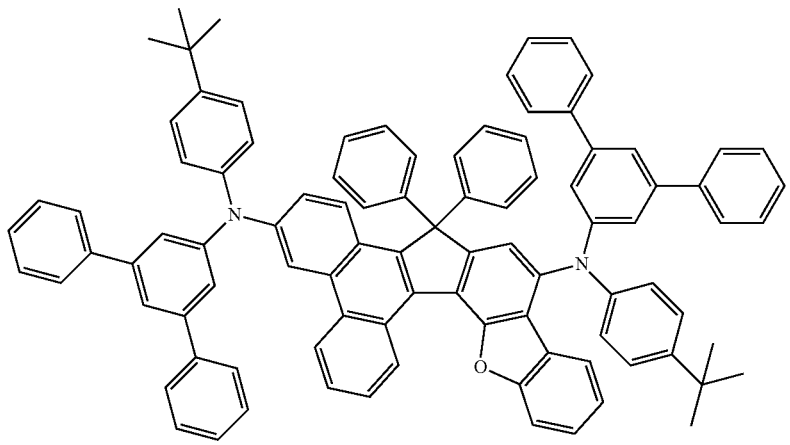
<Chemical Formula 110>
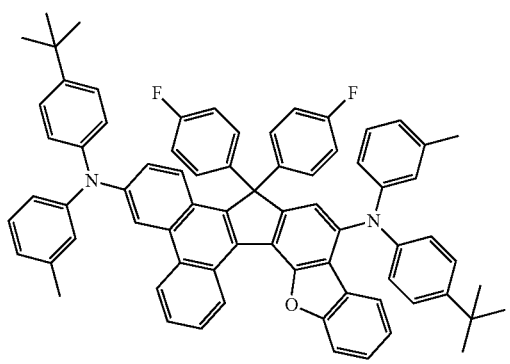
<Chemical Formla 111>
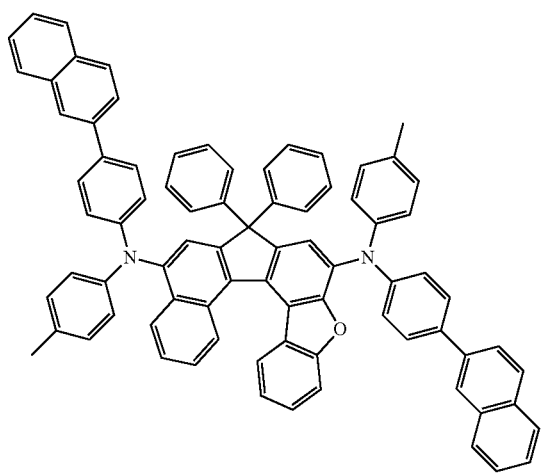
<Chemical Formula 112>

-continued
<Chemical Formula 113>
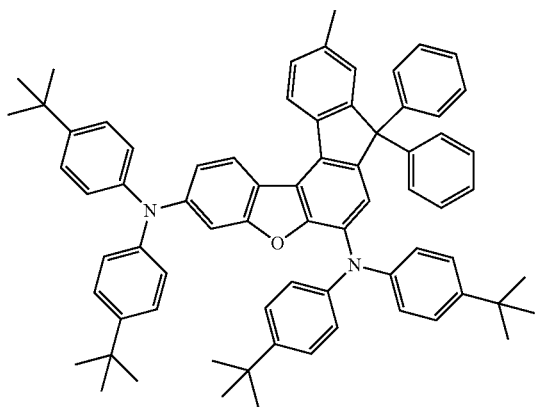
<Chemical Formula 114>
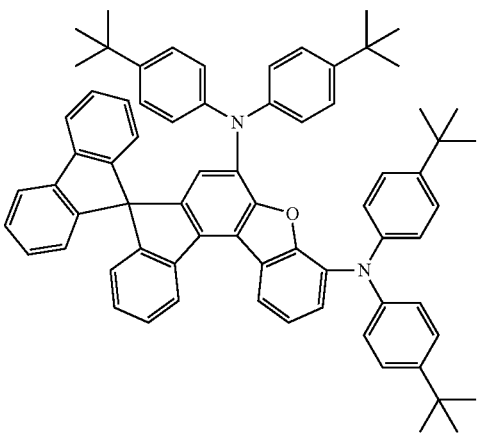
<Chemical Formula 115>
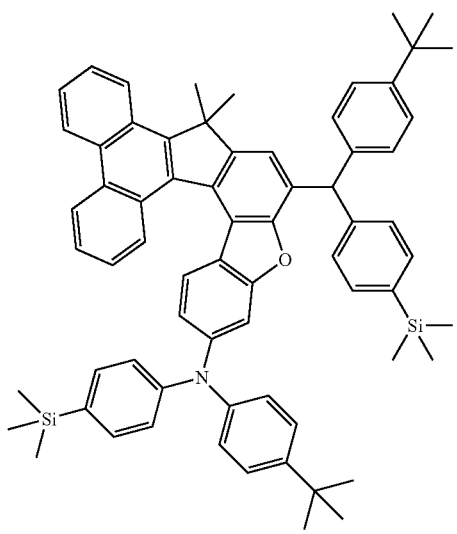
<Chemical Formula 116>
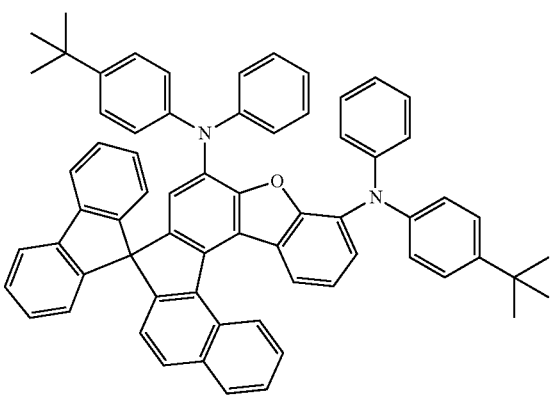
<Chemical Formula 117>
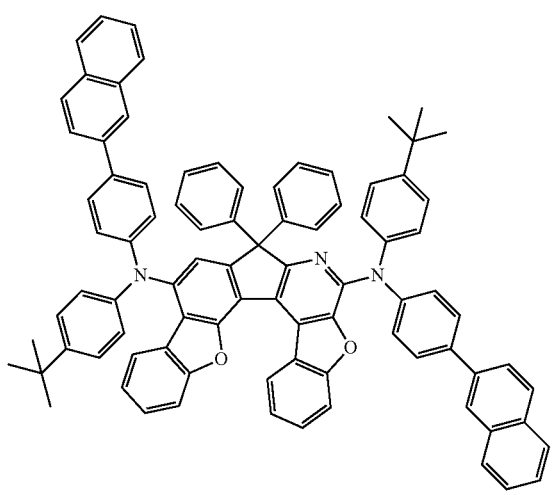
<Chemical Formula 118>
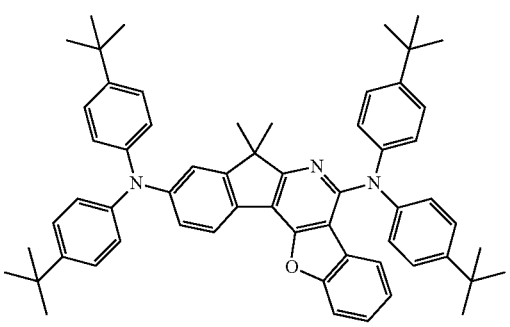

-continued
<Chemical Formula 119>
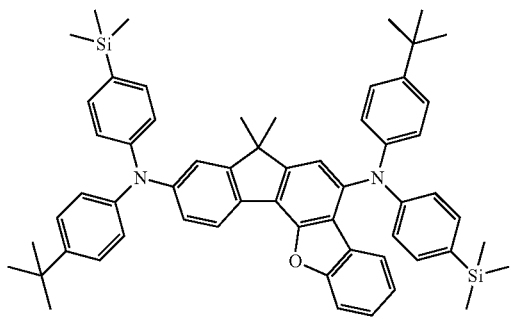
<Chemical Formula 120>
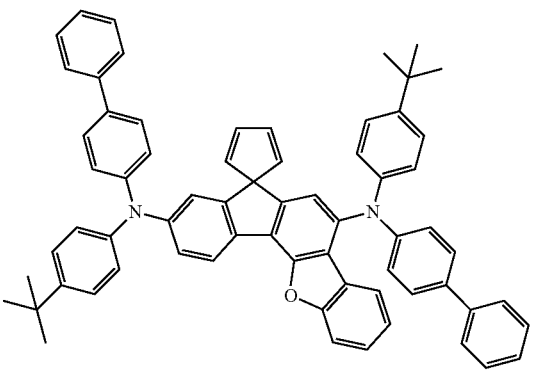
<Chemical Formula 121>
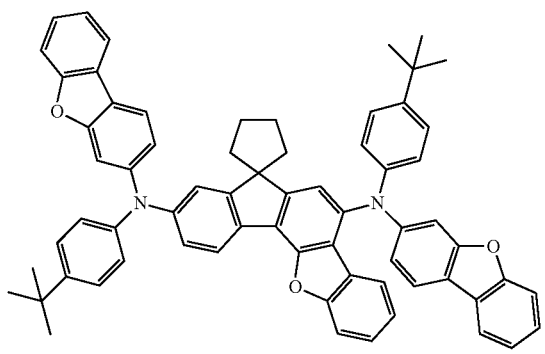
<Chemical Formula 122>
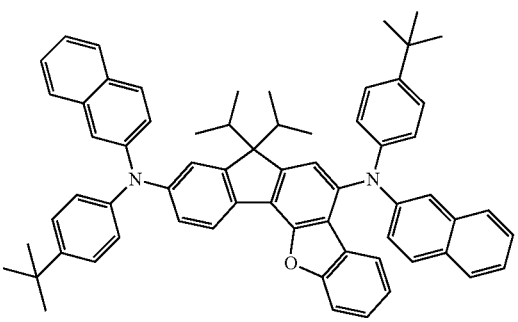
<Chemical Formula 123>
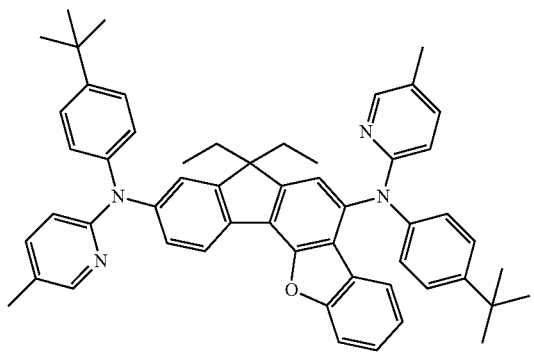
<Chemical Formula 124>
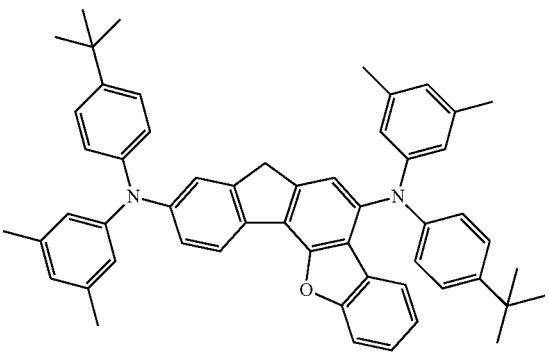
<Chemical Formula 125>
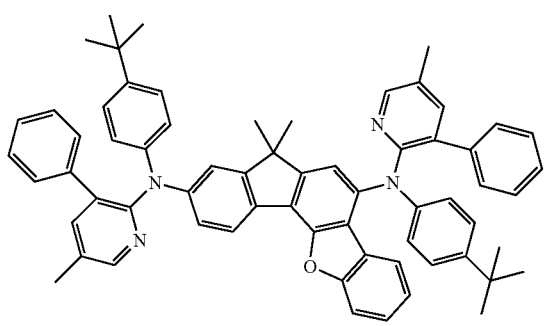

<Chemical Formula 126>
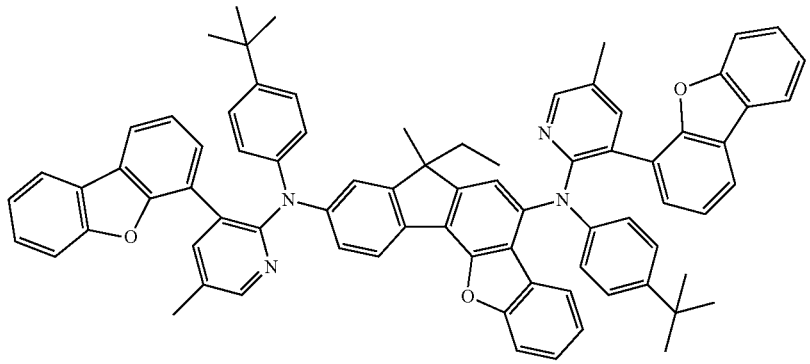
<Chemical Formula 127>
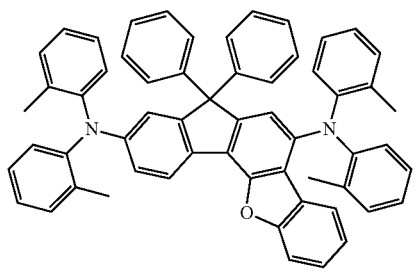
<Chemical Formula 128>
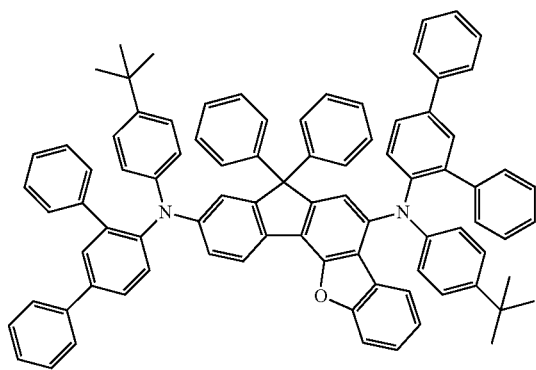
<Chemical Formula 129>
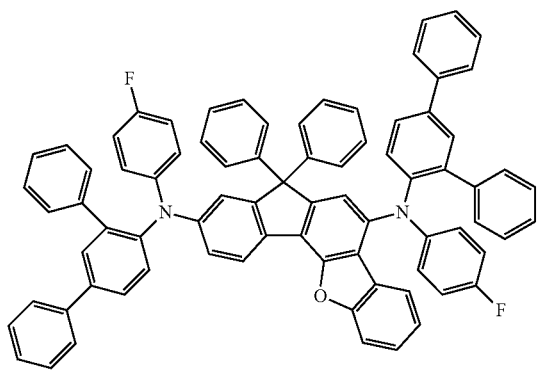
<Chemical Formula 130>
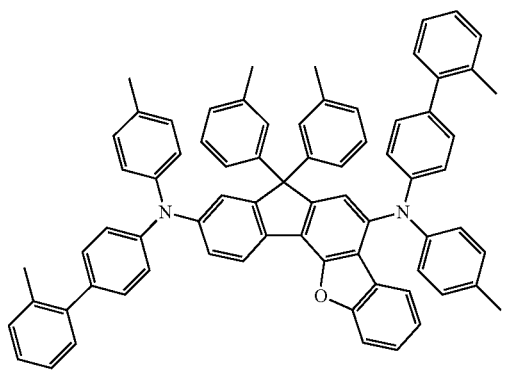
<Chemical Formua 131>
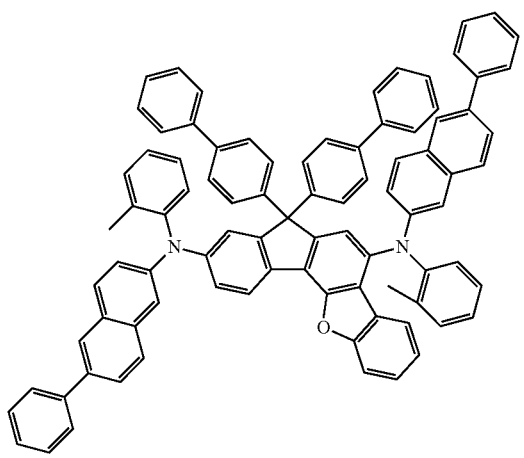
<Chemical Formula 132>
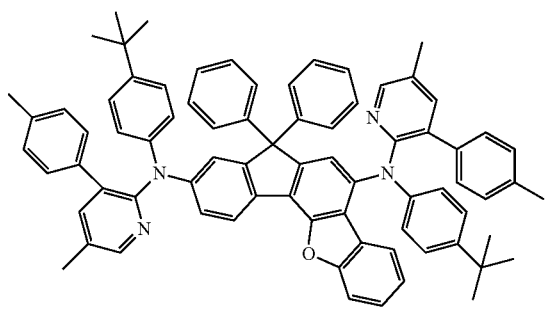

-continued
<Chemical Formula 133>
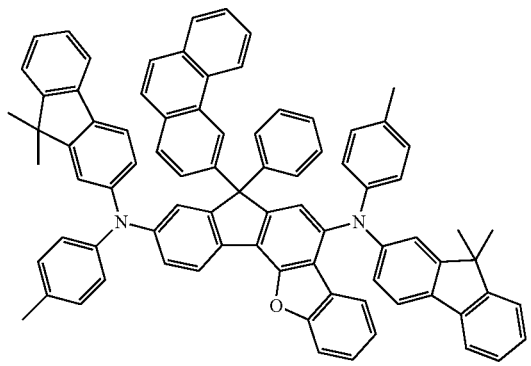
<Chemical Formula 134>
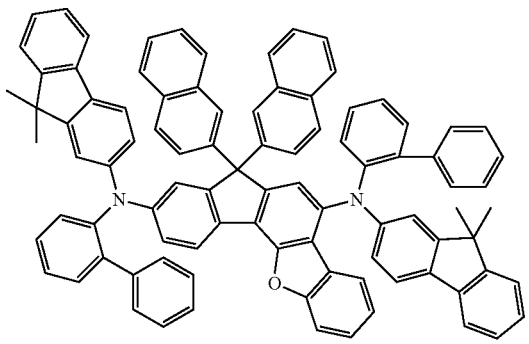
<Chemical Formula 135>
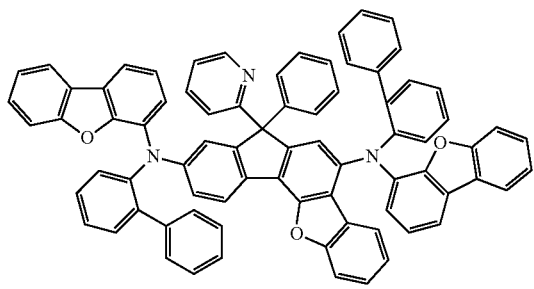
<Chemical Formula 136>
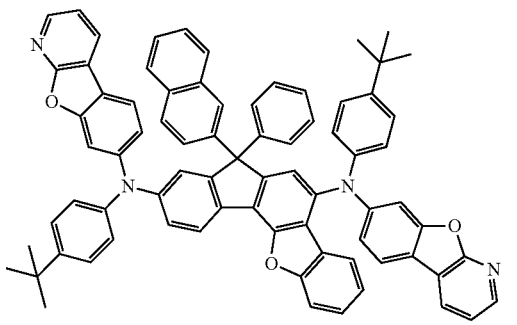
<Chemical Formula 137>
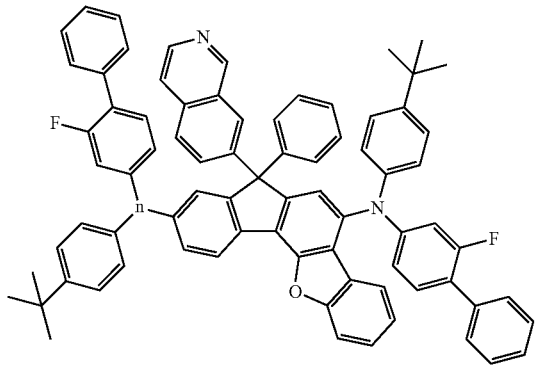
<Chemical Formula 138>
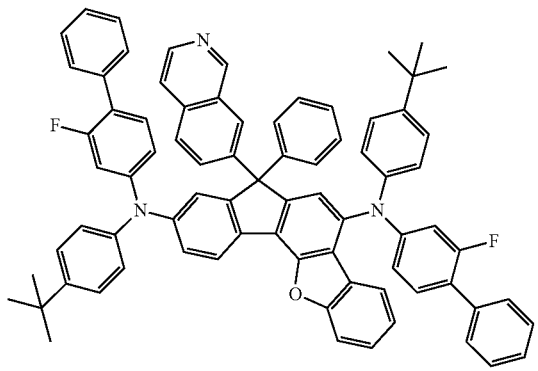
<Chemical Formula 139>
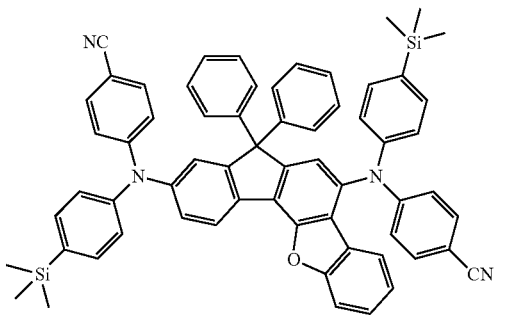

<Chemical Formulla 140>
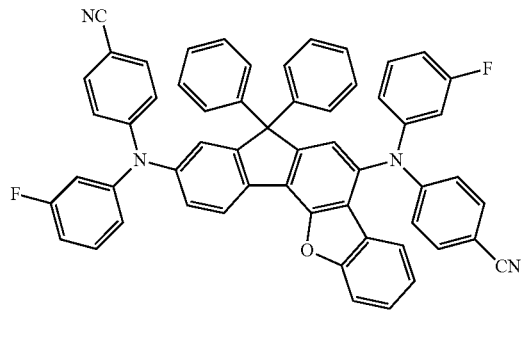
<Chemical Formula 141>
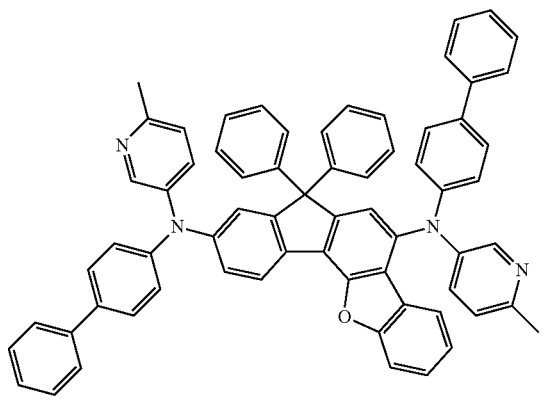
<Chemical Formula 142>
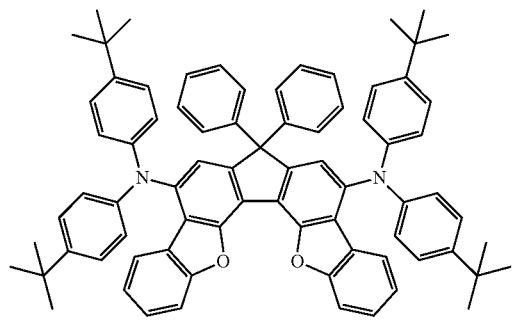
<Chemical Formula 143>
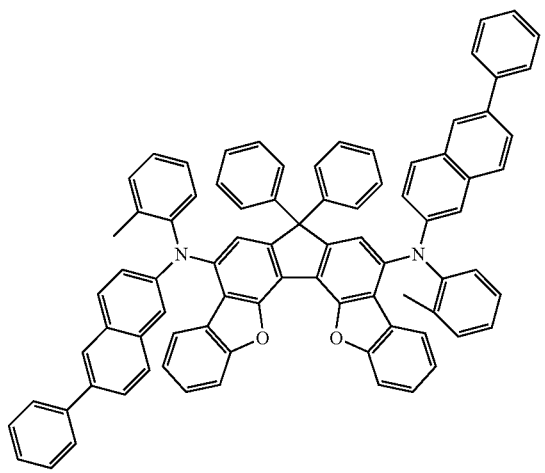
<Chemical Formula 144>
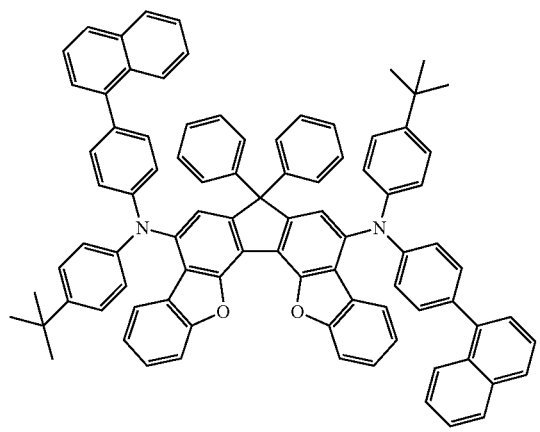

<Chemical Formula 145>
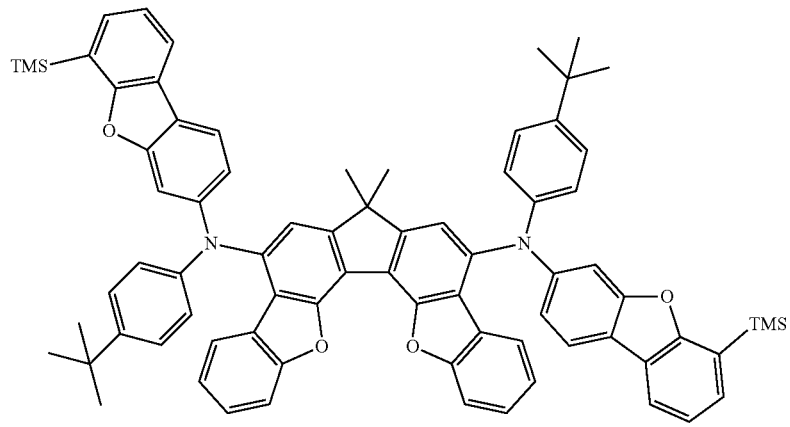
<Chemical Formula 146>
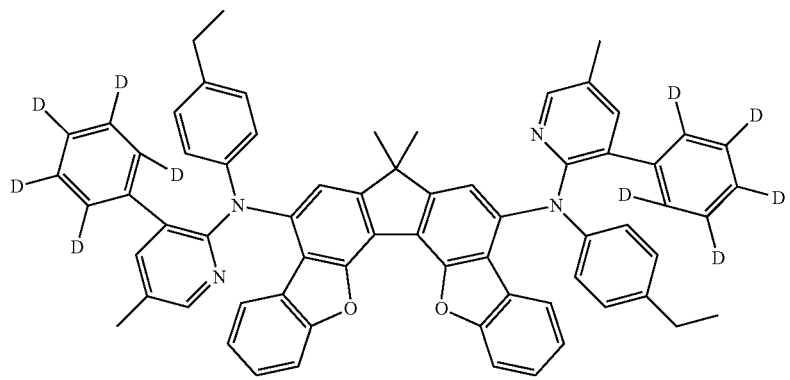
<Chemical Formula 147>
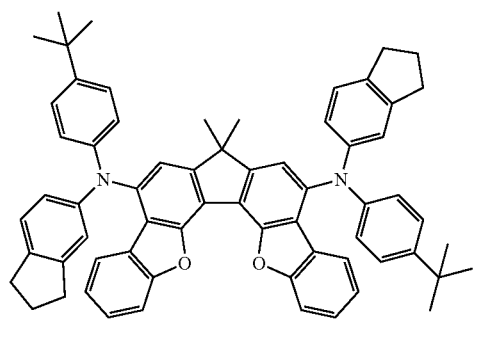
<Chemical Formula 148>
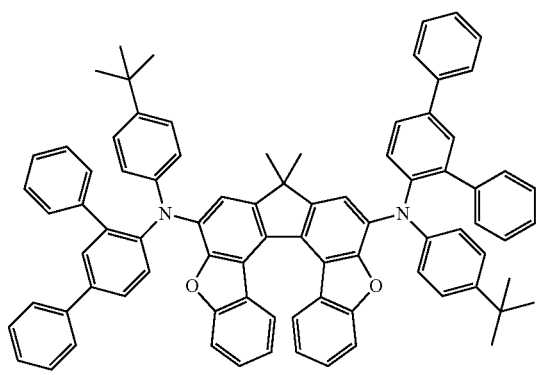
<Chemical Formula 149>
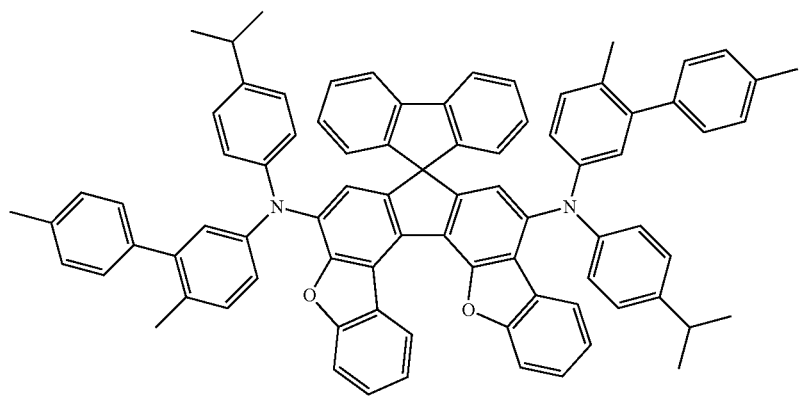

-continued
<Chemical Formula 150>
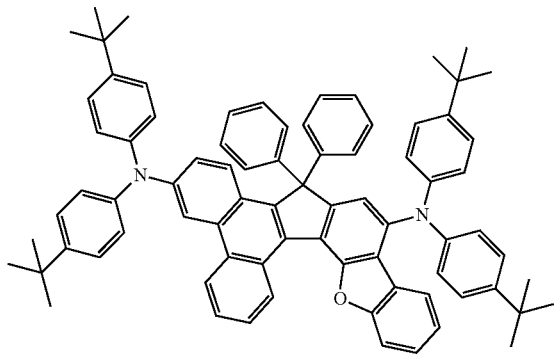
<Chemical Formula 151>
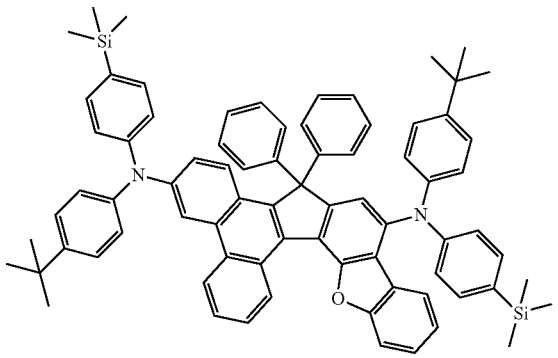
<Chemical Formula 152>
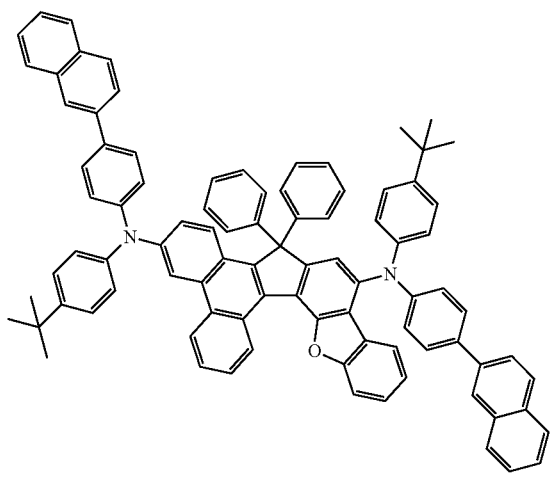
<Chemical Formula 153>
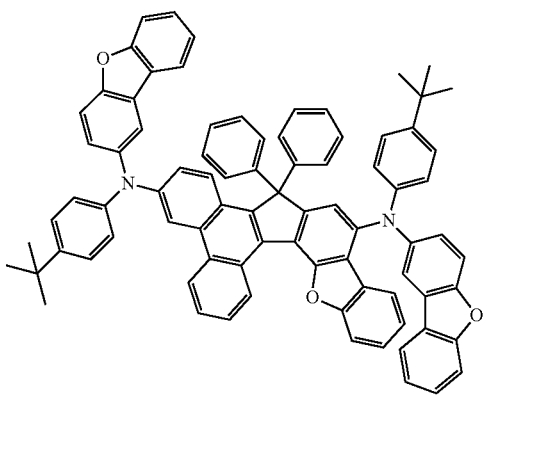
<Chemical Formula 154>
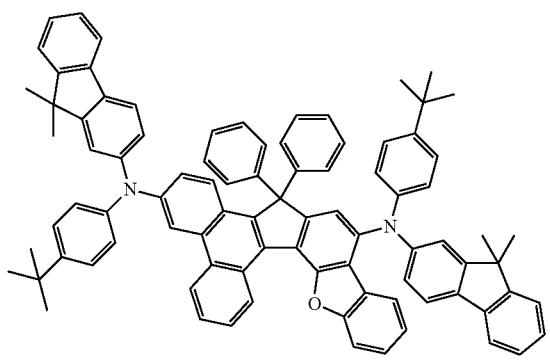
<Chemical Formula 155>
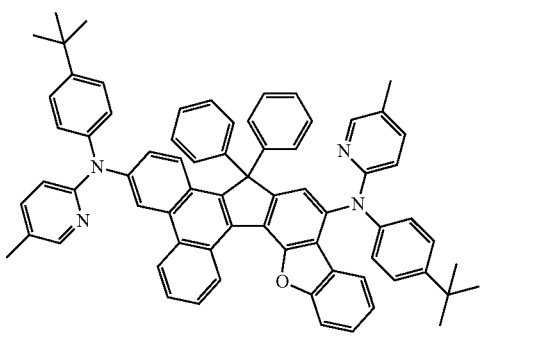
<Chemical Formula 156>
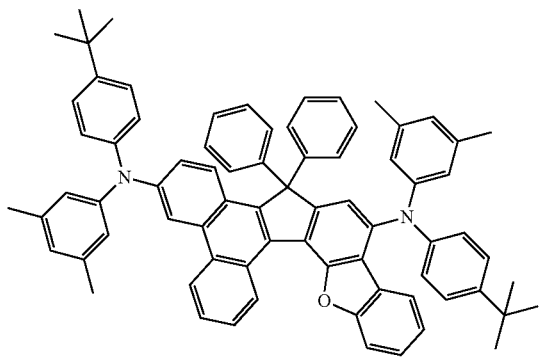

-continued
<Chemical Formula 157>
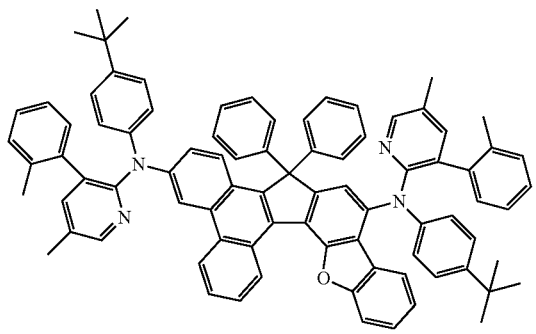
<Chemical Formula 158>
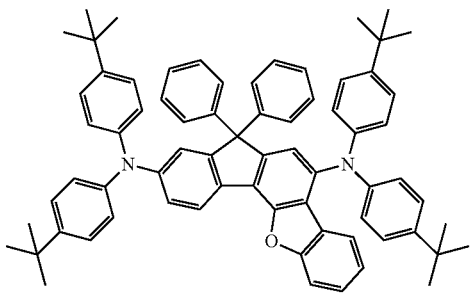
<Chemical Formula 159>
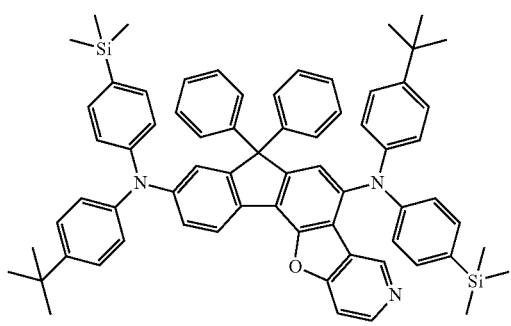
<Chemical Formula 160>
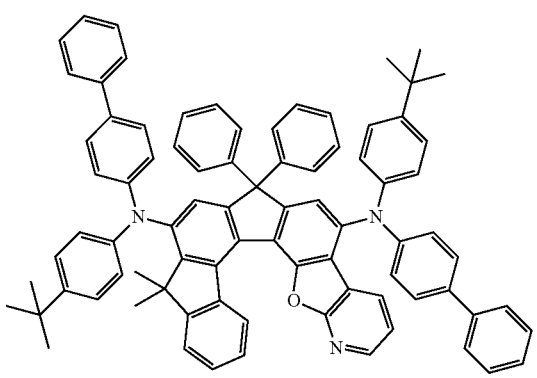
<Chemical Formula 161>
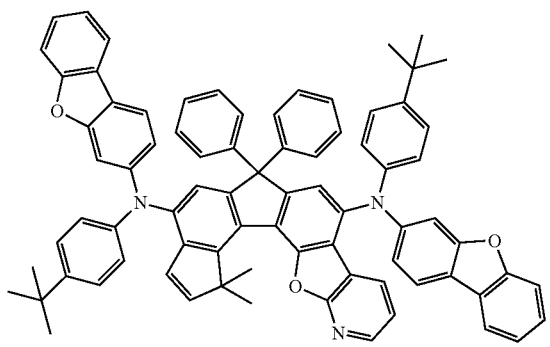
<Chemical Formula 162>
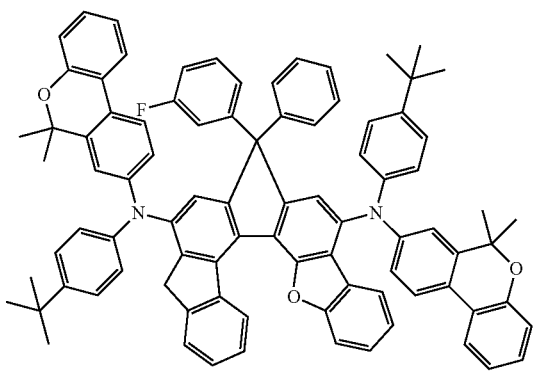
<Chemical Formula 163>
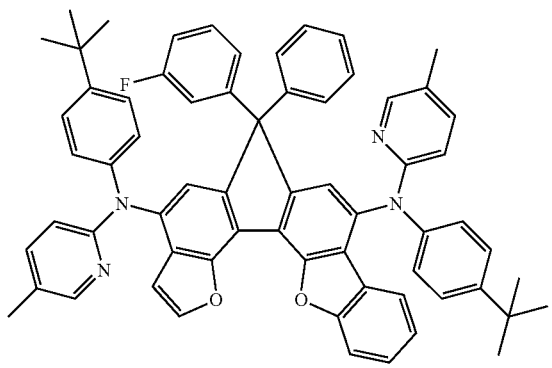
<Chemical Formula 164>
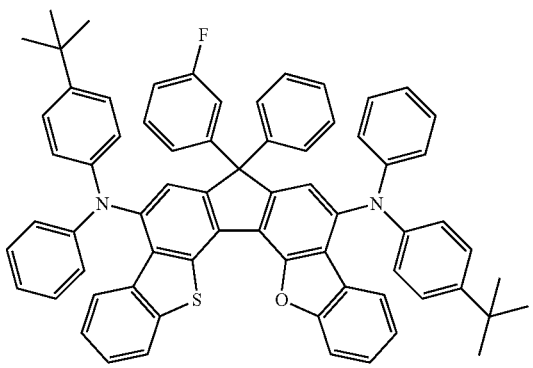

-continued
<Chemical Formula 165>
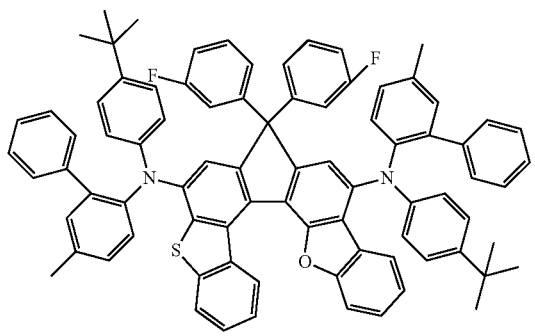
<Chemical Formula 166>
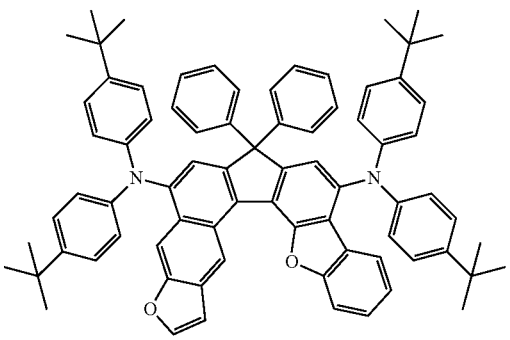
<Chemical Formula 167>
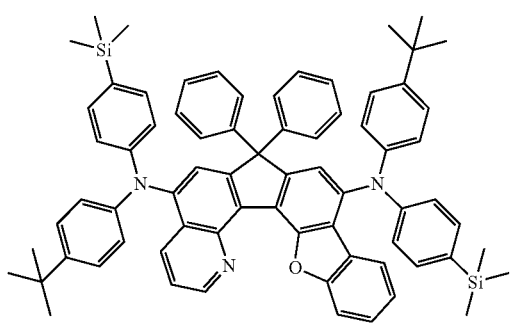
<Chemical Formula 168>
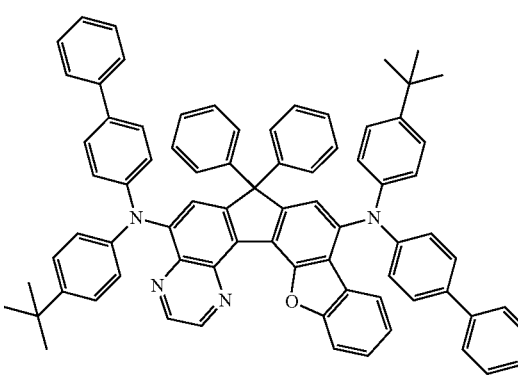
<Chemical Formula 169>
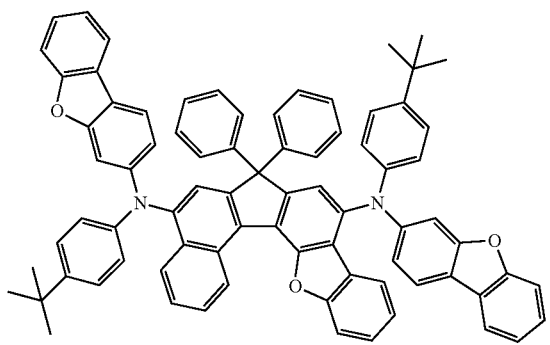
<Chemical Formula 170>
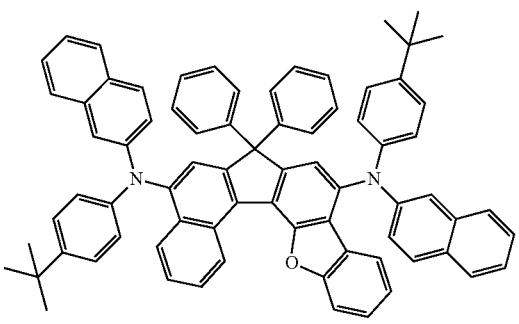
<Chemical Formula 171>
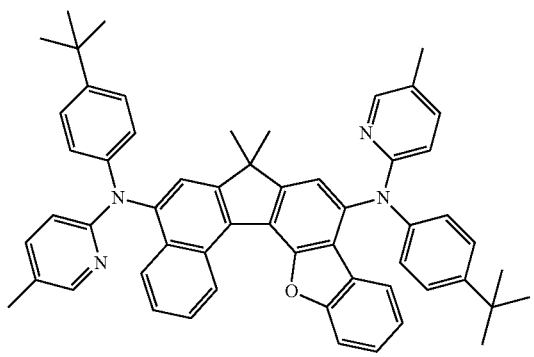
<Chemical Formula 172>
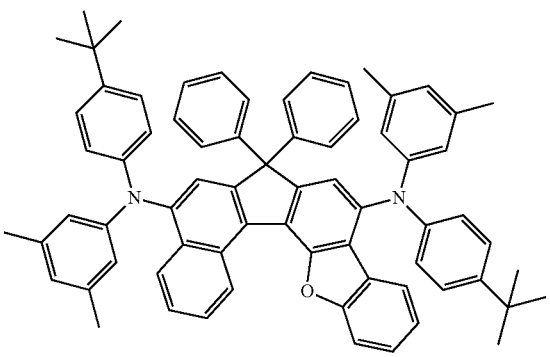

<Chemical Formula 173>
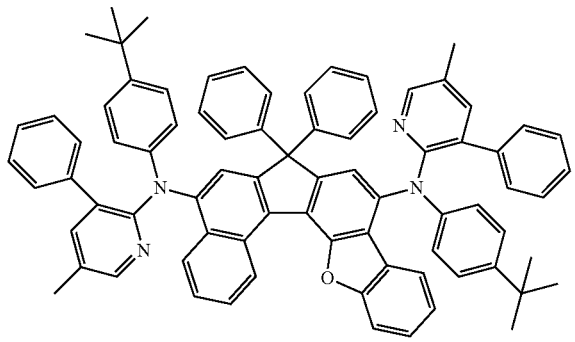
<Chemical Formula 174>
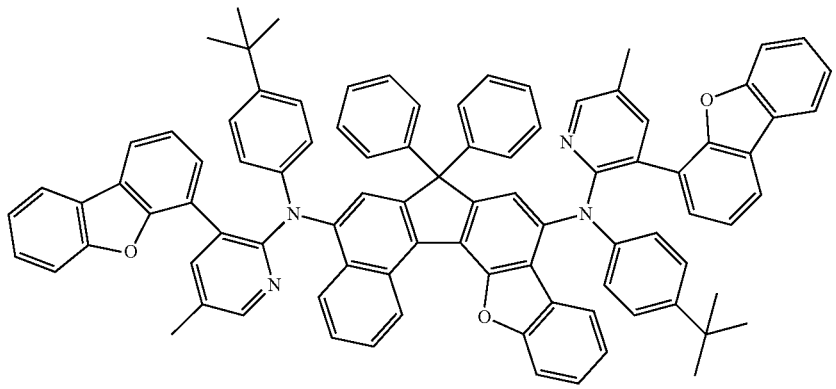
<Chemical Formula 175>
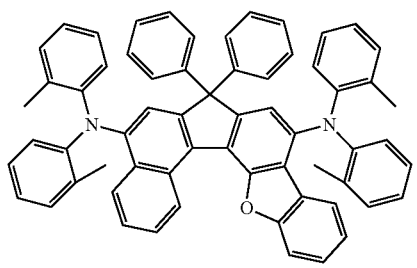
<Chemical Formula 176>
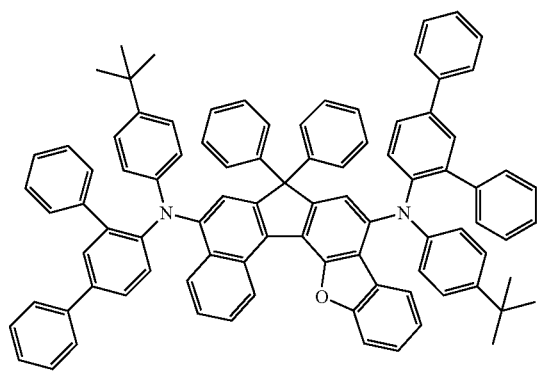
<Chemical Formula 177>
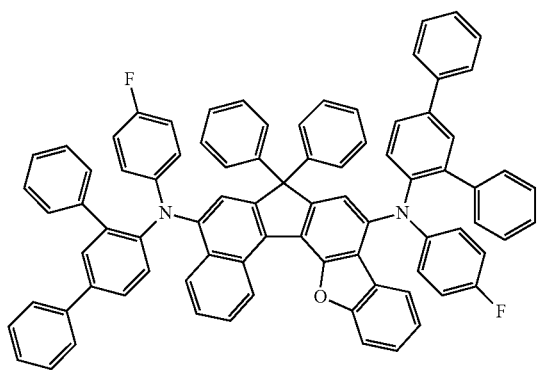
<Chemical Formula 178>
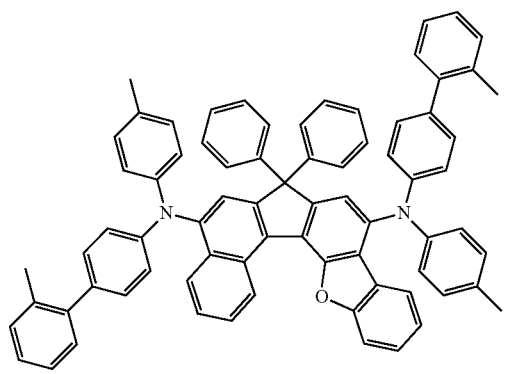

<Chemical Formula 179>
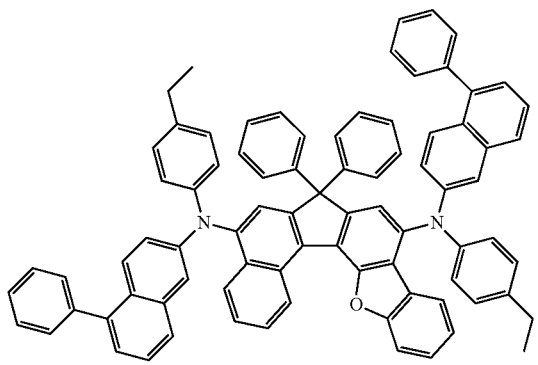
<Chemical Formula 180>
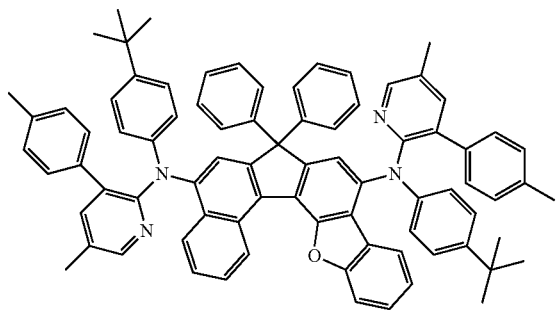
<Chemical Formula 181>
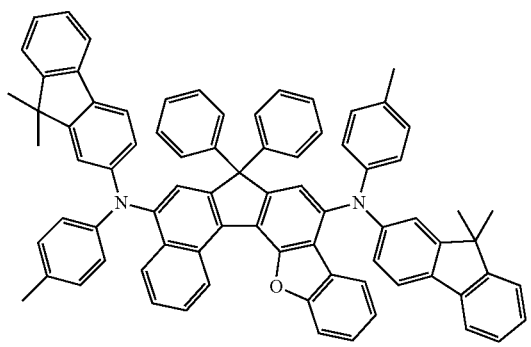
<Chemical Formula 182>
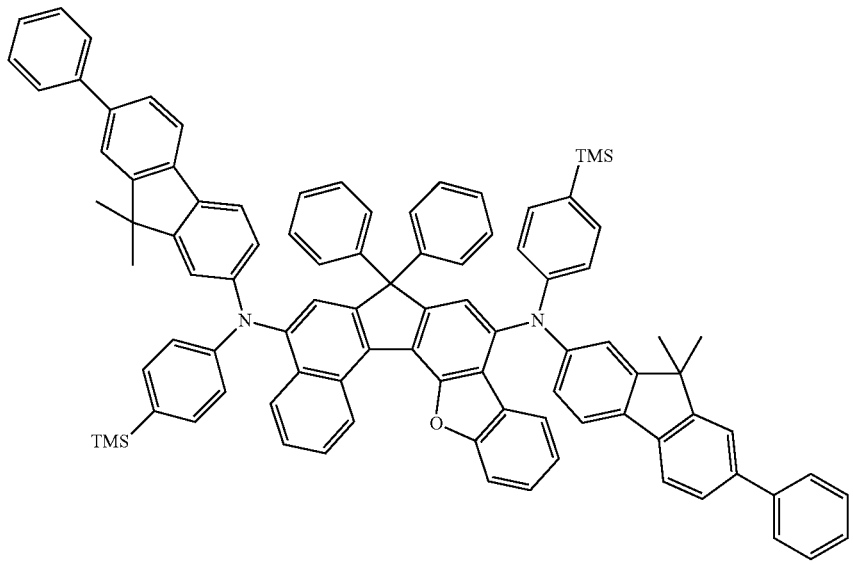
<Chemical Formula 183>
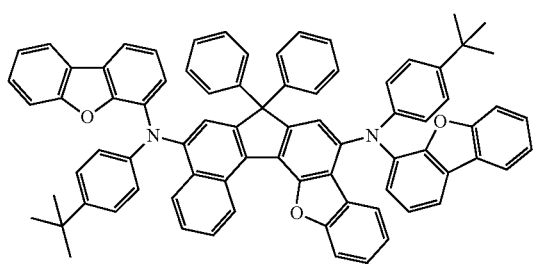
<Chemical Formula 184>
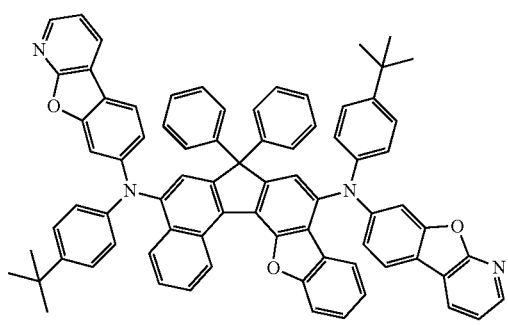

<Chemical Formula 185>
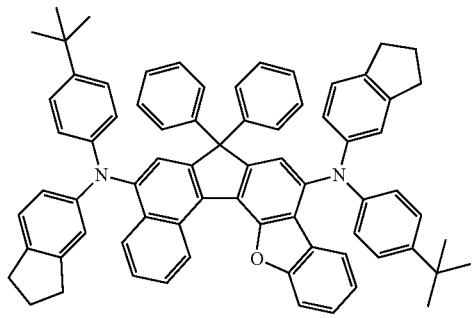
<Chemical Formula 186>
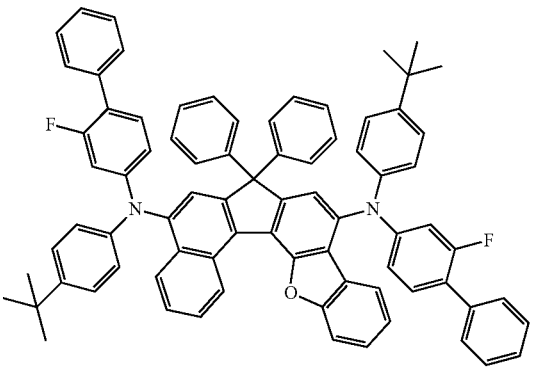
<Chemical Formula 187>
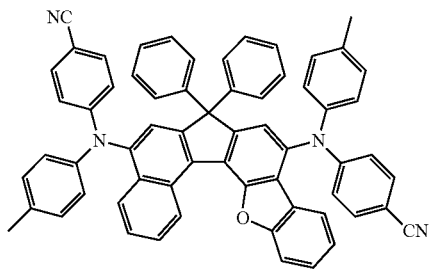
<Chemical Formula 188>
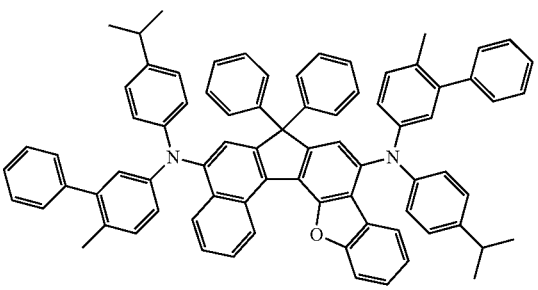
<Chemical Formula 189>
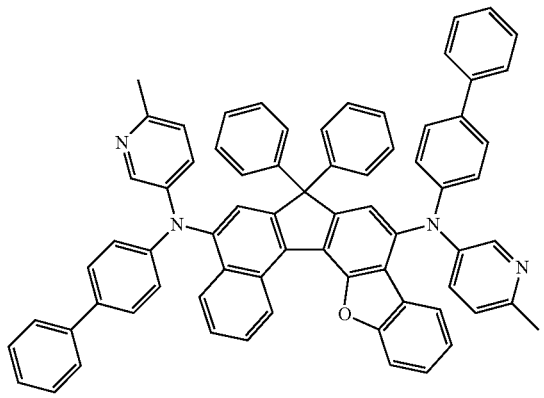
<Chemical Formula 190>
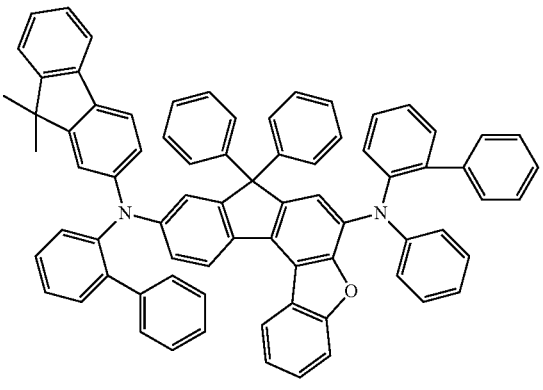
<Chemical Formula 191>
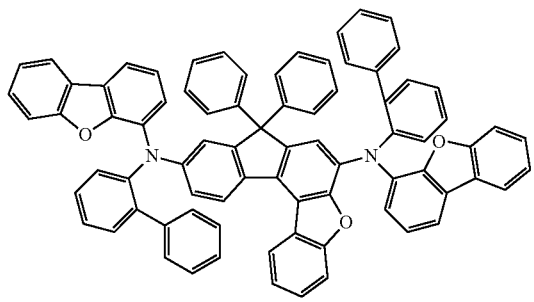
<Chemical Formula 192>
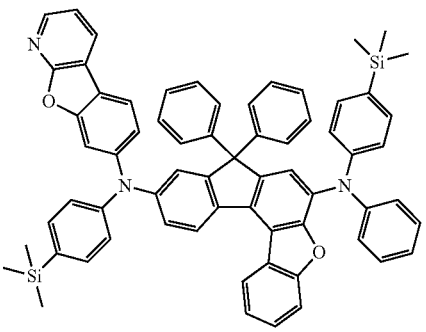

<Chemical Formula 193>
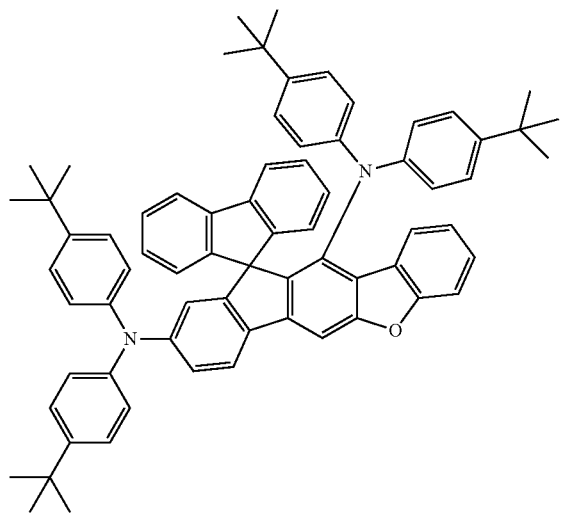
<Chemical Formula 194>
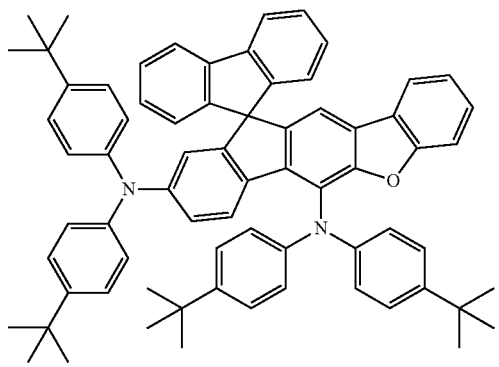
<Chemical Formula 195>
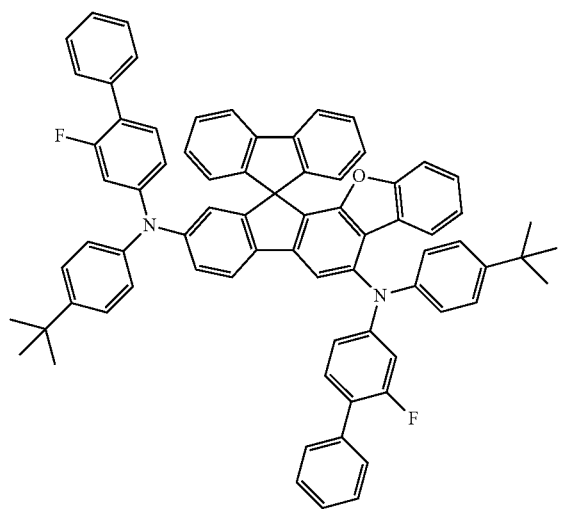
<Chemical Formula 196>
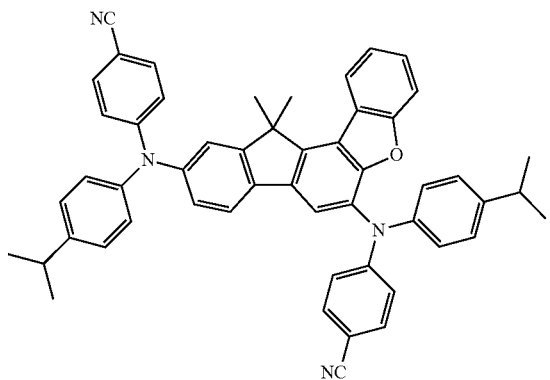

-continued
<Chemical Formula 197>
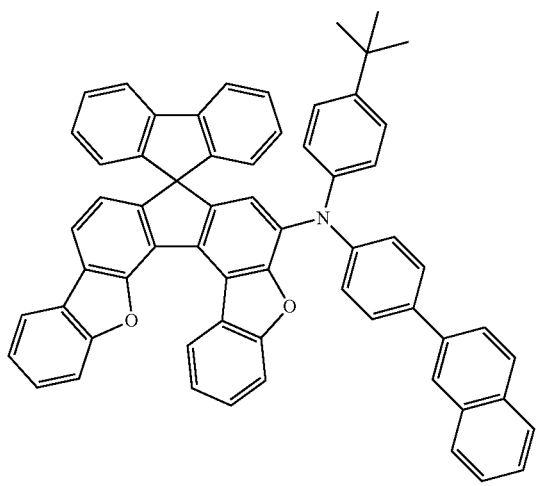
<Chemical Formula 198>
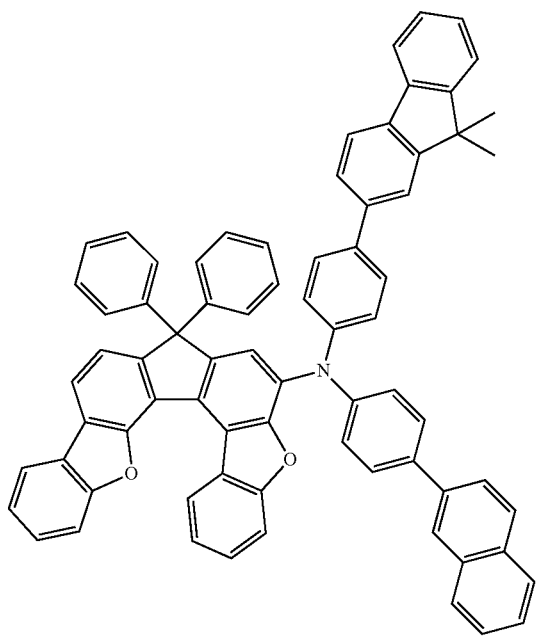
<Chemical Formula 199>
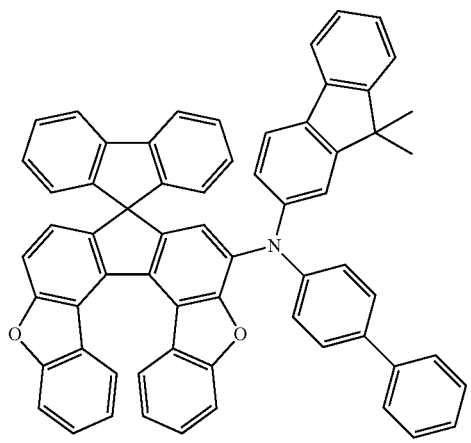
<Chemical Formula 200>
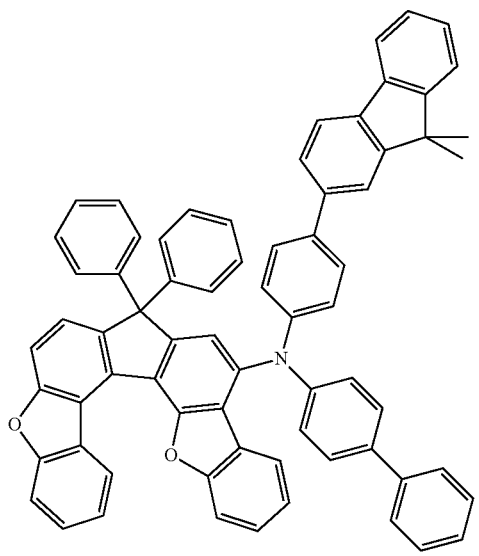

-continued
<Chemical Formula 201>
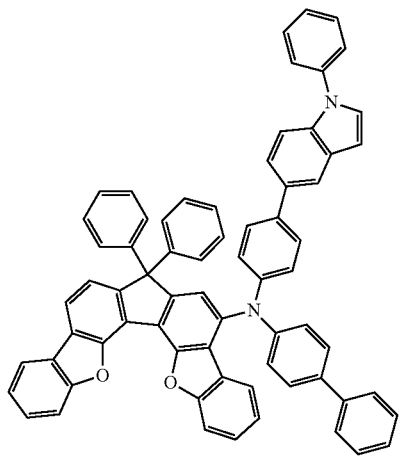
<Chemical Formula 202>
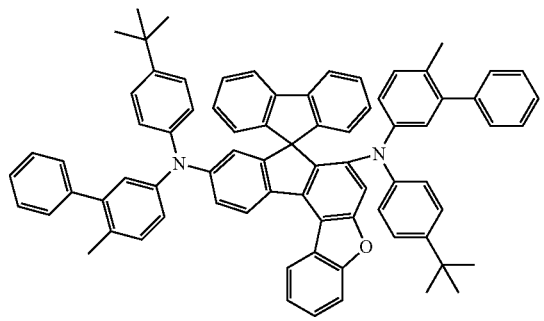
<Chemical Formula 203>
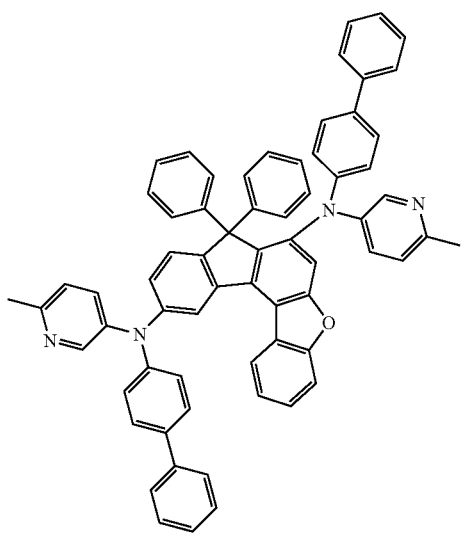
<Chemical Formula 204>
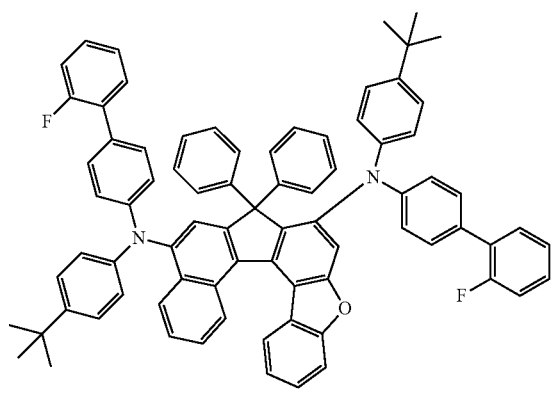
<Chemical Formula 205>
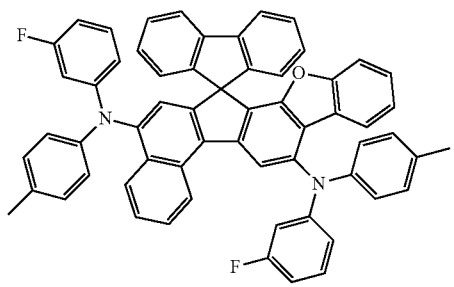
<Chemical Formula 206>
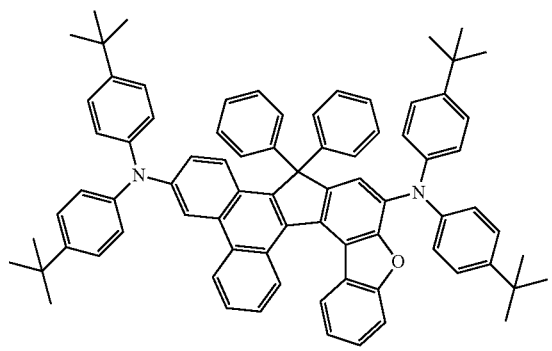

<Chemical Formula 207>
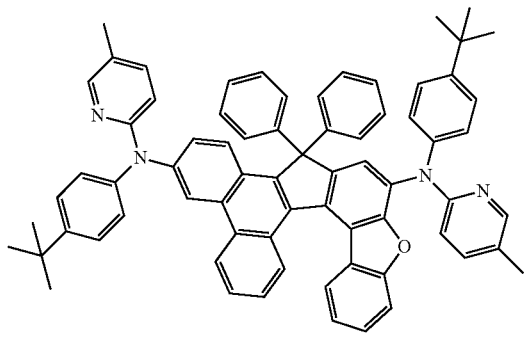
<Chemical Formula 208>
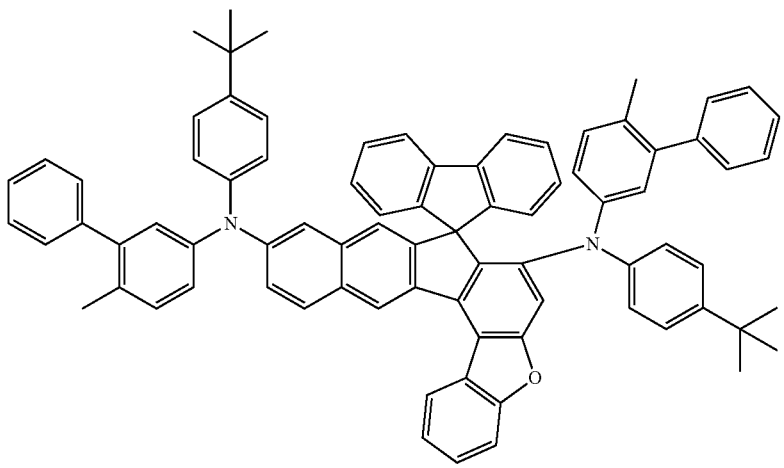
<Chemical Formula 209>
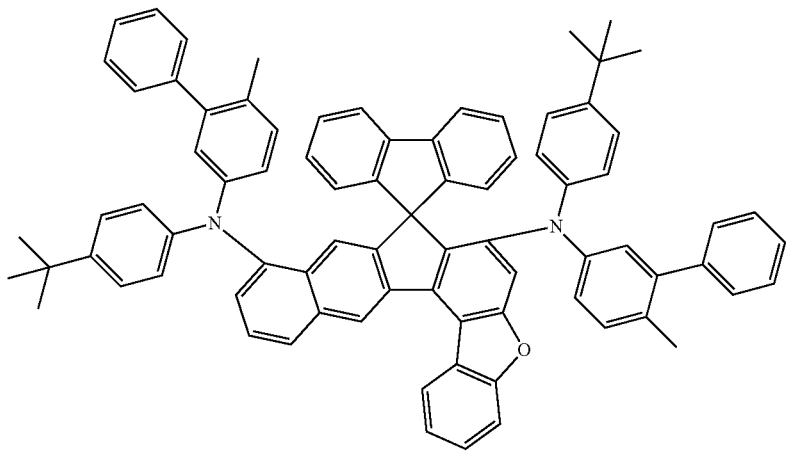
<Chemical Formula 210>
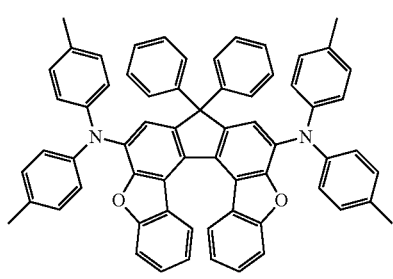
<Chemical Formula 211>
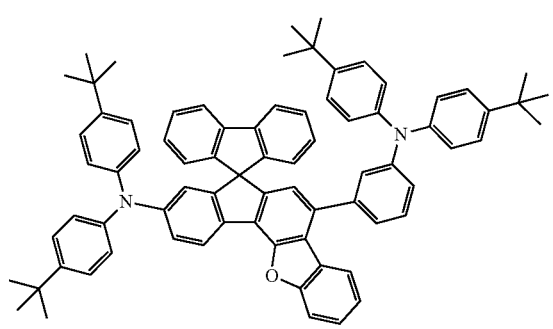

<Chemical Formula 212>
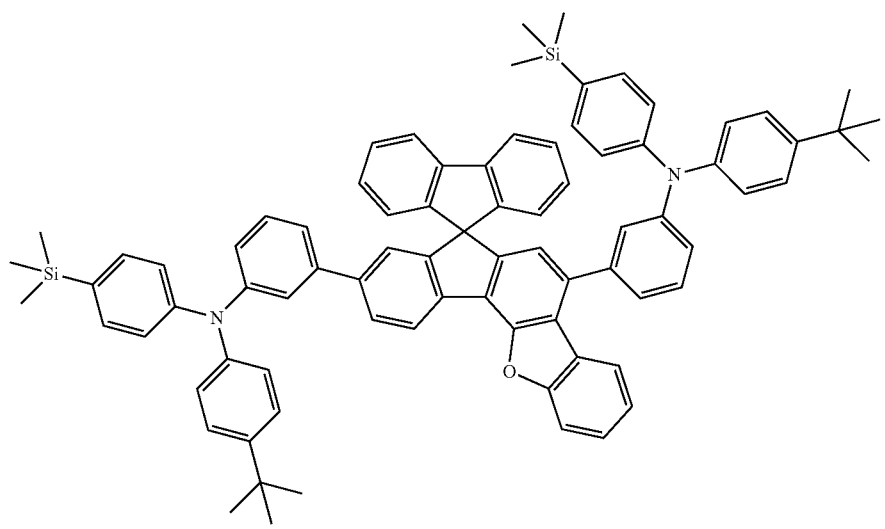
<Chemical Formula 213>
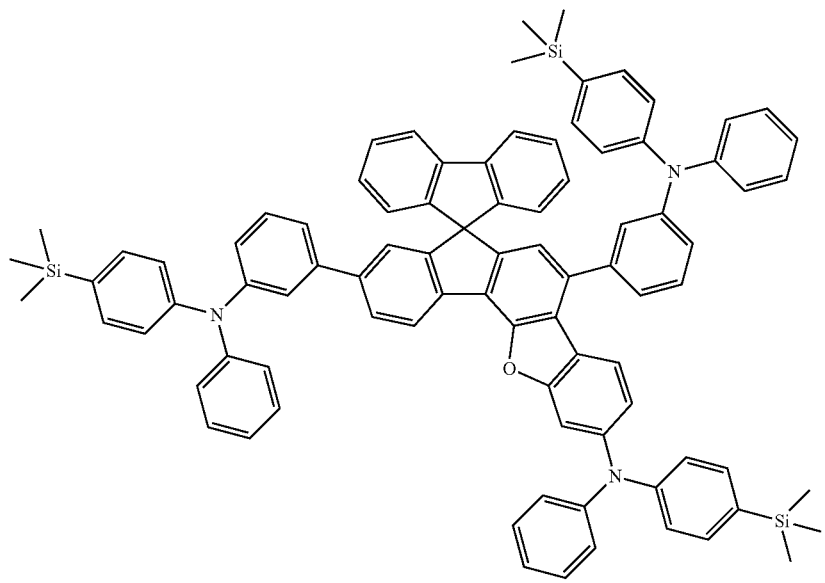
<Chemical Formula 214>
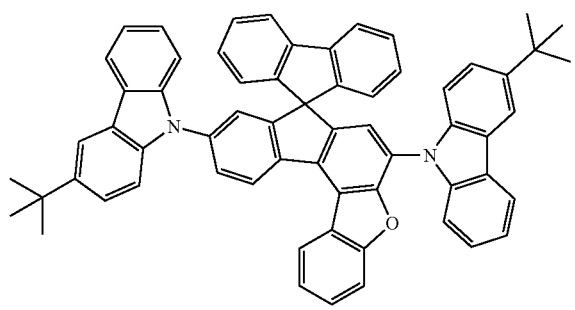

-continued
<Chemical Formula 215>
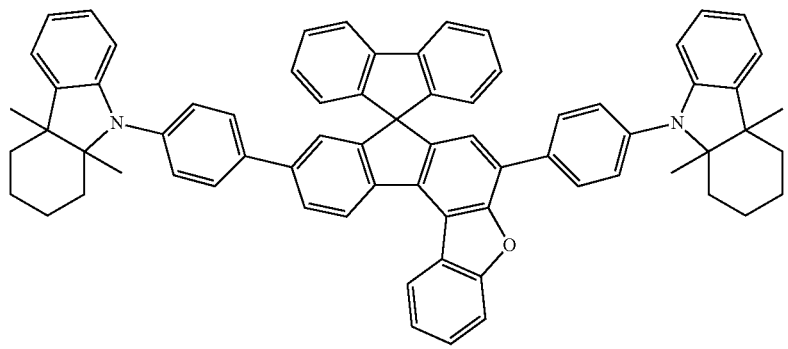
<Chemical Formula 216>
<Chemical Formula 217>
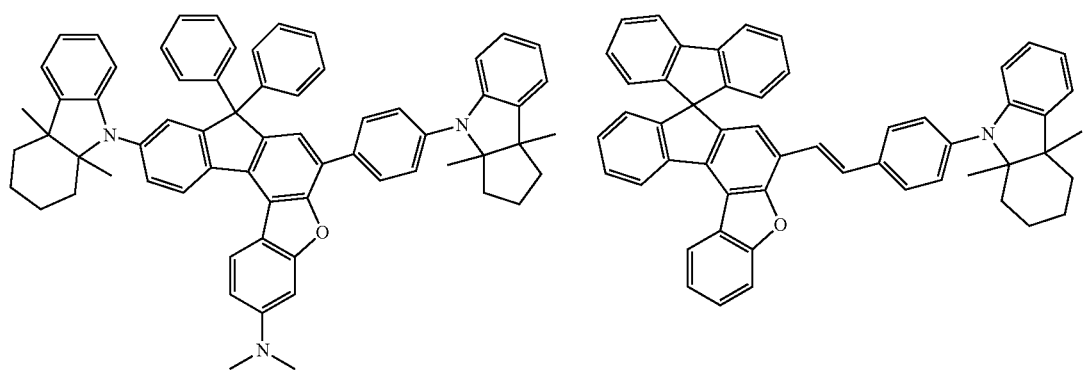
<Chemical Formula 218>
<Chemical Formula 219>
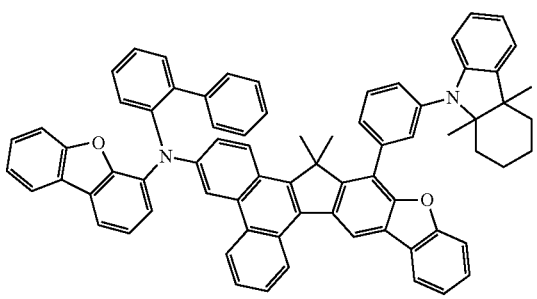
<Chemical Formula 220>
<Chemical Formula 221>
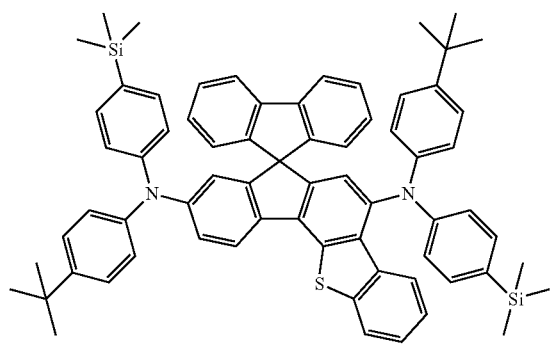
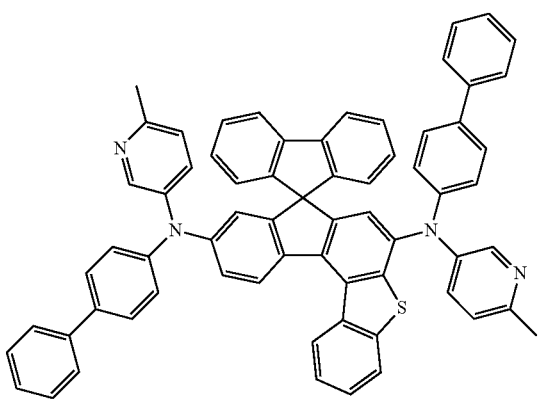

-continued
<Chemical Formula 222>
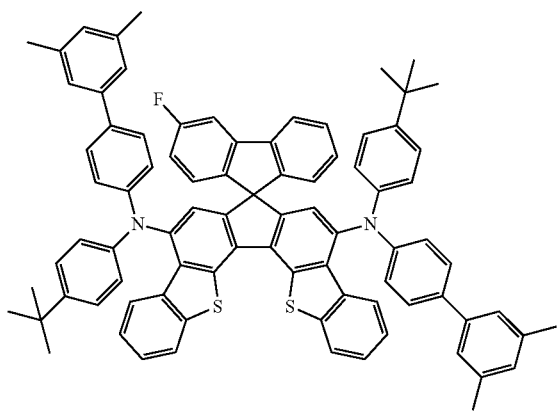
<Chemical Formula 223>
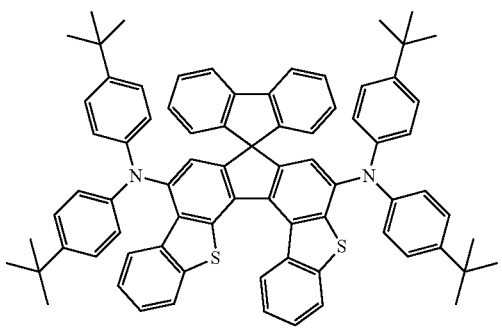
<Chemical Formula 224>
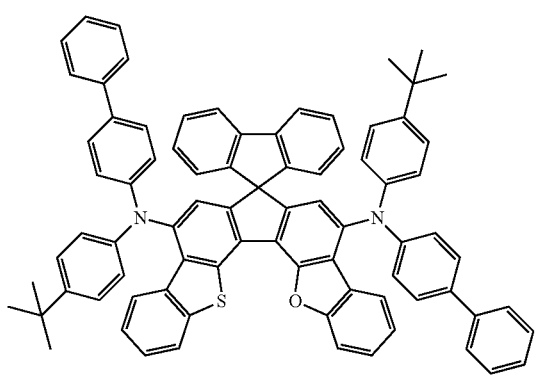
<Chemical Formula 225>
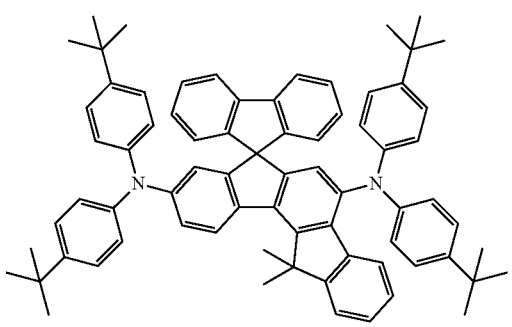
<Chemical Formula 226>
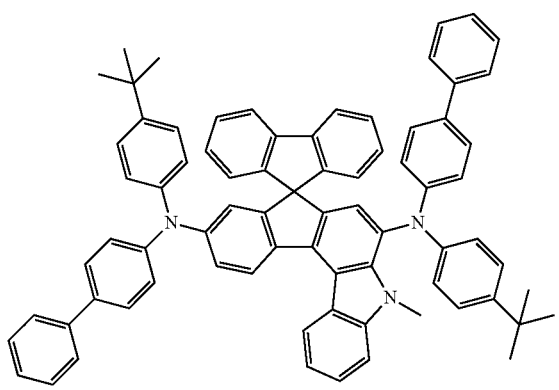
<Chemical Formula 227>
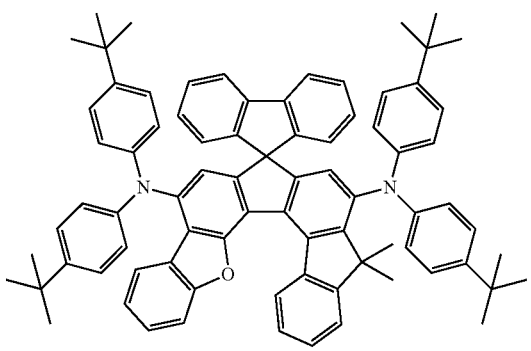
<Chemical Formula 228>
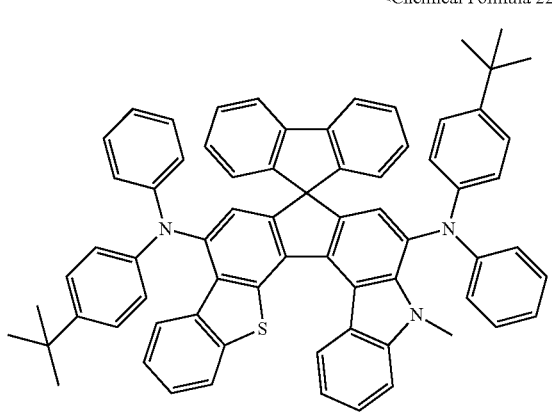
<Chemical Formula 229>
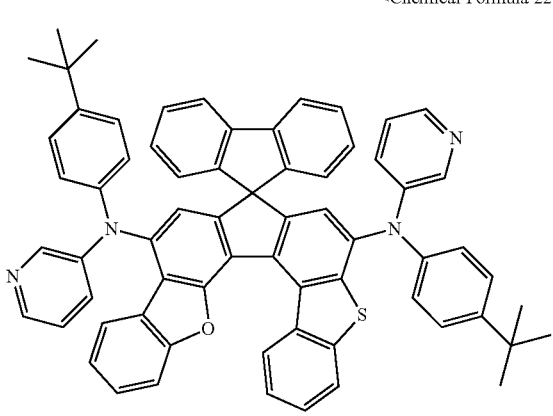

-continued
<Chemical Formula 230>
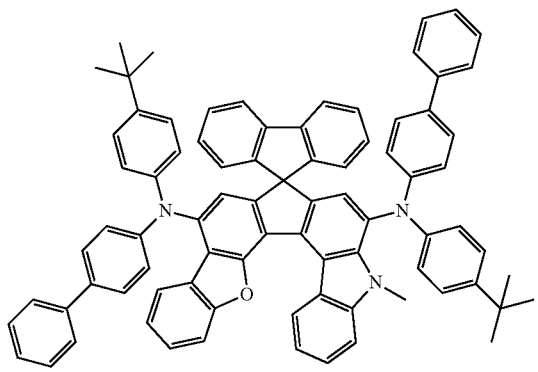
<Chemical Formula 231>
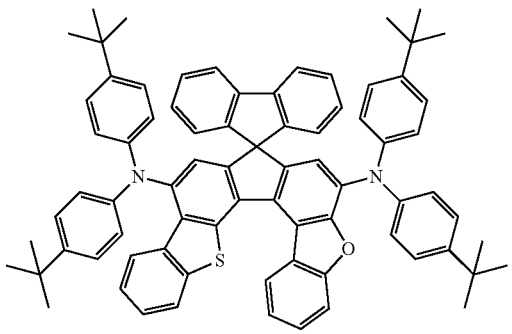
<Chemical Formula 232>
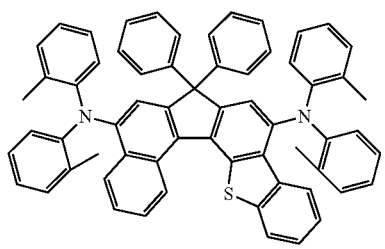
<Chemical Formula 233>
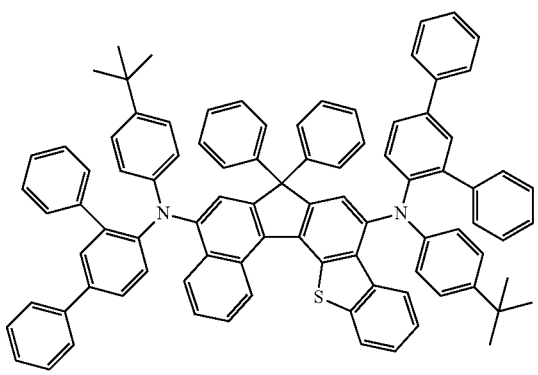
<Chemical Formula 234>
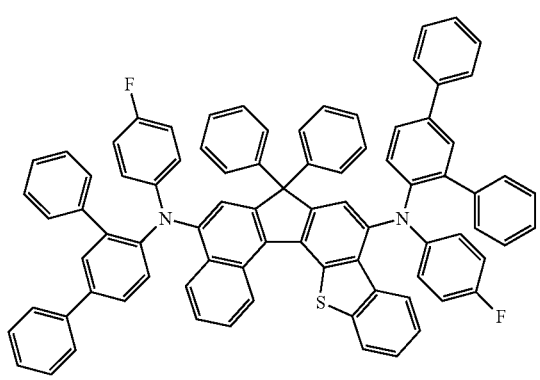
<Chemical Formula 235>
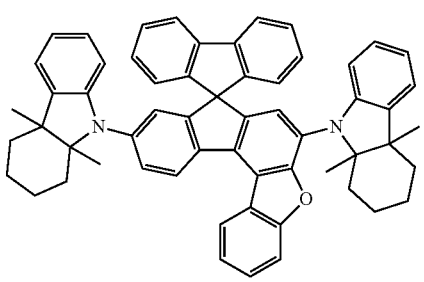
<Chemical Formula 236>
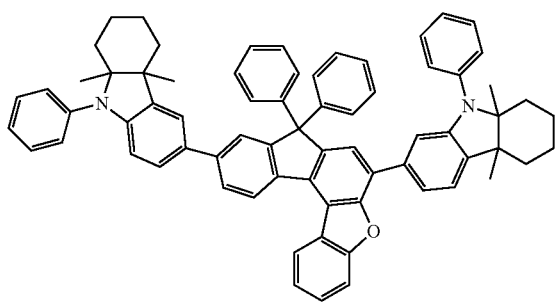
<Chemical Formula 237>
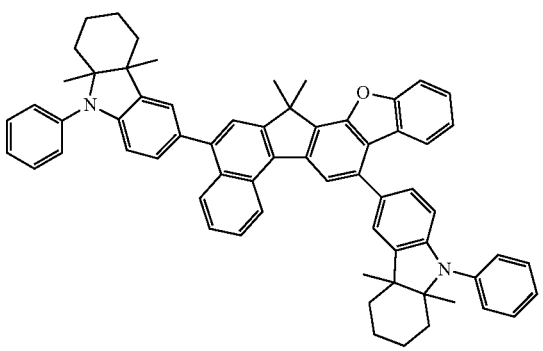

<Chemical Formula 238>

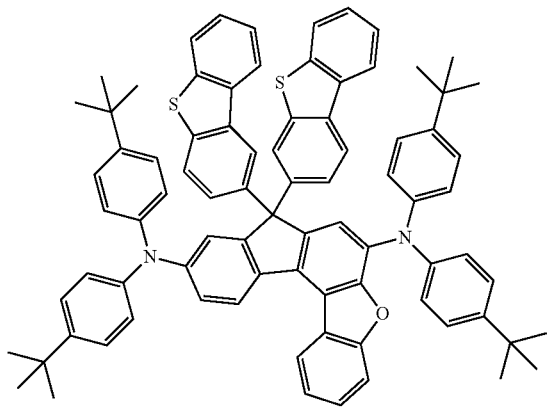

<Chemical Formula 239>

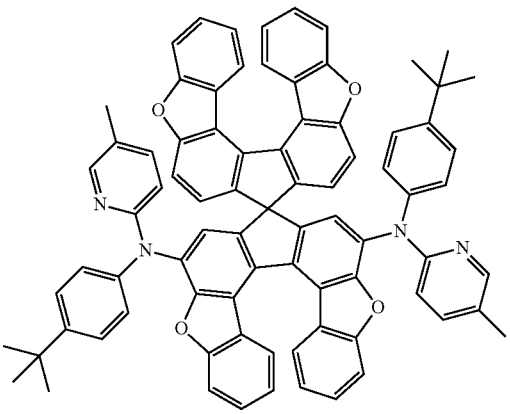

In addition, the compound represented by Chemical Formula D may be any one organic compound selected from among Compounds 1 to 138.

The following Compounds 1 to 138 each of which serves as a host is characterized in that linking occurs between the carbon atom at position 9 of the anthracene moiety and the carbon atom at position 1 or 2 of either phenyl ring of the substituted or unsubstituted dibenzofuran moiety, as shown in the following Diagram 1, through the linker L.

<Compound 1>

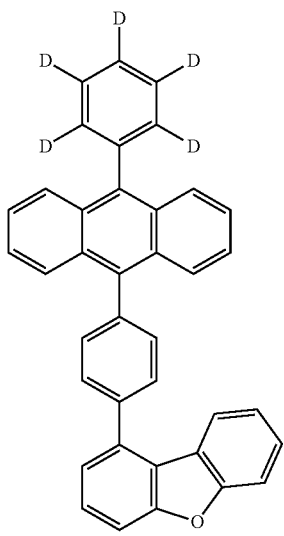

<Compound 2>

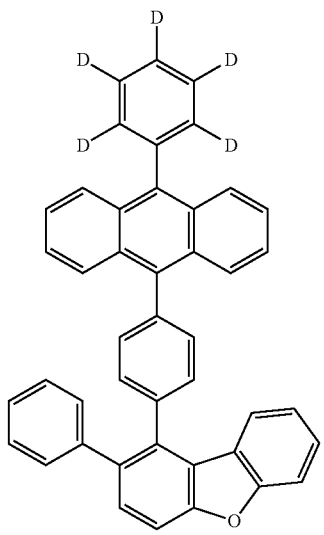

<Compound 3>

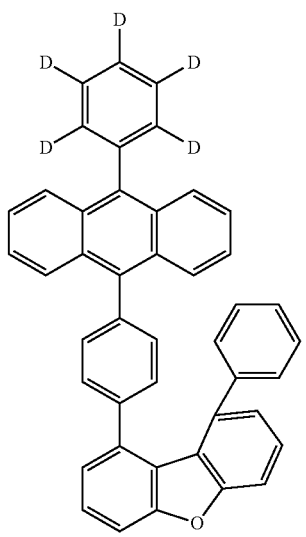

<Compound 4>
<Compound 5>
<Compound 6>
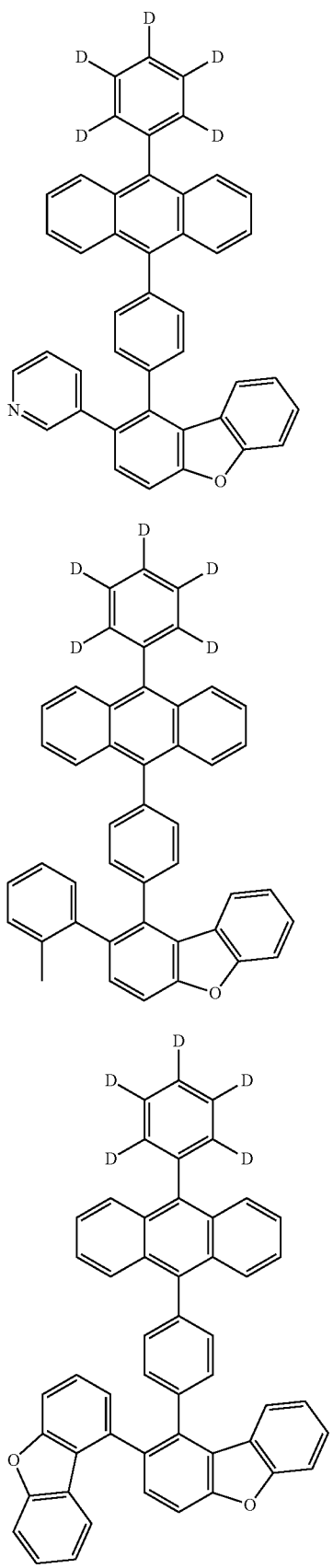
<Compound 7>
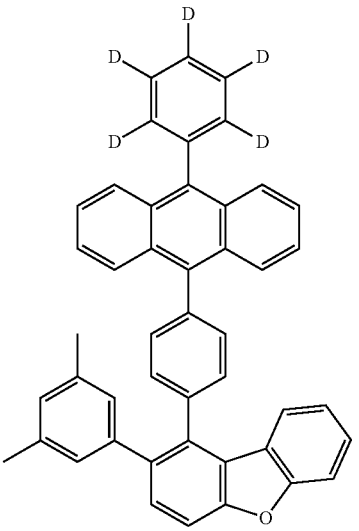
<Compound 8>
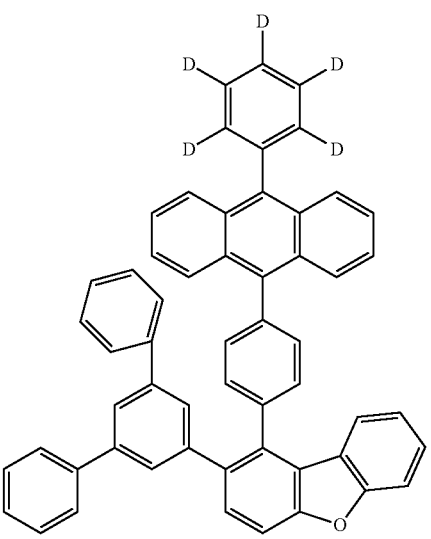
<Compound 9>
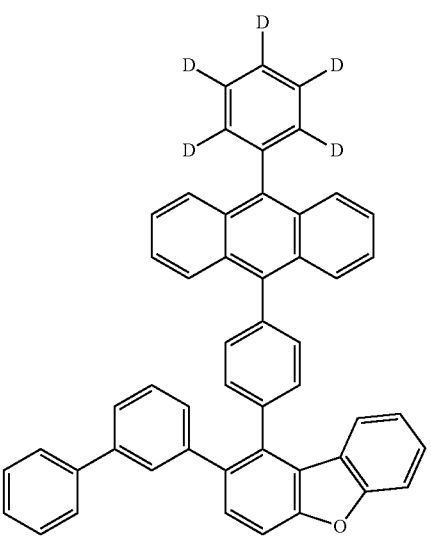

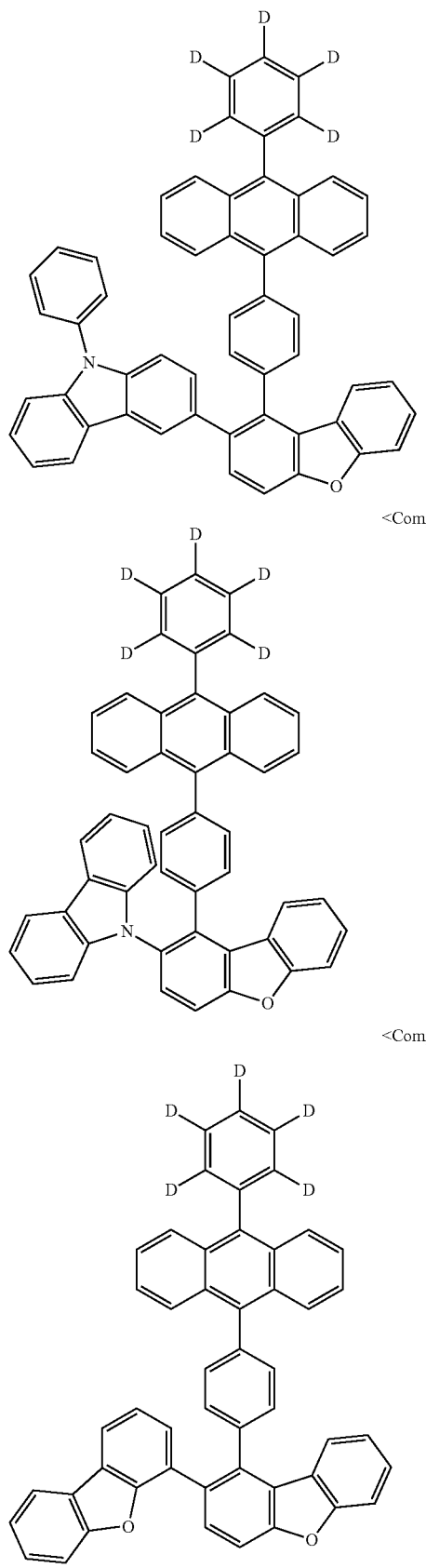
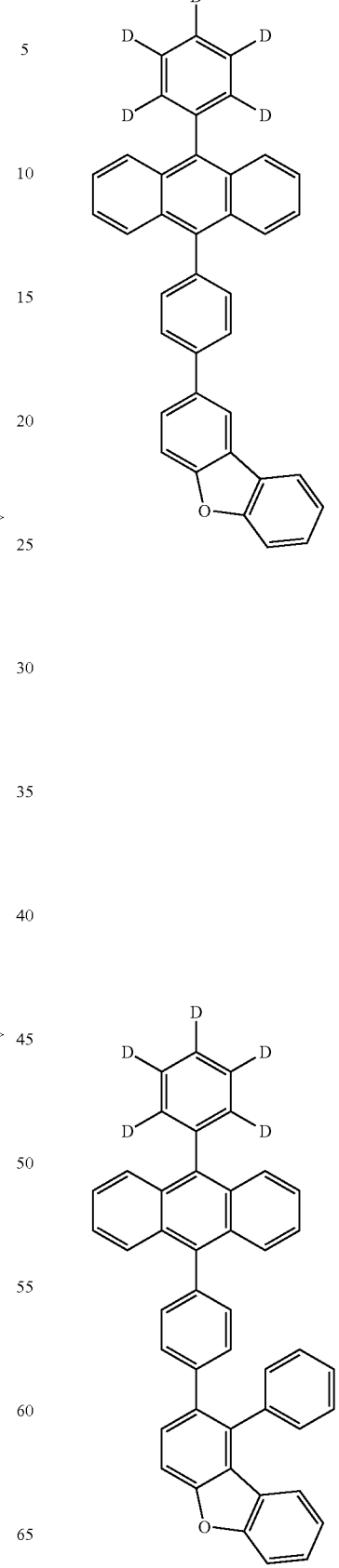

<Compound 15>
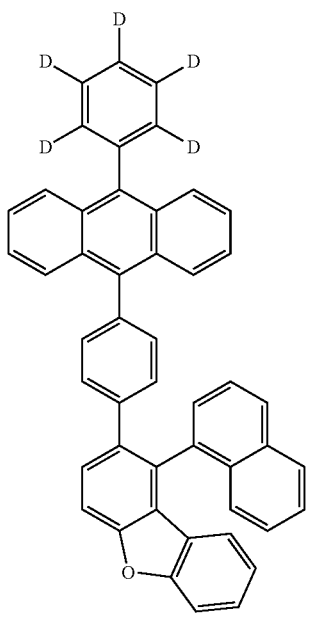
<Compound 16>
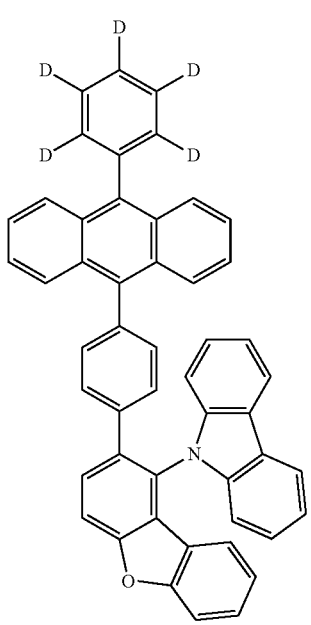
<Compound 17>
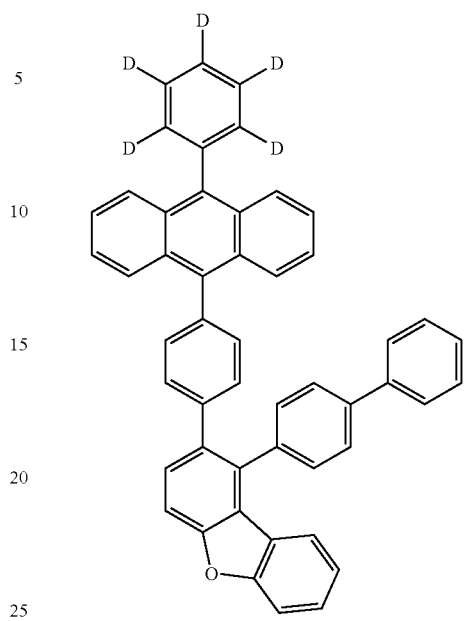
<Compound 18>
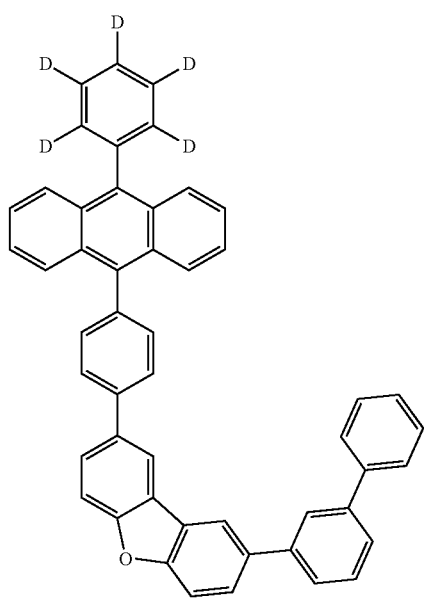

<Compound 19>
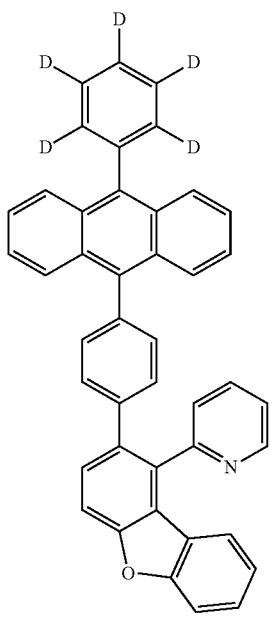
<Compound 20>
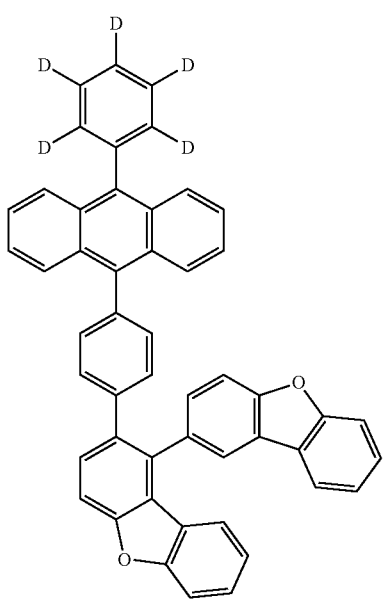
<Compound 21>
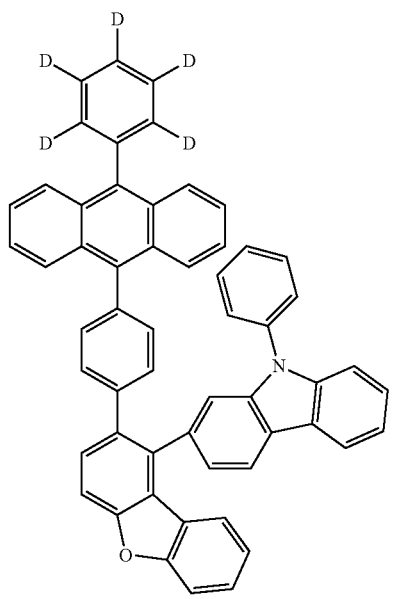
<Compound 22>
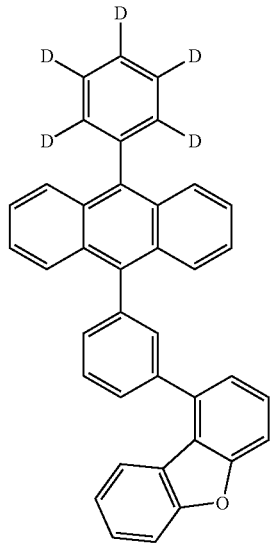

<Compound 23>
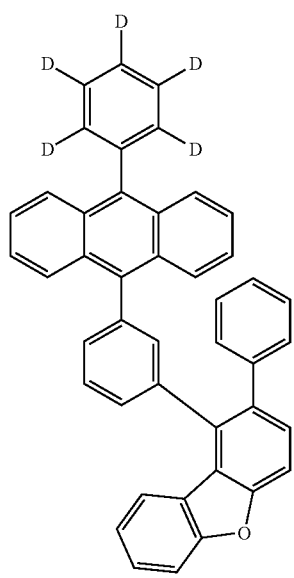
<Compound 25>
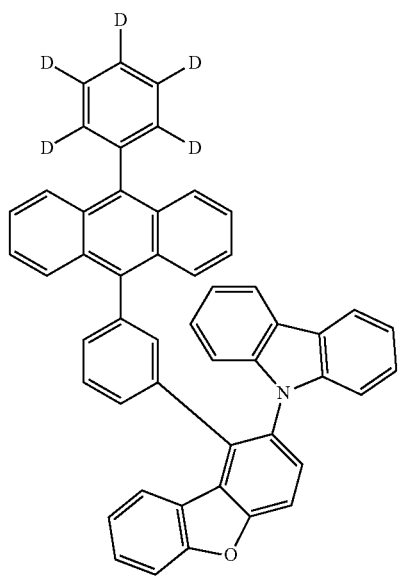
<Compound 24>
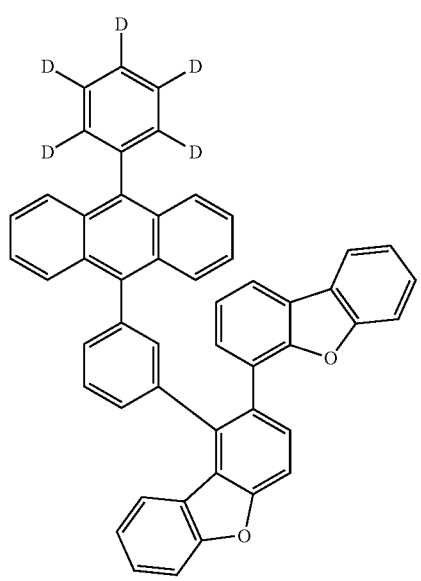
<Compound 26>
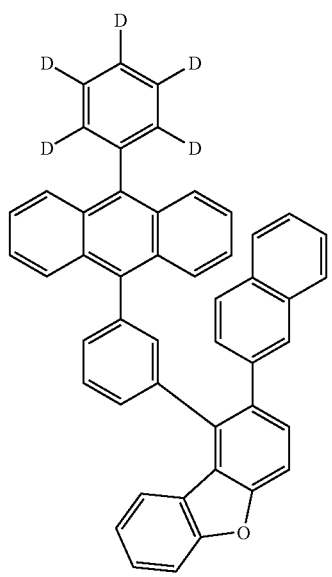

<Compound 27>
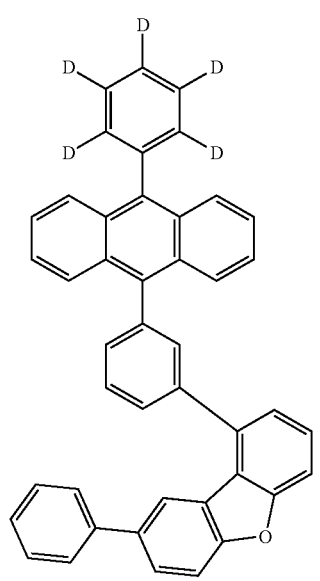
<Compound 29>
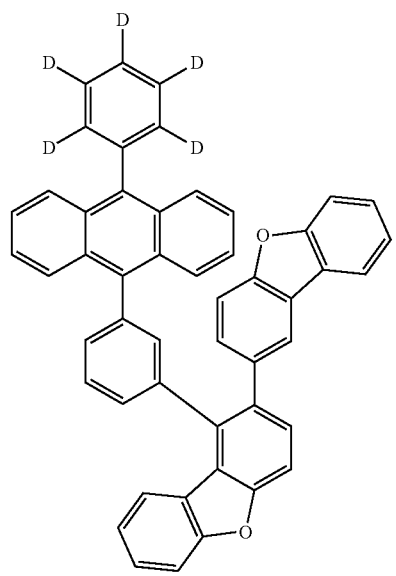
<Compound 28>
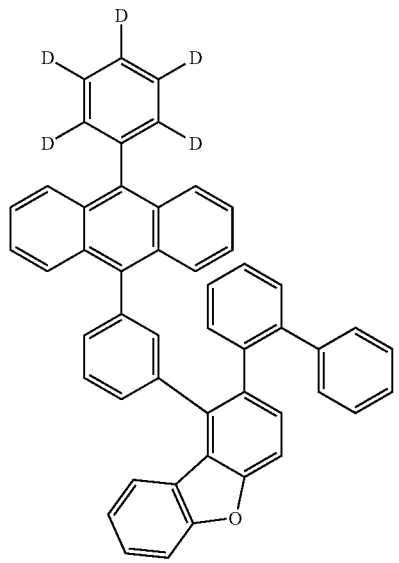
<Compound 30>
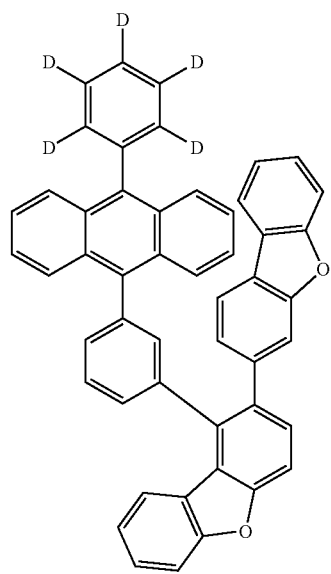

<Compound 31>
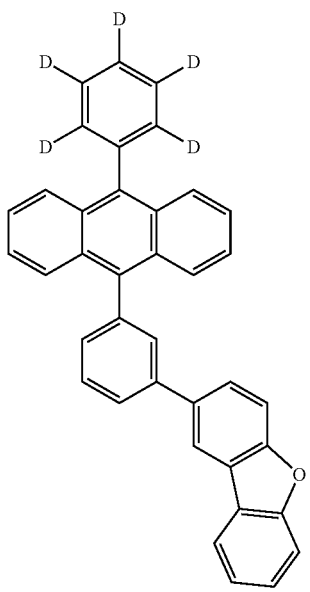
<Compound 33>
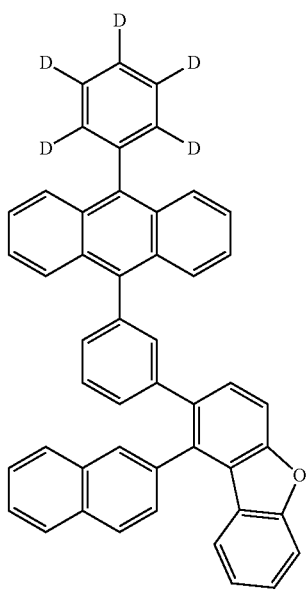
<Compound 32>
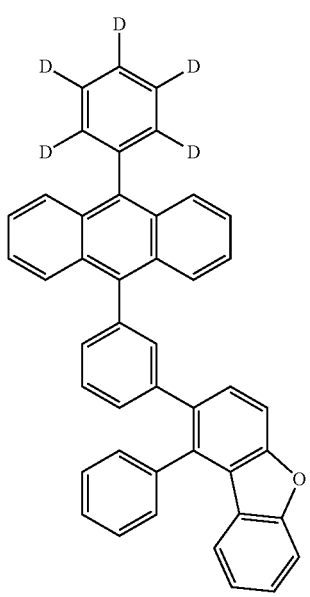
<Compound 34>
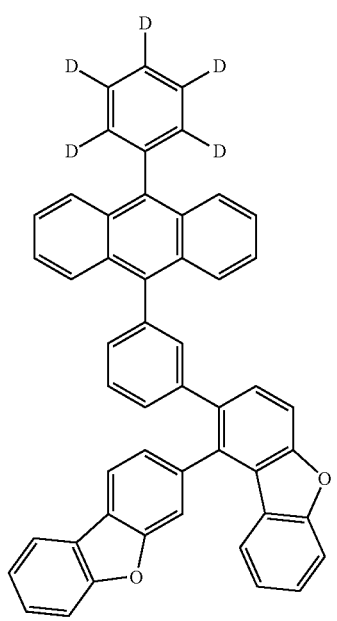

<Compound 35>
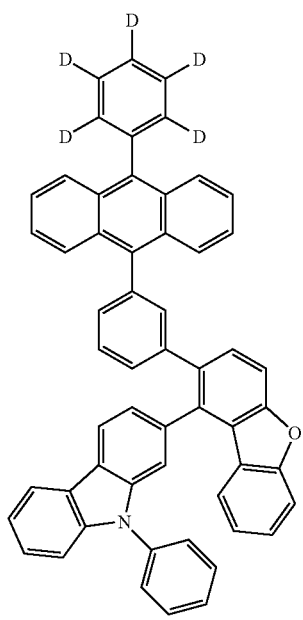
<Compound 36>
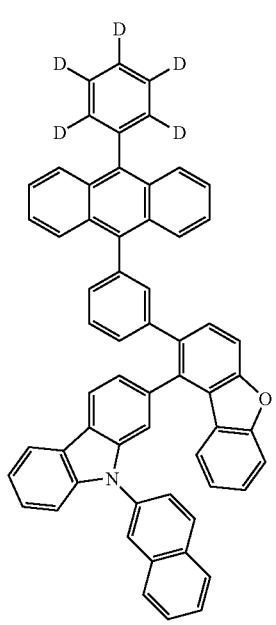
<Compound 37>
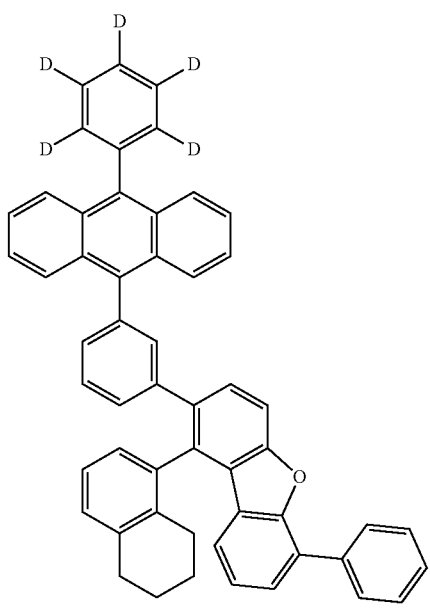
<Compound 38>
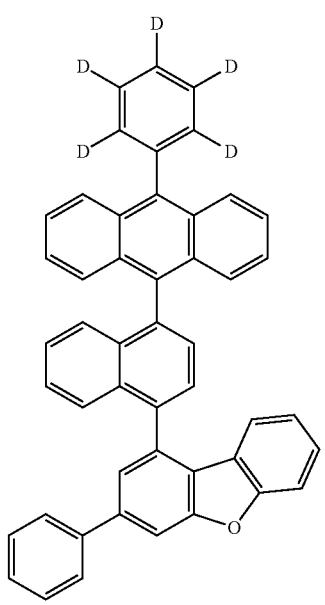

<Compound 39>
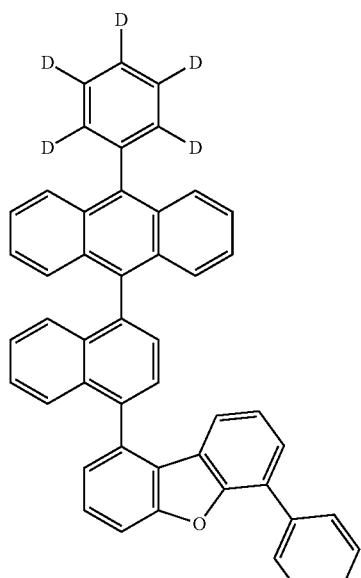
<Compound 40>
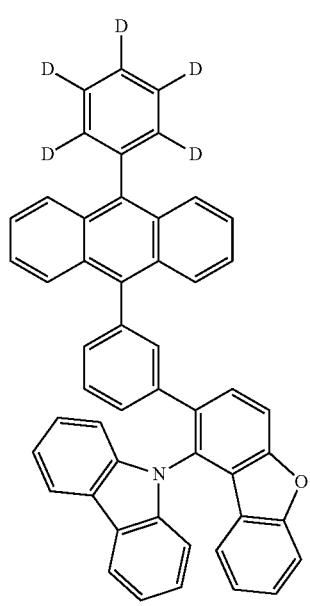
<Compound 41>
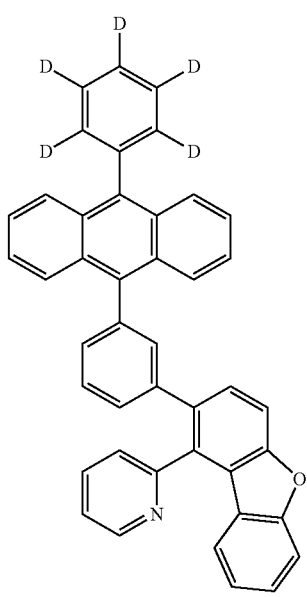
<Compound 42>
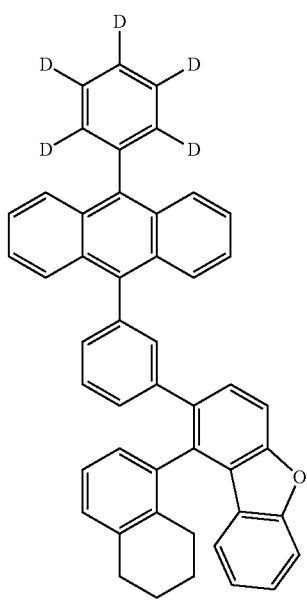

<Compound 43>
<Compound 44>
<Compound 45>
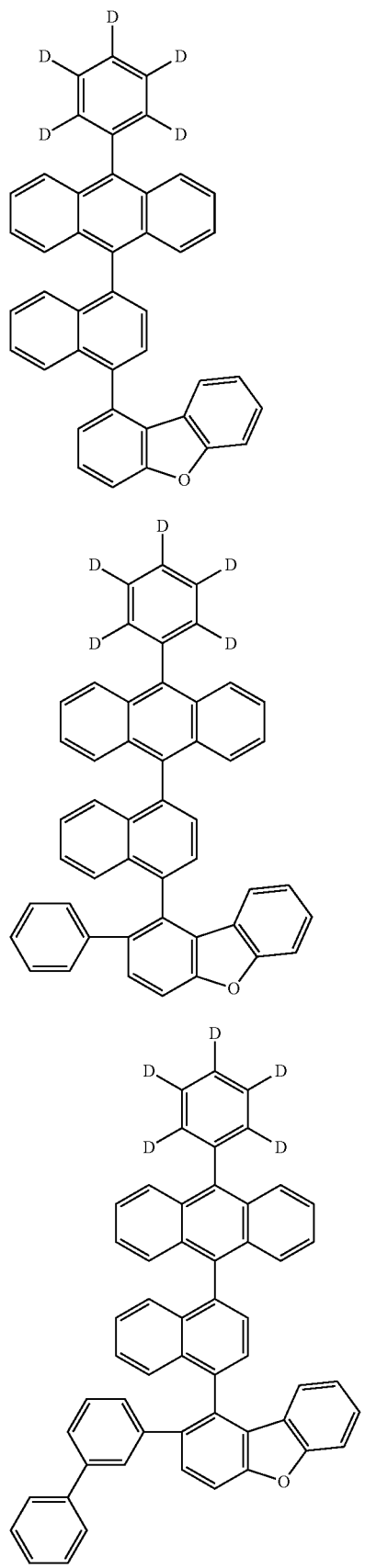
<Compound 46>
<Compound 47>

<Compound 48>
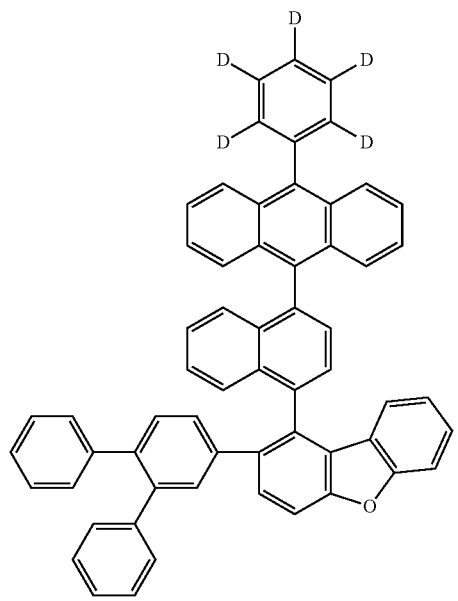
<Compound 49>
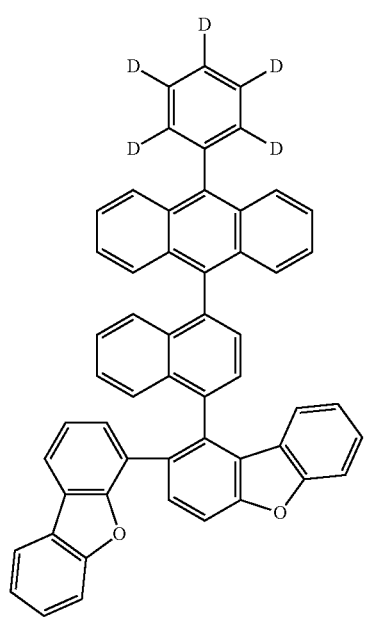
<Compound 50>
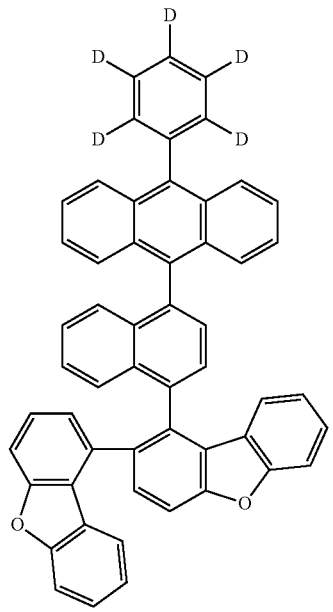
<Compound 51>
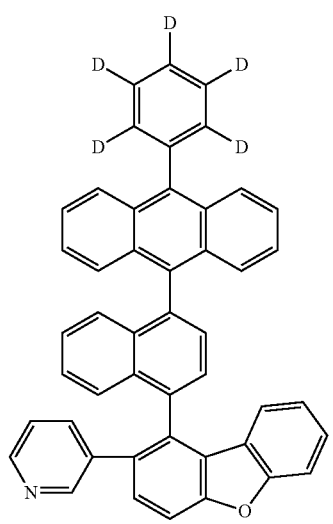

<Compound 52>
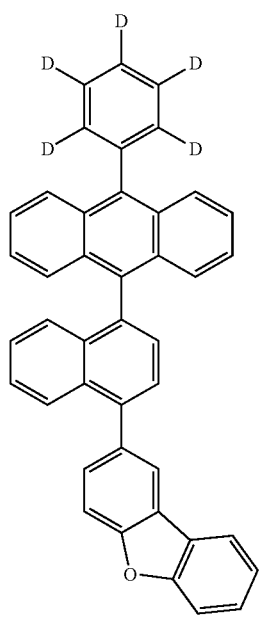
<Compound 54>
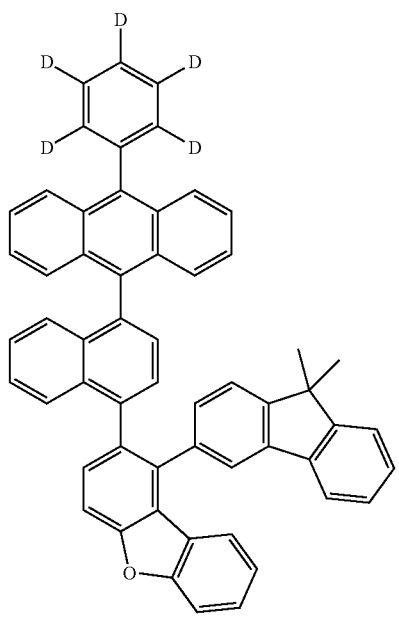
<Compound 53>
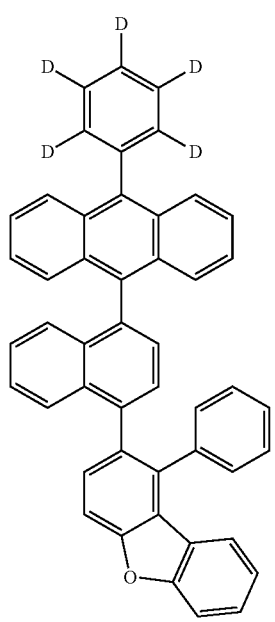
<Compound 55>
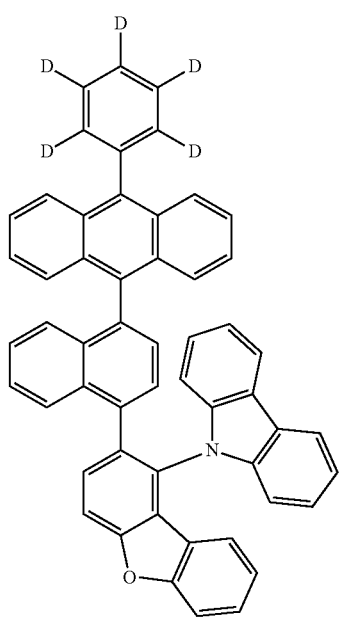

<Compound 56>
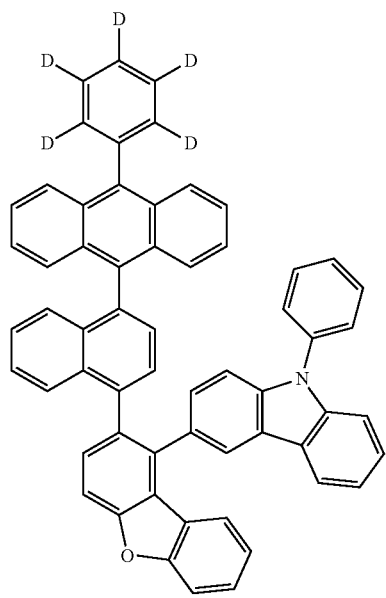
<Compound 58>
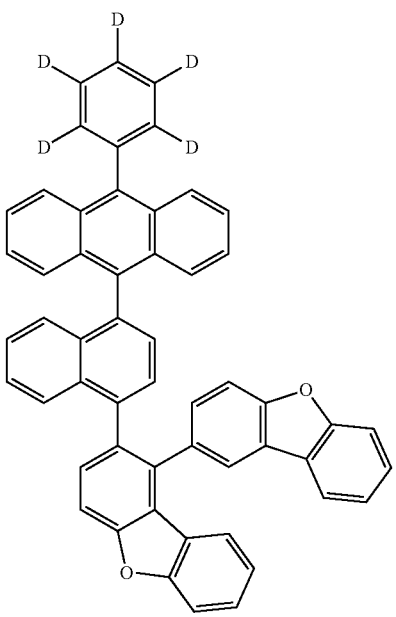
<Compound 57>
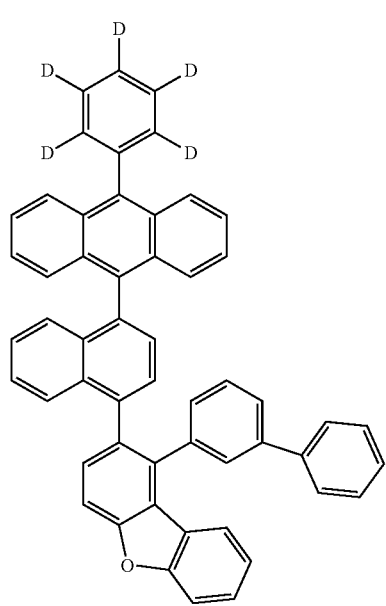
<Compound 59>
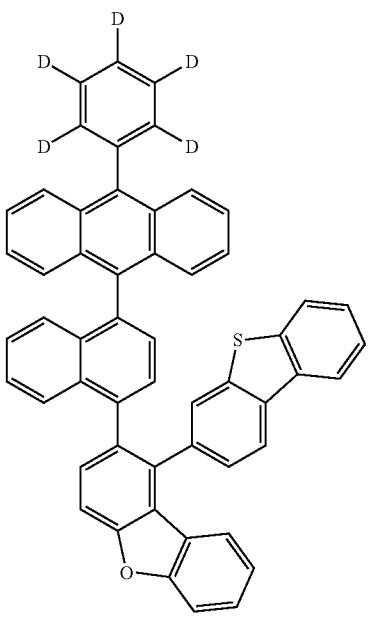

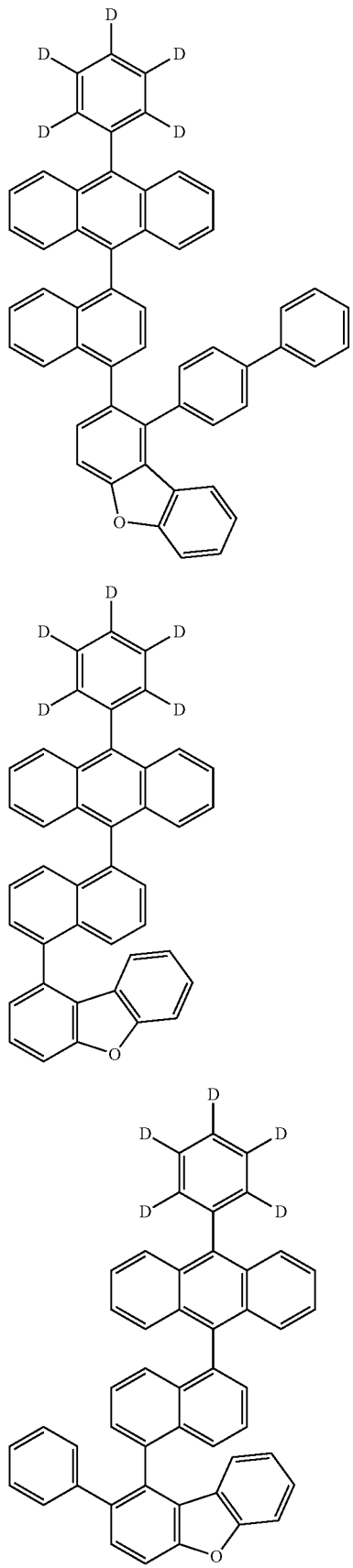
<Compound 60>
<Compound 61>
<Compound 62>
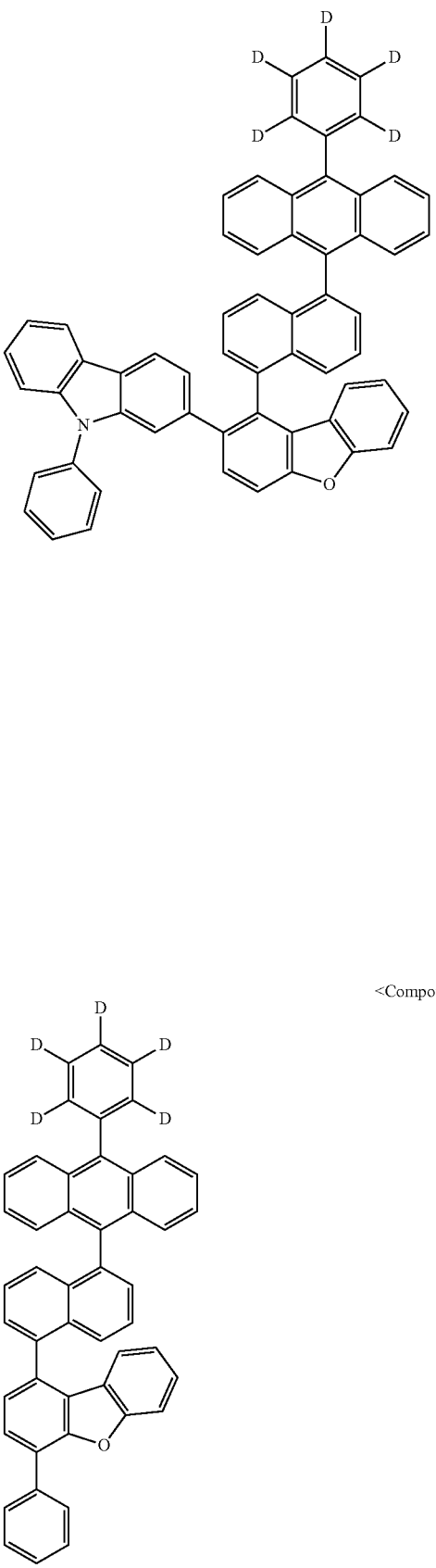
<Compound 63>
<Compound 64>

<Compound 65>
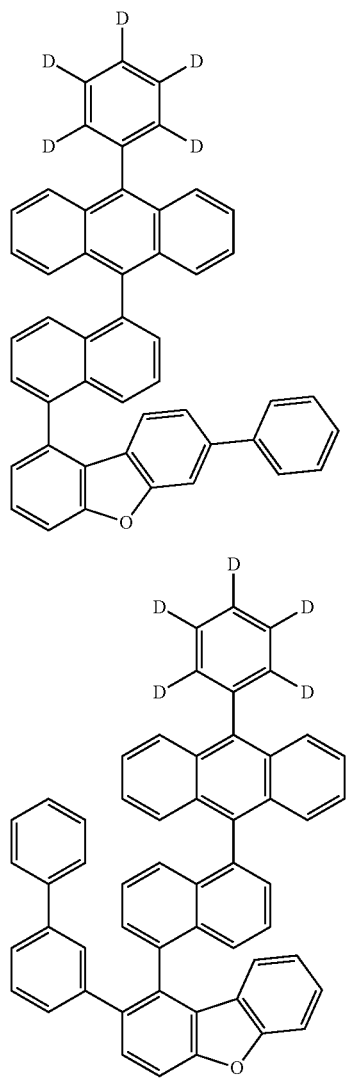
<Compound 66>
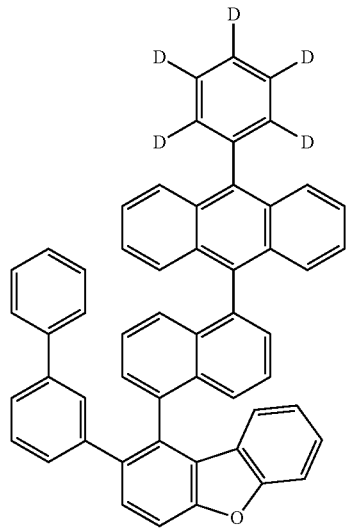
<Compound 67>
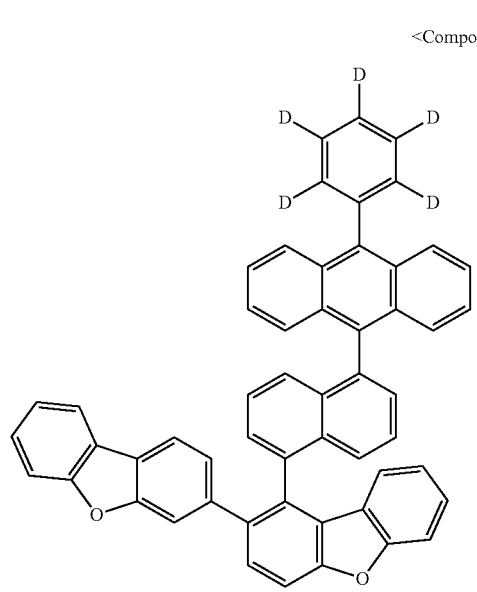
<Compound 68>
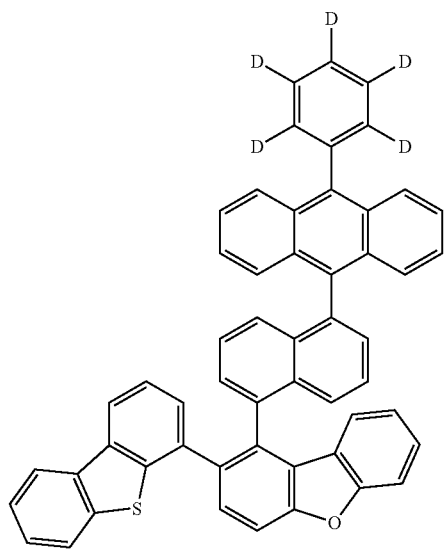
<Compound 69>
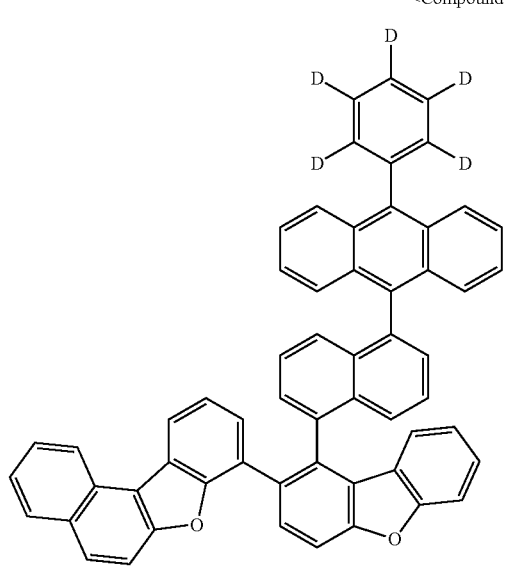

<Compound 70>
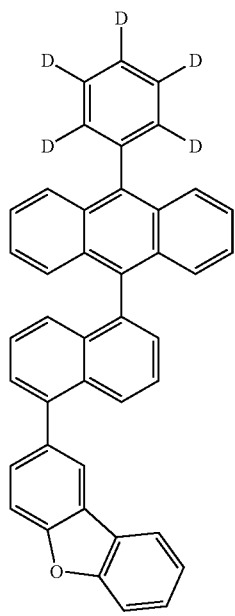
<Compound 72>

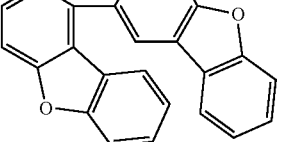
<Compound 71>
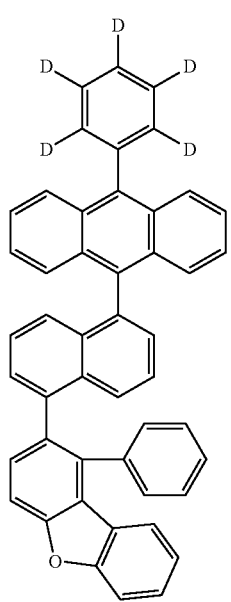
<Compound 73>
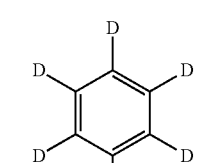
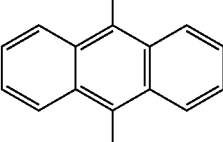
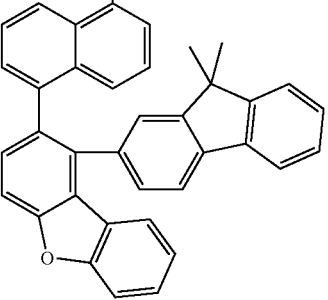

<Compound 74>
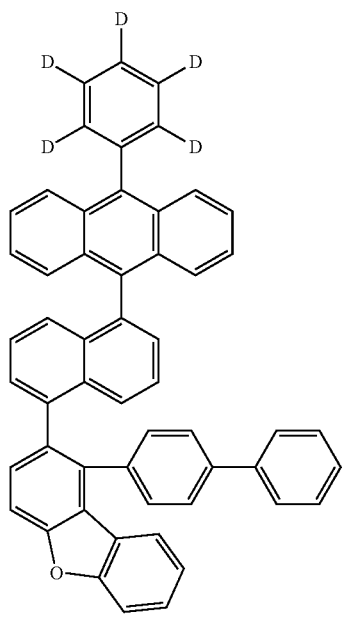
<Compound 75>
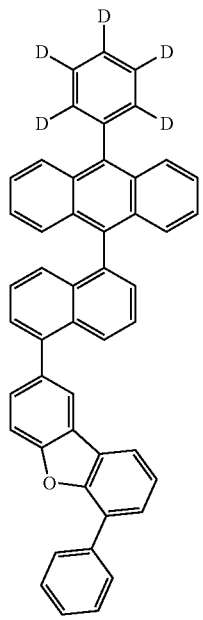
<Compound 76>
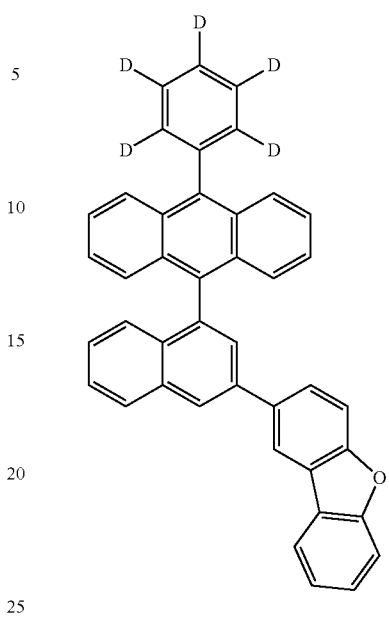
<Compound 77>
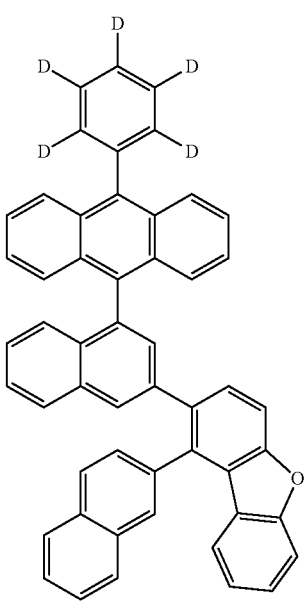

<Compound 78>
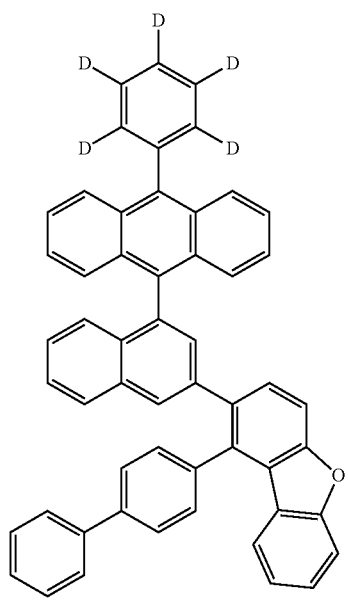
<Compound 79>
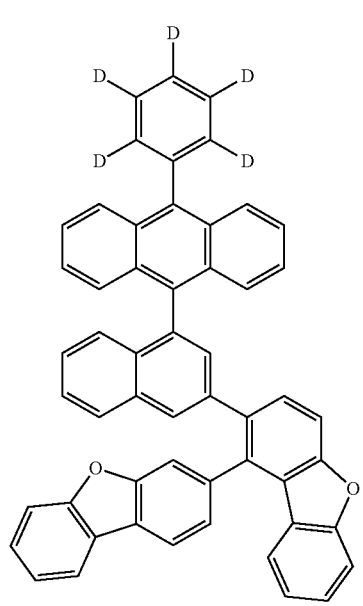
<Compound 80>
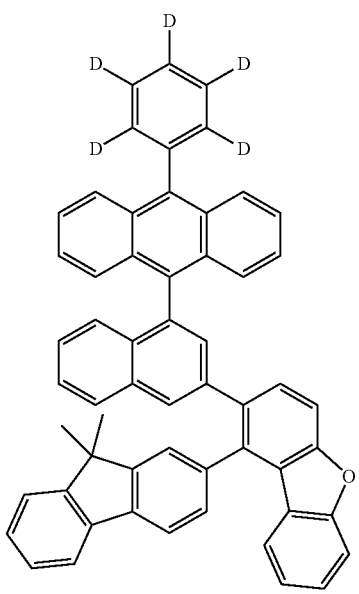
<Compound 81>
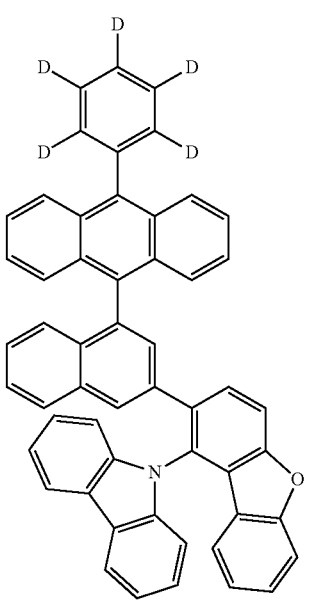

<Compound 82>
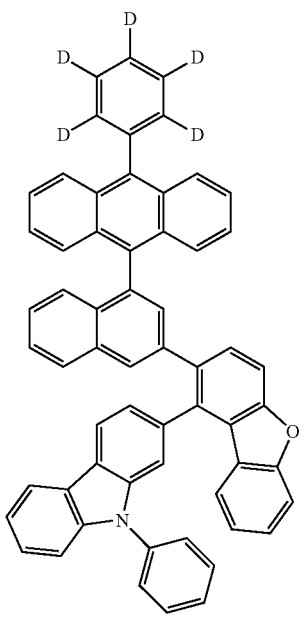
<Compound 84>
<Compound 85>
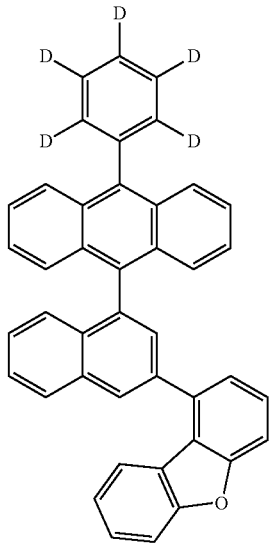
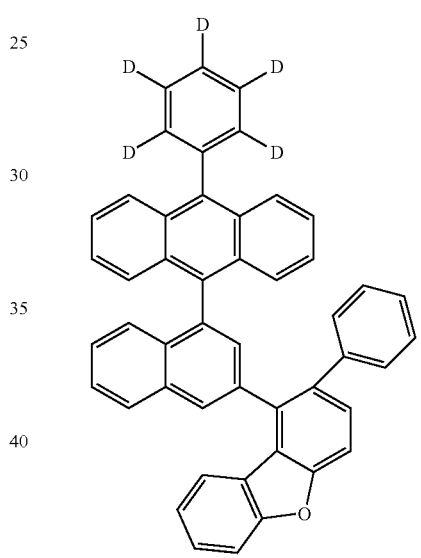
<Compound 83>
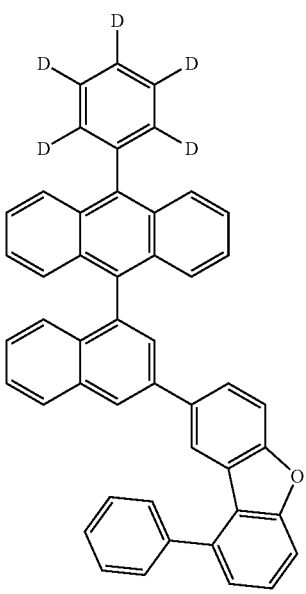
<Compound 86>

<Compound 87>
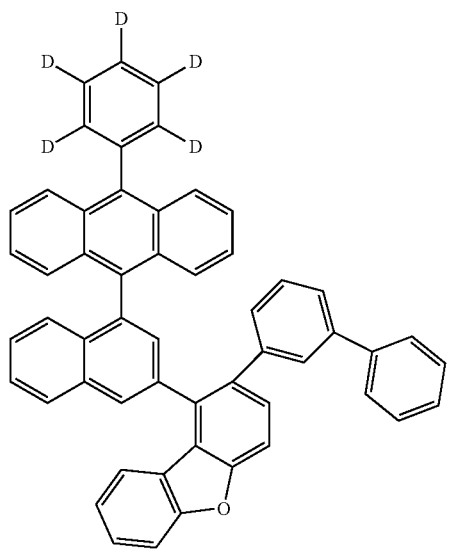
<Compound 88>
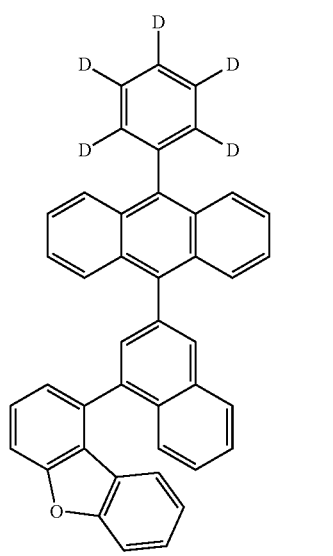
<Compound 89>
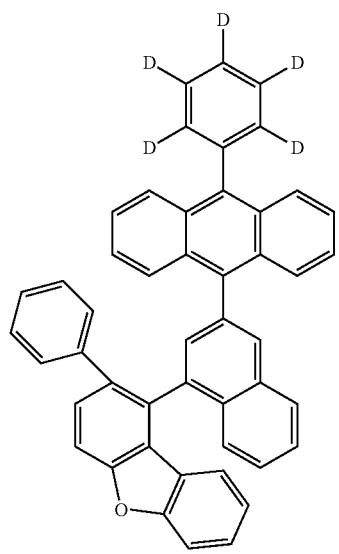
<Compound 90>
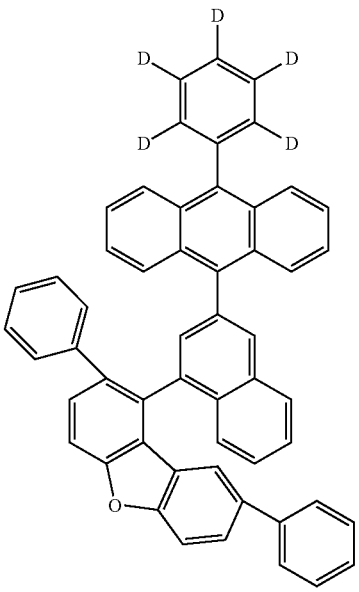
<Compound 91>
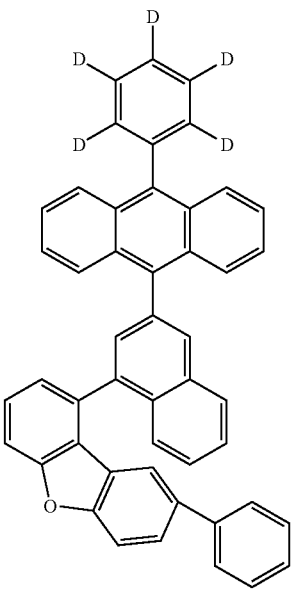

<Compound 92>
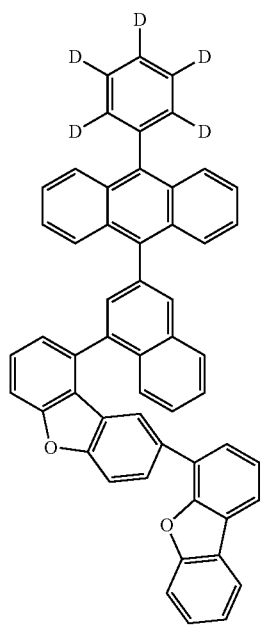
<Compound 93>
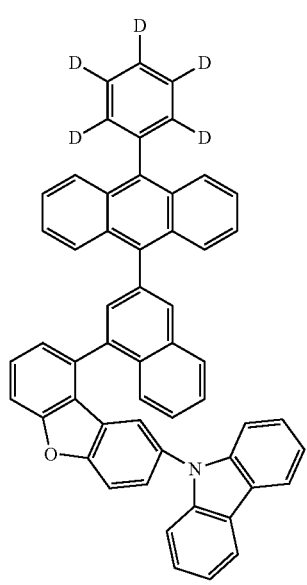
<Compound 94>
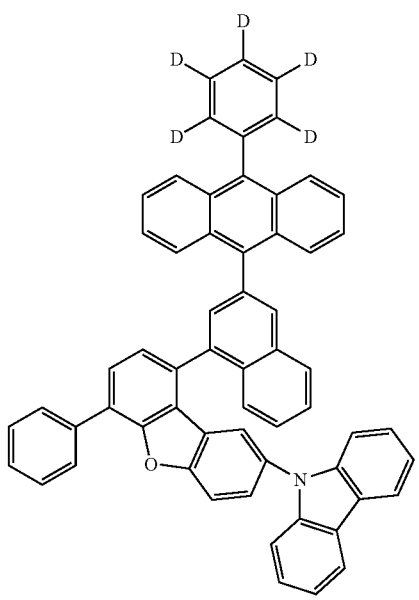
<Compound 95>
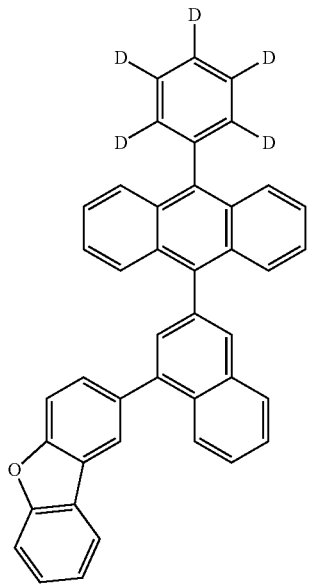

<Compound 96>
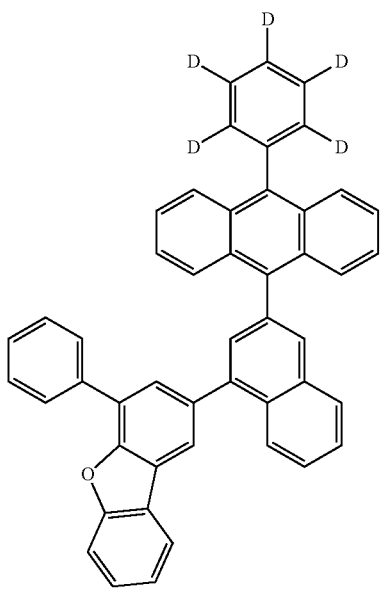
<Compound 98>
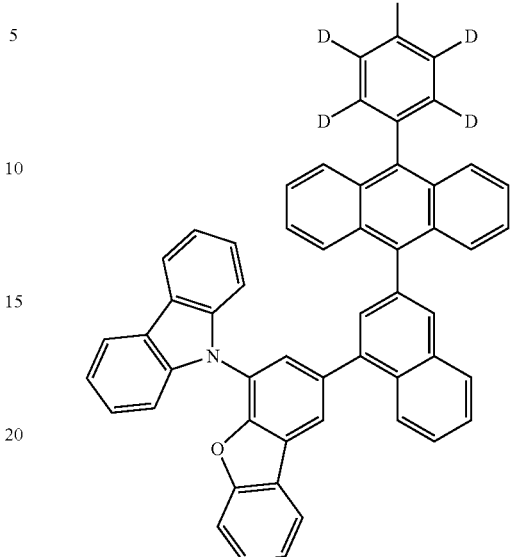
<Compound 97>
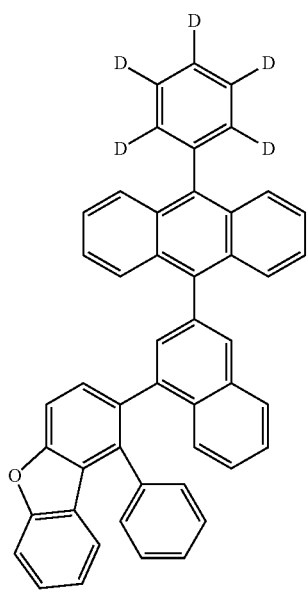
<Compound 99>
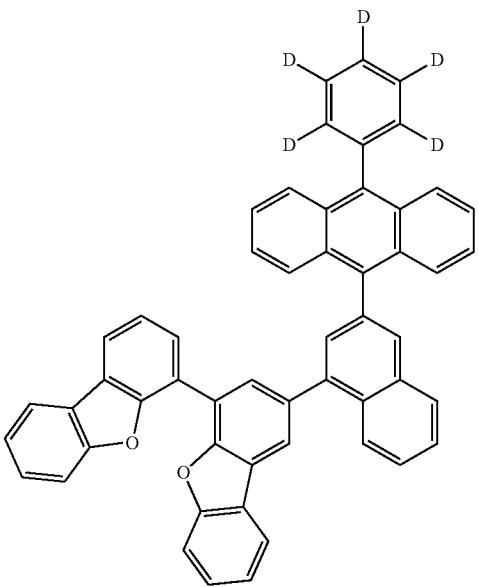

<Compound 100>
<Compound 101>
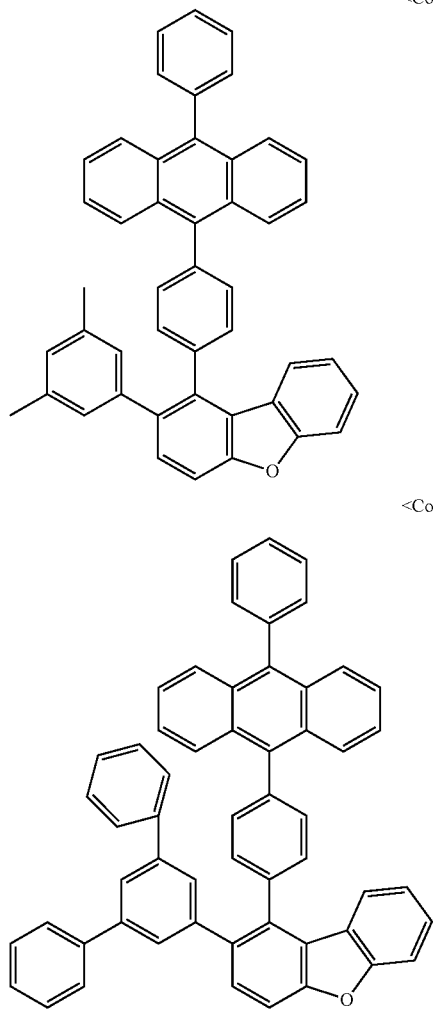
<Compound 102>
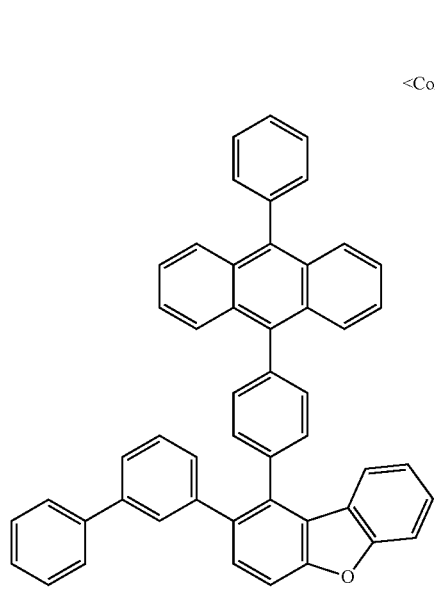
<Compound 103>
<Compound 104>
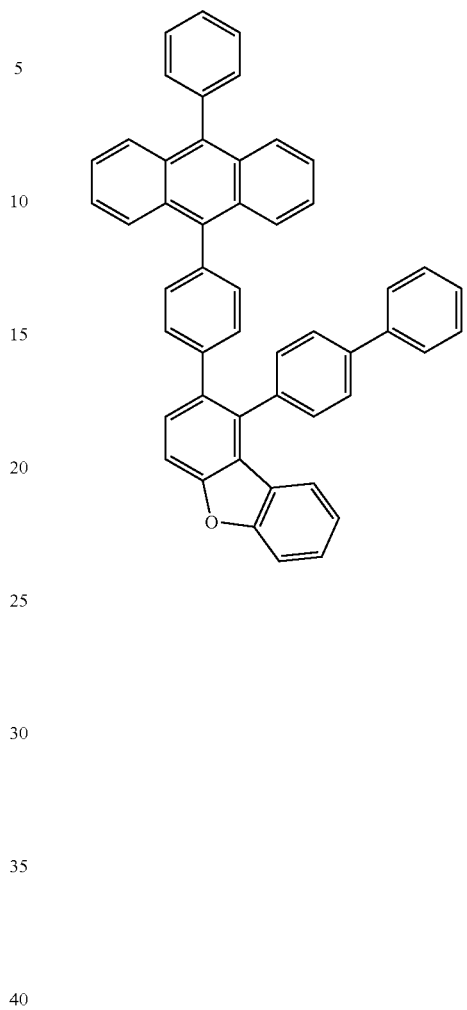

<Compound 105>
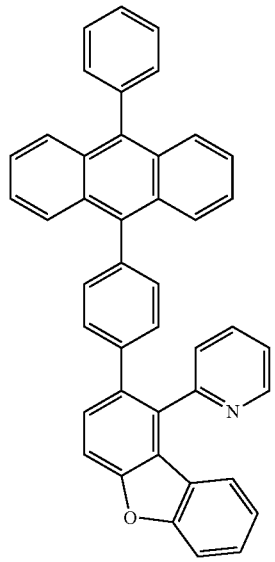
<Compound 106>
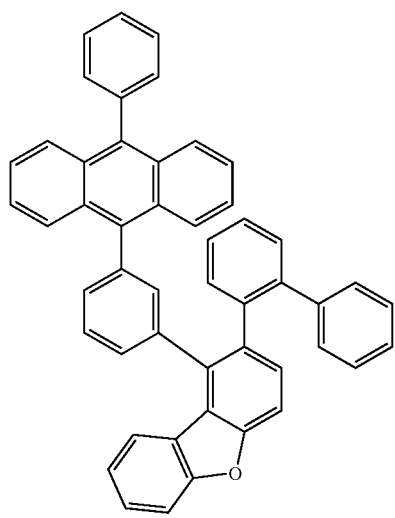
<Compound 107>
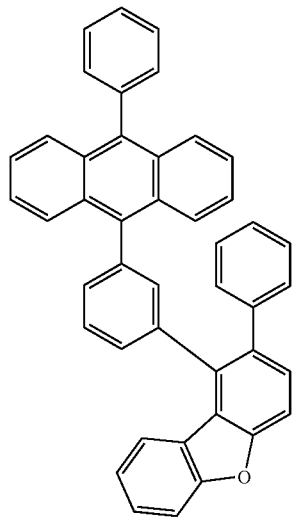
<Compound 108>
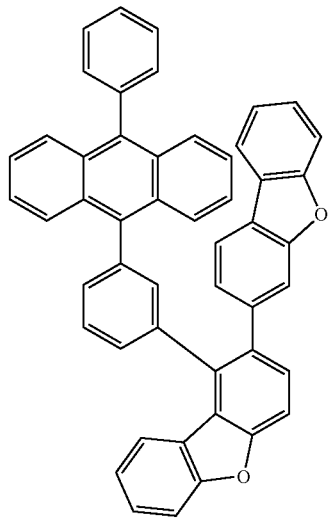
<Compound 109>
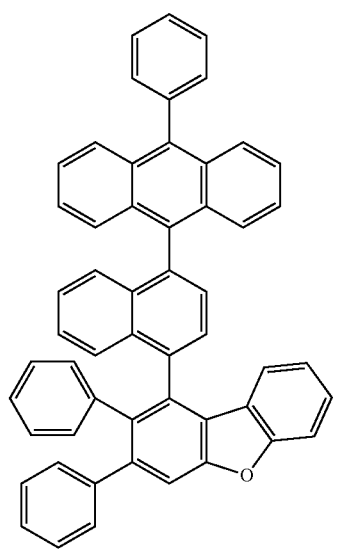
<Compound 110>
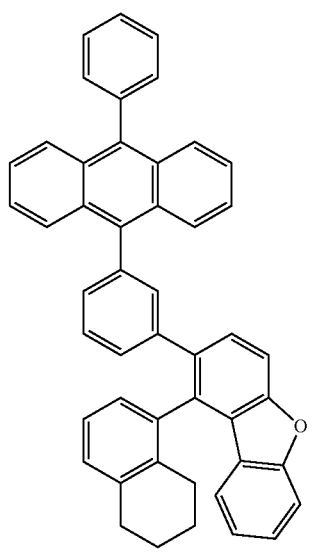

<Compound 111>
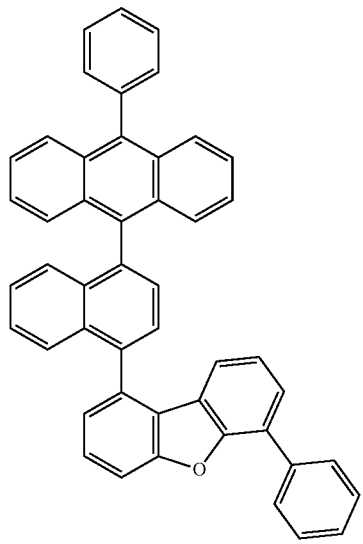
<Compound 112>
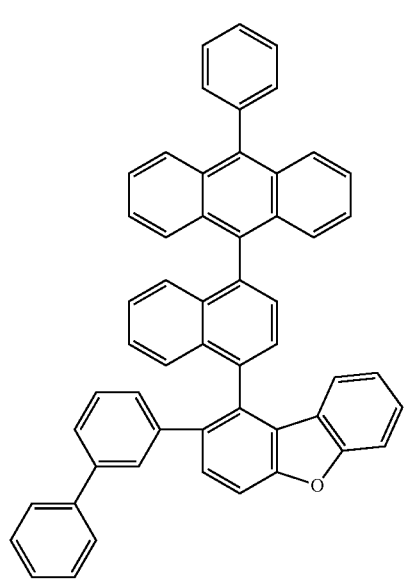
<Compound 113>
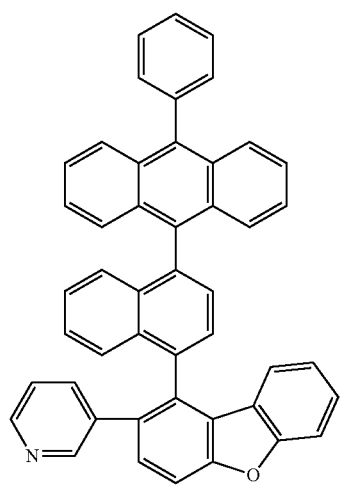
<Compound 114>
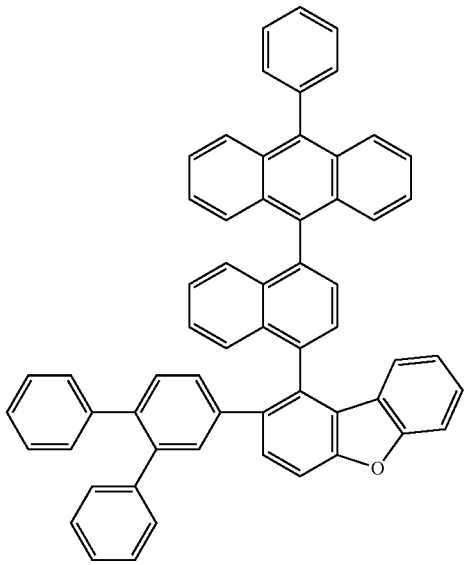
<Compound 115>
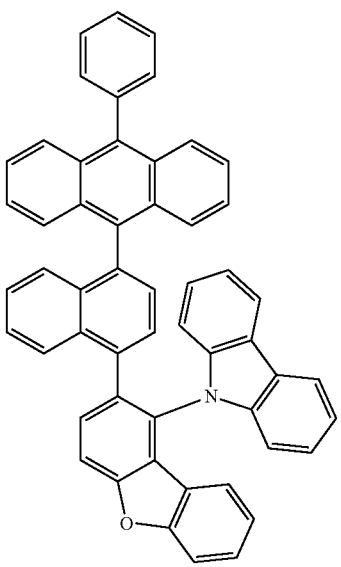

<Compound 116>
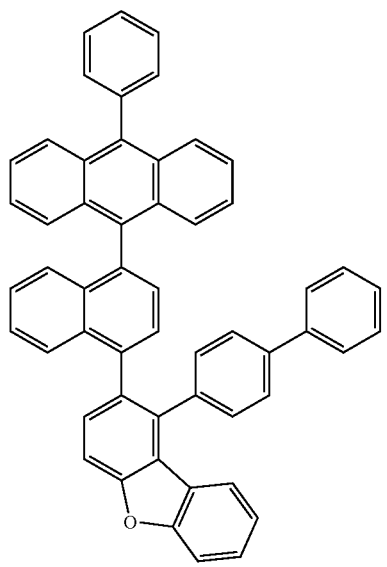
<Compound 117>
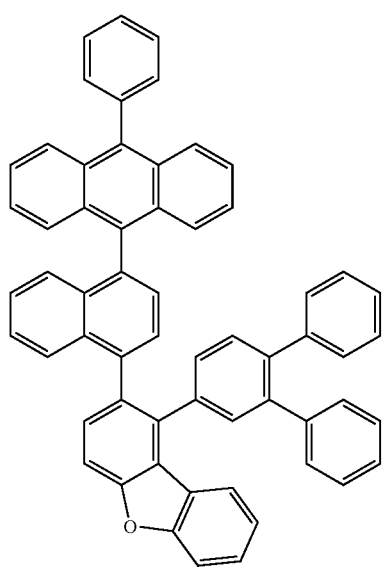
<Compound 118>
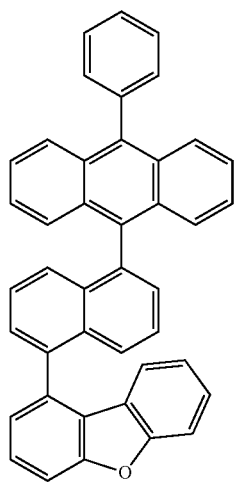
<Compound 119>
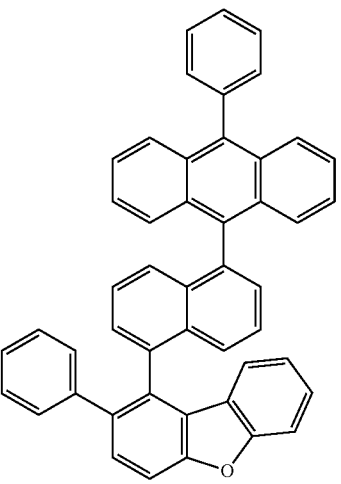
<Compound 120>
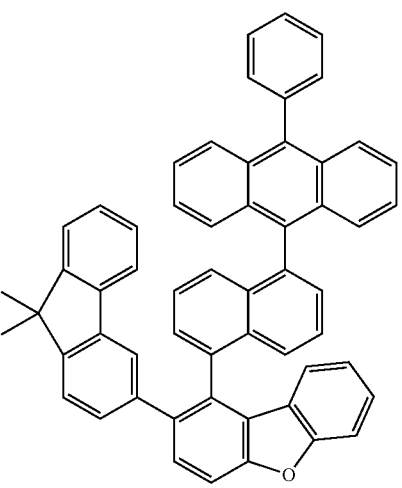
<Compound 121>
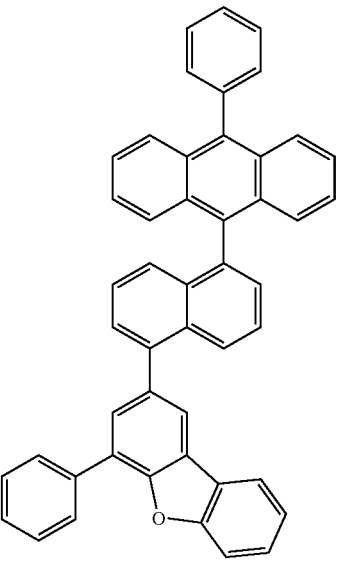

<Compound 122>
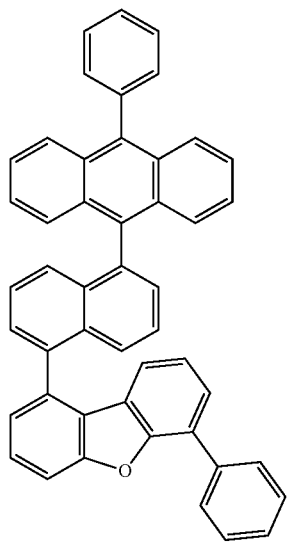
<Compound 123>
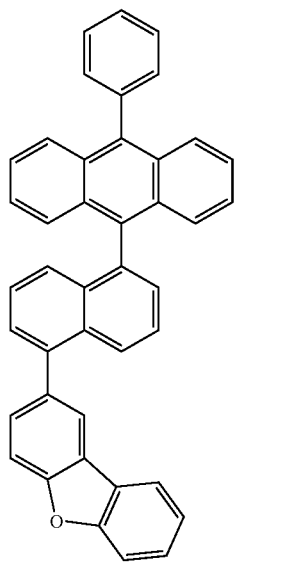
<Compound 124>
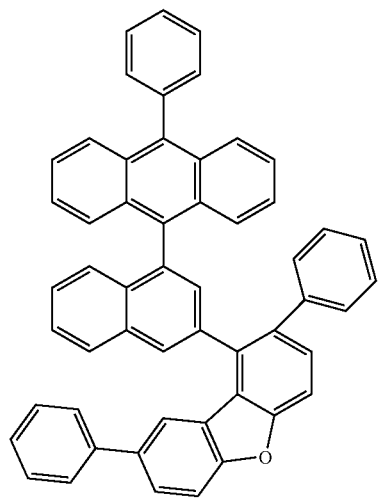
<Compound 125>
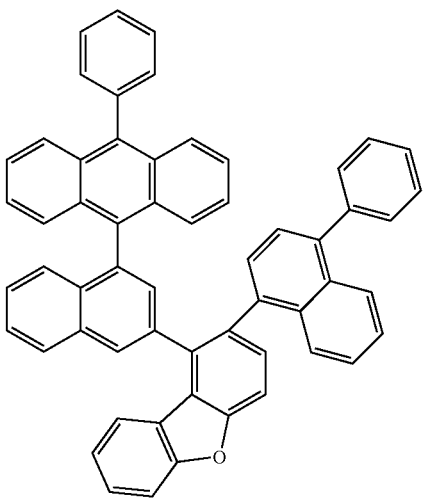
<Compound 126>
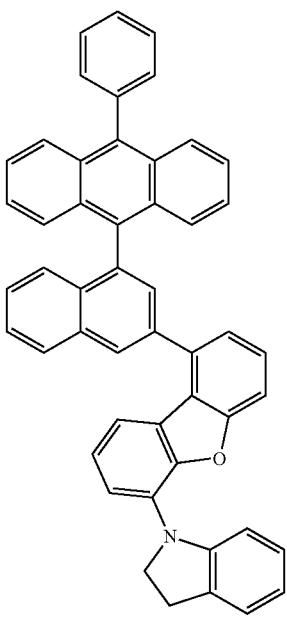

<Compound 127>
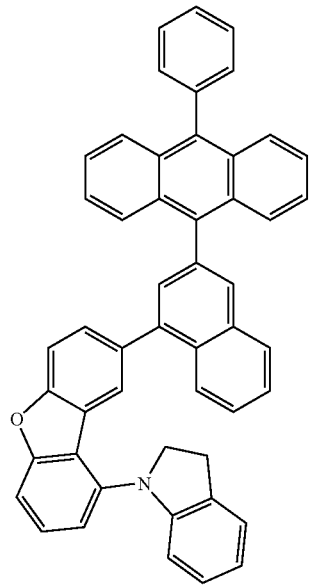
<Compound 128>
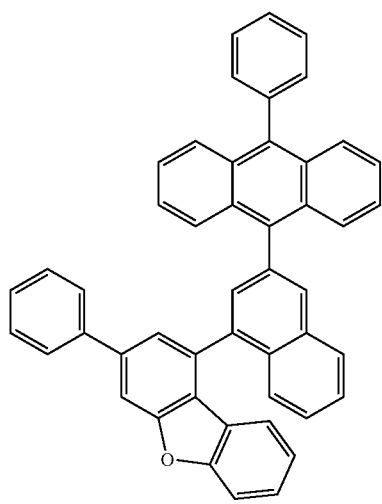
<Compound 129>
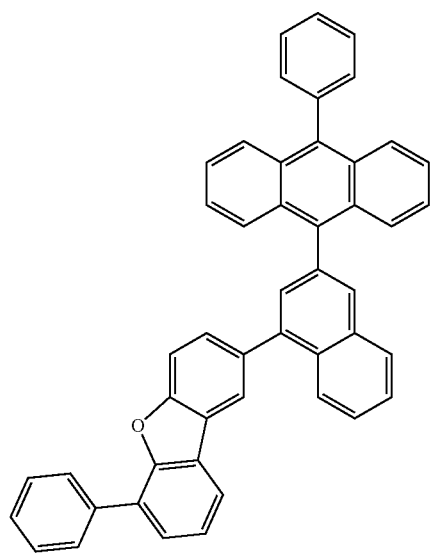
<Compound 130>
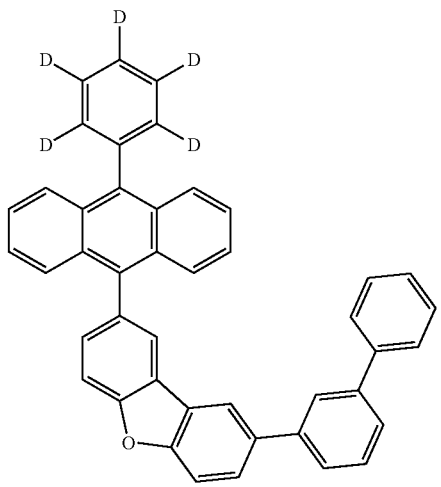
<Compound 131>
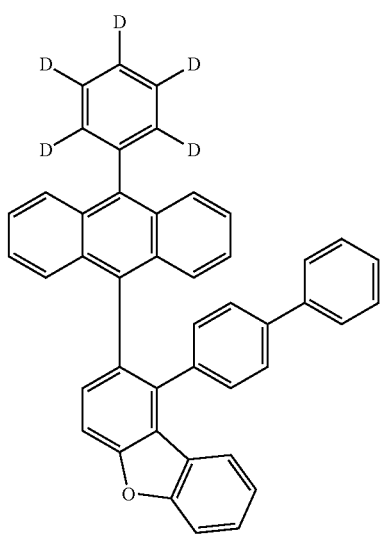
<Compound 132>
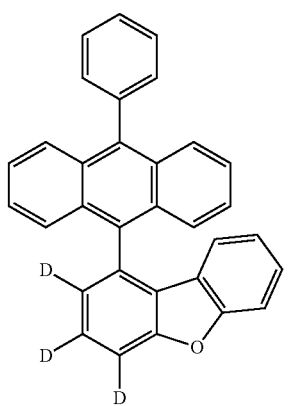

<Compound 133>
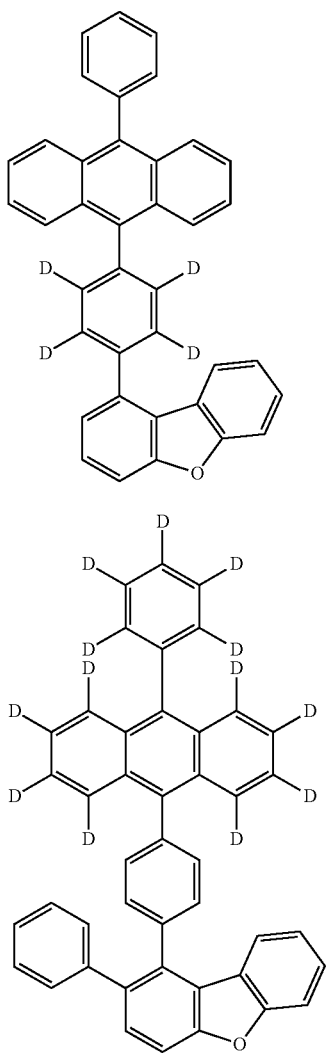
<Compound 134>
<Compound 135>
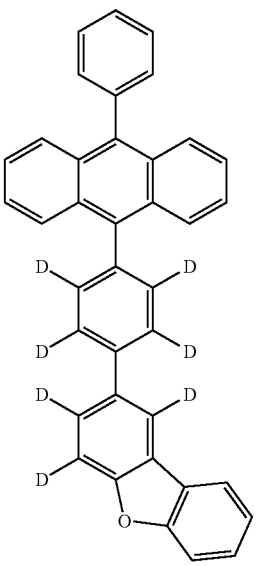
<Compound 136>
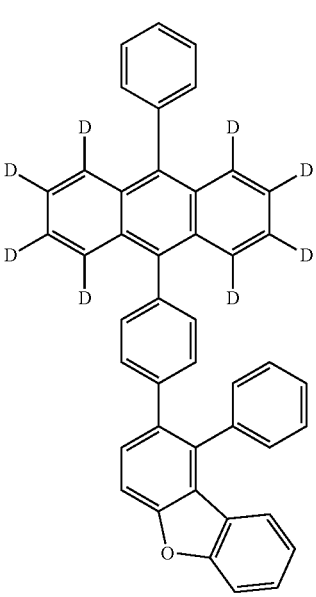
<Compound 137>
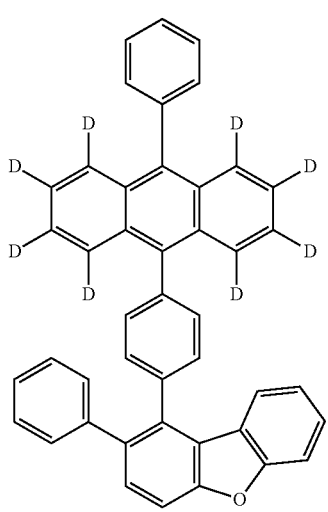

<Compound 138>

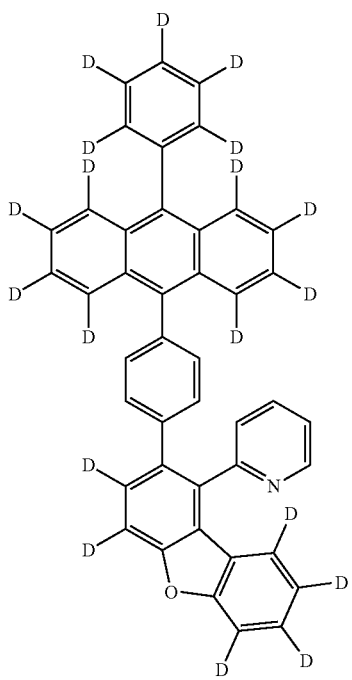

In accordance with more particular embodiments thereof, the present disclosure addresses an organic light-emitting diode, comprising a first electrode, a second electrode facing the first electrode, and an organic layer interposed therebetween, wherein the organic layer includes a light-emitting layer containing as a host at least one of the amine compounds represented by Chemical Formula A or B and as a dopant the compound represented by Chemical Formula D.

As used herein, the expression "(the organic layer) . . . containing at least one organic compound" is construed to mean that the organic layer may contain one organic compound falling within the scope of the present disclosure or two or more different compounds falling within the scope of the present disclosure.

The amount of the dopant in the light-emitting layer may range from about 0.01 to about 20 weight parts, based on 100 weight parts of the host, but is not limited thereto.

In addition to the above-mentioned dopants and hosts, the light-emitting layer may further include various hosts and dopant materials.

Selection of an appropriate amine compound represented by Chemical Formula A or B as a dopant and an appropriate compound of Chemical Formula D as a host in the light-emitting layer can impart a low driving voltage property and longevity to the light-emitting diode of the present disclosure, and can control color coordinate CIEy values of the light emitted from the light-emitting layer.

In some embodiments of the present disclosure, the organic light-emitting diode may comprise two or more light-emitting layers which include at least one layer employing a phosphorescent material and at least one layer employing as a dopant the compound represented by Chemical Formula A or B and as a host the compound of Chemical Formula D.

According to some particular embodiments of the present disclosure, the organic light-emitting diode may comprise at least one of a hole injection layer, a hole transport layer, a functional layer capable of both hole injection and hole transport, an electron transport layer, and an electron injection layer, in addition to the light-emitting layer.

A material for use in the electron transport layer functions to stably carry the electrons injected from the electron injection electrode (cathode), and may be an electron transport material known in the art. Examples of the electron transport material known in the art include quinoline derivatives, particularly, tris(8-quinolinorate)aluminum (Alq3), TAZ, Balq, beryllium bis(benzoquinolin-10-olate) (Bebq2), ADN, Compound 201, Compound 202, BCP, and oxadiazole derivatives such as PBD, BMD, BND, etc., but are not limited thereto.

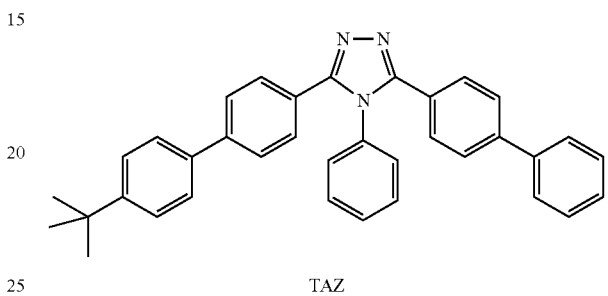

TAZ

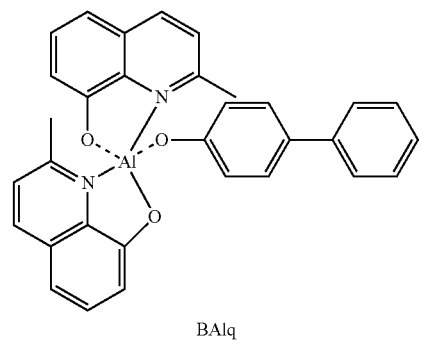

BAlq

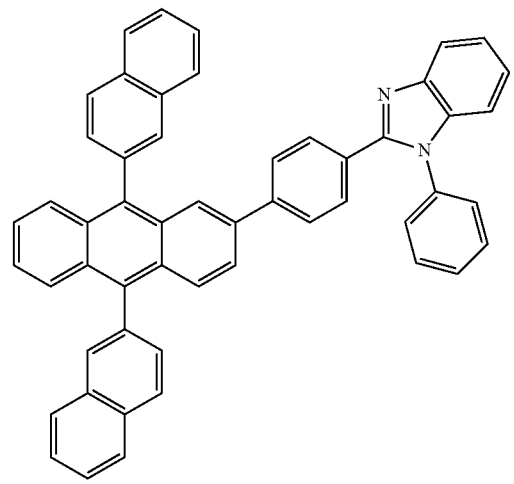

<Compound 201>

<Compound 202>

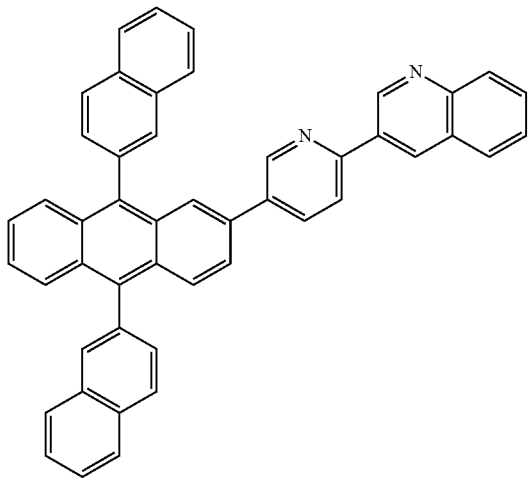

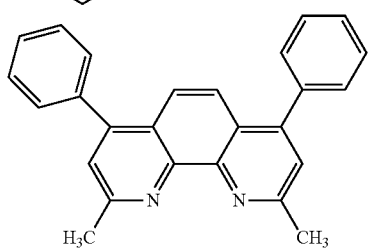
<BCP>

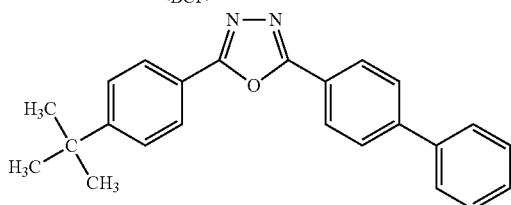
PBD

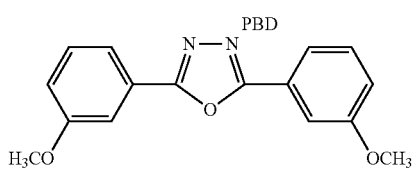
BMD

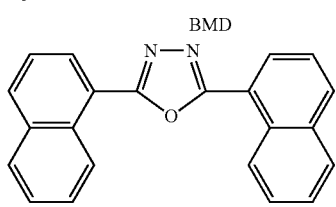
BND

In addition, the electron transport layer may be made of the organic metal compound represented by Chemical Formula F, either alone or in combination with the aforementioned material.

[Chemical Formula F]

$Y_m$-M-(OA)$_n$ wherein,

Y is a ligand that contains two moieties respectively responsible for forming a single bond with M through a direct bond M and for forming a coordinate bond with M, each moiety being selected from among C, N, O and S, and which is chelated by the single bond and the coordinate bond;

M is an alkali metal, an alkaline earth metal, aluminum (Al), or a boron (B) atom, with the proviso that:

OA is a monodentate ligand capable of forming a single bond or a coordinate bond with M, wherein O is oxygen, and A is selected from among a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing as a heteroatom at least one selected from among O, N, S and Si;

when M is an alkali metal, m=1, n=0 when M is an alkaline earth metal, m=1, n=1, or m=2, n=0, when M is aluminum or a boron, m is an integer of 1 to 3 and n is an integer of 0 to 2, satisfying the relationship m+n=3;

The term 'substituted' in the expression 'substituted or unsubstituted' means having at least one substituent selected from the group consisting of a deuterium atom, a cyano, a halogen, a hydroxy, a nitro, an alkyl, an alkoxy, an alkylamino, an arylamino, a hetero arylamino, an alkylsilyl, an arylsilyl, an aryloxy, an aryl, a heteroaryl, germanium, phosphorus, and boron.

In the present disclosure, the Y's may be the same or different and are each independently selected from among the following Structural Formulas C1 to C39, but are not limited thereto:

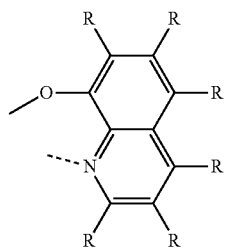
[Structural Formula C1]

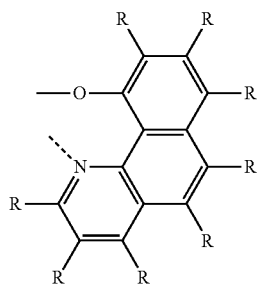
[Structural Formula C2]

[Structural Formula C3]
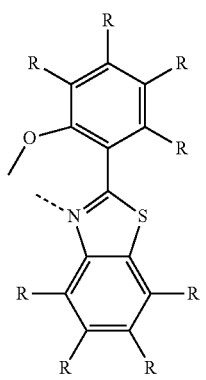
[Structural Formula C4]
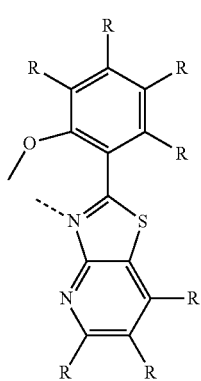
[Structural Formula C5]
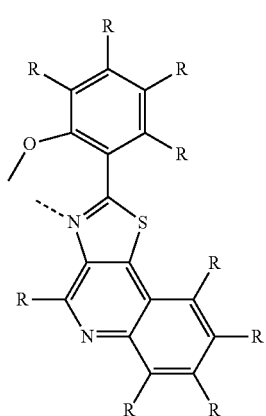
[Structural Formula C6]
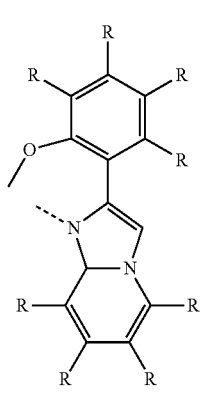
[Structural Formula C7]
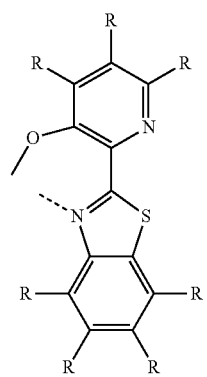
[Structural Formula C8]
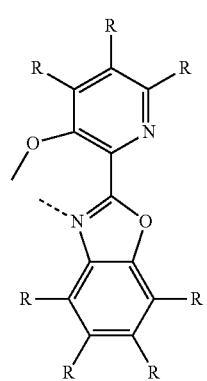
[Structural Formula C9]
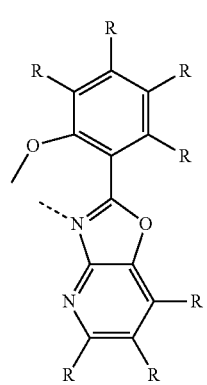
[Structural Formula C10]
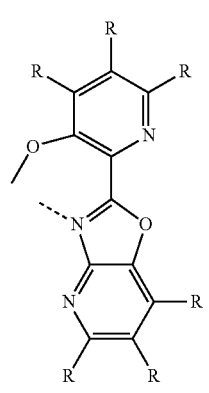

-continued
[Structural Formula C11]
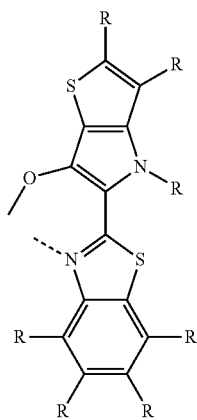
[Structural Formula C12]
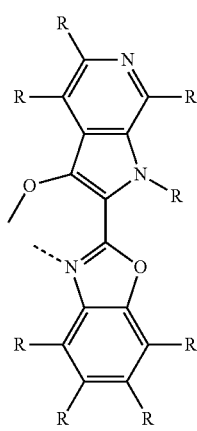
[Structural Formula C13]
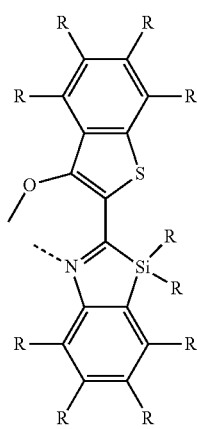
[Structural Formula C14]
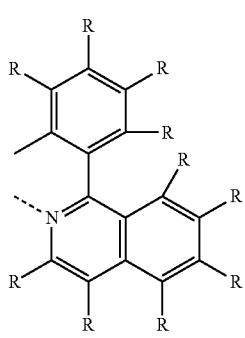
-continued
[Structural Formula C15]
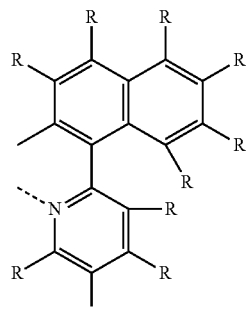
[Structural Formula C16]
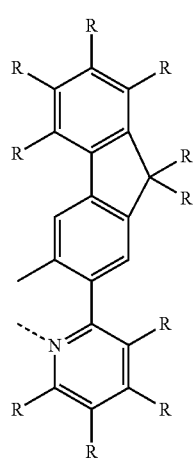
[Structural Formula C17]
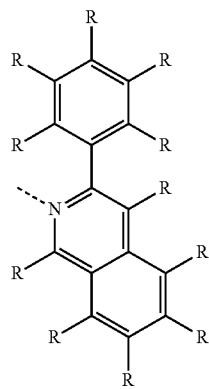
[Structural Formula C18]
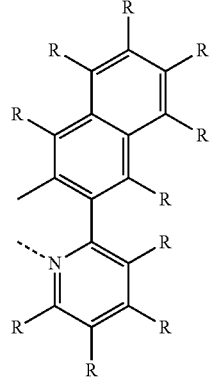

[Structural Formula C19]
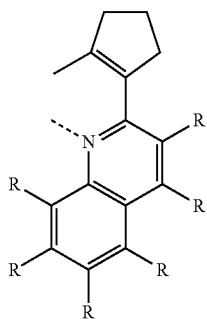
[Structural Formula C20]
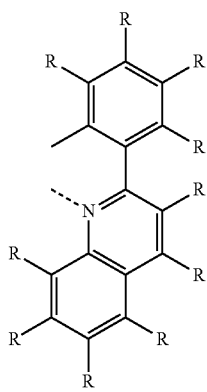
[Structural Formula C21]
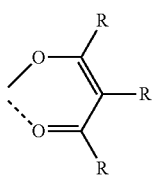
[Structural Formula C22]
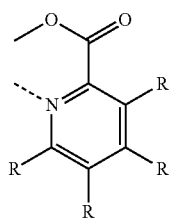
[Structural Formula C23]
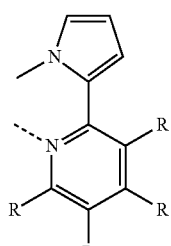
[Structural Formula C24]
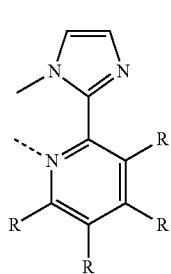
[Structural Formula C25]
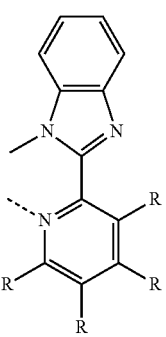
[Structural Formula C26]
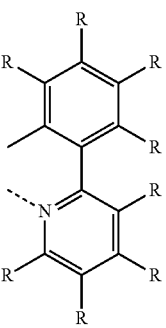
[Structural Formula C27]
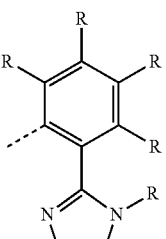
[Structural Formula C28]
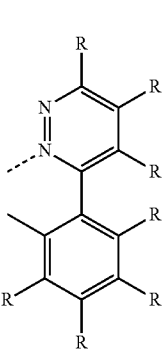
[Structural Formula C29]
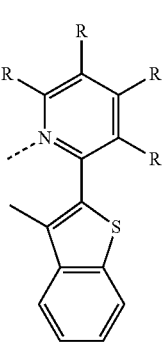

[Structural Formula C30]

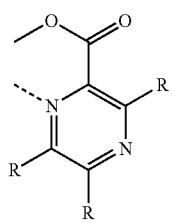

[Structural Formula C31]

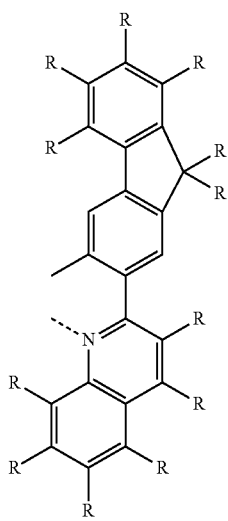

[Structural Formula C32]

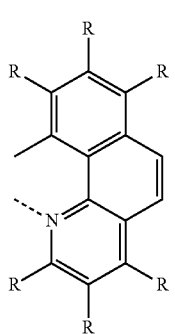

[Structural Formula C33]

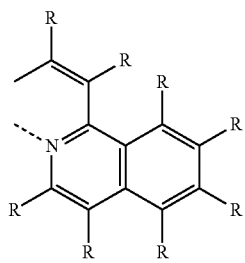

[Structural Formula C34]

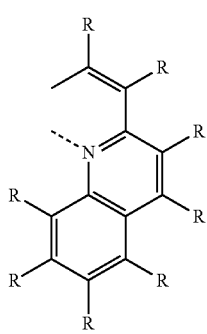

[Structural Formula C35]

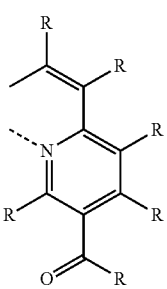

[Structural Formula C36]

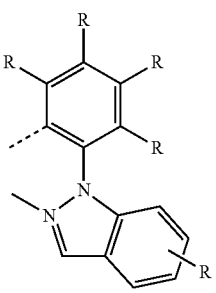

[Structural Formula C37]

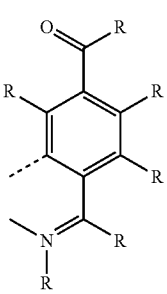

[Structural Formula C38]

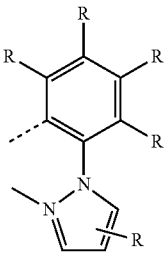

[Structural Formula C39]

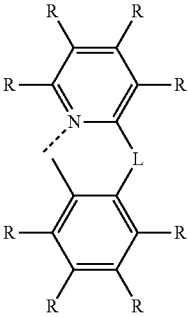

wherein,

R's, which may be the same or different, are each independently selected from among halogen, deuterium, halogen, cyano, a substituted or unsubstituted alkyl of 1 to 30 carbon atoms, a substituted or unsubstituted aryl of 6 to 60 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted dialkylsilyl of 1 to 30 carbon atoms, a substituted or unsubstituted arylamino of 6 to 60 carbon atoms, and a substituted or unsubstituted arylsilyl of 6 to 60 carbon atoms, and may form a spiro or fused ring with an adjacent substituent via an alkylene or alkenylene linker.

Below, the organic light-emitting diode of the present disclosure is explained with reference to FIG. 1.

FIG. 1 is a schematic cross-sectional view of the structure of an organic light-emitting diode according to some embodiments of the present disclosure. The organic light-emitting diode comprises an anode 20, a hole transport layer 40, an organic light-emitting layer 50, an electron transport layer 60, and a cathode 80, and optionally a hole injection layer 30 and an electron injection layer 70. In addition, one or two Intermediate layers may be further formed in the organic light-emitting diode, or a hole barrier layer or an electron barrier layer may also be employed.

Reference is made to FIG. 1 with regard to the organic light-emitting diode of the present disclosure and the fabrication thereof. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide (SnO2), or zinc oxide (ZnO), which are transparent and superior in terms of conductivity, may be used.

A hole injecting layer material is applied on the anode electrode 20 by thermal deposition in a vacuum or by spin coating to form a hole injecting layer 30. Subsequently, thermal deposition in a vacuum or by spin coating may also be conducted to form a hole transport layer 40 with a hole transport layer material on the hole injecting layer 30.

No particular limitations are imposed on the hole injection layer material, as long as it is one that is typically used in the art. For example, mention may be made of 2-TNATA [4,4',4"-tris(2-naphthylphenyl-phenylamino)-triphenylamine], NPD [N,N'-di(1-naphthyl)-N,N'-diphenylbenzidine], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine].

So long as it is typically used in the art, any material may be selected for the hole transport layer without particular limitation. Examples include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenyl-benzidine (a-NPD).

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifetime of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitation. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present disclosure, the light-emitting layer particularly ranges in thickness from 50 to 2,000 Å.

Further, one or more layers selected from among a hole injection layer, a hole transport layer, a functional layer capable of both hole injection and hole transport, an electron barrier layer, a light-emitting layer, a hole barrier layer, an electron transport layer, and an electron injection layer may be deposited using a single-molecule deposition process or a solution process. Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the present disclosure may be obtained through the following examples which are set forth to illustrate, but are not to be construed as limiting the present disclosure.

Example I. Preparation of Dopant Compounds

Synthesis Example 1: Synthesis of Compound of Chemical Formula 1

Synthesis Example 1-(1): Synthesis of Intermediate 1-a

Intermediate 1-a was synthesized as illustrated in the following Reaction Scheme 1.

<Reaction Scheme 1>

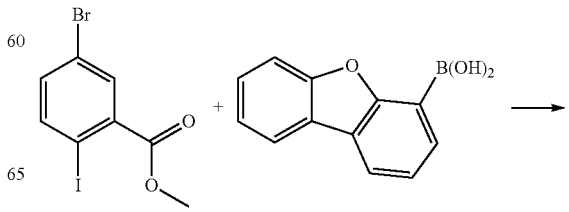

-continued

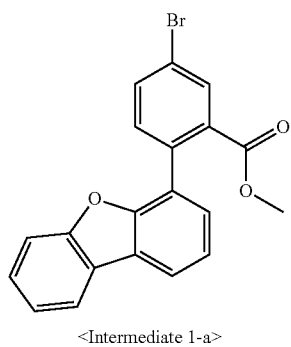

<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a>. (75.0 g, 60.1%).

Synthesis Example 1-(2): Synthesis of Intermediate 1-b

Intermediate 1-b was synthesized as illustrated in the following Reaction Scheme 2:

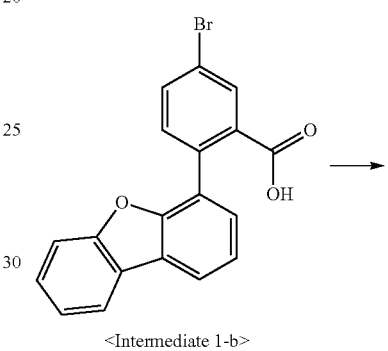

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 1-b>. (14.5 g, 88.6%)

Synthesis Example 1-(3): Synthesis of Intermediate 1-c

Intermediate 1-c was synthesized as illustrated in the:

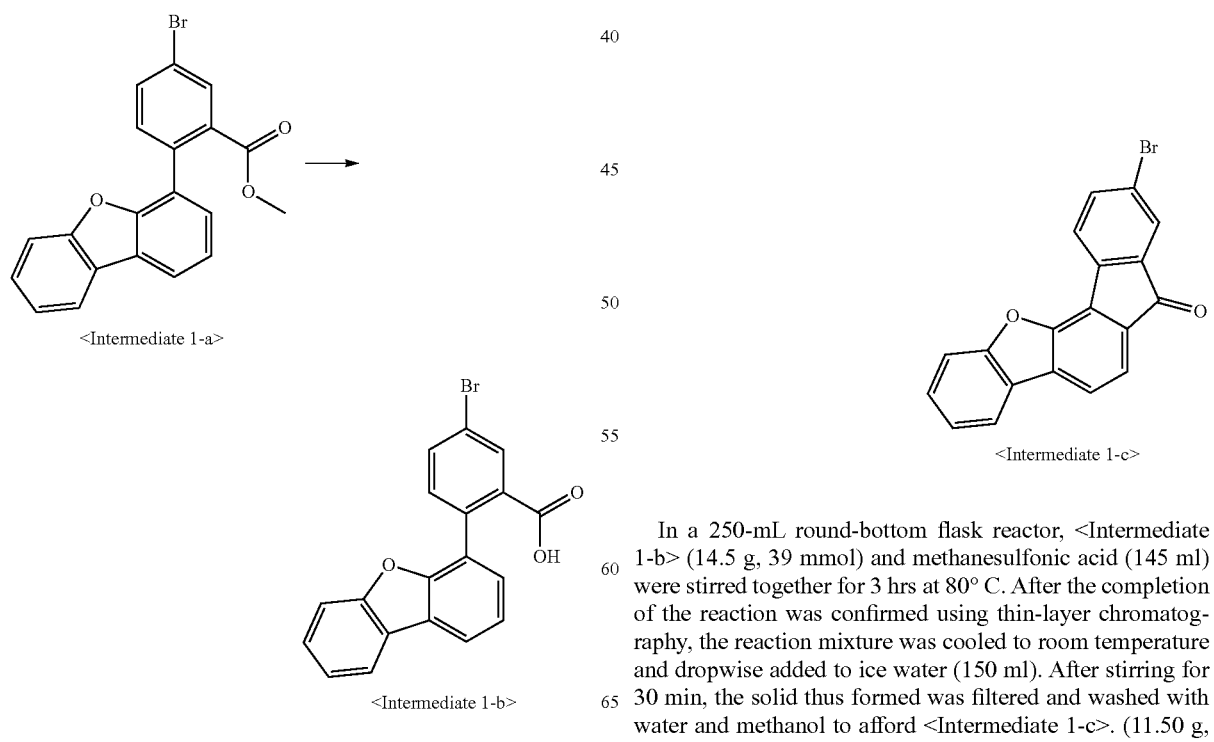

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the solid thus formed was filtered and washed with water and methanol to afford <Intermediate 1-c>. (11.50 g, 83.4%)

Synthesis Example 1-(4): Synthesis of Intermediate 1-d

Intermediate 1-d was synthesized as illustrated in the following Reaction Scheme 4:

<Reaction Scheme 4>

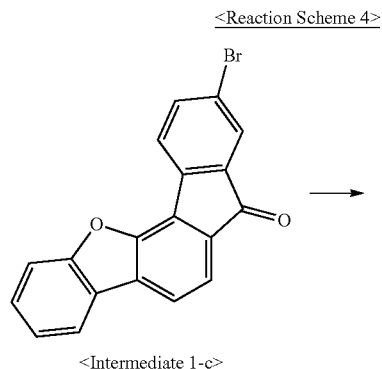

<Intermediate 1-c>

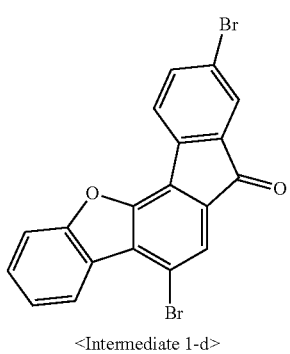

<Intermediate 1-d>

In a 1-L round-bottom flask reactor, <Intermediate 1-c> (11.5 g, 33 mmol> and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered and washed with acetone. Recrystallization in monochlorobenzene afforded <Intermediate 1-d>. (11.0 g, 78%)

Synthesis Example 1-(5): Synthesis of Intermediate 1-e

Intermediate 1-e was synthesized as illustrated in the following Reaction Scheme 5:

<Reaction Scheme 5>

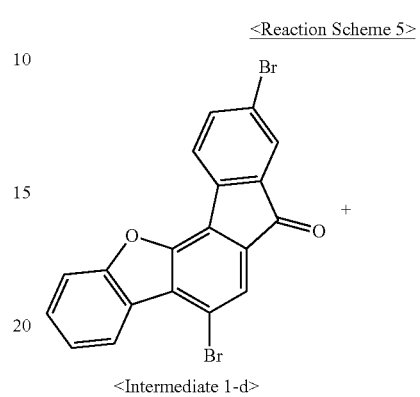

<Intermediate 1-e>

In a 250-ml round-bottom flask reactor, 2-bromobiphenyl (8.4 g, 0.036 mol) and tetrahydrofuran (110 ml) were frozen at −78° C. in a nitrogen atmosphere. At the same temperature, n-butyl lithium (19.3 ml, 0.031 mol) was dropwise added to the reaction solution, which was then stirred for 2 hrs. Thereafter, <Intermediate 1-d> (11.0 g, 0.026 mol) was added little by little to the reaction solution and stirred at room temperature. When the reaction mixture started to change color, the reaction was monitored via TLC. After the reaction was stopped with H$_2$O (50 ml), extraction was conducted with ethyl acetate and water. The organic layer was separated, concentrated in a vacuum, and recrystallized in acetonitrile to afford <Intermediate 1-e> as a solid. (12.2 g, 81.5%)

Synthesis Example 1-(6): Synthesis of Intermediate 1-f

Intermediate 1-f was synthesized as illustrated in the following Reaction Scheme 6:

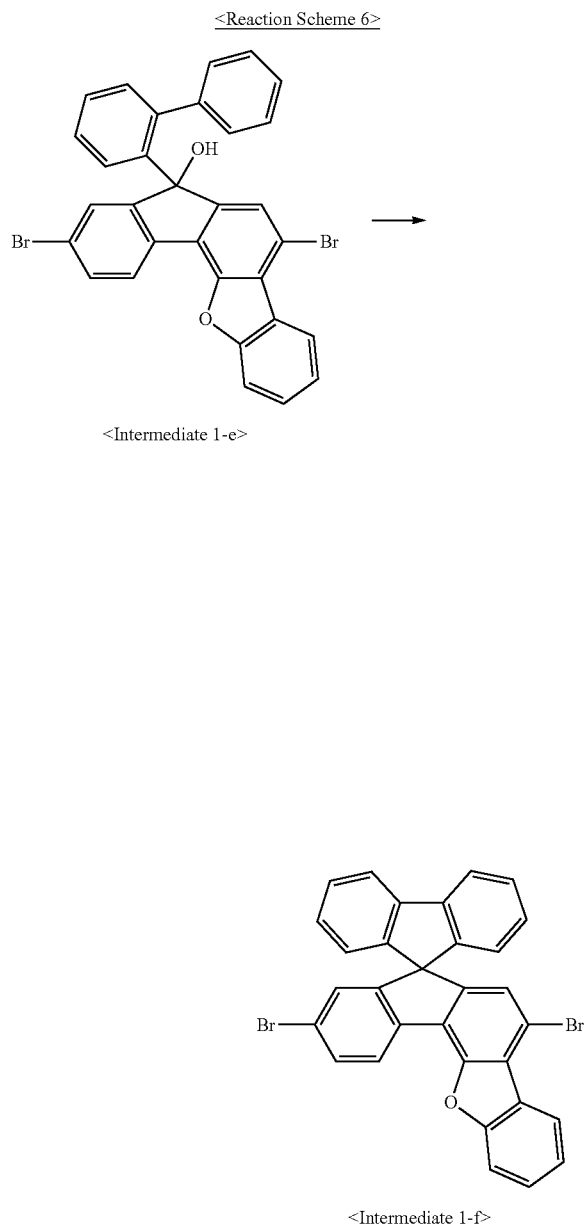

<Reaction Scheme 6>

<Intermediate 1-e>

<Intermediate 1-f>

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin-layer chromatography. The reaction mixture was then cooled to room temperature and filtered. The filtrate was washed with H₂O and methanol and dissolved in monochlorobenzene. Following silica gel chromatography, the fraction was concentrated and cooled to room temperature to give <Intermediate 1-f>. (10.7 g, 90%>

Synthesis Example 1-(7): Synthesis of Compound of Chemical Formula 1

The compound of Chemical Formula 1 was synthesized as illustrated in the following Reaction Scheme 7:

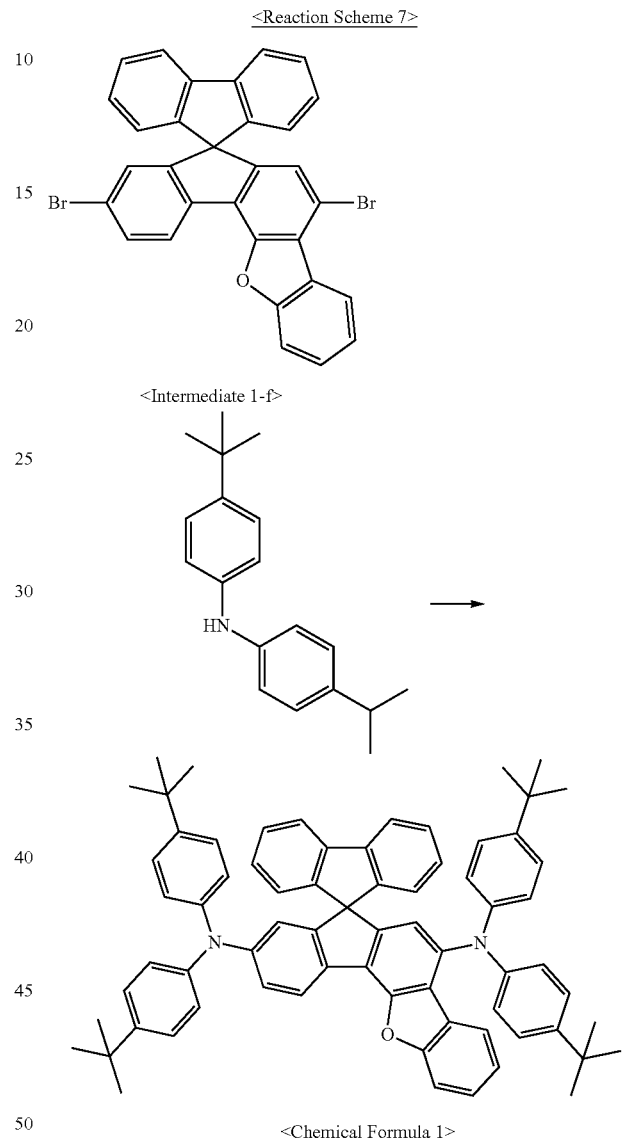

<Reaction Scheme 7>

<Intermediate 1-f>

<Chemical Formula 1>

In a 250-ml round-bottom flask reactor, a mixture of <Intermediate 1-f> (5.0 g, 0.009 mol), bis(4-tert-butylphenyl)amine (6.0 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 1 as a solid (3.1 g, 38%).

MS (MALDI-TOF): m/z 964.5 [M⁺]

Synthesis Example 2: Synthesis of Compound of Chemical Formula 33

Synthesis Example 2-(1): Synthesis of Intermediate 2-a

Intermediate 2-a was synthesized as illustrated in the following Reaction Scheme 8:

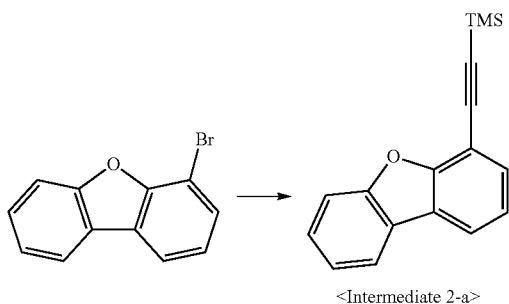

In a 2-L round bottom flask, 4-bromodibenzofuran (100.0 g, 0.405 mol), ethynyl trimethylsilane (47.7 g, 0.486 mol), [1,1'-bis(diphenylphosphino)ferrocene]dichloropalladium (9.92 g, 0.012 mol), copper iodide (2.31 g, 0.012 mol), triphenylphosphine (10.6 g, 0.040 mol), and triethylamine (700 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 2-a> (130 g, 84%).

Synthesis Example 2-(2): Synthesis of Intermediate 2-b

Intermediate 2-b was synthesized as illustrated in the following Reaction Scheme 9:

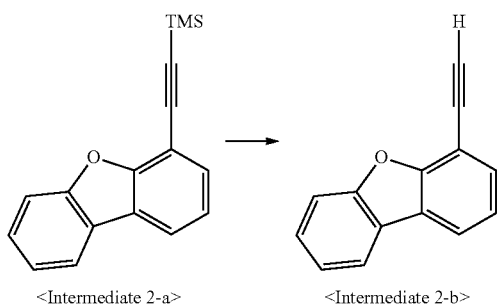

In a 2-L round-bottom flask reactor, <Intermediate 2-a> (130 g, 0.492 mol), potassium carbonate (101.9 g, 0.738 mol), methanol (650 ml), and tetrahydrofuran (650 ml) were stirred together for 2 hrs at room temperature. After completion of the reaction, heptane (500 ml) was added to terminate the reaction. The reaction mixture was filtered and the filtrate was extracted with ethyl acetate and water. The organic layer thus formed was isolated and dried over magnesium sulfate. Filtration and vacuum concentration afforded <Intermediate 2-b> as an oil (82 g, 84%).

Synthesis Example 2-(3): Synthesis of Intermediate 2-c

Intermediate 2-c was synthesized as illustrated in the following Reaction Scheme 10:

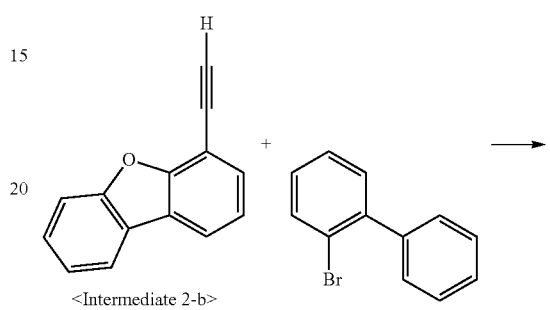

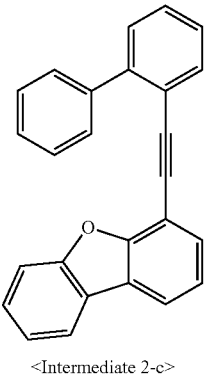

In a 2-L round-bottom flask reactor, 2-bromobiphenyl (66.0 g, 0.283 mol), <Intermediate 2-b> (65.3 g, 0.340 mol), [1,1'-bis(diphenylphosphino)ferrocene]dichloropalladium (6.94 g, 0.008 mol), copper iodide (1.62 g, 0.008 mol), triphenylphosphine (7.4 g, 0.028 mol), and triethylamine (500 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 2-c> (80 g, 82%).

Synthesis Example 2-(4): Synthesis of Intermediate 2-d

Intermediate 2-d was synthesized as illustrated in the following Reaction Scheme 11:

<Reaction Scheme 11>

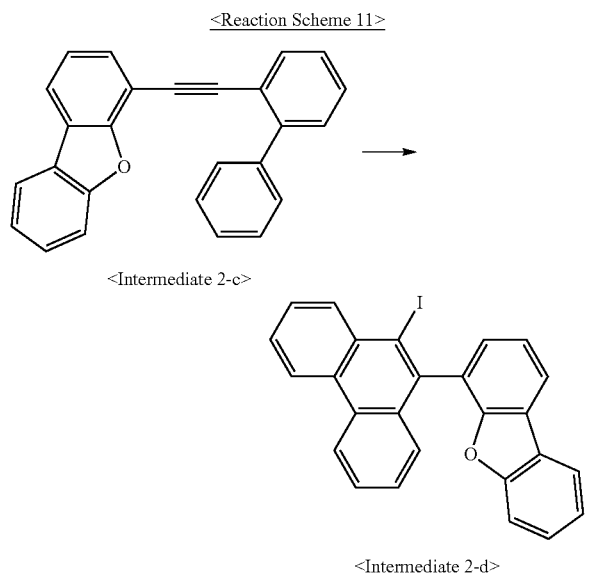

<Intermediate 2-c>

<Intermediate 2-d>

In a 2-L round-bottom flask reactor, a solution of <Intermediate 2-c> (80.0 g, 0.232 mol) in dichloromethane (960 ml) was cooled to −78° C. under a nitrogen atmosphere. Iodine monochloride (278.4 ml, 0.279 mol) was dropwise added to the chilled solution, which was then stirred at room temperature for 12 hrs. After completion of the reaction, the reaction mixture was stirred together with an aqueous saturated sodium thiosulfate solution. Following extraction with dichloromethane and water, the organic layer was isolated, concentrated in a vacuum, and washed with methanol to afford <Intermediate 2-d> as a crystal (67 g, 61.3%).

Synthesis Example 2-(5): Synthesis of Intermediate 2-e

Intermediate 2-e was synthesized as illustrated in the following Reaction Scheme 12:

<Reaction Scheme 12>

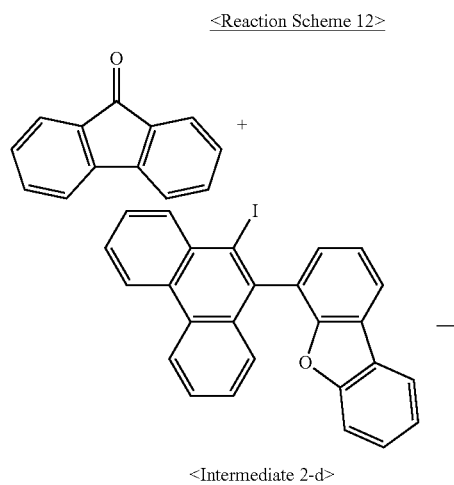

<Intermediate 2-d>

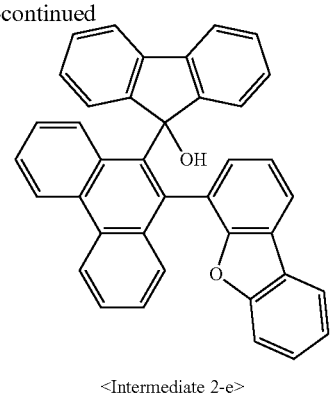

<Intermediate 2-e>

In a 500-mL round-bottom flask reactor, a solution of <Intermediate 2-d> (54.8 g, 0.117 mol) in tetrahydrofuran (150 ml) was cooled to −78° C. under a nitrogen atmosphere. At the same temperature, 1.6 M n-butyl lithium (62.4 ml, 0.1 mol) was dropwise added to the chilled solution and stirred for 1 hr. Then, a solution of 9-fluorenone (15.0 g, 0.083 mol) in tetrahydrofuran (50 ml) was dropwise added before stirring at room temperature for 8 hrs. After completion of the reaction, extraction was performed with ethyl acetate and water. The organic layer thus formed was isolated and dried over magnesium sulfate. Vacuum concentration subsequent to filtration afforded <Intermediate 2-e> as an oil (33.2 g, 76%).

Synthesis Example 2-(6): Synthesis of Intermediate 2-f

Intermediate 2-f was synthesized as illustrated in the following Reaction Scheme 13:

<Reaction Scheme 13>

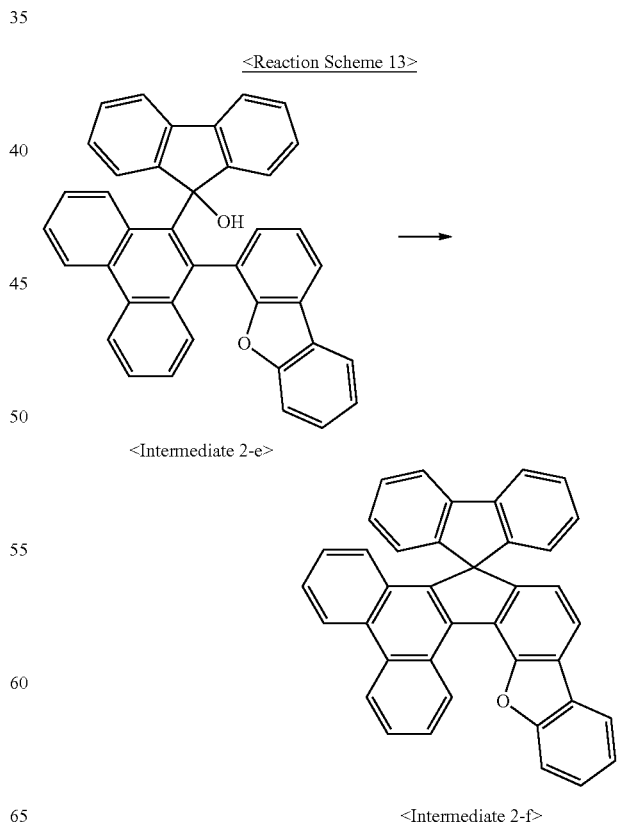

<Intermediate 2-e>

<Intermediate 2-f>

In a 1-L round-bottom flask reactor, <Intermediate 2-e> (33.3 g, 0.063 mol), acetic acid (330 ml), and sulfuric acid (3 ml) were stirred together for 3 hrs under reflux. After the completion of the reaction was confirmed using thin-layer chromatography, the reaction mixture was cooled to room temperature. The precipitates thus formed were filtered and washed with $H_2O$ and methanol to afford <Intermediate 2-f> (28.6 g, 88%>.

Synthesis Example 2-(7): Synthesis of Intermediate 2-g

Intermediate 2-g was synthesized as illustrated in the following Reaction Scheme 14:

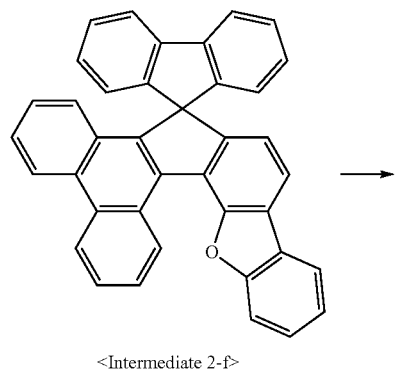

<Reaction Scheme 14>

<Intermediate 2-f>

<Intermediate 2-g>

In a 1-L round-bottom flask reactor, a solution of <Intermediate 2-f> (20.0 g, 0.039 mol) in dichloromethane (200 ml) was added with drops of a dilution of bromine (6 ml, 0.118 mol) in dichloromethane (40 ml) while stirring. After completion of the reaction for 12 hrs of stirring at room temperature, the addition of methanol (100 ml) produced precipitates which were then washed with methanol. Recrystallization in 1,2-dichlorobenzene and acetone afforded <Intermediate 2-g> (16 g, 60%).

Synthesis Example 2-(8): Synthesis of Compound of Chemical Formula 33

The compound of Chemical Formula 33 was synthesized as illustrated in the following Reaction Scheme 15:

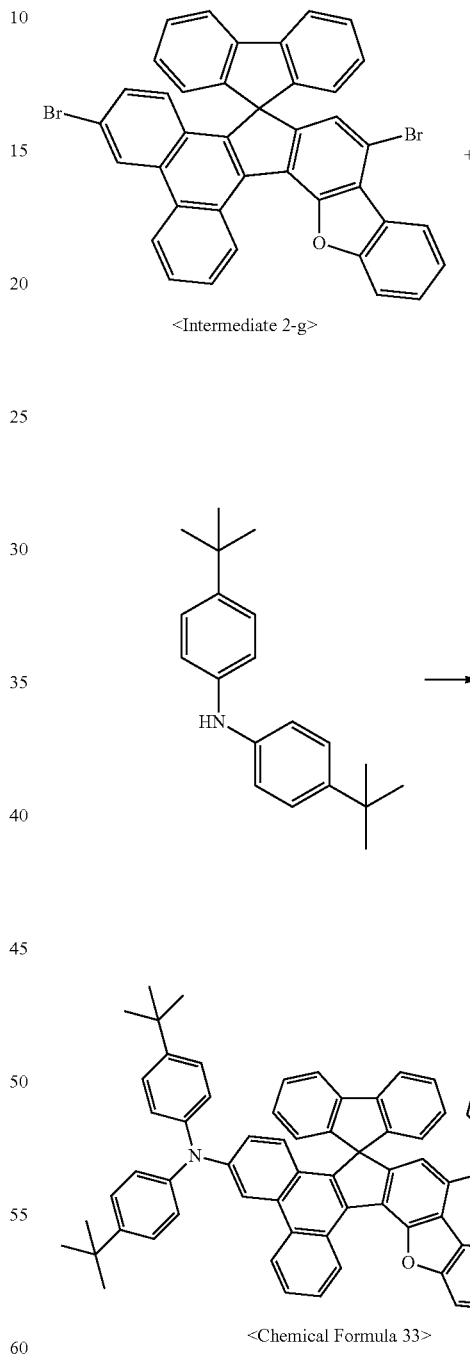

<Reaction Scheme 15>

<Intermediate 2-g>

<Chemical Formula 33>

The same procedure was conducted as in Synthesis Example 1-(7), with the exception of using <Intermediate 2-g> instead of <Intermediate 1-f>, to synthesize the compound of <Chemical Formula 33> (2.5 g, 31%).

MS (MALDI-TOF): m/z 1064.5 [$M^+$]

Synthesis Example 3: Synthesis of Compound of Chemical Formula 49

Synthesis Example 3-(1): Synthesis of Intermediate 3-a

Intermediate 3-a was synthesized as illustrated in the following Reaction Scheme 16:

<Reaction Scheme 16>

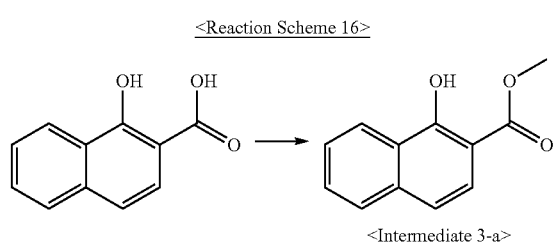

<Intermediate 3-a>

In a 2-L round-bottom flask reactor, 1-hydroxy 2-naphthalic acid (50 g, 266 mmol), methanol (1000 ml), and sulfuric acid (100 ml) were stirred together for 100 hrs under reflux. The completion of the reaction was confirmed by TLC before the reaction mixture was cooled to room temperature. The mixture was concentrated in a vacuum and extracted with dichloromethane and water. The organic layer was isolated, dried over magnesium sulfate, and filtered. The filtrate was concentrated at a reduced pressure and crystallized in an excess of heptane to afford <Intermediate 3-a> (39 g, 72.6%).

Synthesis Example 3-(2): Synthesis of Intermediate 3-b

Intermediate 3-b was synthesized as illustrated in the following Reaction Scheme 17:

<Reaction Scheme 17>

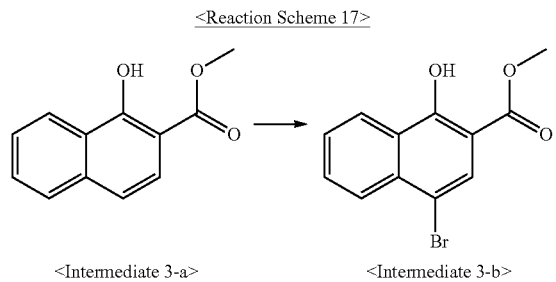 [SMILES: COC(=O)c1ccc2ccccc2c1O ; COC(=O)c1cc(Br)c2ccccc2c1O]

<Intermediate 3-a>  <Intermediate 3-b>

In a 1-L round-bottom flask reactor, <Intermediate 3-a> (39.0 g, 193 mmol) was stirred together with acetic acid (390 ml) at room temperature. A dilution of acetic acid (80 ml) in bromine (11.8 ml, 231 mmol) was added dropwise thereto. The resulting reaction solution was stirred for 5 hrs at room temperature. After completion of the reaction, the precipitates thus formed were filtered and slurried in heptane to afford <Intermediate 3-b> (50 g, 90%).

Synthesis Example 3-(3): Synthesis of Intermediate 3-c

Intermediate 3-c was synthesized as illustrated in the following Reaction Scheme 18:

<Reaction Scheme 18>

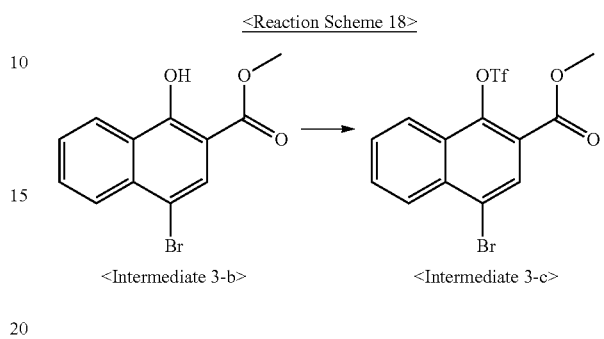

<Intermediate 3-b>  <Intermediate 3-c>

In a 2-L round-bottom flask reactor, <Intermediate 3-b> (50 g, 178 mmol) was stirred together with dichloromethane. Under a nitrogen atmosphere, pyridine (28.1 g, 356 mmol) was added and stirred at room temperature for 20 min. The resulting solution was cooled to 0° C. and then added with drops of trifluoromethanesulfonic anhydride (65.24 g, 231 mmol) under a nitrogen atmosphere. After 3 hrs of stirring, the completion of the reaction was confirmed by TLC. Water (20 ml) was added, and the mixture was stirred for 10 min. The reaction mixture was concentrated in a vacuum, followed by purification through column chromatography to afford <Intermediate 3-c> (45 g, 61%).

Synthesis Example 3-(4): Synthesis of Intermediate 3-d

Intermediate 3-d was synthesized as illustrated in the following Reaction Scheme 19:

<Reaction Scheme 19>

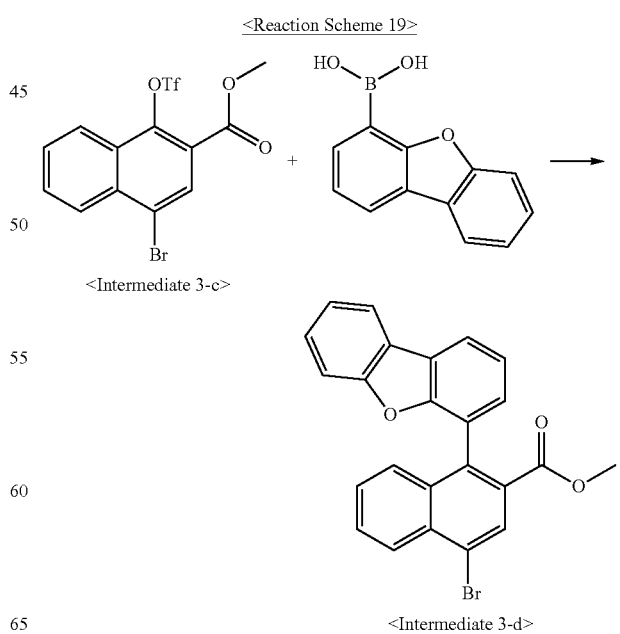

<Intermediate 3-c>

<Intermediate 3-d>

In a 1-L round-bottom flask reactor, a mixture of <Intermediate 3-c> (45.0 g, 0.109 mol), 4-dibenzoboronic acid (25.4 g, 0.120 mol), tetrakis (triphenylphosphine)palladium (2.5 g, 0.22 mmol), and potassium carbonate (30.1 g, 0.218 mol) was stirred together with toluene (300 mL), ethanol (130 mL) and water (90 mL) at 80° C. for 5 hrs. After completion of the reaction, the reaction mixture was cooled to room temperature and extracted with ethyl acetate. The organic layer was isolated and concentrated in a vacuum. Purification through column chromatography afforded Intermediate 3-d. (22.0 g, 46.1%)

Synthesis Example 3-(5): Synthesis of Intermediate 3-e

Intermediate 3-e was synthesized as illustrated in the following Reaction Scheme 20:

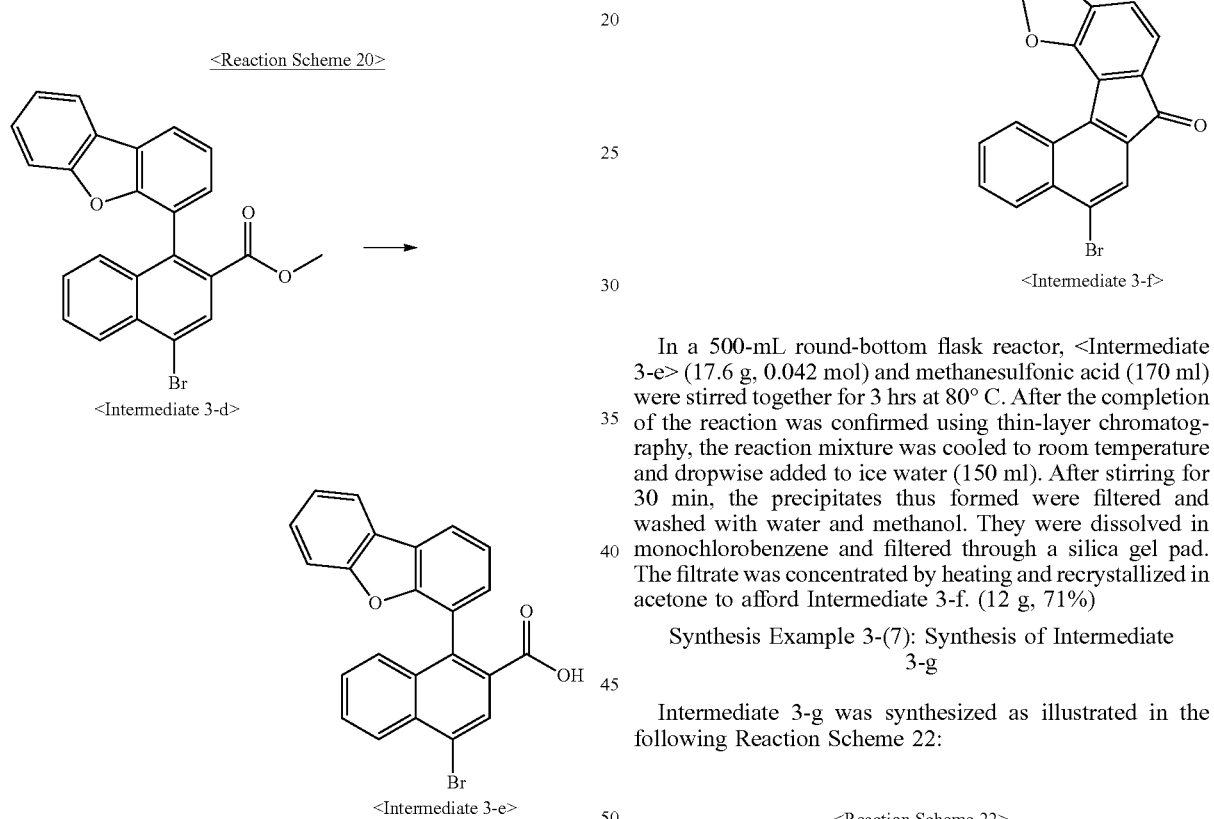

In a 1-L round-bottom flask reactor, <Intermediate 3-d> (22.0, 0.051 mol) was stirred together with sodium hydroxide (2.65 g, 0.066 mol) for 48 hrs under reflux. After completion of the reaction, the reaction mixture was cooled to room temperature. The chilled solution was acidified with drops of 2-N HCl, followed by stirring for 30 min. The solid thus formed was filtered and recrystallized in dichloromethane and n-hexane to afford Intermediate 3-e. (17.6 g, 82.7%)

Synthesis Example 3-(6): Synthesis of Intermediate 3-f

Intermediate 3-f was synthesized as illustrated in the following Reaction Scheme 21:

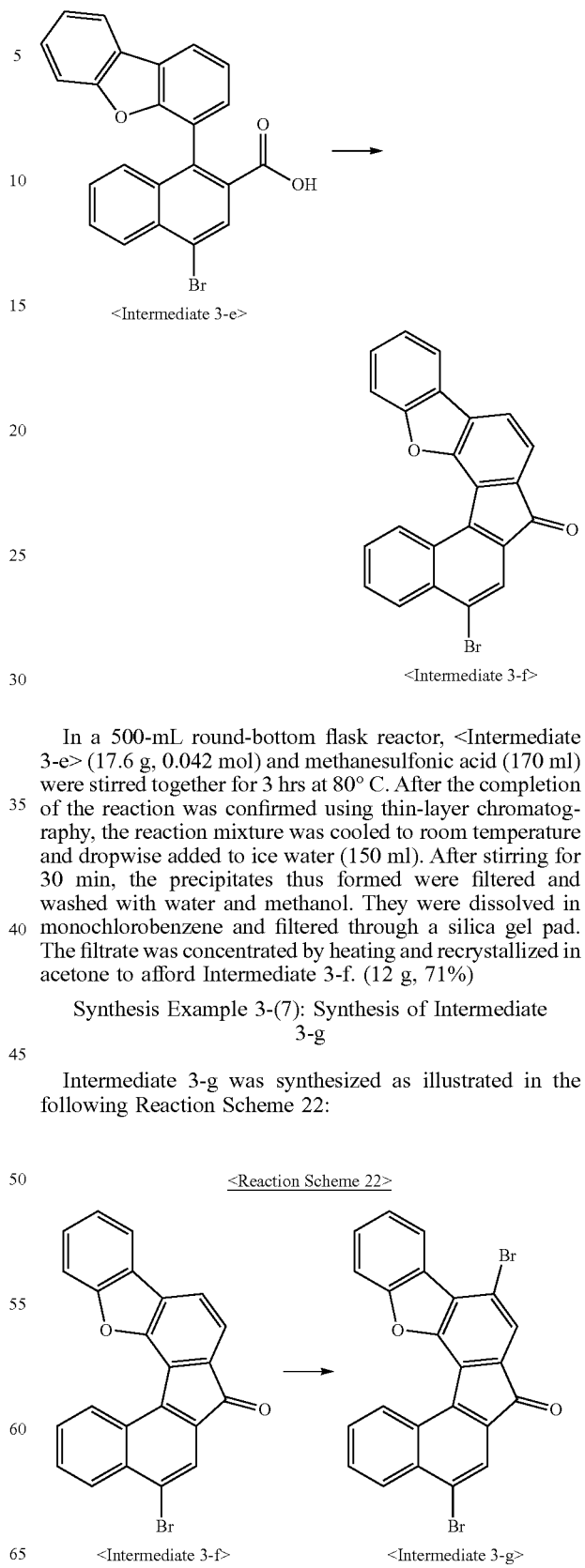

In a 500-mL round-bottom flask reactor, <Intermediate 3-e> (17.6 g, 0.042 mol) and methanesulfonic acid (170 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the precipitates thus formed were filtered and washed with water and methanol. They were dissolved in monochlorobenzene and filtered through a silica gel pad. The filtrate was concentrated by heating and recrystallized in acetone to afford Intermediate 3-f. (12 g, 71%)

Synthesis Example 3-(7): Synthesis of Intermediate 3-g

Intermediate 3-g was synthesized as illustrated in the following Reaction Scheme 22:

In a 1-L round-bottom flask reactor, Intermediate 3-f (12.0 g, 0.030 mol) and dichloromethane (360 ml) were stirred together at room temperature. A dilution of bromine (3.1 ml, 0.06 mol) in dichloromethane (40 ml) was dropwise added, followed by stirring at room temperature for 12 hrs. After completion of the reaction, methanol (100 ml) was added to induce the formation of precipitates. They were then filtered and washed with methanol. Recrystallization in 1,2-dichlorobenzene and acetone afforded Intermediate 3-g (10.3 g, 71.7%).

Synthesis Example 3-(8): Synthesis of Intermediate 3-h

Intermediate 3-h was synthesized as illustrated in the following Reaction Scheme 23:

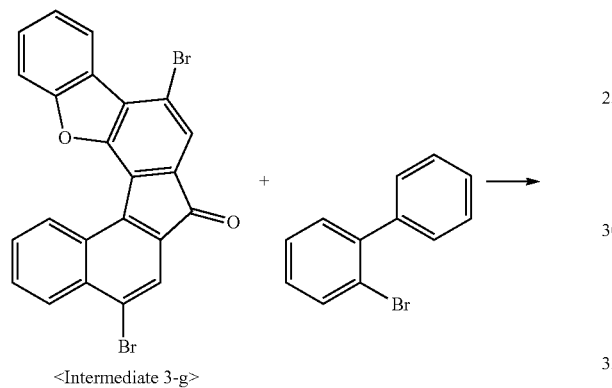

The same procedure was conducted as Synthetic Example 1-(5), with the exception of using <Intermediate 3-g> instead of <Intermediate 1-d>, to synthesize <Intermediate 3-h> (10.0 g, 73.4%).

Synthesis Example 3-(9): Synthesis of Intermediate 3-i

Intermediate 3-i was synthesized as illustrated in the following Reaction Scheme 24:

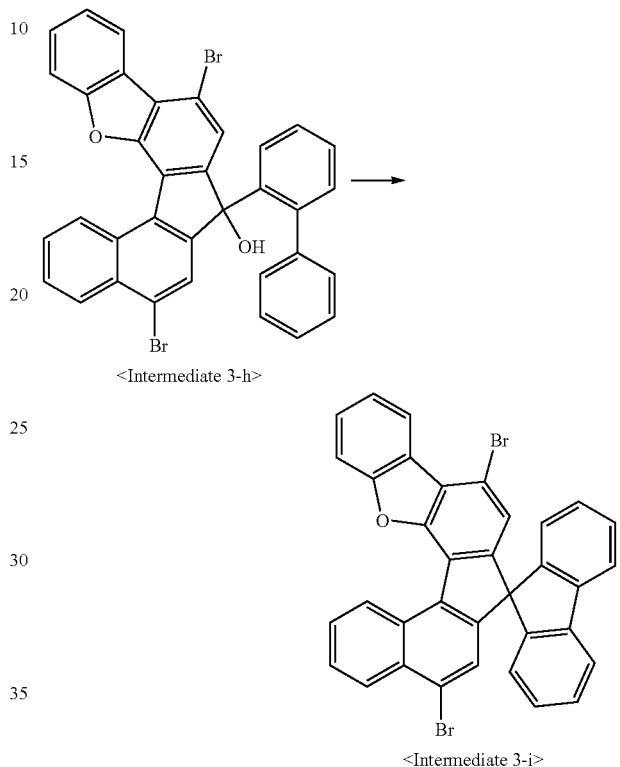

The same procedure was conducted as Synthetic Example 1-(6), with the exception of using <Intermediate 3-h> instead of <Intermediate 1-e>, to synthesize <Intermediate 3-i> (6.3 g, 64.8%).

Synthesis Example 3-(10): Synthesis of Compound of Chemical Formula 49

Chemical Formula 49 was synthesized as illustrated in the following Reaction Scheme 25:

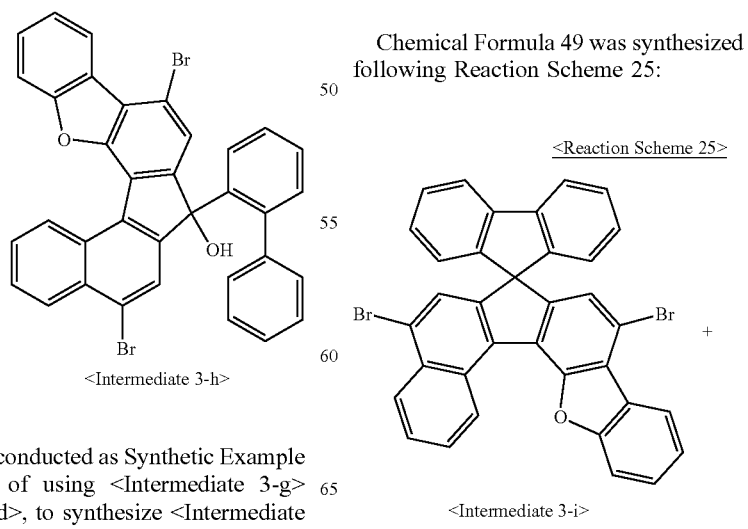

-continued

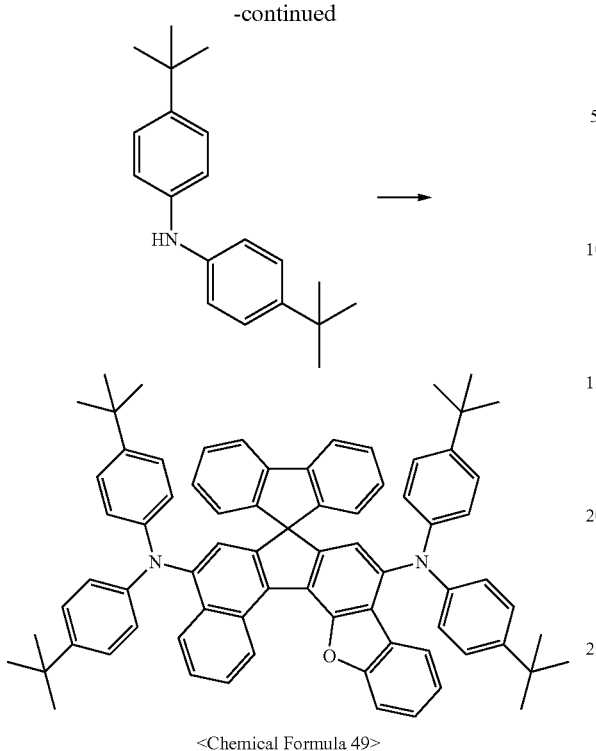

<Chemical Formula 49>

The same procedure was conducted as Synthetic Example 1-(7), with the exception of using <Intermediate 3-i> instead of <Intermediate 1-f>, to synthesize <Chemical Formula 49> (3.0 g, 36.1%).
MS (MALDI-TOF): m/z 1014.5 [M$^+$]

Synthesis Example 4: Synthesis of Compound of Chemical Formula 76

Synthesis Example 4-(1): Synthesis of Intermediate 4-a

Intermediate 4-a was synthesized as illustrated in the following Reaction Scheme 26:

<Reaction Scheme 26>

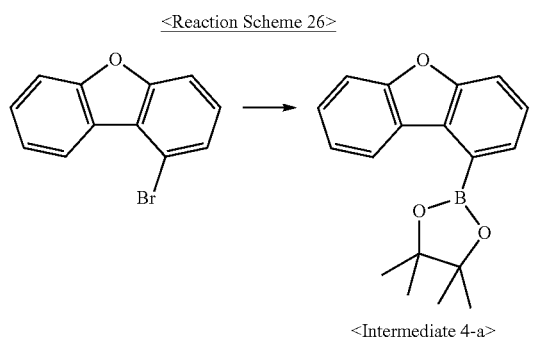 [SMILES: Brc1cccc2oc3ccccc3c12 ; CC1(C)OB(c2cccc3oc4ccccc4c23)OC1(C)C]

<Intermediate 4-a>

In a 500-mL round-bottom flask reactor, 1-bromodibenzofuran (20.0 g, 0.081 mmol), bis(pinacolato)diboron (26.7 g, 0.105 mol), [1,1'-bis(diphenylphosphino)ferrocene]dichloropalladium (1.3 g, 0.002 mol), potassium acetate (19.9 g, 0.202 mol), and 1,4-dioxane (200 ml) were stirred together for 10 hrs under reflux.

After completion of the reaction, filtration was performed through a celite pad. The filtrate was concentrated in a vacuum, purified by column chromatography, and recrystallized in dichloromethane and heptane to afford <Intermediate 4-a> (17.0 g, 70%).

Synthesis Example 4-(2): Synthesis of Intermediate 4-b

Intermediate 4-b was synthesized as illustrated in the following Reaction Scheme 27:

<Reaction Scheme 27>

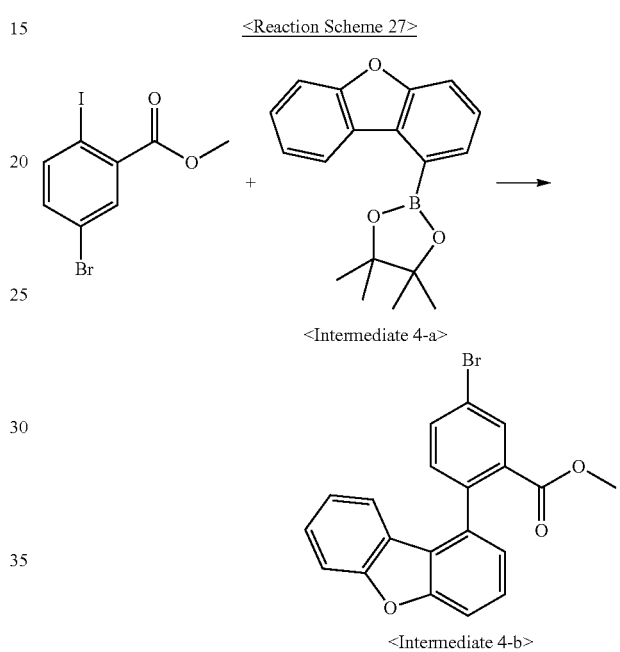

<Intermediate 4-a>

<Intermediate 4-b>

The same procedure was conducted as in Synthesis Example 1-(1), with the exception of using <Intermediate 4-a> instead of 4-dibenzobronic acid, to synthesize <Intermediate 4-b> (13.1 g, 68.9%).

Synthesis Example 4-(3): Synthesis of Intermediate 4-c

Intermediate 4-c was synthesized as illustrated in the following Reaction Scheme 28:

<Reaction Scheme 28>

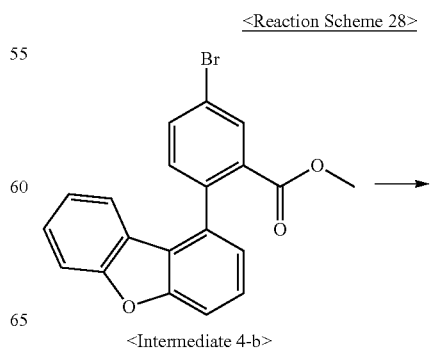

<Intermediate 4-b>

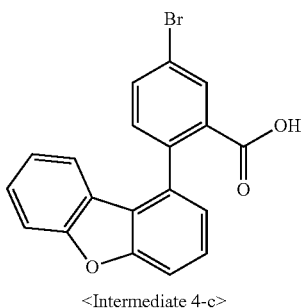

<Intermediate 4-c>

The same procedure was conducted as in Synthesis Example 1-(2), with the exception of using <Intermediate 4-b> instead of <Intermediate 1-a>, to synthesize <Intermediate 4-c> (11 g, 87%).

Synthesis Example 4-(4): Synthesis of Intermediate 4-d

Intermediate 4-d was synthesized as illustrated in the following Reaction Scheme 29:

<Reaction Scheme 29>

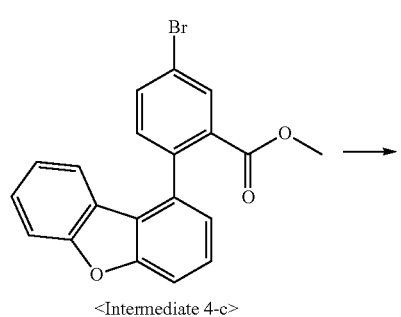

<Intermediate 4-c>

↓

<Intermediate 4-d>

The same procedure as in Synthesis Example 1-(3), with the exception of using <Intermediate 4-c> instead of <Intermediate 1-b>, was conducted to synthesize <Intermediate 4-d> (9.0 g, 86%).

Synthesis Example 4-(5): Synthesis of Intermediate 4-e

Intermediate 4-e was synthesized as illustrated in the following Reaction Scheme 30:

<Reaction Scheme 30>

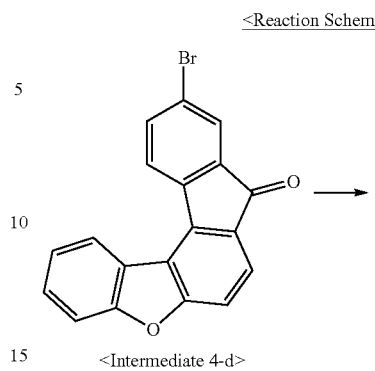

<Intermediate 4-d>

<Intermediate 4-e>

The same procedure as in Synthesis Example 1-(4), with the exception of using <Intermediate 4-d>, instead of <Intermediate 1-c>, was conducted to synthesize <Intermediate 4-e> (6.7 g, 60.7%).

Synthesis Example 4-(6): Synthesis of Intermediate 4-f

Intermediate 4-f was synthesized as illustrated in the following Reaction Scheme 31:

<Reaction Scheme 31>

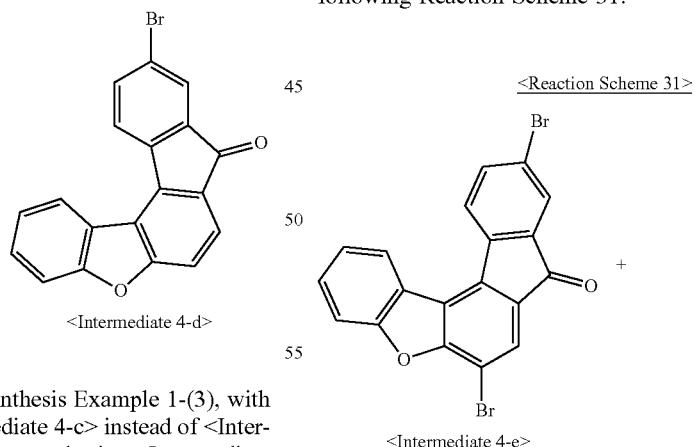

<Intermediate 4-e>

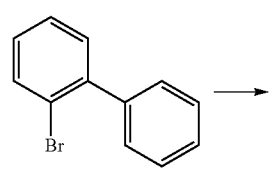

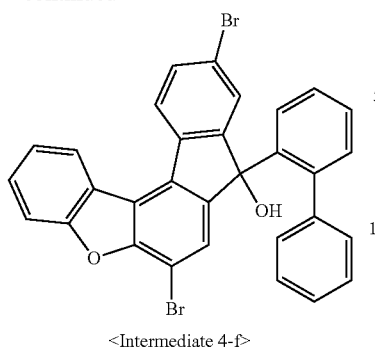

<Intermediate 4-f>

The same procedure as in Synthesis Example 1-(5), with the exception of using <Intermediate 4-e> instead of <Intermediate 1-d>, was conducted to synthesize <Intermediate 4-f> (5.2 g, 55%).

Synthesis Example 4-(7): Synthesis of Intermediate 4-g

Intermediate 4-g was synthesized as illustrated in the following Reaction Scheme 32:

<Reactin Scheme 32>

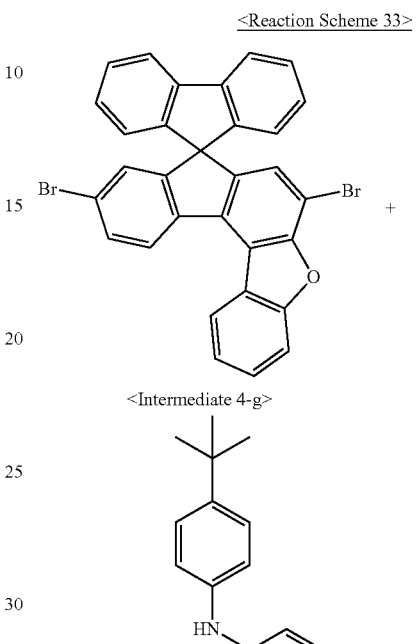

<Intermediate 4-f>

<Intermediate 4-g>

The same procedure as in Synthesis Example 1-(6), with the exception of using <Intermediate 4-f> instead of <Intermediate 1-e>, was conducted to synthesize <Intermediate 4-g> (4.3 g, 85.3%).

Synthesis Example 4-(8): Synthesis of Compound of Chemical Formula 76

The compound of Chemical Formula 76 was synthesized as illustrated in the following Reaction Scheme 33:

<Reaction Scheme 33>

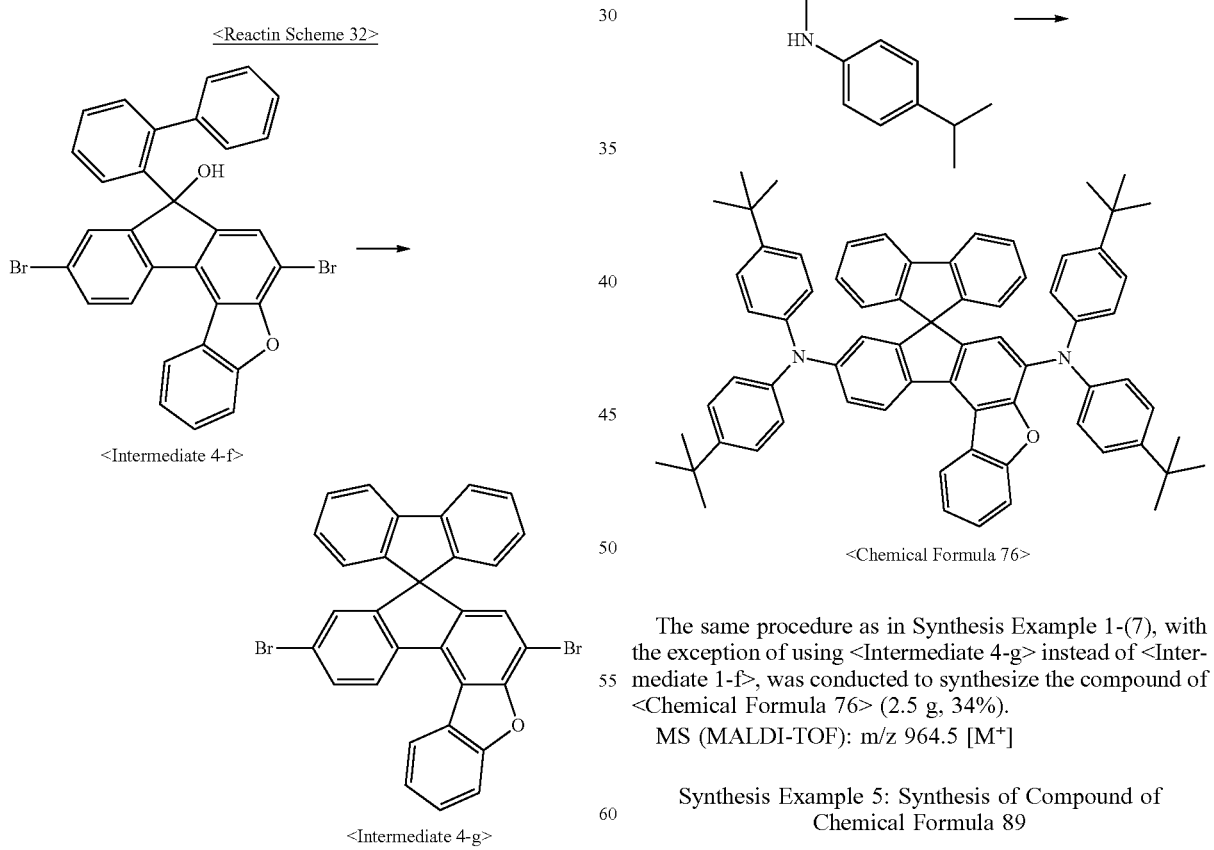

<Chemical Formula 76>

The same procedure as in Synthesis Example 1-(7), with the exception of using <Intermediate 4-g> instead of <Intermediate 1-f>, was conducted to synthesize the compound of <Chemical Formula 76> (2.5 g, 34%).

MS (MALDI-TOF): m/z 964.5 [M$^+$]

Synthesis Example 5: Synthesis of Compound of Chemical Formula 89

Synthesis Example 5-(1): Synthesis of Intermediate 5-a

Intermediate 5-a was synthesized as illustrated in the following Reaction Scheme 34:

<Reaction Scheme 34>

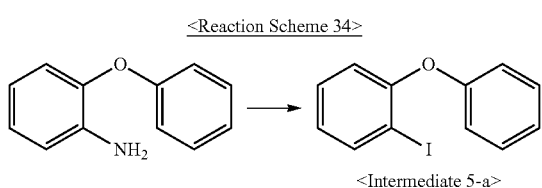 [SMILES: Nc1ccccc1Oc1ccccc1 ; Ic1ccccc1Oc1ccccc1]

<Intermediate 5-a>

In a 1-L round-bottom flask reactor, a mixture of 2-phenoxyaniline (25.0, 0.135 mol), HCl (30 ml), and water (150 ml) was cooled to 0° C. and stirred for 1 hr. At the same temperature, an aqueous solution (75 ml) of sodium nitrite (11.2 g, 0.162 mol) was added and then stirred for 1 hr. An aqueous solution (75 ml) of potassium iodide (44.8 g, 0.270 mol) was dropwise added, with care not to increase the temperature of the reaction solution above 5° C. Stirring was continued for 5 hrs at room temperature, and after completion of the reaction, the reaction mixture was washed with an aqueous sodium thiosulfate solution and extracted with ethyl acetate and water. The organic layer was separated and concentrated in a vacuum. Purification through column chromatography gave <Intermediate 5-a> (22.6 g, 56.5%).

Synthesis Example 5-(2): Synthesis of Intermediate 5-b

Intermediate 5-b was synthesized as illustrated in the following Reaction Scheme 35:

<Reaction Scheme 35>

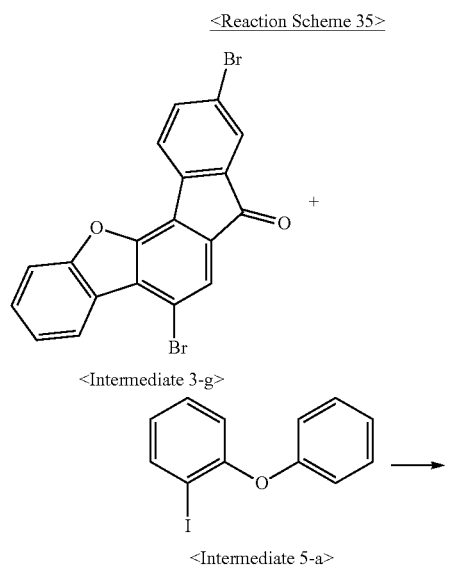

The same procedure as in Synthesis Example 1-(5), with the exception of using <Intermediate 3-g> instead of <Intermediate 1-d>, was conducted to synthesize <Intermediate 5-b> (19.6 g, 70.4%).

Synthesis Example 5-(3): Synthesis of Intermediate 5-c

Intermediate 5-c was synthesized as illustrated in the following Reaction Scheme 36:

<Reaction Scheme 36>

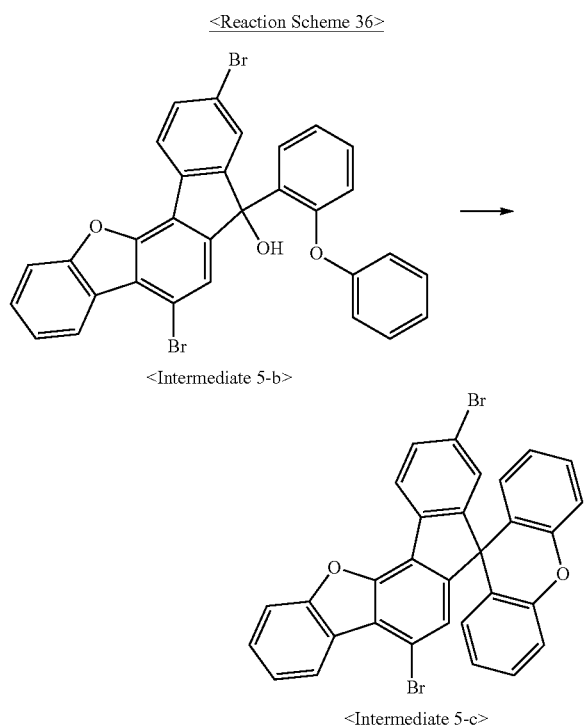

The same procedure as in Synthesis Example 1-6), with the exception of using <Intermediate 5-b> instead of <Intermediate 1-e>, was conducted to synthesize <Intermediate 5-c> (14.2 g, 74.7%).

Synthesis Example 5-(4): Synthesis of Compound of Chemical Formula 89

The compound of Chemical Formula 89 was synthesized as illustrated in the following Reaction Scheme 37:

<Reaction Scheme 37>

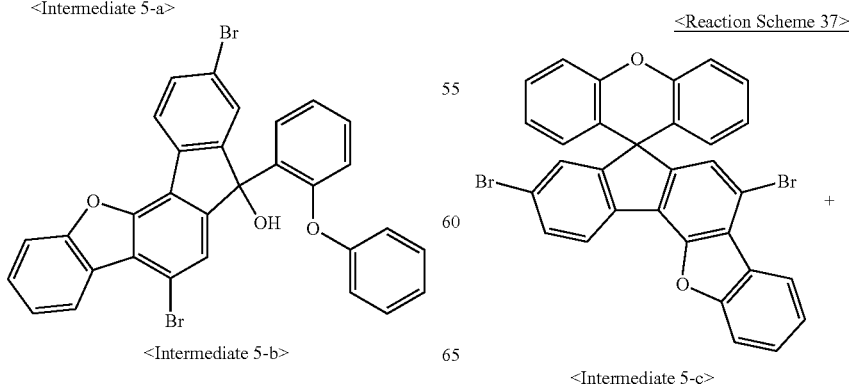

<Intermediate 5-c>

-continued

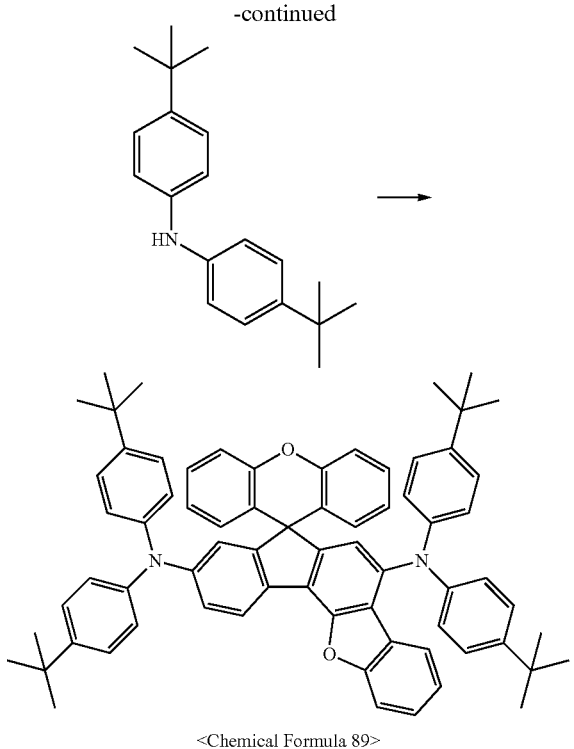

<Chemical Formula 89>

The same procedure as in Synthesis Example 1-(7), with the exception of using <Intermediate 5-c> and 1,1'-(4-methylphenyl-4-tert-butylphenyl)amine respectively instead of <Intermediate 1-f> and bis(4-tert-butylphenyl)amine, was conducted to synthesize the compound of <Chemical Formula 89> (2.4 g, 28%).

MS (MALDI-TOF): m/z 980.5 [M$^+$]

Synthesis Example 6: Synthesis of Compound of Chemical Formula 97

Synthesis Example 6-(1): Synthesis of Intermediate 6-a

Intermediate 6-a was synthesized as illustrated in the following Reaction Scheme 38:

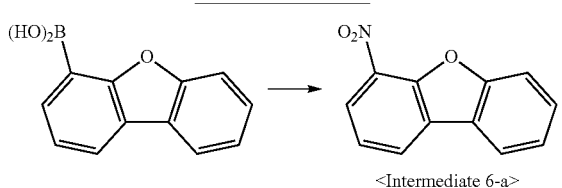

<Reaction Scheme 38>

<Intermediate 6-a>

In a 2-L round-bottom flask reactor, 4-dibenzoboronic acid (85.0 g, 0.401 mol), bismuth (III) nitrate pentahydrate (99.2 g, 0.200 mol), and toluene (400 ml) were stirred together at 70° C. for hrs under a nitrogen atmosphere. After completion of the reaction, the reaction mixture was cooled to room temperature, and the precipitates thus formed were filtered and washed with toluene to afford <Intermediate 6-a> (61.5 g, 72%).

Synthesis Example 6-(2): Synthesis of Intermediate 6-b

Intermediate 6-b was synthesized as illustrated in the following Reaction Scheme 39:

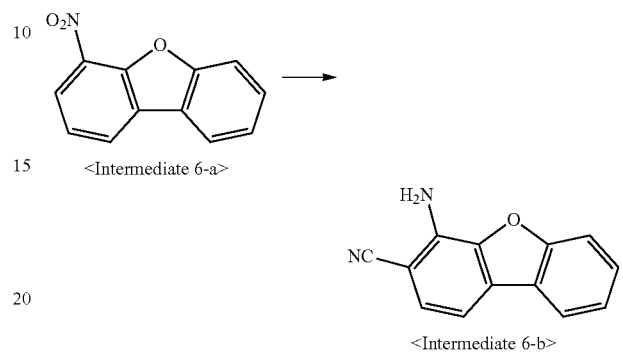

<Reaction Scheme 39>

<Intermediate 6-a>

<Intermediate 6-b>

In a 2-L round-bottom flask reactor, ethylcyanoacetate (202.9 g, 1.794 mol) and dimethylformamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. <Intermediate 6-a> (127.5 g, 0.737 mol) was added little by little to the reaction solution, followed by stirring at 50° C. for 72 hrs. After completion of the reaction, an aqueous sodium hydroxide solution (25%, 200 ml) was added to the reaction solution, which was then stirred for 3 hrs under reflux and cooled to room temperature. Extraction was performed using ethyl acetate and water. The organic layer was isolated and concentrated in a vacuum. Purification through column chromatography afforded <Intermediate 6-b> (20.0 g, 16%).

Synthesis Example 6-(3): Synthesis of Intermediate 6-c

Intermediate 6-c was synthesized as illustrated in the following Reaction Scheme 40:

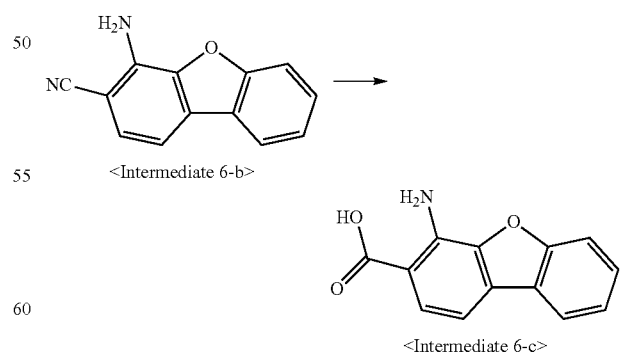

<Reaction Scheme 40>

<Intermediate 6-b>

<Intermediate 6-c>

In a 2-L round-bottom flask reactor, <Intermediate 6-b> (20.0 g, 0.096 mol), ethanol (600 ml), and an aqueous potassium hydroxide solution (142.26 g, 2.53 mol, 170 ml) were stirred together for 12 hrs under reflux. After completion of the reaction, the reaction mixture was cooled to room temperature and acidified with 6-N HCl (400 ml). The solid thus formed was stirred for 20 min and filtered. The filtrate was washed with ethanol to afford <Intermediate 6-c> (17.0 g, 88.5%).

Synthesis Example 6-(4): Intermediate 6-d

Intermediate 6-d was synthesized as illustrated in the following Reaction Scheme 41:

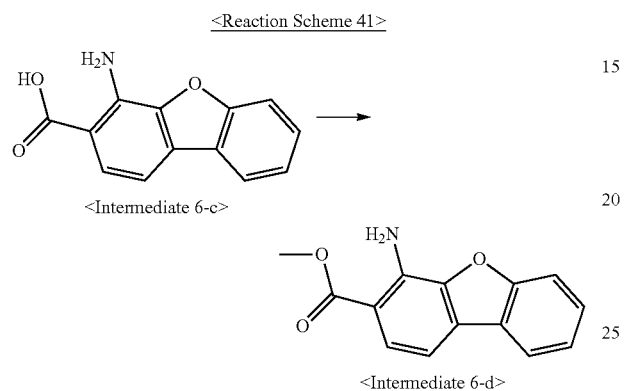

In a 2-L round-bottom flask reactor, <Intermediate 6-c> (17.0 g, 0.075 mol) and sulfuric acid (15 ml) were stirred together for 72 hrs under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford <Intermediate 6-d> (14.0 77.6%).

Synthesis Example 6-(5) Synthesis of Intermediate 6-e

Intermediate 6-d was synthesized as illustrated in the following Reaction Scheme 42:

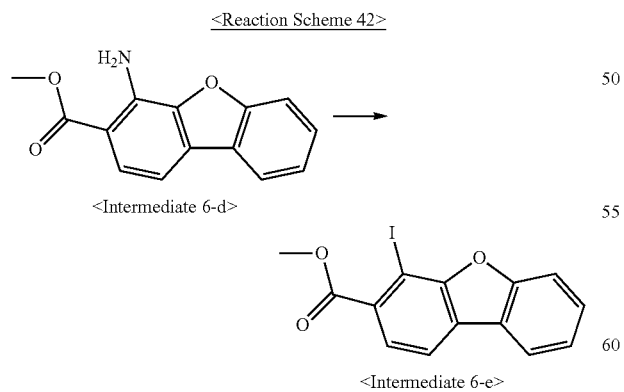

The same procedure was conducted as in Synthesis Example 5-(1), with the exception of using <Intermediate 6-d> instead of 2-phenoxyaniline, to synthesize <Intermediate 6-e> (9.1 g, 48%).

Synthesis Example 6-(6): Synthesis of Intermediate 6-f

Intermediate 6-f was synthesized as illustrated in the following Reaction Scheme 43:

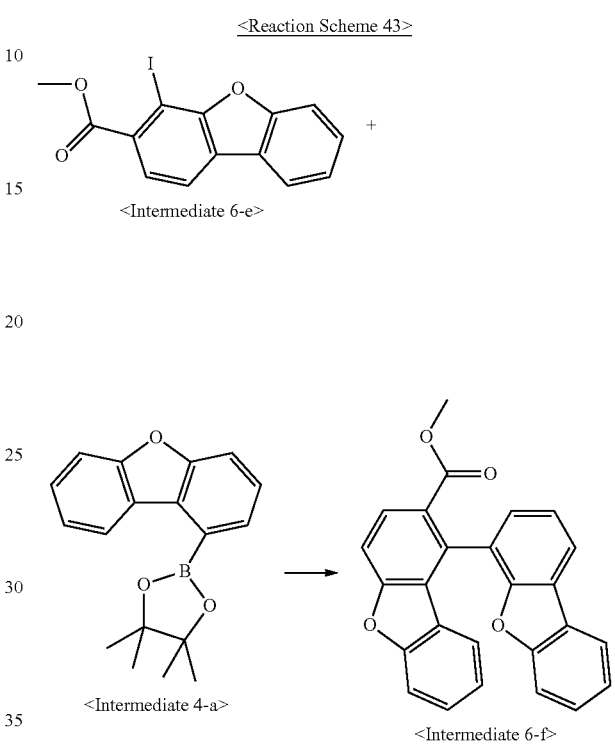

The same procedure as in Synthesis Example 4-(2), with the exception of using <Intermediate 6-e> instead of methyl 5-bromo-2-iodobenzoate, was conducted to synthesize <Intermediate 6-f> (5.3 g, 52.3%).

Synthesis Example 6-(7): Synthesis of Intermediate 6-g

Intermediate 6-g was synthesized as illustrated in the following Reaction Scheme 44:

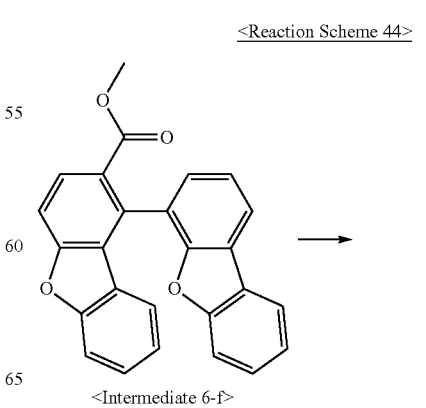

-continued

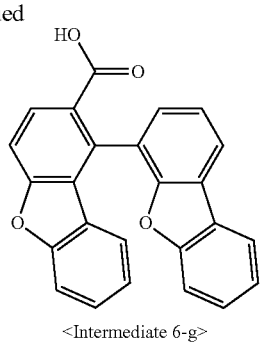

<Intermediate 6-g>

The same procedure as in Synthesis Example 1-(2), with the exception of using <Intermediate 6-f> instead of <Intermediate 1-a>, was conducted to synthesize <Intermediate 6-g> (4.5 g, 88.1%).

Synthesis Example 6-(8): Synthesis of Intermediate 6-h

Intermediate 6-h was synthesized as illustrated in the following Reaction Scheme 45:

<Reaction Scheme 45>

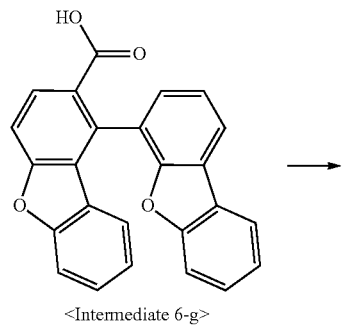

<Intermediate 6-g>

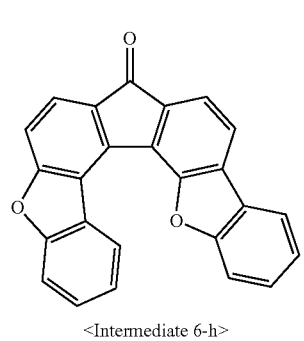

<Intermediate 6-h>

The same procedure as in Synthesis Example 1-(3), with the exception of using <Intermediate 6-g> instead of <Intermediate 1-b>, was conducted to synthesize <Intermediate 6-h> (3.8 g, 88.8%).

Synthesis Example 6-(9): Synthesis of Intermediate 6-i

Intermediate 6-i was synthesized as illustrated in the following Reaction Scheme 46:

<Reaction Scheme 46>

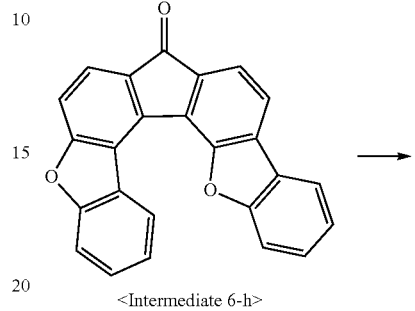

<Intermediate 6-h>

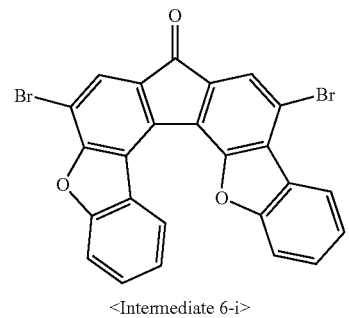

<Intermediate 6-i>

The same procedure as in Synthesis Example 1-(4), with the exception of using <Intermediate 6-h> instead of <Intermediate 1-c>, was conducted to synthesize <Intermediate 6-i> (3 g, 55%).

Synthesis Example 6-(10): Synthesis of Intermediate 6-j

Intermediate 6-j was synthesized as illustrated in the following Reaction Scheme 47:

<Reaction Scheme 47>

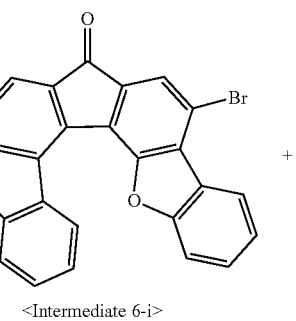

<Intermediate 6-i>

+

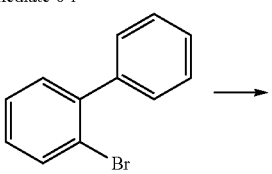

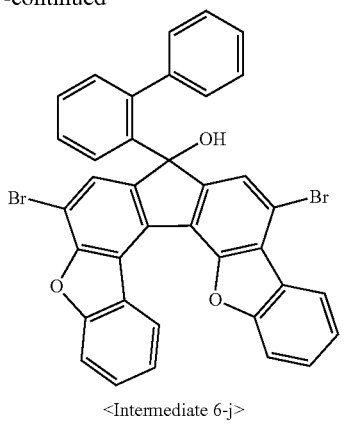

<Intermediate 6-j>

The same procedure was conducted as in Synthesis Example 1-(5), with the exception of using <Intermediate 6-i> instead of <Intermediate 1-d>, to synthesize <Intermediate 6-j> (2.5 g, 64%).

Synthesis Example 6-(10): Synthesis of Intermediate 6-k

Intermediate 6-k was synthesized as illustrated in the following Reaction Scheme 48:

<Reaction Scheme 48>

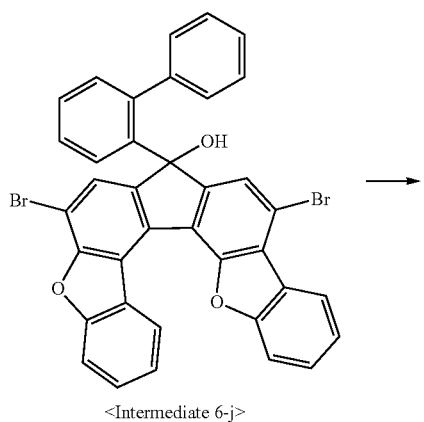

<Intermediate 6-j>

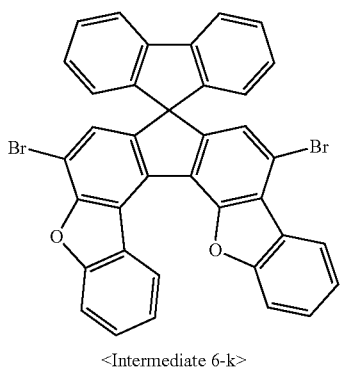

<Intermediate 6-k>

The same procedure as in Synthesis Example 1-(6), with the exception of using <Intermediate 6-j> instead of <Intermediate 1-e>, was conducted to synthesize <Intermediate 6-k> (2.2 g, 90.4%).

Synthesis Example 6-(11): Synthesis of Intermediate 6-l

Intermediate 6-l was synthesized as illustrated in the following Reaction Scheme 49:

<Reaction Scheme 49>

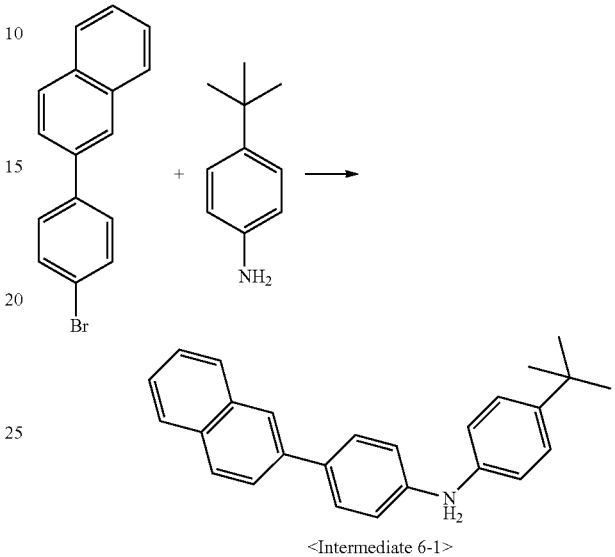

<Intermediate 6-l>

In a 250-ml round-bottom flask reactor, 1-bromo-4-(2-naphthyl)benzene (10.0 g, 0.035 mol), 4-tert-butyl aniline (5.8 g, 0.039 mol), tris(dibenzylidne acetone)dipalladium(0) (0.65 g, 0.0007 mol), sodium tert-butoxide (6.79 g, 0.0706 mol), 2,2'-bis(diphenylphosphino)-1,1'-binaphthalene (0.44 g, 0.0007 mol), and toluene (100 ml) were stirred together for 3 hrs under reflux. After completion of the reaction, the reaction mixture was cooled to room temperature and extracted with ethyl acetate and water. The organic layer was isolated, dried over magnesium sulfate, and concentrated in a vacuum. Purification through column chromatography gave <Intermediate 6-l> (10 g, 80%).

Synthesis Example 6-(12): Synthesis of Compound of Chemical Formula 97

The compound of Chemical Formula 97 was synthesized as illustrated in the following Reaction Scheme 50:

<Reaction Scheme 50>

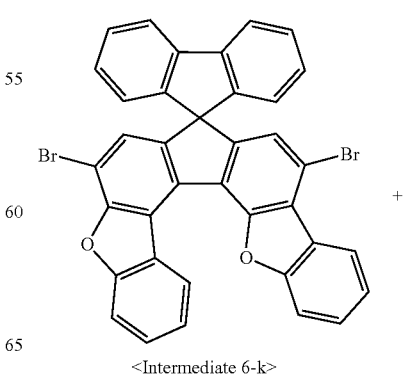

<Intermediate 6-k>

193
-continued

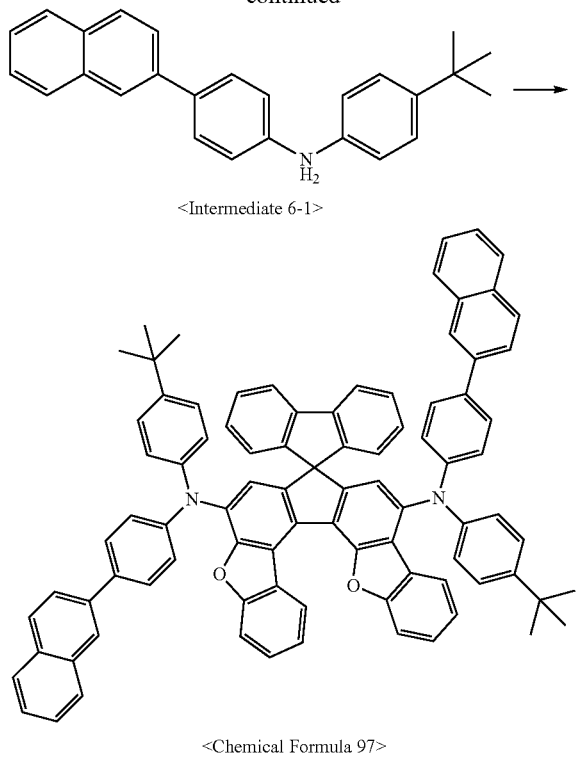

<Intermediate 6-1>

<Chemical Formula 97>

The same procedure as in Synthesis Example 1-(7), with the exception of using <Intermediate 6-k> and <Intermediate 6-l> respectively instead of <Intermediate 1-f> and bis(4-tert-butylphenyl)amin, was conducted to synthesize <Chemical Formula 97> (1.6 g, 38%).

MS (MALDI-TOF): m/z 1194.5 [M$^+$]

II. Preparation Example of Host Compounds

Synthesis Example 1: Synthesis of Compound 1

Synthesis Example 1-(1): Synthesis of Intermediate 1-a

Intermediate 1-a was synthesized as illustrated in the following Reaction Scheme 1:

<Reaction Scheme 1>

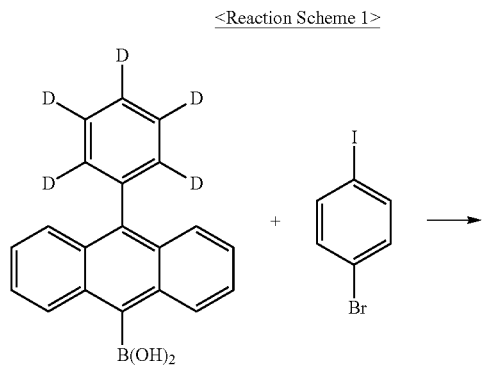

194
-continued

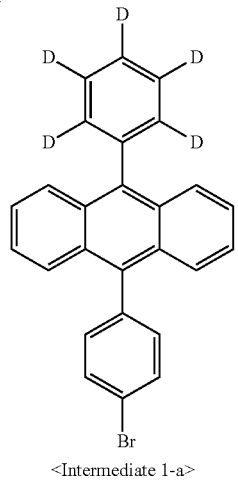

<Intermediate 1-a>

In a 500-mL round-bottom flask reactor, (10-phenyl(d5)-anthracene-9-boronic acid (38.6 g, 127 mmol), 1-bromo-4-iodobenzene (30.0 g, 106 mmol), tetrakis(triphenylphosphine)palladium (3.43 g, 3 mmol), and potassium carbonate (27.35 g, 197.9 mmol) were placed, followed by toluene (150 mL), tetrahydrofuran (150 mL), and water (60 mL). The temperature of the reactor was increased to 90° C. and stirring was conducted overnight. After completion of the reaction, the reaction mixture was cooled to room temperature and extracted with ethyl acetate. The organic layer thus formed was separated and concentrated in a vacuum, followed by purification through column chromatography to afford <Intermediate 1-a>. (35.0 g, 79.7%)

Synthesis Example 1-(2): Synthesis of Intermediate 1-b

Intermediate 1-b was synthesized as illustrated in the following Reaction Scheme 2:

<Reaction Scheme 2>

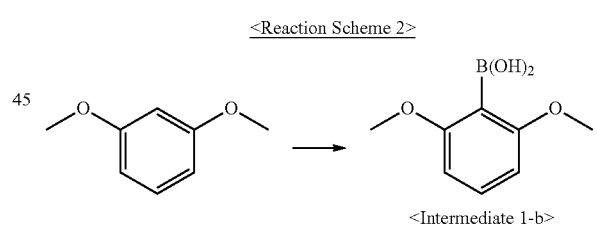

<Intermediate 1-b>

In a well-dried 2-L round-bottom flask reactor, 1,3-dimethoxy benzene (100.0 g, 0.724 mol) was dissolved in tetrahydrofuran (800 ml). The solution was chilled to −10° C. in a nitrogen atmosphere and then added slowly with drops of n-butyl lithium (543 ml, 0.868 mol). After 4 hrs of stirring at the same temperature, the temperature was decreased to −78° C. While this temperature was maintained, drops of trimethyl borate (112.8 g, 1.086 mol) were slowly added over 30 min, followed by stirring overnight at room temperature. After completion of the reaction, 2 N HCl was dropwise added for acidification. Extraction was made with water and ethyl acetate, and the organic layer thus formed was dried over magnesium sulfate. Subsequent to vacuum concentration, crystallization was conducted in heptane. The solid thus formed was filtered and washed with heptane to afford <Intermediate 1-b>. 92.0 g, 69%)

Synthesis Example 1-(3): Synthesis of Intermediate 1-c

Intermediate 1-c was synthesized as illustrated in the following Reaction Scheme 3:

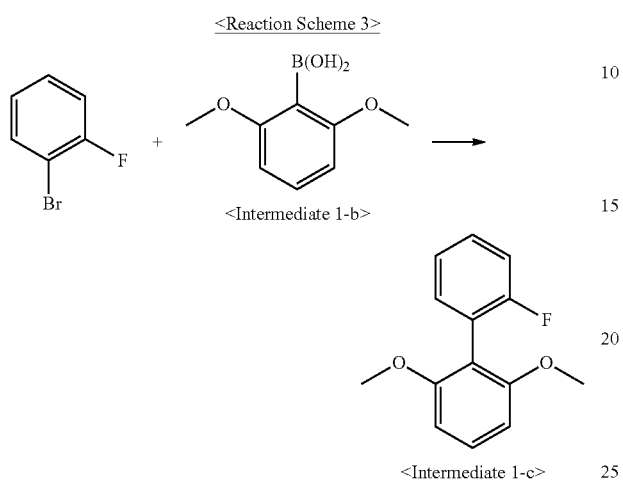

<Reaction Scheme 3>

<Intermediate 1-b>

<Intermediate 1-c>

In a 2-L round-bottom flask reactor, 1-bromo-2-fluorobenzene (80.0 g, 0.457 mol), <Intermediate 1-b> (91.5 g, 0.503 mol), tetrakis(triphenylphosphine)palladium (11.6 g, 0.01 mol), and potassium carbonate (126.4 g, 0.914 mol) were placed, followed by toluene (400 mL), tetrahydrofuran (400 mL), and water (160 mL). The temperature of the reactor was increased to 80° C. and stirring was conducted overnight. After completion of the reaction, the reaction mixture was cooled to room temperature and extracted with ethyl acetate. The organic layer thus formed was separated and concentrated in a vacuum, followed by purification through column chromatography to afford <Intermediate 1-c>. (85.0 g, 80%)

Synthesis Example 1-(4): Synthesis of Intermediate 1-d

Intermediate 1-d was synthesized as illustrated in the following Reaction Scheme 4:

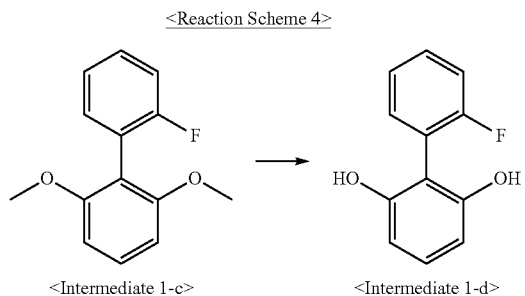

<Reaction Scheme 4>

<Intermediate 1-c>    <Intermediate 1-d>

In a 2-L round-bottom flask reactor, <Intermediate 1-c> (85.0 g, 0.366 mol) was added with acetic acid (510 ml) and hydrobromic acid (340 ml) and stirred overnight under reflux. After completion of the reaction, the reaction mixture was cooled to room temperature and dropwise added little by little to cold water (1000 ml). Extraction was made with water and ethyl acetate and the organic layer thus formed was isolated, washed with an aqueous sodium hydrogen carbonate solution (400 ml), and concentrated in a vacuum. Purification through column chromatography afforded <Intermediate 1-d>. (71 g, 95%)

Synthesis Example 1-(5): Synthesis of Intermediate 1-e

Intermediate 1-e was synthesized as illustrated in the following Reaction Scheme 5:

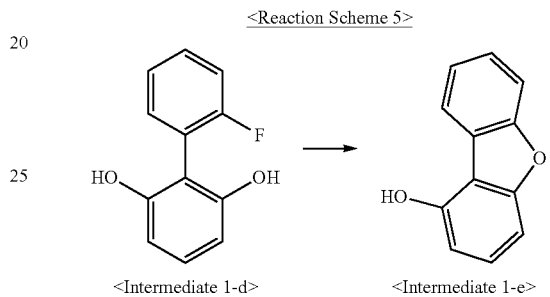

<Reaction Scheme 5>

<Intermediate 1-d>    <Intermediate 1-e>

In a 2-L round-bottom flask reactor, <Intermediate 1-d> (71.0, 39 mmol), potassium carbonate (96.1 g, 0.695 mol), and 1-methyl-2-pyrrolidinone (1060 ml) were stirred together overnight at 120° C. After completion of the reaction, the reaction mixture was cooled to room temperature and dropwise added to cold water (1000 ml). Extraction with water and ethyl acetate formed an organic layer which was then isolated and concentrated in a vacuum. Purification through column chromatography afforded <Intermediate 1-e>. (60.0 g, 93.7%)

Synthesis Example 1-(6): Synthesis of Intermediate 1-f

Intermediate 1-f was synthesized as illustrated in the following Reaction Scheme 6:

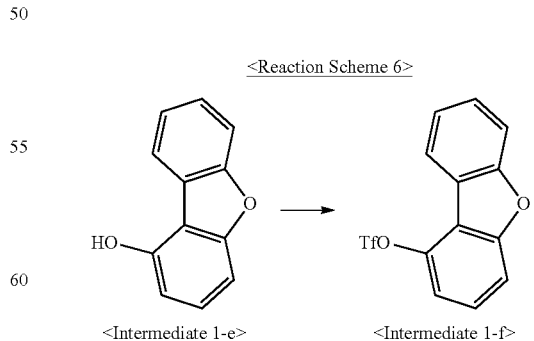

<Reaction Scheme 6>

<Intermediate 1-e>    <Intermediate 1-f>

In a 2-L round-bottom flask reactor, <Intermediate 1-e> (60.0 g, 0.326 mol) was dissolved in methylene chloride (600 ml) and slowed added with pyridine (38.7 g, 0.489 mol)

before stirring at room temperature for 30 min. The solution was cooled to 0° C. and added with drops of trifluoromethane sulfonyl anhydride (137.8 g, 0.489 mol) at the same temperature. After 5 hrs of stirring at room temperature, the reaction solution was added with water (100 ml) and stirred again for 10 min. Extraction with water and ethyl acetate formed an organic layer which was then isolated and concentrated in a vacuum. Purification through column chromatography afforded <Intermediate 1-f>. (87 g, 84.5%)

Synthesis Example 1-(7): Synthesis of Intermediate 1-g

Intermediate 1-g was synthesized as illustrated in the following Reaction Scheme 7:

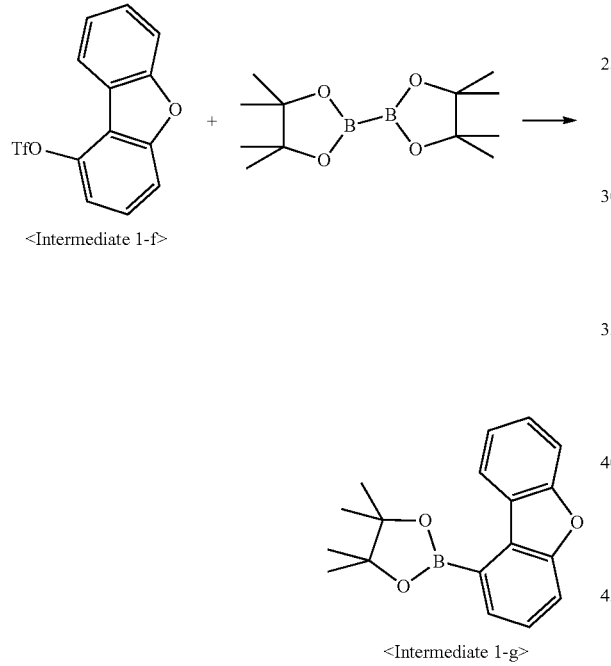

In a 2-L round-bottom flask reactor, <Intermediate 1-f> (87.0 g, 0.275 mol), bis(pinacolato)diboron (83.8 g, 0.330 mol), 1,1'-bis(diphenylphosphino)ferocene-palladium(II) dichloride (4.5 g, 0.006 mol), potassium acetate (54.0 g, 0.550 mol), and 1,4-dioxane (870 ml) were placed and stirred overnight under reflux. After completion of the reaction, the reaction mixture was filtered through a celite pad and the filtrate was concentrated in a vacuum. The concentrate was purified by column chromatography to afford <Intermediate 1-g>. (65.3 g, 80.7%)

Synthesis Example 1-(8): Synthesis of Compound 1

Compound 1 was synthesized as illustrated in the following Reaction Scheme 8:

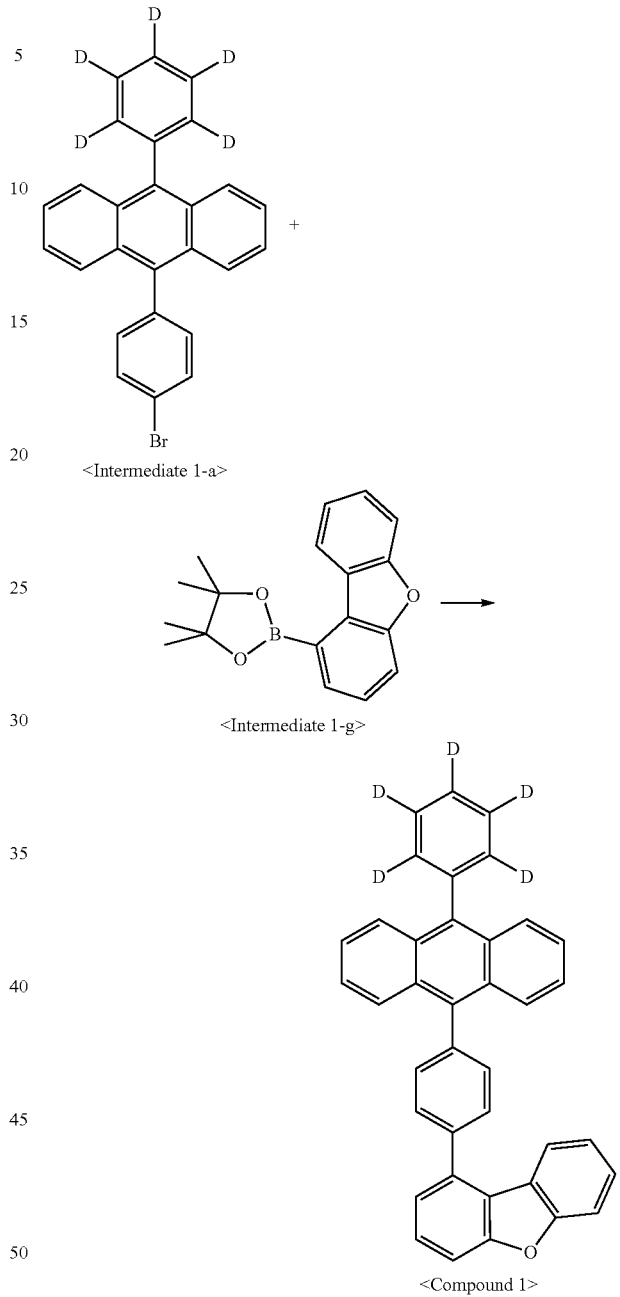

In a 250-mL round-bottom flask reactor, <Intermediate 1-a> (5.5 g, 13 mmol), <Intermediate 1-g> (4.7 g, 16 mmol), tetrakis(triphenylphosphine)palladium (0.46 g, 3 mmol), and potassium carbonate (3.67 g, 26.5 mmol) were placed, followed by toluene (30 mL), 1,4-dioxane (30 mL) and water (11 mL). The temperature of the reactor was elevated to 90° C. before stirring overnight. After completion of the reaction, the reaction mixture was cooled to room temperature and extracted with ethyl acetate. The organic layer thus formed was isolated and concentrated in a vacuum, followed by purification through column chromatography. Recrystallization in toluene and acetone afforded <Compound 1>. (3.2 g, 48%)

MS: m/z 502.2 [M$^+$]

Synthesis Example 2: Synthesis of Compound 13

Synthesis Example 2-(1): Synthesis of Intermediate 2-a

Intermediate 2-a was synthesized as illustrated in the following Reaction Scheme 9:

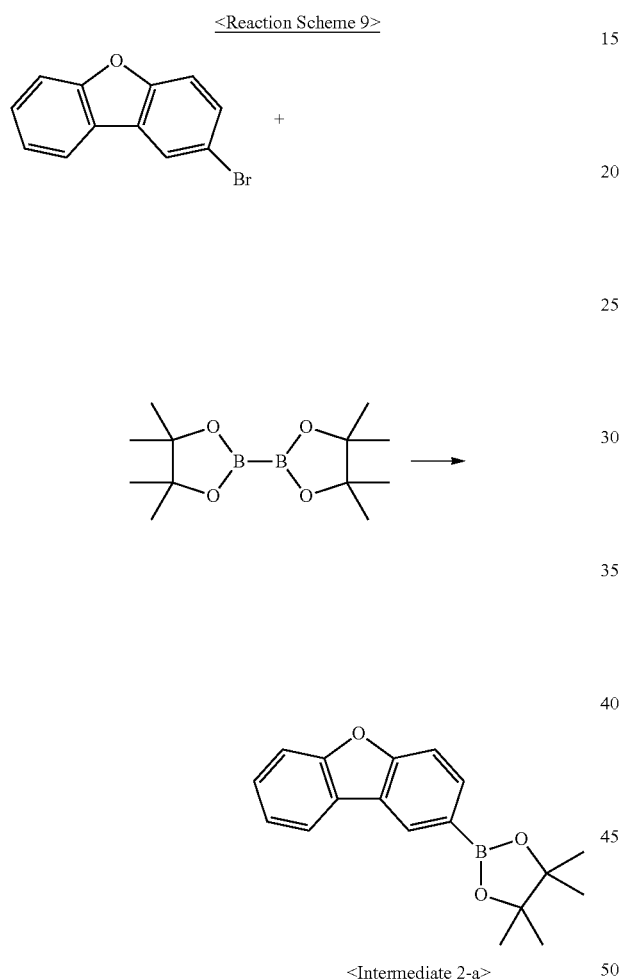

<Reaction Scheme 9>

<Intermediate 2-a>

In a 2-L round-bottom flask reactor, a mixture of 2-bromodibenzofuran (70.0 g, 0.283 mol), bis(pinacolato)diboron (86.3 g, 0.340 mol), 1,1'-bis(diphenylphosphino)ferocene-palladium(II) dichloride (4.6 g, 0.006 mol), potassium acetate (56.6 g, 0.567 mol), and 1,4-dioxane (700 ml) was stirred overnight under reflux. After completion of the reaction, the reaction mixture was filtered through a celite pad and the filtrate was concentrated in a vacuum. The concentrate was purified using column chromatography to afford <Intermediate 2-a>. (66.4 g, 79%)

Synthesis Example 2-(2): Synthesis of Compound 13

Compound 13 was synthesized as illustrated in the following Reaction Scheme 10:

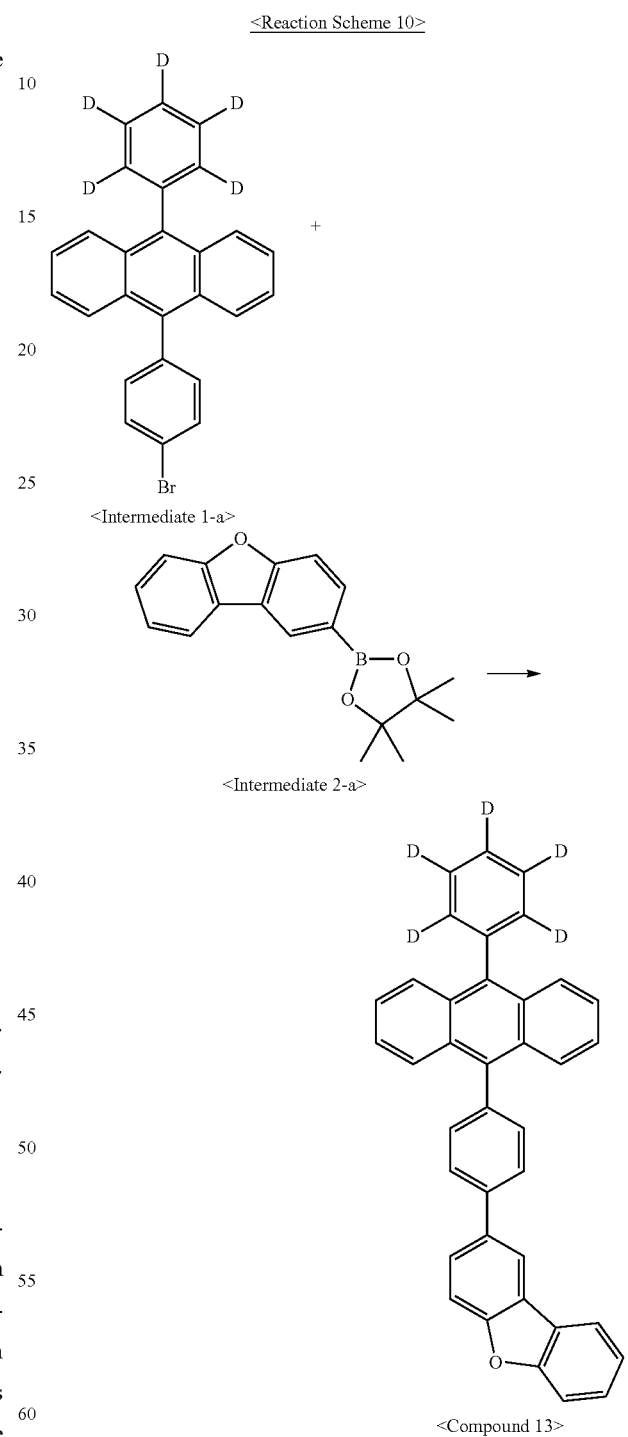

<Reaction Scheme 10>

<Intermediate 1-a>

<Intermediate 2-a>

<Compound 13>

The same procedure was carried out as in Synthesis Example 1-(8), with the exception of using Intermediate 2-a instead of Intermediate 1-g, to afford <Compound 13>. (3.0 g, 66.1%).

MS: m/z 502.2 [M+]

Synthesis Example 3: Synthesis of Compound 22

Synthesis Example 3-(1): Synthesis of Intermediate 3-a

Intermediate 3-a was synthesized as illustrated in the following Reaction Scheme 11:

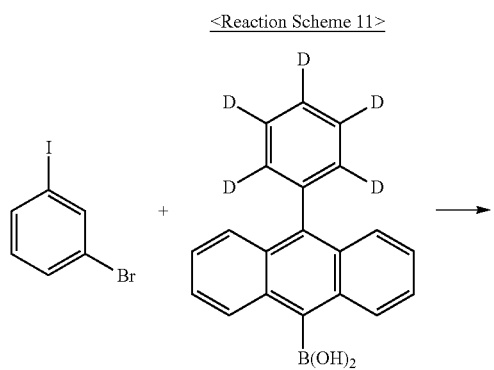

<Reaction Scheme 11>

<Intermediate 3-a>

The same procedure was carried out as in Synthesis Example 1-(1), with the exception of using 1-bromo-3-iodobenzene instead of 1-bromo-4-iodobenzene, to afford <Intermediate 3-a>. (32 g, 72.8%)

Synthesis Example 3-(2): Synthesis of Compound 22

Compound 22 was synthesized as illustrated in the following Reaction Scheme 12:

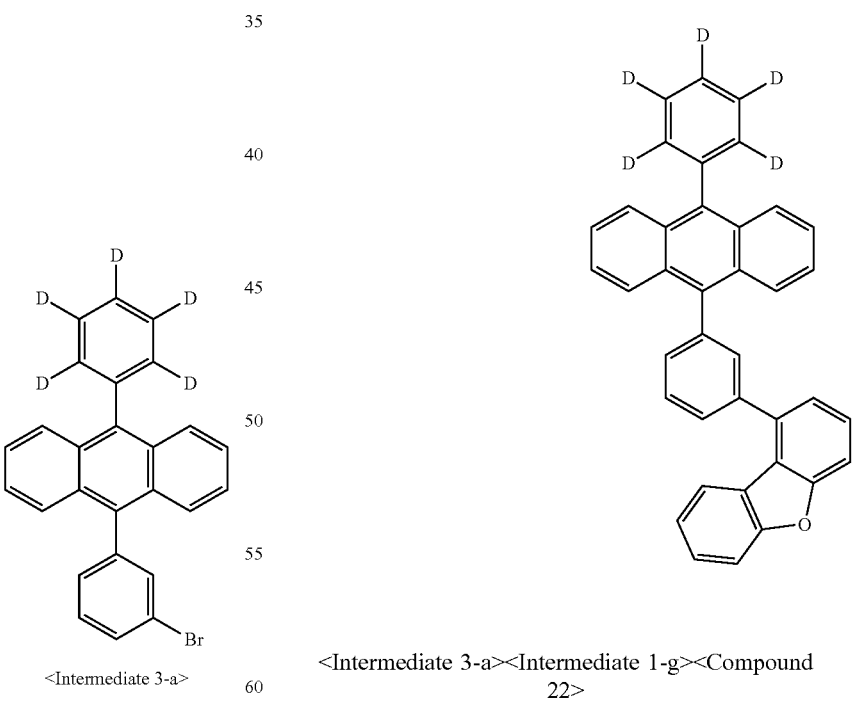

<Reaction Scheme 12>

<Intermediate 3-a><Intermediate 1-g><Compound 22>

The same procedure was carried out as in Synthesis Example 1-(8), with the exception of using Intermediate 3-a instead of Intermediate 1-a, to afford <Compound 22>. (3.5 g, 57.8%)

MS: m/z 502.2 [M+]

Synthesis Example 4: Synthesis of Compound 31

Synthesis Example 4-(1): Synthesis of Compound 31

Compound 31 was synthesized as illustrated in the following Reaction Scheme 13:

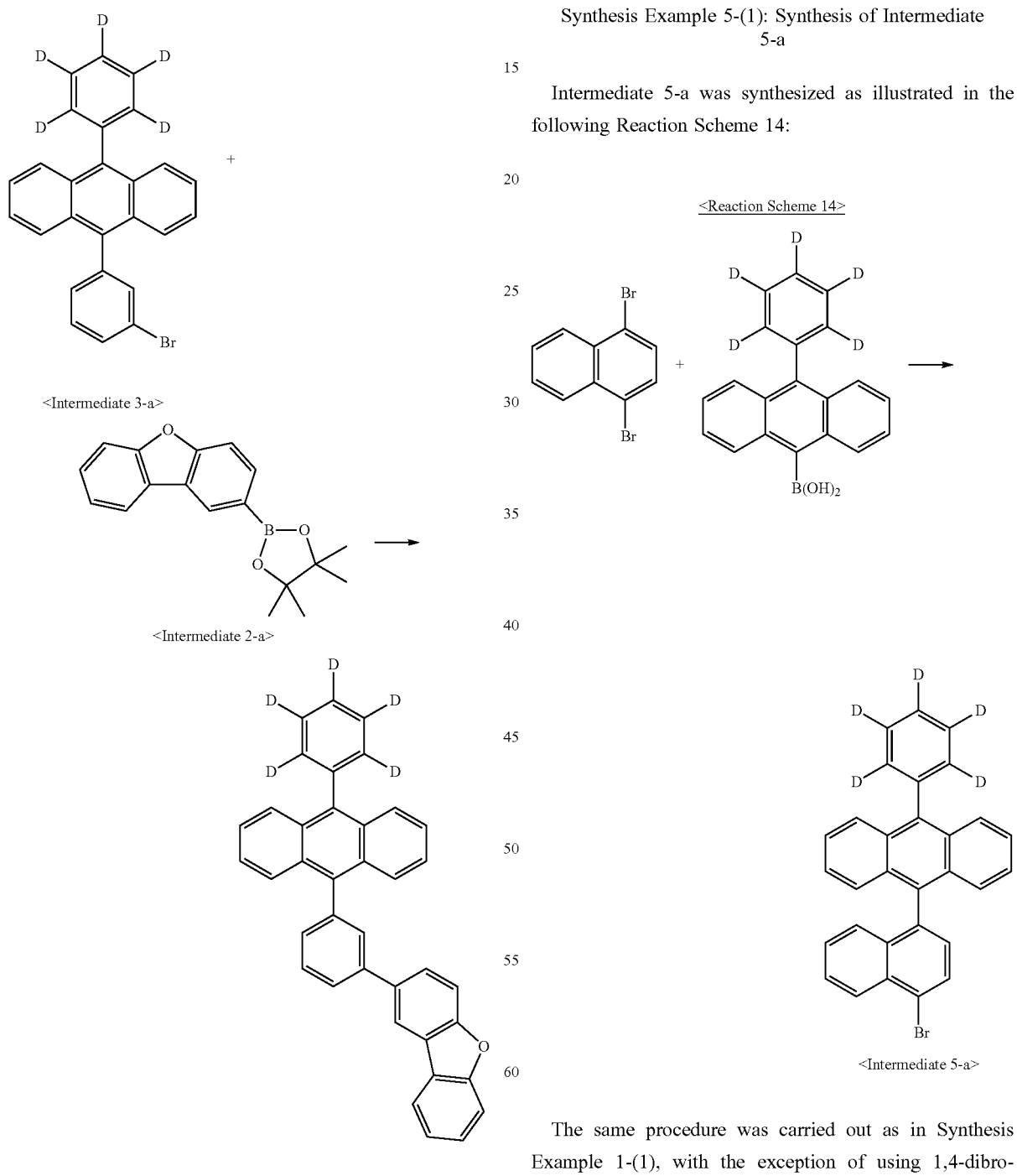

<Compound 31>

The same procedure was carried out as in Synthesis Example 2-(2), with the exception of using Intermediate 3-a instead of Intermediate 1-a, to afford <Compound 31>. (2.7 g, 44.6%)

MS: m/z 502.2 [M+]

Synthesis Example 5: Synthesis of Compound 43

Synthesis Example 5-(1): Synthesis of Intermediate 5-a

Intermediate 5-a was synthesized as illustrated in the following Reaction Scheme 14:

The same procedure was carried out as in Synthesis Example 1-(1), with the exception of using 1,4-dibromonaphthalene instead of 1-bromo-4-iodobenzene, to afford <Intermediate 5-a>. (29 g, 59.5%)

Synthesis Example 5-(2): Synthesis of Compound 43

Compound 43 was synthesized as illustrated in the following Reaction Scheme 15:

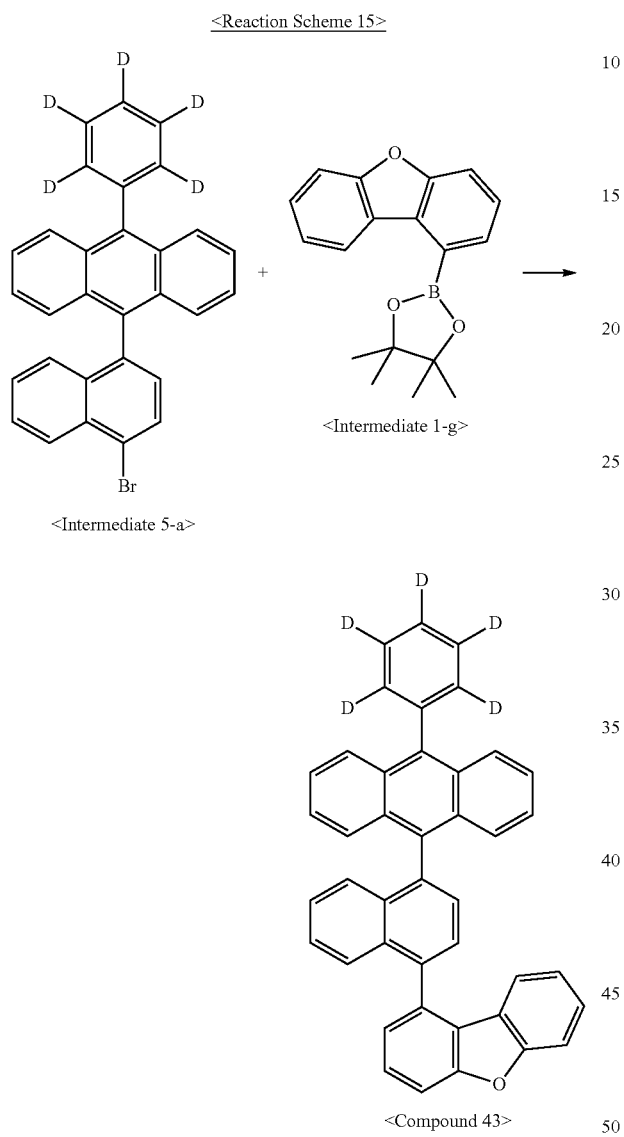

<Compound 43>

The same procedure was carried out as in Synthesis Example 1-(8), with the exception of using Intermediate 5-a instead of Intermediate 1-a, to afford <Compound 43>. (4.2 g, 69.4%)

MS: m/z 552.2 [M+]

Synthesis Example 6: Synthesis of Compound 52

Synthesis Example 6-(1): Synthesis of Compound 52

Compound 52 was synthesized as illustrated in the following Reaction Scheme 16:

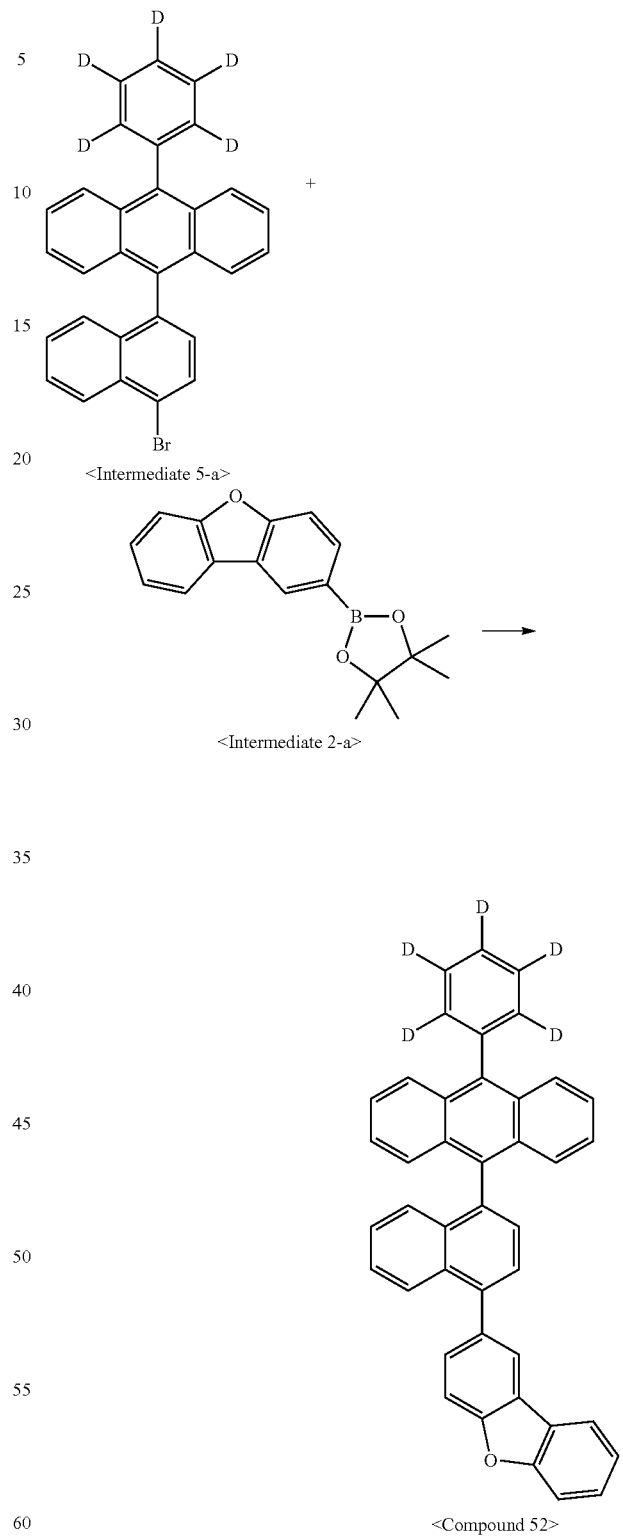

<Compound 52>

The same procedure was carried out as in Synthesis Example 2-(2), with the exception of using Intermediate 5-a instead of Intermediate 1-a, to afford <Compound 52>. (4.0 g, 67.4%)

MS: m/z 552.2 [M+]

Synthesis Example 7: Synthesis of Compound 61

Synthesis Example 7-(1): Synthesis of Intermediate 7-a

Intermediate 7-a was synthesized as illustrated in the following Reaction Scheme 17:

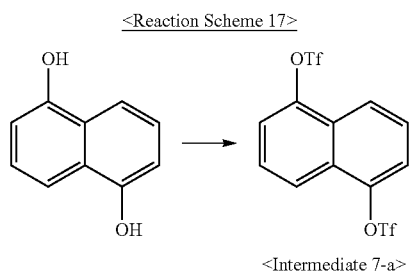 [SMILES: Oc1cccc2c(O)cccc12 ; O=S(=O)(Oc1cccc2c(OS(=O)(=O)C(F)(F)F)cccc12)C(F)(F)F]

<Intermediate 7-a>

The same procedure was carried out as in Synthesis Example 1-(6), with the exception of using 1,4-dihydroxynaphthalene instead of Intermediate 1-e, to afford <Intermediate 7-a>. (244 g, 95%)

Synthesis Example 7-(2): Synthesis of Intermediate 7-b

Intermediate 7-b was synthesized as illustrated in the following Reaction Scheme 18:

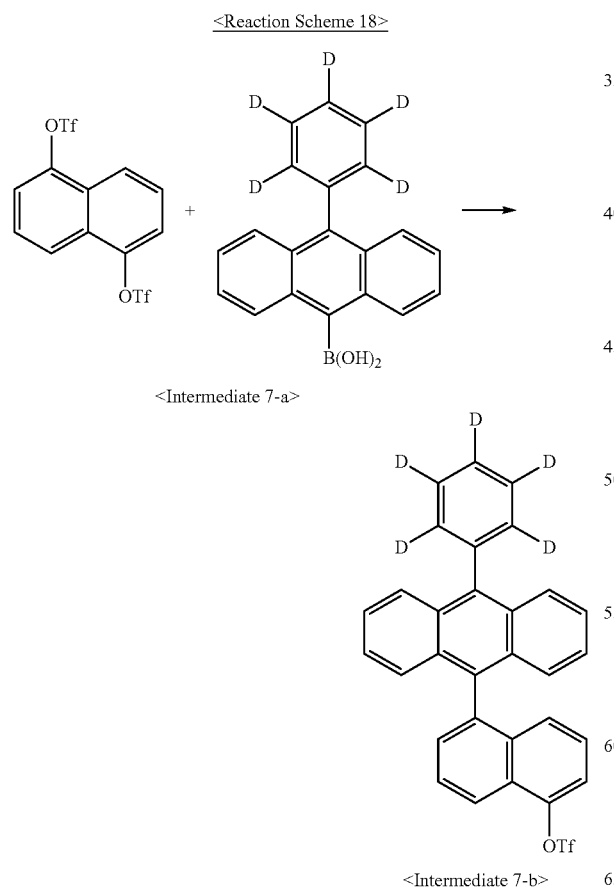

<Intermediate 7-b>

In a 2-L round-bottom flask reactor, Intermediate 7-a (110.0 g, 0.259 mol), 10-phenyl(d5)-anthracene-9-boronic acid (78.6 g, 0.259 mol), tetrakis(triphenylphosphine)palladium (6.0 g, 5 mmol), and potassium carbonate (71.7 g, 0.519 mol) were placed, followed by toluene (770 mL), ethanol (330 mL) and water (220 mL). The mixture was heated to 60° C. and stirred for 1 hr. After completion of the reaction, the reaction mixture was cooled to room temperature and the precipitates were filtered off. The filtrate was extracted with water and ethyl acetate and the organic layer was separated and concentrated in a vacuum. The concentrate was dissolved in toluene and recrystallized in methanol to afford <Intermediate 7-b>. (100.0 g, 72.3%)

Synthesis Example 7-(3): Synthesis of Compound 61

Compound 61 was synthesized as illustrated in the following Reaction Scheme 19:

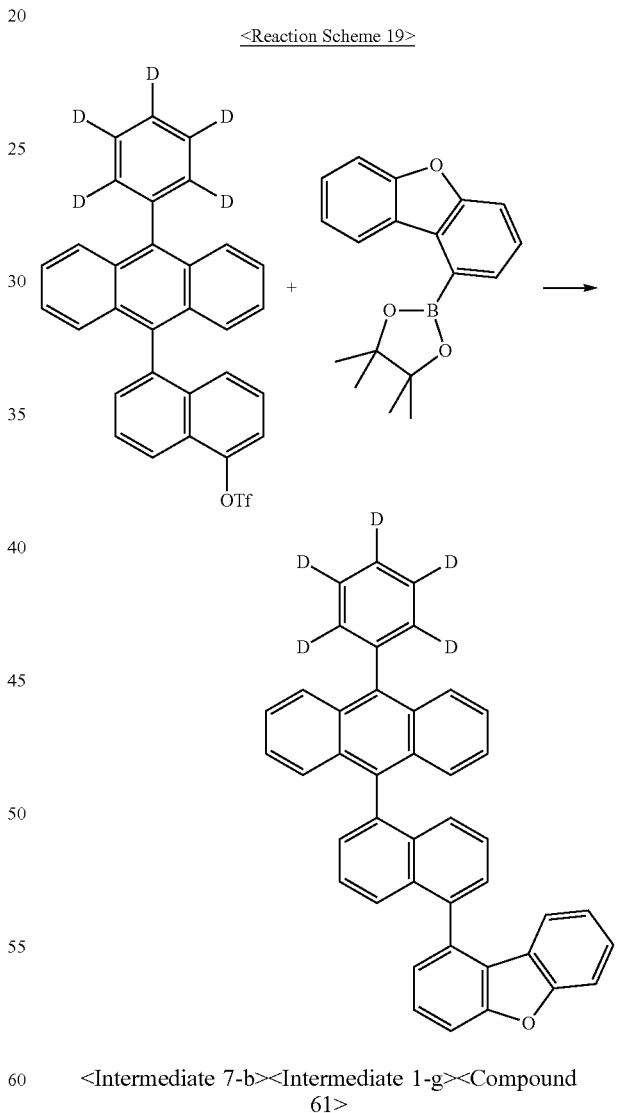

<Intermediate 7-b><Intermediate 1-g><Compound 61>

The same procedure was carried out as in Synthesis Example 1-(8), with the exception of using Intermediate 7-b instead of Intermediate 1-a, to afford <Compound 61>. (2.8 g, 54%)

MS: m/z 552.2 [M+]

Synthesis Example 8: Synthesis of Compound 70

Synthesis Example 8-(1): Synthesis of Compound 70

Compound 70 was synthesized as illustrated in the following Reaction Scheme 20:

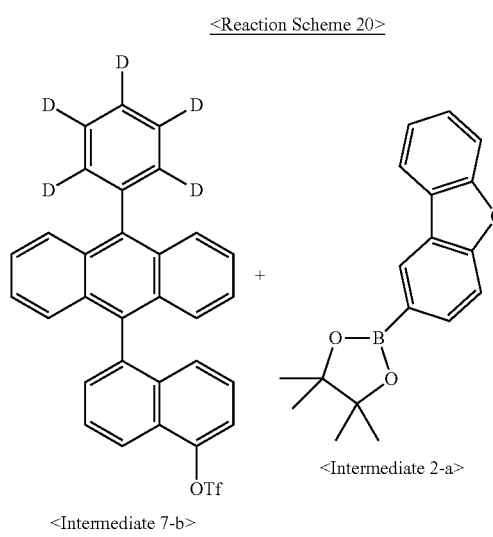

<Reaction Scheme 20>

<Compound 70>

The same procedure was carried out as in Synthesis Example 2-(2), with the exception of using Intermediate 7-b instead of Intermediate 1-a, to afford <Compound 70>. (2.4 g, 46%).

MS: m/z 552.2 [M+]

Synthesis Example 9: Synthesis of Compound 118

Synthesis Example 9-(1): Synthesis of Compound 118

Compound 118 was synthesized as illustrated in the following Reaction Scheme 21:

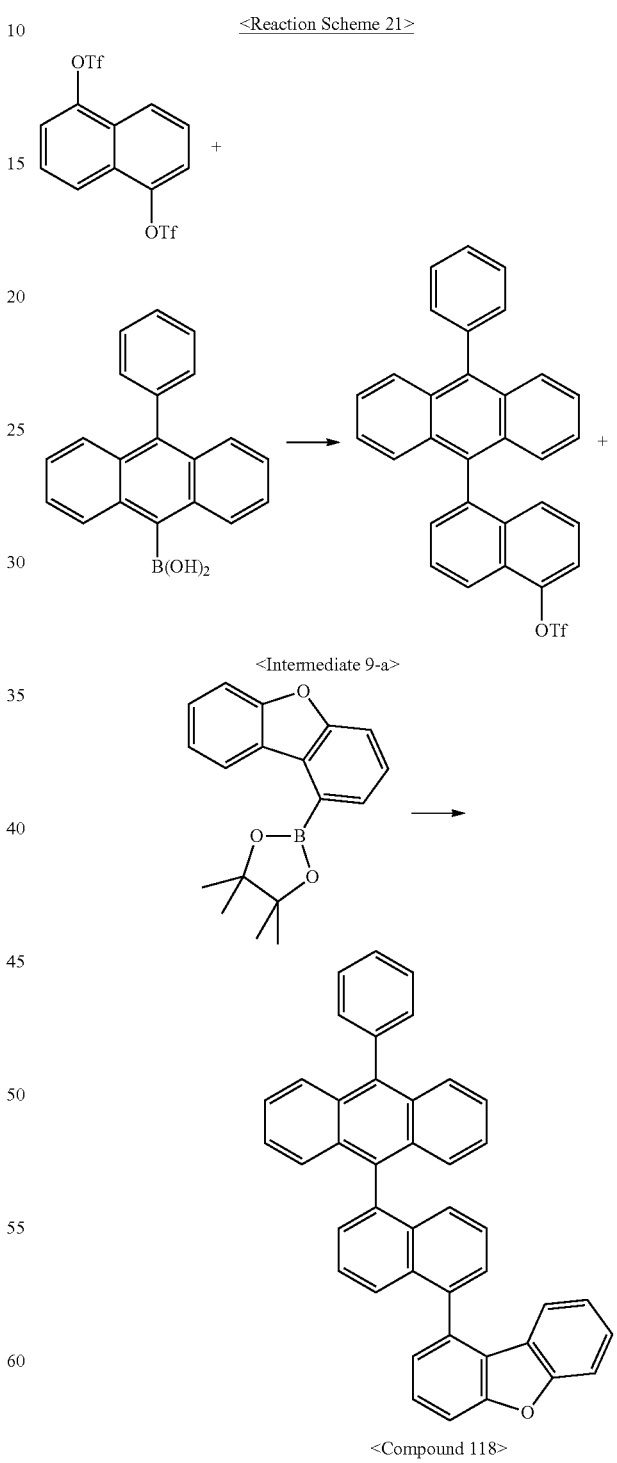

<Reaction Scheme 21>

<Intermediate 9-a>

<Compound 118>

The same procedure was carried out as in Synthesis Examples 7-(2) and 7-(3), with the exception of using 10-phenyl(H5)-anthracene-9-boronic acid and Intermediate 9-a instead of 10-phenyl(d5)-anthracene-9-boronic acid and Intermediate 7-b, respectively, to afford <Compound 118>. (3.5 g, 58%)

Synthesis Example 10: Synthesis of Compound 84

Synthesis Example 10-(1): Synthesis of Compound 84

Intermediate 10-a was synthesized as illustrated in the following Reaction Scheme 22:

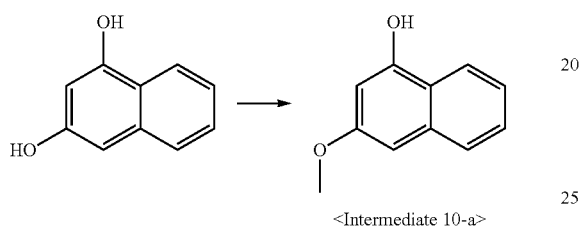

In a 1-L round-bottom flask reactor, 1,2-dihydroxynaphthalene (50.0 g 0.312 mol), HCl (17 ml), and methanol (500 ml) were placed and stirred at room temperature for three days. After completion of the reaction, the reaction solution was concentrated in a vacuum and purified through column chromatography to afford <Intermediate 10-a> (40.0 g, 73%).

Synthesis Example 10-(2): Synthesis of Intermediate 10-b

Intermediate 10-b was synthesized as illustrated in the following Reaction Scheme 23:

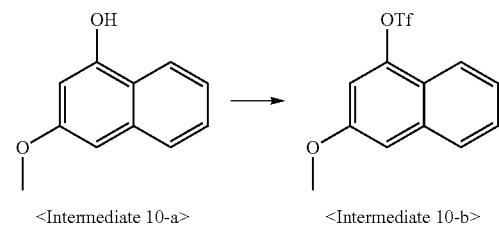

The same procedure was conducted as in Synthesis Example Synthesis Example 1-(6) with the exception of using <Intermediate 10-a> instead of <Intermediate 1-e>, to synthesize <Intermediate 10-b> (65.2 g, 92%).

Synthesis Example 10-(3): Synthesis of Intermediate 10-c

Intermediate 10-c was synthesized as illustrated in the following Reaction Scheme 24:

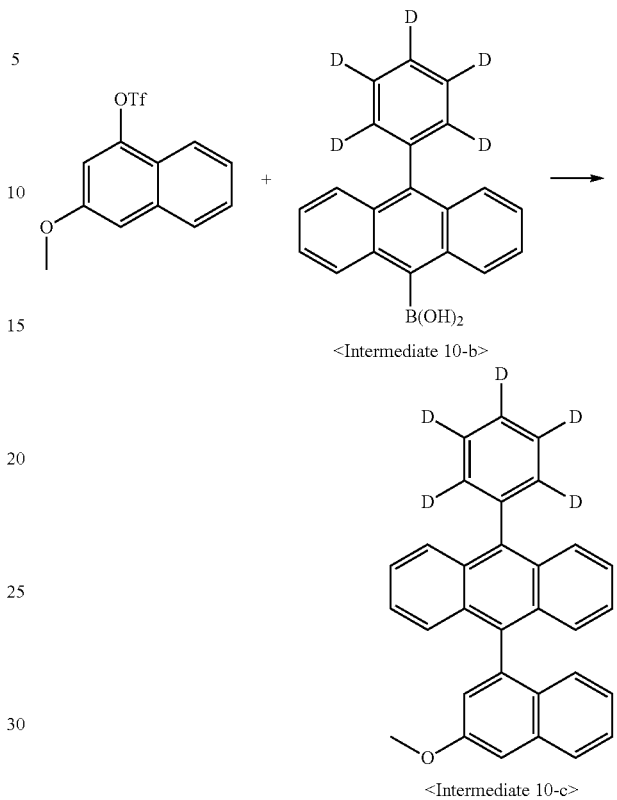

The same procedure was conducted as in Synthesis Example 7-(2), with the exception of using <Intermediate 10-b> instead of <Intermediate 7-a>, to synthesize <Intermediate 10-c> (12.0 g, 59%).

Synthesis Example 10-(4): Synthesis of Intermediate 10-d

Intermediate 10-d was synthesized as illustrated in the following Reaction Scheme 25:

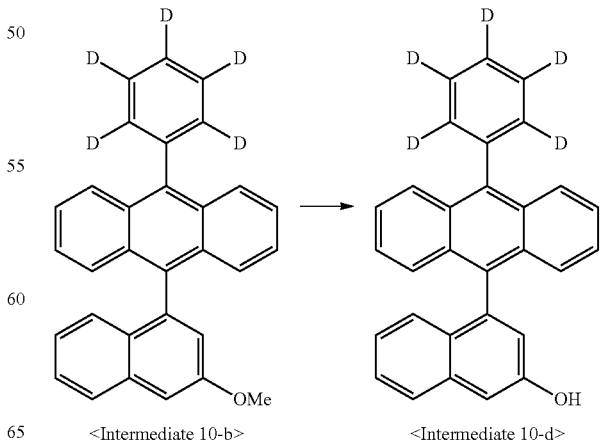

In a 500-ml round-bottom flask reactor, a solution of <Intermediate 10-b> (12.0 g, 0.028 mol) in dichloromethane (180 ml) was chilled to 0° C. The chilled solution was slowly added with drops of boron bromide (43.3 g, 0.043 mol) and stirred at room temperature. After completion of the reaction, the reaction solution was cooled to 0° C., slowly added with drops of water (20 ml), and then extracted with water and ethyl acetate. The organic layer thus formed was separated, concentrated in a vacuum, and recrystallized in acetonitrile and acetone to afford <Intermediate 10-d> (10.0 g, 86.2%).

Synthesis Example 10-(5): Synthesis of Intermediate 10-e

Intermediate 10-e was synthesized as illustrated in the following Reaction Scheme 26:

<Reaction Scheme 26>

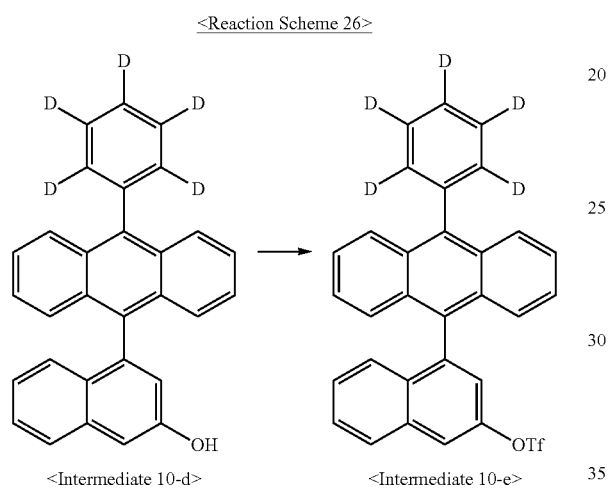

<Intermediate 10-d>    <Intermediate 10-e>

The same procedure was conducted as in Synthesis Example 1-(6), with the exception of using <Intermediate 10-d> instead of <Intermediate 1-e>, to synthesize <Intermediate 10-e> (11.2 g, 84%).

Synthesis Example 10-(6): Synthesis of Compound of Chemical Formula 84

Chemical Formula 84 was synthesized as illustrated in the following Reaction Scheme 27:

<Reaction Scheme 27>

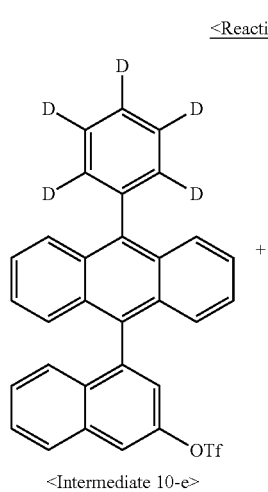

<Intermediate 10-e>

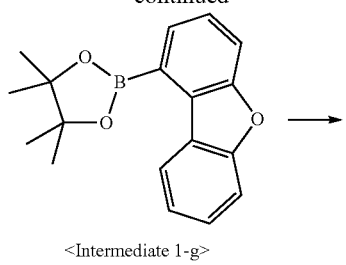

<Intermediate 1-g>

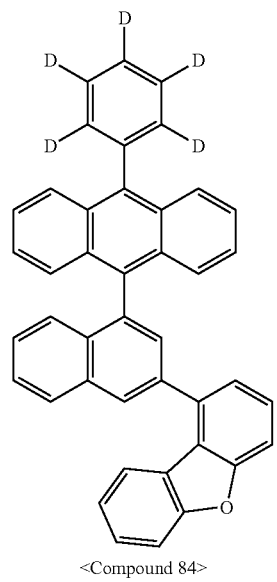

<Compound 84>

The same procedure was conducted as in Synthesis Example 1-(8), with the exception of using <Intermediate 10-e> instead of <Intermediate 1-a>, to synthesize <Compound 84> (3.8 g, 54%).

MS: m/z 552.2 [M$^+$]

Examples 1-7: Fabrication of OLEDs

An ITO glass substrate was patterned to have a translucent area of 2 mm×2 mm and cleansed. The ITO glass was mounted in a vacuum chamber that was then set to have a base pressure of 1×10$^{-7}$ torr. On the ITO glass substrate, films were formed of HAT-CN (50 Å) and a-NPD (600 Å) in that order. A light-emitting layer (200 Å) was formed of a mixture including each of hosts and dopants listed in Table 1. Then, [Chemical Formula E-1] and [Chemical Formula E-2] were deposited at a ratio of 1:1 to form an electron transport layer 300 Å thick, on which an electron injection layer of [Chemical Formula E-1] (10 Å thick) was formed and then covered with an Al layer (1000 Å) to fabricate an organic light-emitting diode. The organic light-emitting diodes thus obtained were measured at 0.4 mA for luminescence properties.

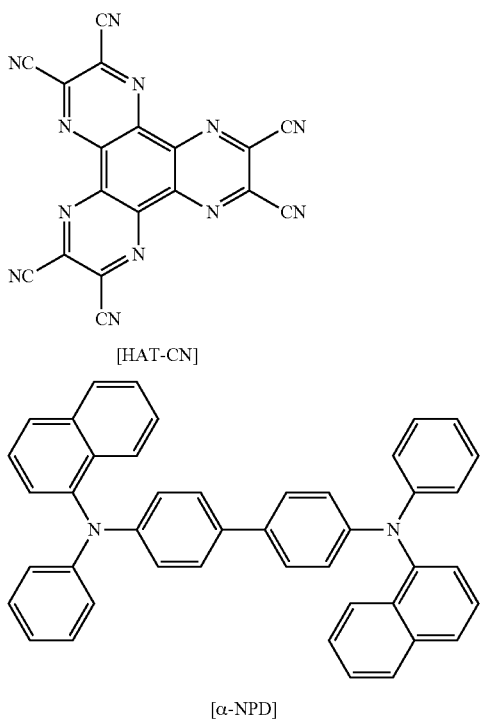

[HAT-CN]

[α-NPD]

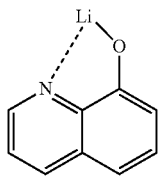

[Chemical FormulaE-1]

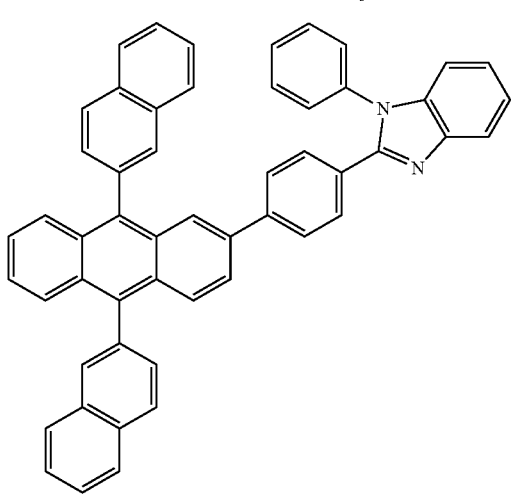

[Chemical FormulaE-2]

Comparative Examples 1-7

Organic light-emitting diodes were fabricated in the same manner as in Examples 1 to 7, with the exception that [BD1] was used, instead of the dopant compounds used in Examples 1 to 7. The structure of [BD1] is as follows:

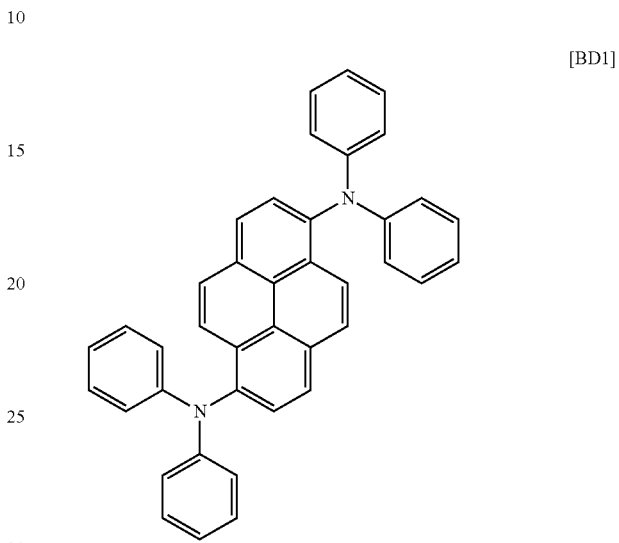

[BD1]

Comparative Examples 8-11

Organic light-emitting diodes were fabricated in the same manner as in Comparative Example 1, with the exception that the host compounds [BH1] to [BH4] were used, instead of the host compound used in Comparative Example 1. The structures of [BH1] to [BH4] are as follows:

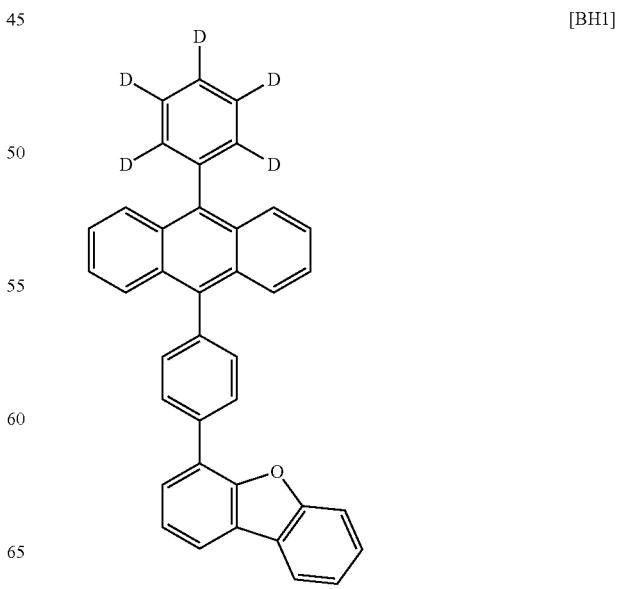

[BH1]

-continued

[BH2]

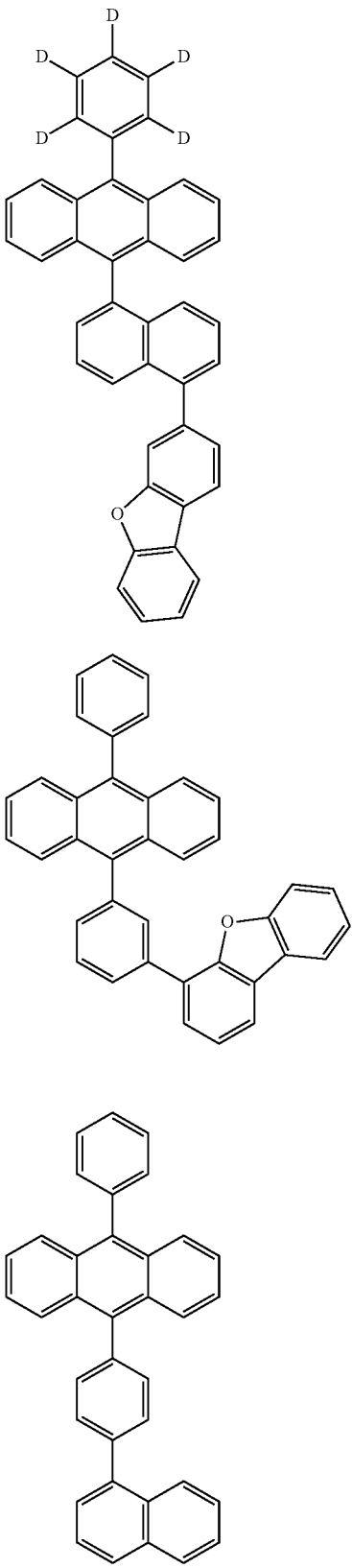

[BH3]

[BH4]

The OLEDs fabricated in Examples 1 to 7 and Comparative Examples 1 to 11 were measured for driving voltage, and the results are summarized in Table 1, below. In Table 1, T97 refers to the time taken for the initial luminance to decrease to 97% thereof.

TABLE 1

|  | Host | Dopant | Driving Volt. (V) | Efficiency (cd/A) | T97 (hr) |
| --- | --- | --- | --- | --- | --- |
| Example 1 | Cpd. 1 | Chemical Formula1 | 3.58 | 5.7 | 40 |
| Example 2 | Cpd. 13 | Chemical Formula33 | 3.54 | 6.5 | 50 |
| Example 3 | Cpd. 22 | Chemical Formula49 | 3.73 | 6.2 | 52 |
| Example 4 | Cpd. 31 | Chemical Formula76 | 3.76 | 6.4 | 55 |
| Example 5 | Cpd. 84 | Chemical Formula97 | 3.62 | 7.0 | 52 |
| Example 6 | Cpd. 52 | Chemical Formula97 | 3.53 | 6.7 | 47 |
| Example 7 | Cpd. 70 | Chemical Formula97 | 3.5 | 6.5 | 40 |
| C. Example 1 | Cpd. 1 | BD1 | 3.6 | 5.5 | 25 |
| C. Example 2 | Cpd. 13 | BD1 | 3.55 | 6.0 | 30 |
| C. Example 3 | Cpd. 22 | BD1 | 3.73 | 5.8 | 35 |
| C. Example 4 | Cpd. 31 | BD1 | 3.75 | 6.2 | 37 |
| C. Example 5 | Cpd. 84 | BD1 | 3.6 | 6.5 | 35 |
| C. Example 6 | Cpd. 52 | BD1 | 3.53 | 6.2 | 30 |
| C. Example 7 | Cpd. 70 | BD1 | 3.51 | 6.1 | 25 |
| C. Example 8 | BH1 | BD1 | 3.97 | 6.2 | 30 |
| C. Example 9 | BH2 | BD1 | 3.83 | 7.3 | 20 |
| C. Example 10 | BH3 | BD1 | 3.98 | 6.5 | 30 |
| C. Example 11 | BH4 | BD1 | 3.9 | 7.0 | 35 |

As is understood from the data of Table 1, the OLEDs according to the present disclosure could operate at lower voltages and exhibited longer lifespan than conventional OLEDs using the compounds of Comparative Examples 1 to 11 as hosts and dopant, thereby demonstrating their high applicability to organic electroluminescence devices.

INDUSTRIAL APPLICABILITY

The present disclosure is industrially applicable as it enables the fabrication of OLEDs that have the excellent diode property of operating at low driving voltages.

The invention claimed is:
1. An organic light-emitting diode, comprising:
a first electrode;
a second electrode facing the first electrode; and
a light-emitting layer interposed therebetween,
wherein the light-emitting layer contains at least one of the amine compounds represented by the following Chemical Formula A or Chemical Formula B, plus the compound represented by Chemical Formula D:

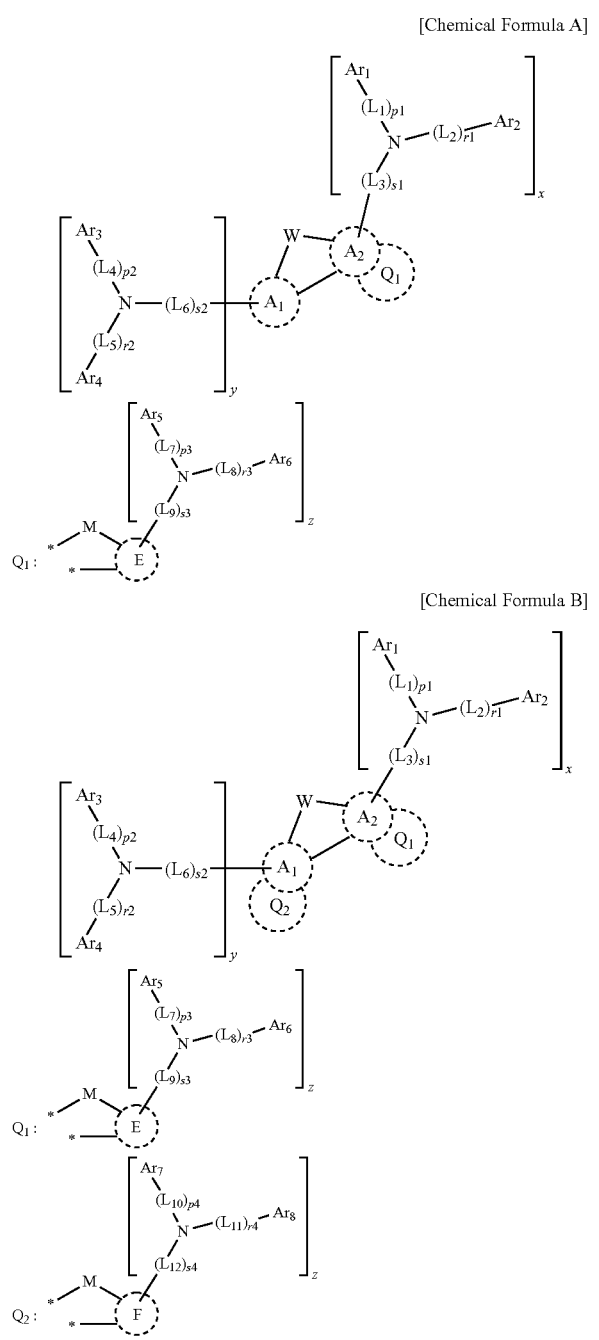

[Chemical Formula A]

[Chemical Formula B]

wherein

A1, A2, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring A1 and two adjacent carbon atoms of the aromatic ring A2 form a 5-membered fused ring together with W;

linkers L1 to L12 may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

W is selected from among $CR_1R_2$, $SiR_1R_2$, $GeR_1R_2$, O, and S;

M is any one selected from among N—$R_3$, $CR_4R_5$, $SiR_6R_7$, $GeR_8R_9$, O, S, and Se;

$R_1$ to $R_9$, and Ar1 to Ar8 may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, with the proviso that $R_1$ and $R_2$ may be bonded to each other to form a mono- or polycyclic aliphatic or aromatic ring, which may be a heterocyclic ring containing a heteroatom selected from among N, O, P, Si, S, Ge, Se, and Te as a ring member;

p1 to p4, $r_1$ to r4, and s1 to s4 are each independently an integer of 1 to 3, with the proviso that when any of them is 2 or greater, the corresponding linkers may be the same or different, x is an integer of 1 or 2, and y and z may be the same or different and are each independently an integer of 0 to 3; and Ar1 may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring,

[Chemical Formula D]

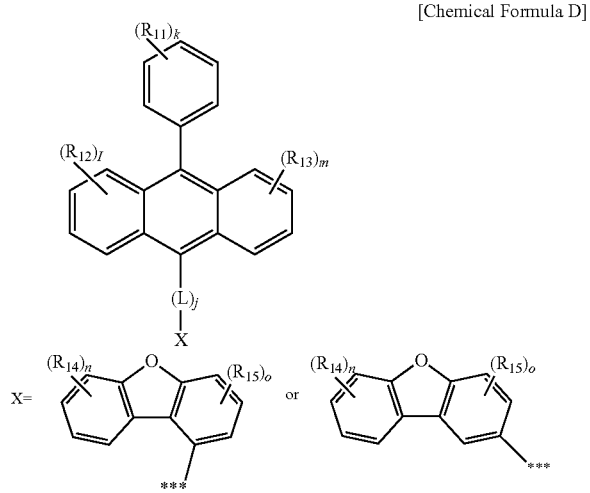

wherein $R_{11}$ to $R_{15}$ may be the same or different and are each independently any one selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxyl of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N or S as a heteroatom, a cyano, a nitro, a halogen a substituted or unsubstituted silyl of 1 to 30 carbon atoms, a substituted or unsubstituted alkylgermanium of 1 to 30 carbon atoms, wherein each of unsubstituted carbon atoms of $R_{11}$ to $R_{15}$ is bound with a hydrogen atom or a deuterium atom;

linker L is a single bond, or a substituted or unsubstituted arylene of 6 to 60 carbon atoms;

j is an integer of 0 to 2, with the proviso that when j is 2 or greater, corresponding L's may be the same or different;

k is an integer of 1 to 5, l to n may be the same or different and are each independently an integer of 1 to 4, o is an integer of 1 to 3, with the proviso that when k to o are each an integer of 2 or greater, corresponding $R_{11}$'s to $R_{15}$'s may be individually the same or different, and "***" of X denotes a bonding site to be linked to linker L, wherein the term 'substituted' in the expression 'substituted or unsubstituted' used in Chemical Formulas A, B and D means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

2. The organic light-emitting diode as set forth in claim 1, wherein the light-emitting layer contains a host and a dopant, wherein the dopant is selected from among the amine compounds represented by Chemical Formulas A and B and the host is the compound represented by Chemical Formula D.

3. The organic light-emitting diode as set forth in claim 2, wherein the linker L in Chemical Formula D may each be a single bond or any one selected from among the following Structural Formulas 22 to 30:

[Structural Formula 22]

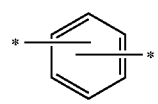

[Structural Formula 23]

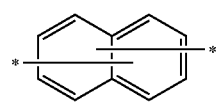

[Structural Formula 24]

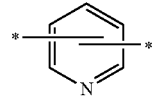

[Structural Formula 25]

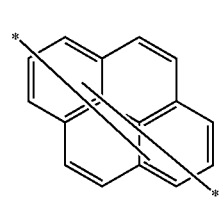

[Structural Formula 26]

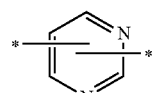

[Structural Formula 27]

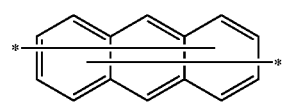

[Structural Formula 28]

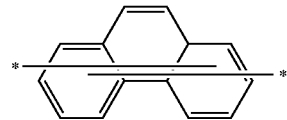

[Structural Formula 29]

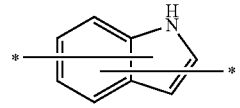

-continued

[Structural Formula 30]

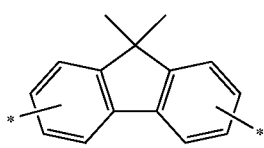

wherein each of the unsubstituted carbon atoms of the aromatic ring moiety in L may be bound with a hydrogen atom or a deuterium atom.

4. The organic light-emitting diode as set forth in claim 1, wherein $A_1$, $A_2$, E, and F in Chemical Formula A or B may be same or different and are each independently substituted or unsubstituted aromatic hydrocarbon rings of 6 to 50 carbon atoms.

5. The organic light-emitting diode as set forth in claim 4, wherein the substituted or unsubstituted aromatic hydrocarbon rings of 6 to 50 carbon atoms may be same or different and are each independently selected from among compounds represented by Structural Formulas 10 to 21:

[Structural Formula 10]

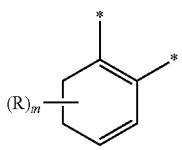

[Structural Formula 11]

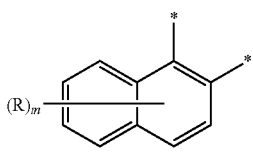

[Structural Formula 12]

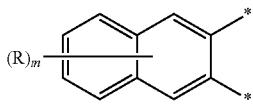

[Structural Formula 13]

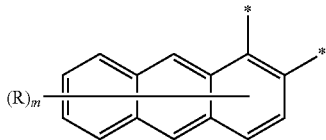

[Structural Formula 14]

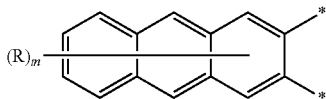

[Structural Formula 15]

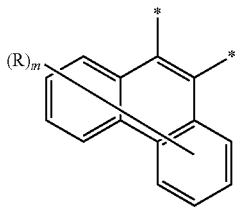

-continued

[Structural Formula 16]

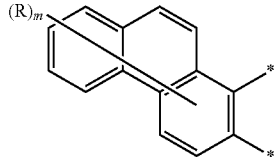

[Structural Formula 17]

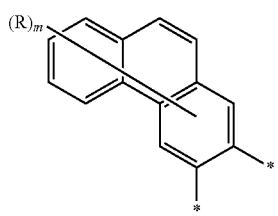

[Structural Formula 18]

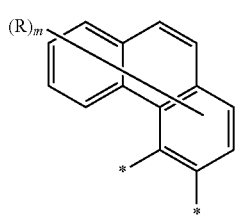

[Structural Formula 19]

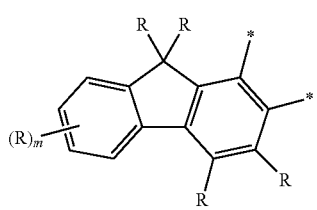

[Structural Formula 20]

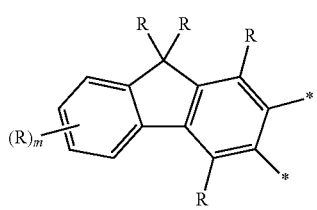

[Structural Formula 21]

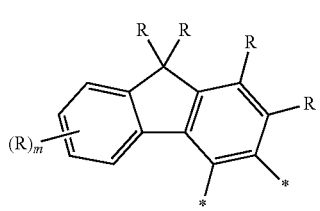

wherein

"-*" denotes a bonding site for forming a 5-membered ring containing W or a bonding site for forming a 5-membered ring containing M of the structural Formula $Q_1$ and $Q_2$;

when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R's are the same as defined above for $R_1$ and $R_2$ in claim 1, and m is an integer of 1 to 8, with a proviso that when m is 2 or greater or when two or more R's exist, the corresponding R's may be the same or different.

6. The organic light-emitting diode as set forth in claim 1, wherein the linkers $L_1$ to $L_{12}$ in Chemical Formulas A and B may be the same or different, and each may be a single bond or any one selected from among the following Structural Formulas 22 to 30:

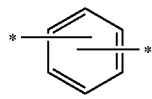

[Structural Formula 22]

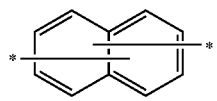

[Structural Formula 23]

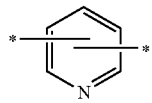

[Structural Formula 24]

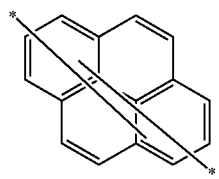

[Structural Formula 25]

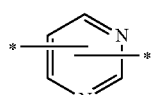

[Structural Formula 26]

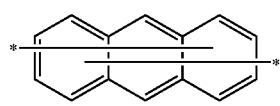

[Structural Formula 27]

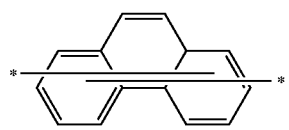

[Structural Formula 28]

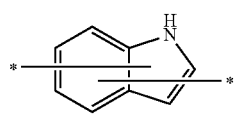

[Structural Formula 29]

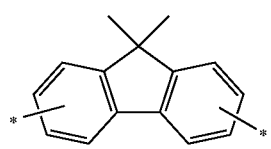

[Structural Formula 30]

wherein each of the unsubstituted carbon atoms of the aromatic ring moiety in L may be bound with a hydrogen atom or a deuterium atom.

7. The organic light-emitting diode as set forth in claim 1, wherein at least one of the substituents $R_{11}$ to $R_{15}$ in Chemical Formula D may contain a deuterium.

8. The organic light-emitting diode as set forth in claim 7, wherein $R_{11}$ is a deuterium, and k is 5.

9. The organic light-emitting diode as set forth in claim 7, wherein $R_{12}$ and/or $R_{13}$ is a deuterium, and l is an integer of 2 or greater or m is an integer of 2 or greater.

10. The organic light-emitting diode as set forth in claim 7, wherein $R_{14}$ and/or $R_{15}$ is a deuterium, and n is an integer of 2 or greater or o is an integer of 2 or greater.

11. The organic light-emitting diode as set forth in claim 1, wherein W in Chemical Formulas A and B is $CR_1R_2$ or $SiR_1R_2$.

12. The organic light-emitting diode as set forth in claim 1, wherein the amine compound is any one selected from among compounds represented by the following Chemical Formulas 1 to 239:

<Chemical Formula 1>

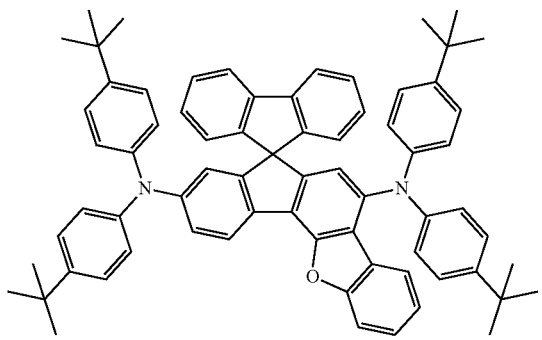

<Chemical Formula 2>

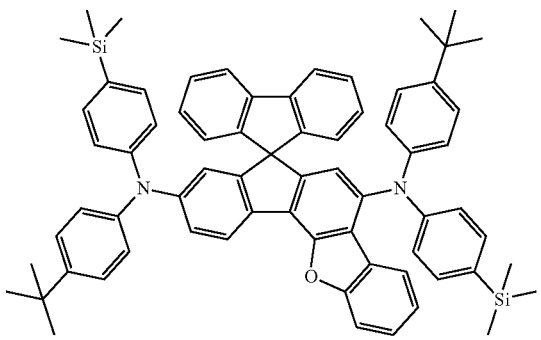

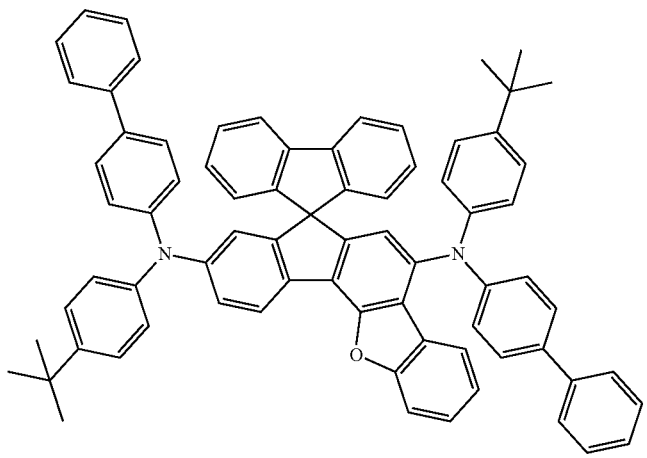
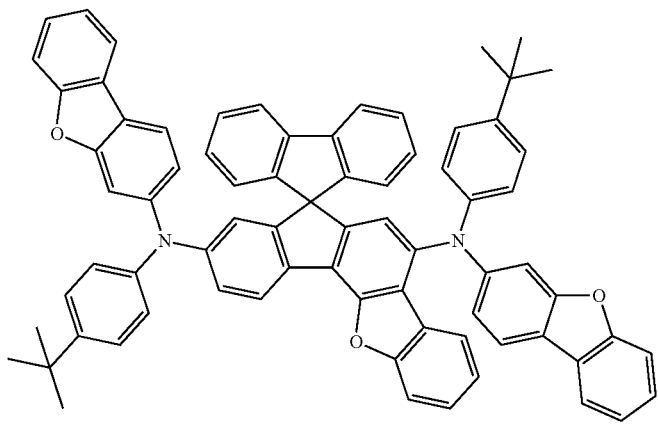
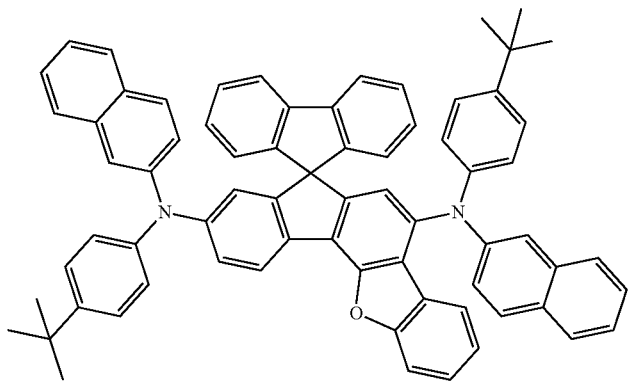
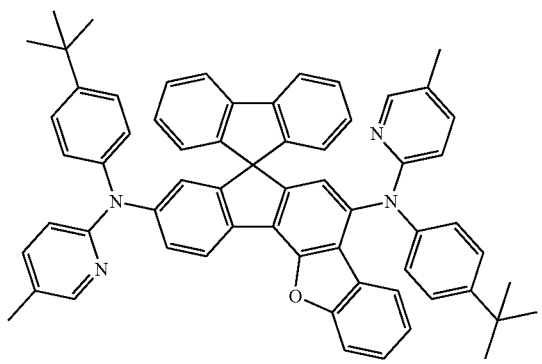
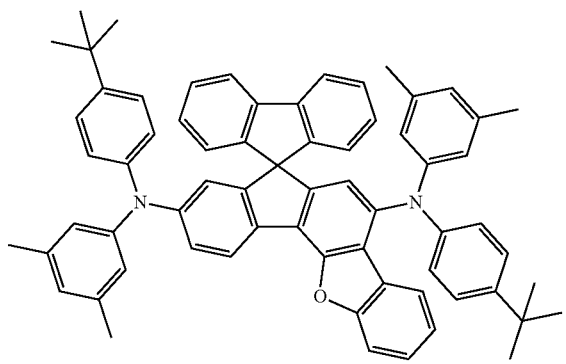

<Chemical Formula 8>
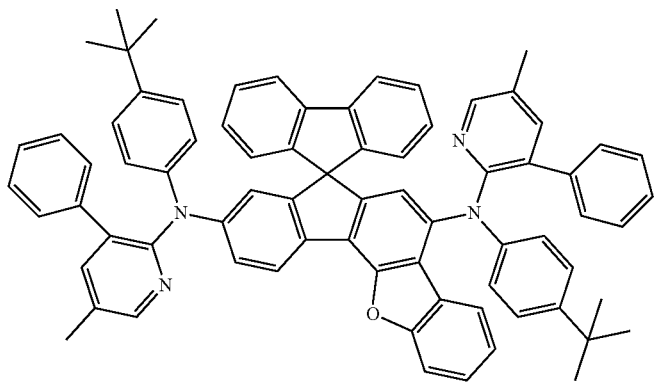
<Chemical Formula 9>
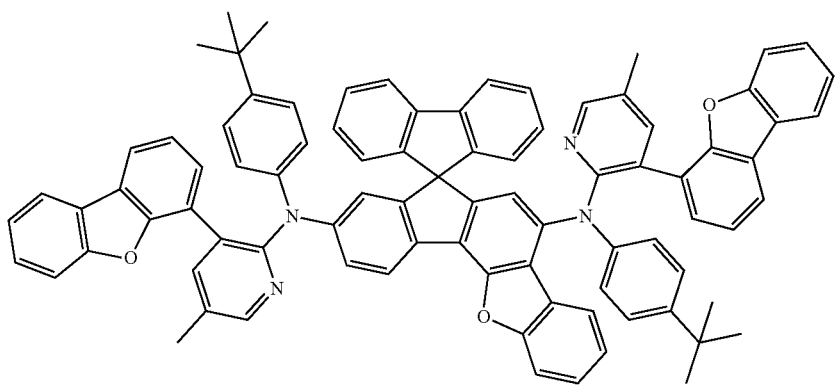
<Chemical Formula 10>
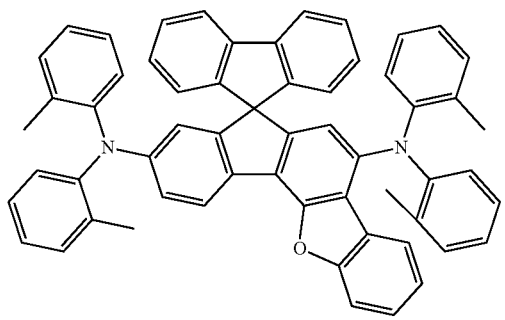
<Chemical Formula 11>
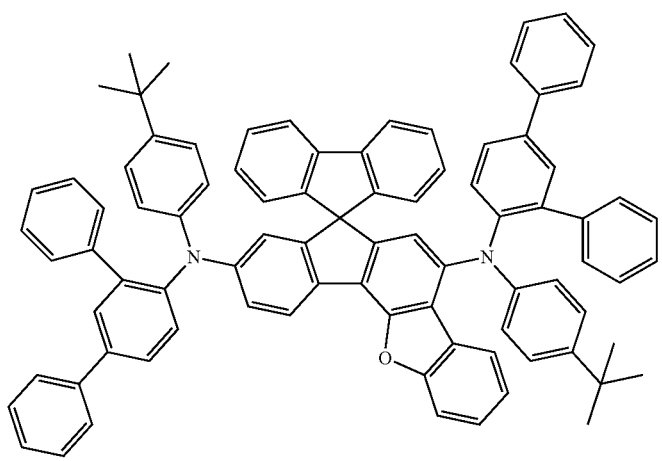

-continued
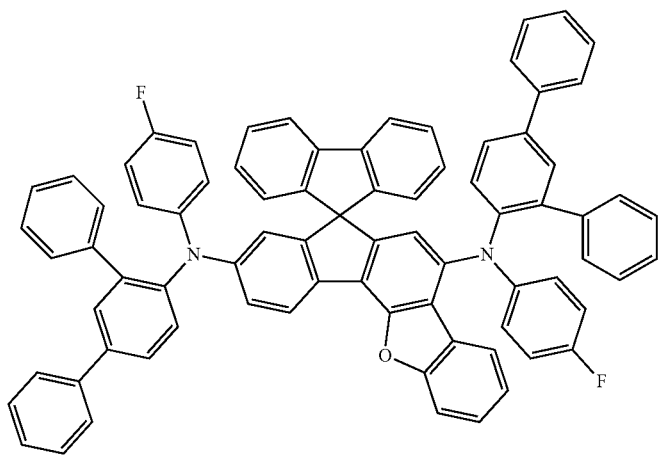
<Chemical Formula 12>
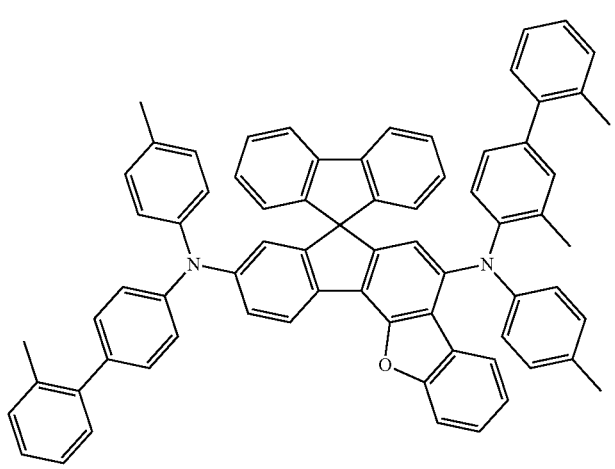
<Chemical Formula 13>
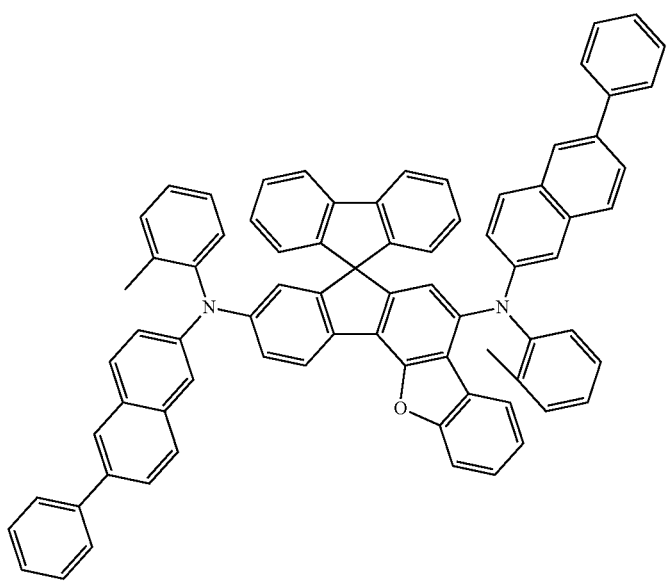
<Chemical Formula 14>

<Chemical Formula 15>
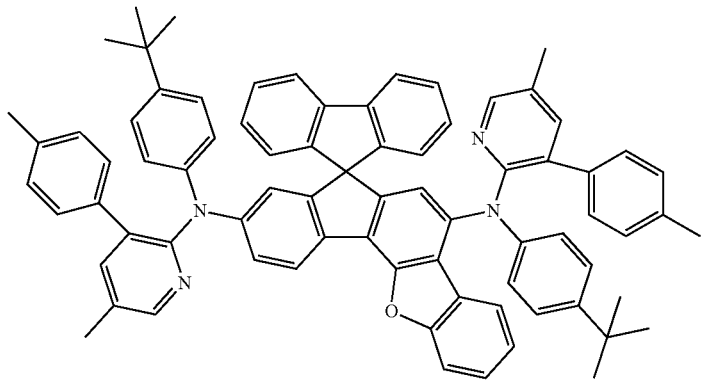
<Chemical Formula 16>
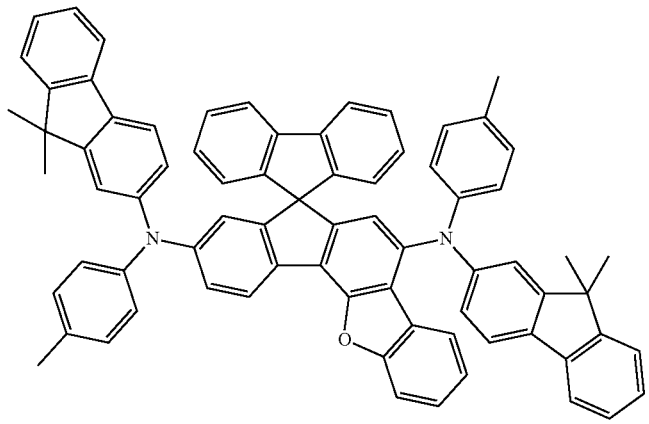
<Chemical Formula 17>
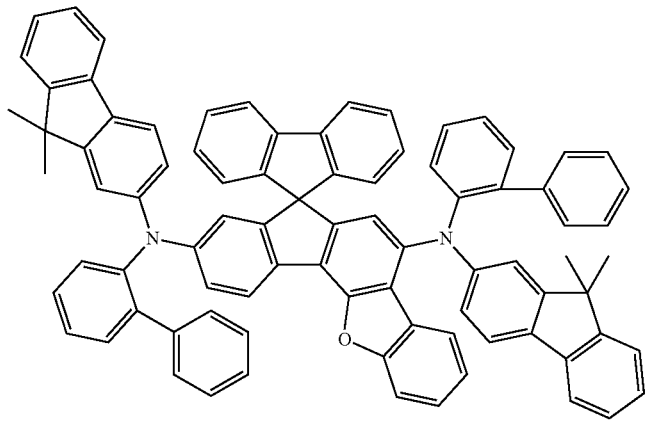
<Chemical Formula 18>
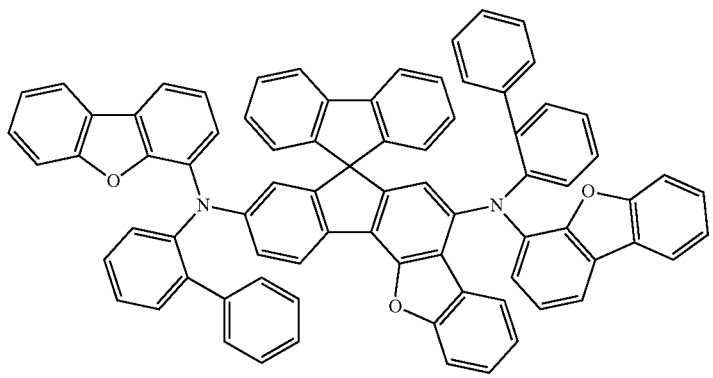

<Chemical Formula 19>
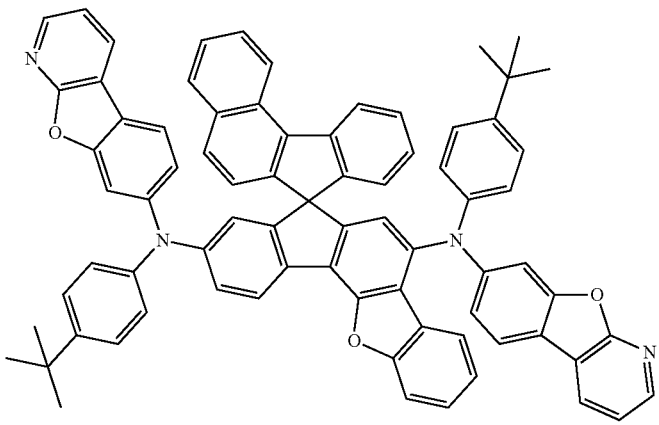
<Chemical Formula 20>
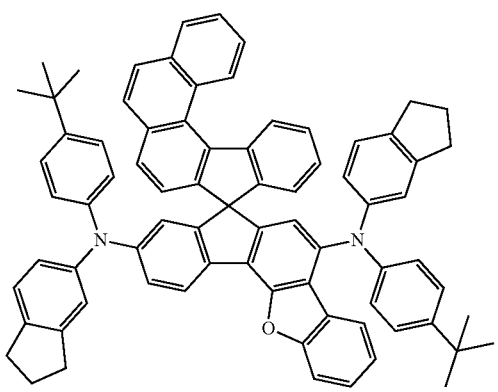
<Chemical Formula 21>
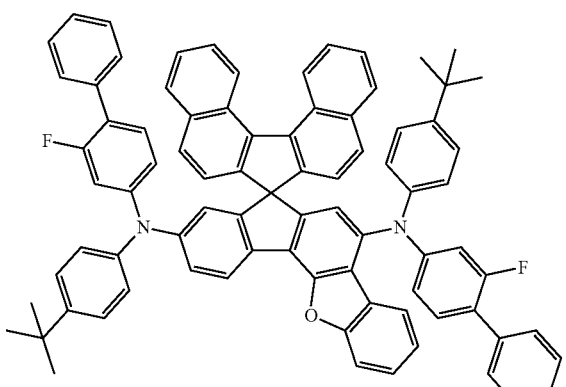
<Chemical Formula 22>
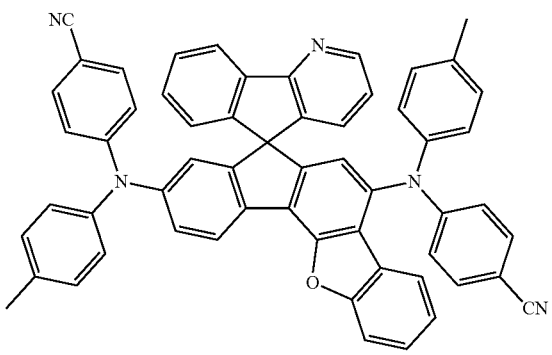
<Chemical Formula 23>
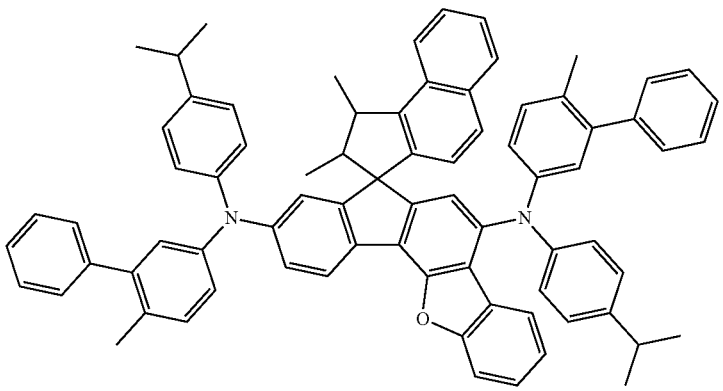

<Chemical Formula 24>
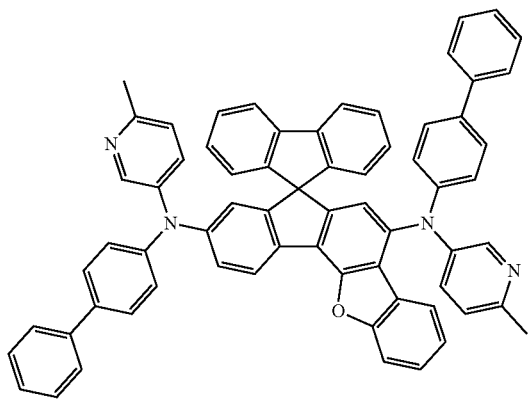
<Chemical Formula 25>
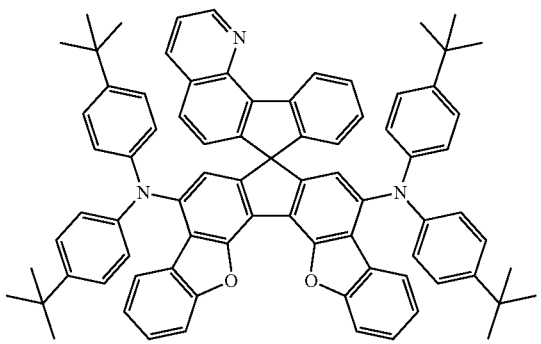
<Chemical Formula 26>
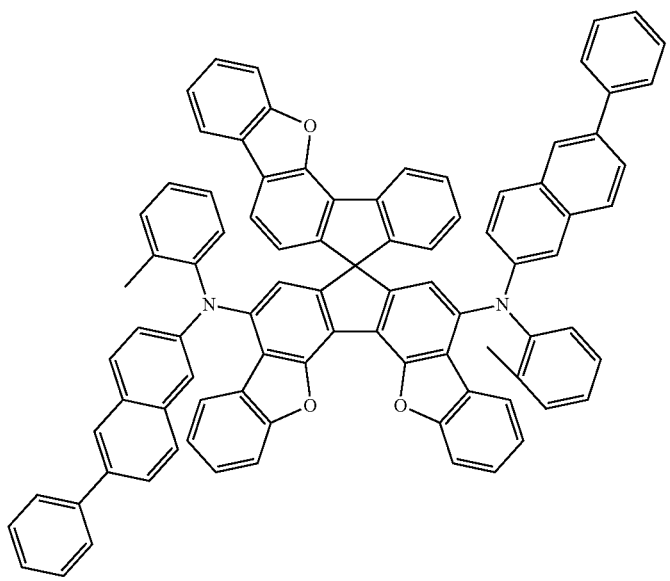
<Chemical Formula 27>
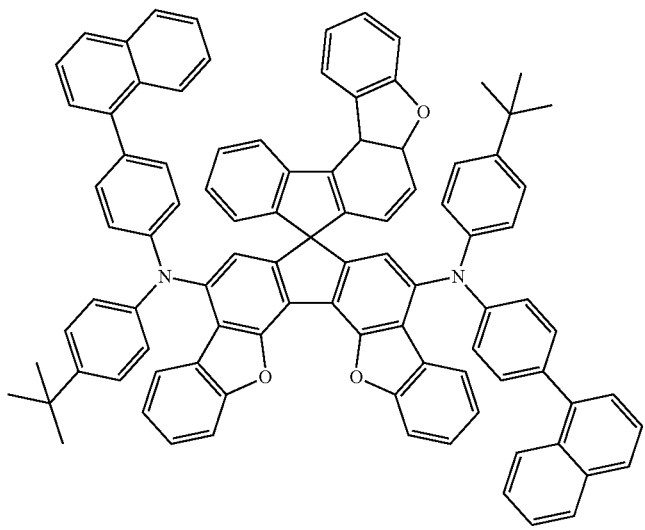

-continued
<Chemical Formula 28>
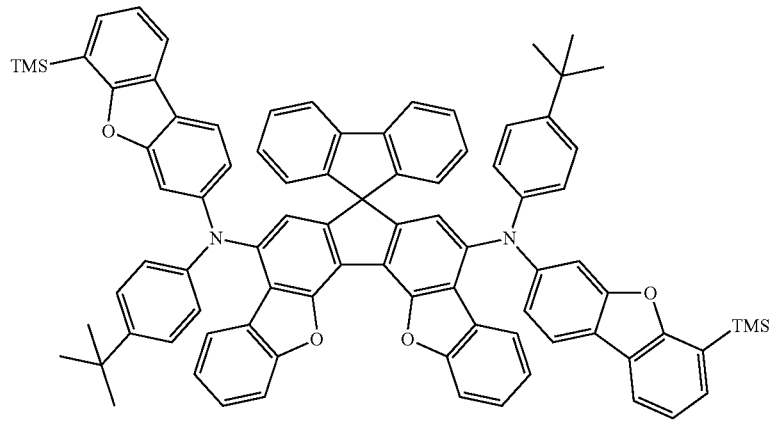
<Chemical Formula 29>
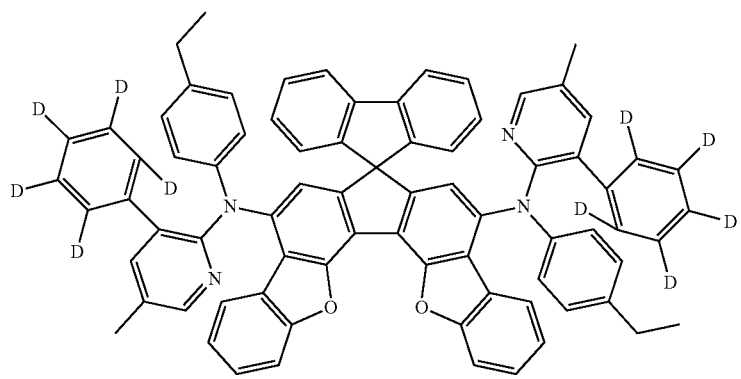
<Chemical Formula 30>
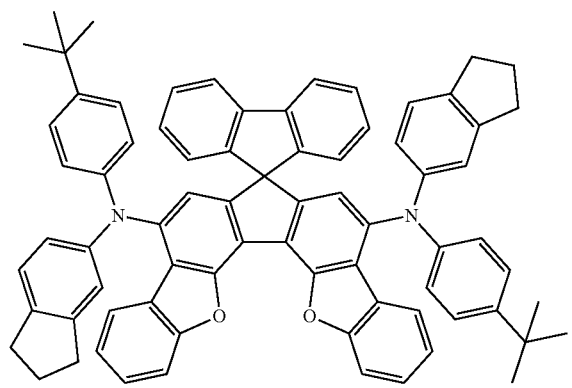
<Chemical Formula 31>
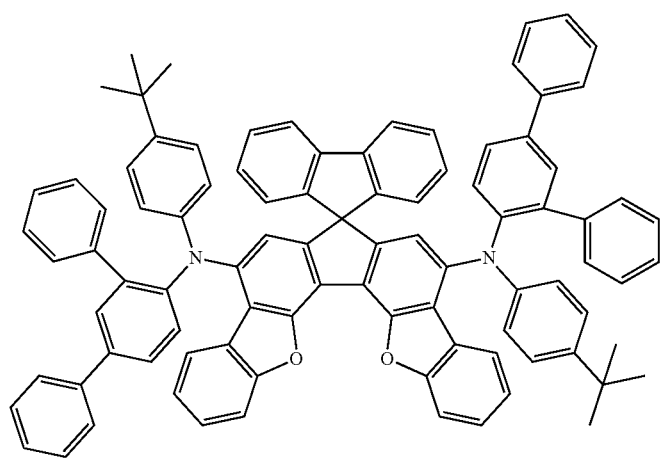

<Chemical Formula 32>
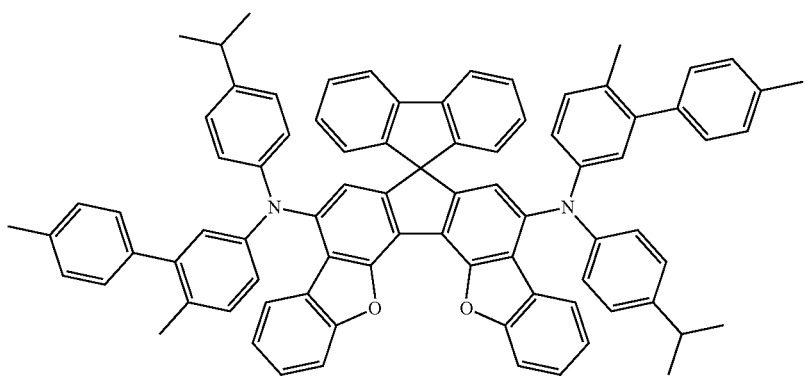
<Chemical Formula 33>
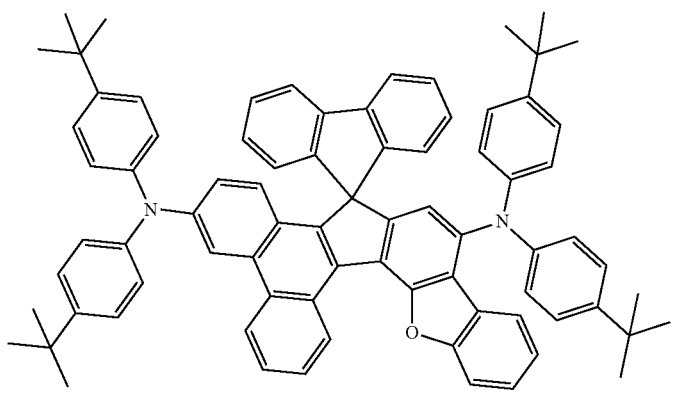
<Chemical Formula 34>
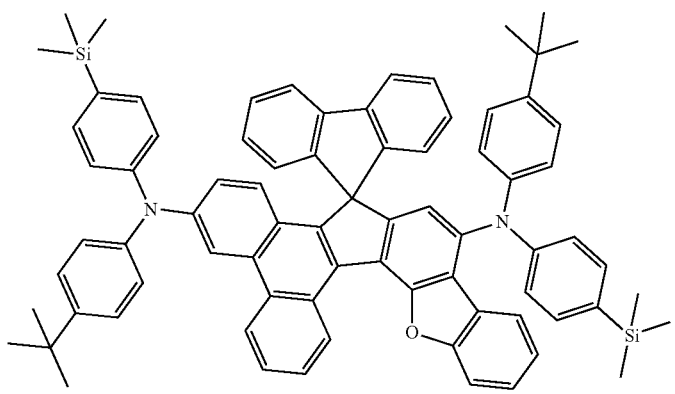

<Chemical Formula 35>
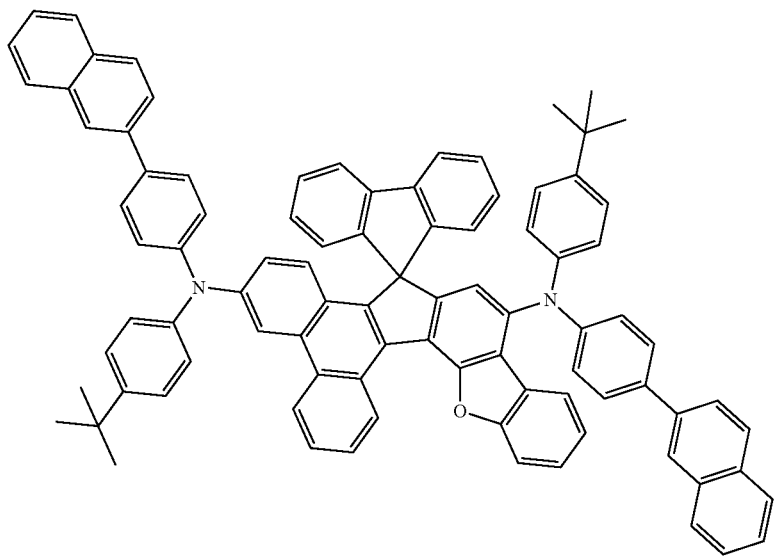
<Chemical Formula 36>
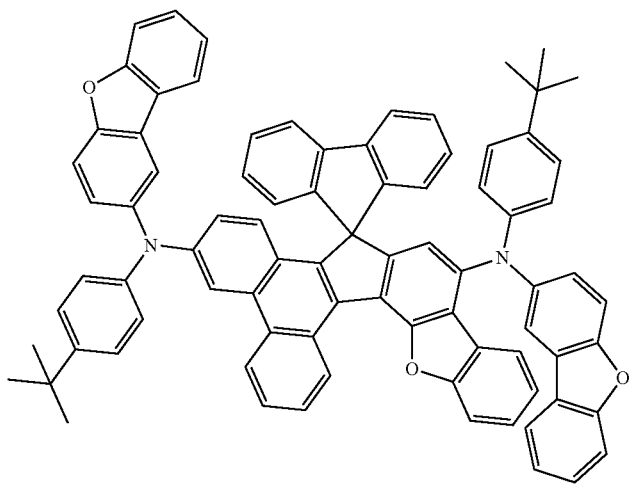
<Chemical Formula 37>
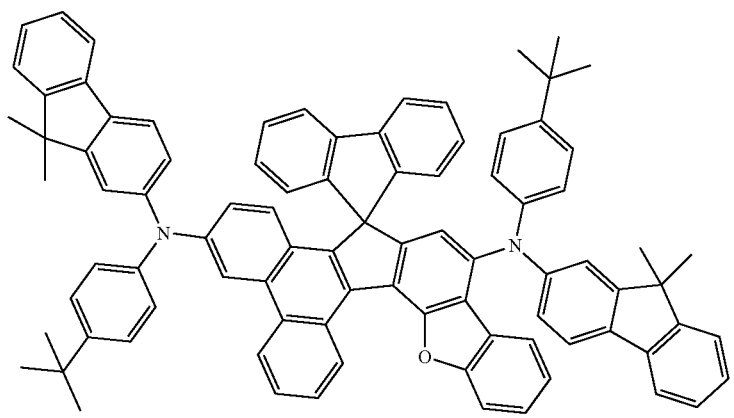

<Chemical Formula 38>
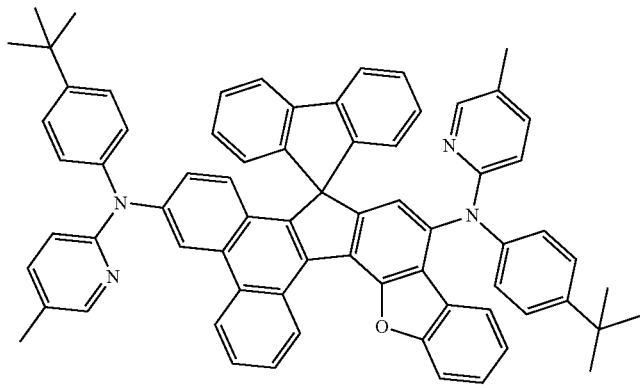
<Chemical Formula 39>
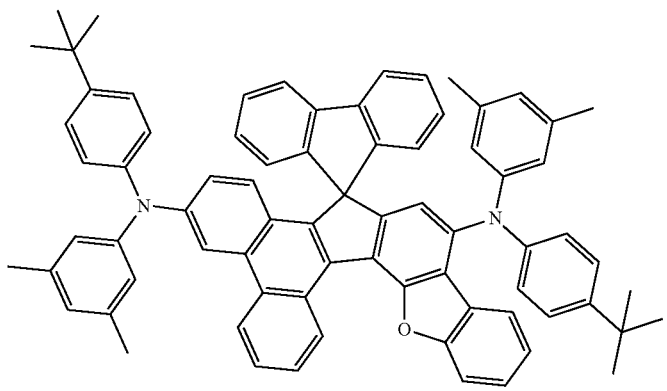
<Chemical Formula 40>
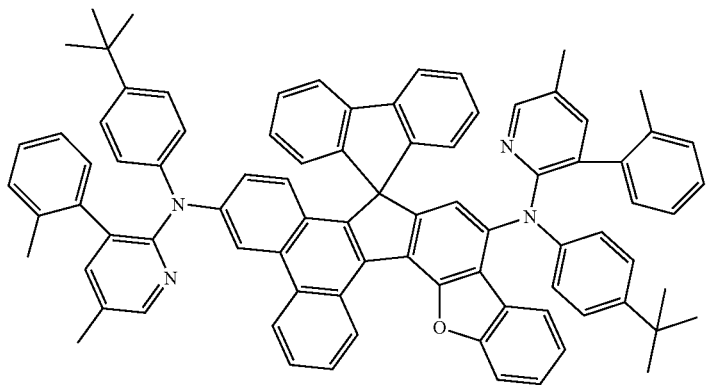
<Chemical Formula 41>
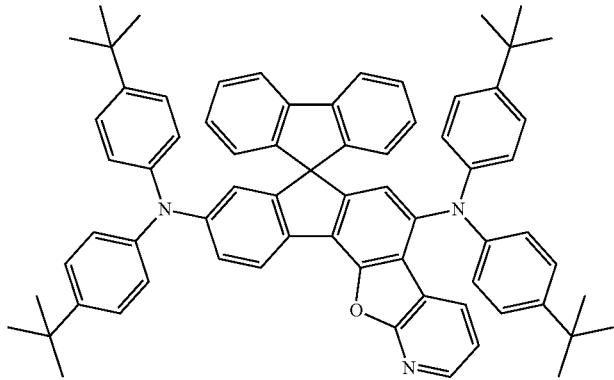

-continued
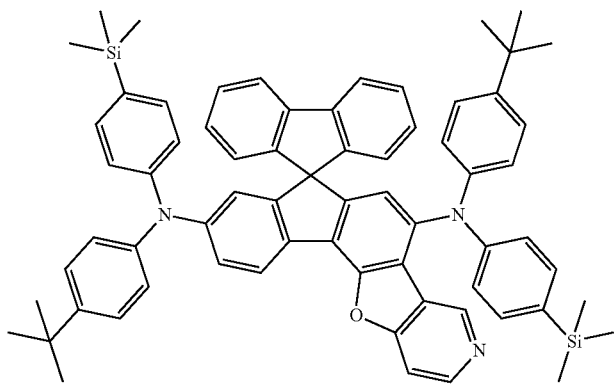
<Chemical Formula 42>
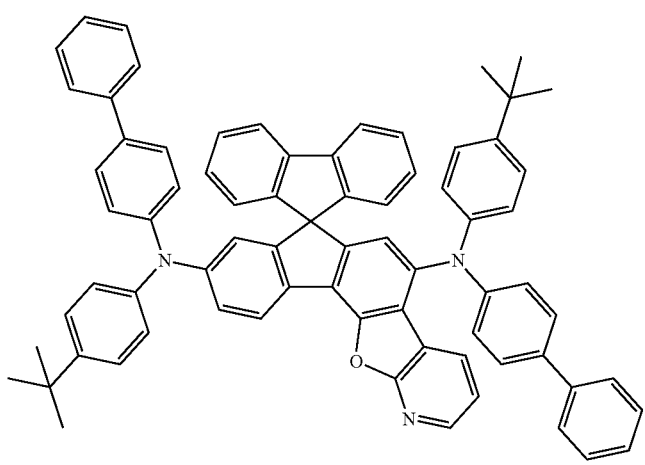
<Chemical Formula 43>
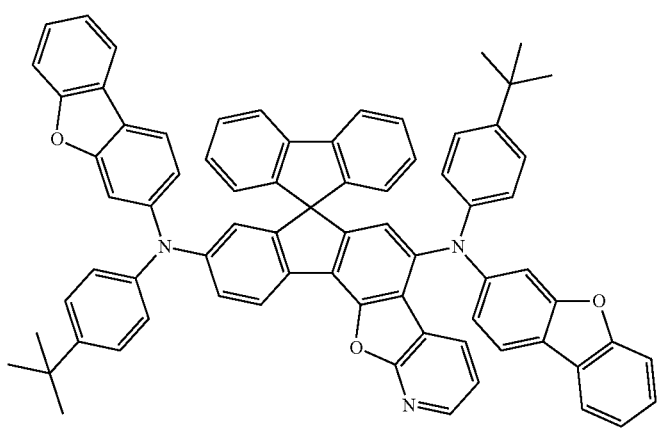
<Chemical Formula 44>

<Chemical Formula 45>
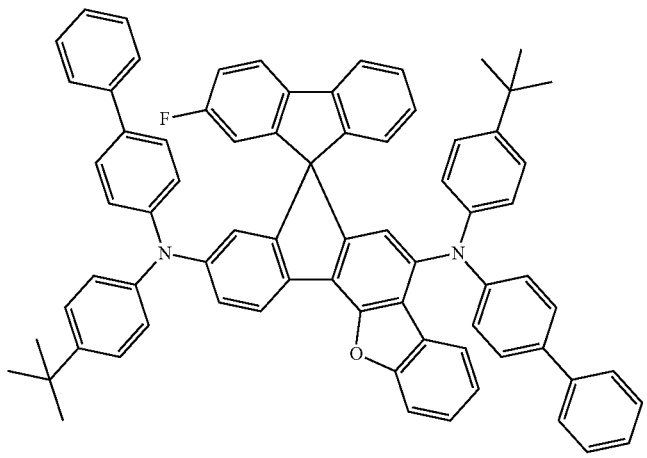
<Chemical Formula 46>
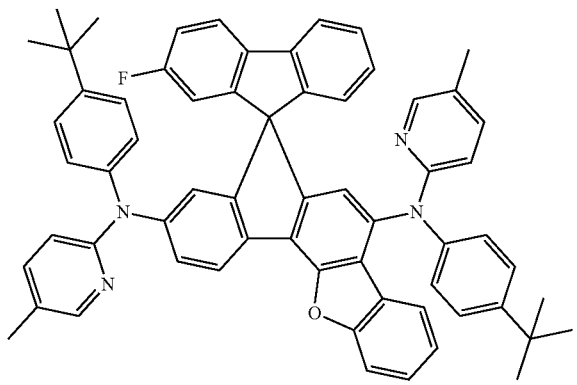
<Chemical Formula 47>
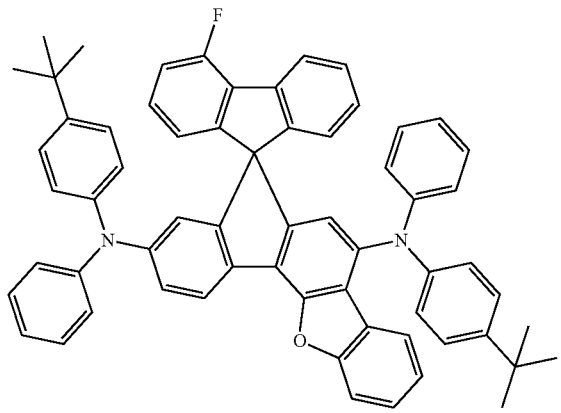
<Chemical Formula 48>
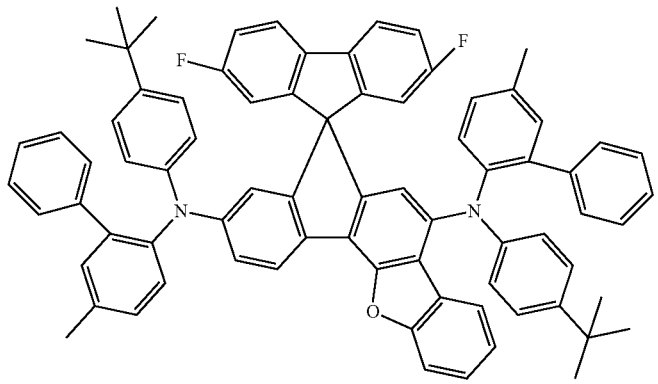

-continued
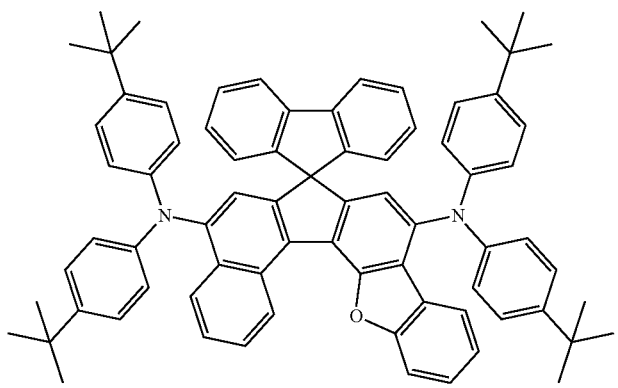
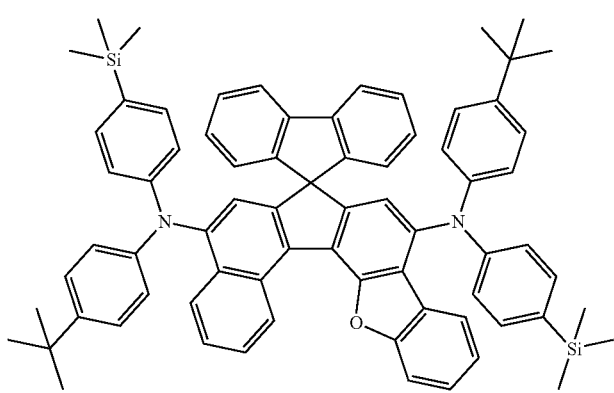
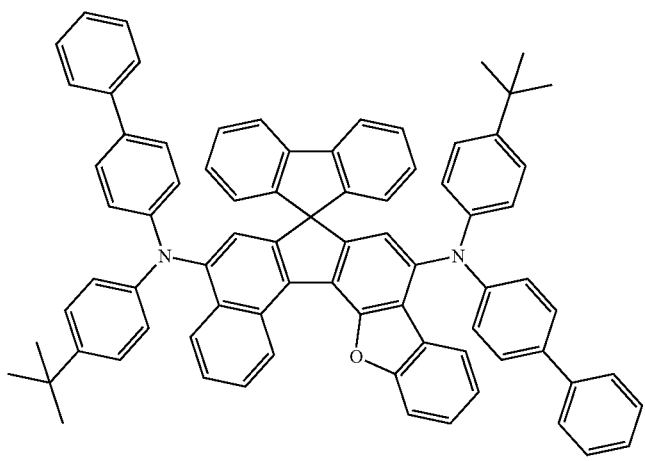
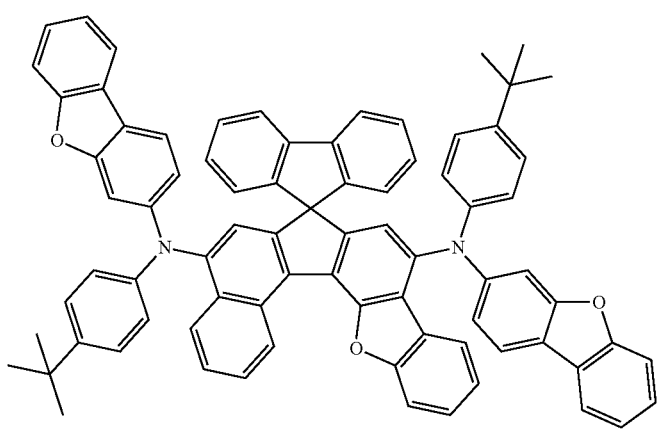
<Chemical Formula 49>
<Chemical Formula 50>
<Chemical Formula 51>
<Chemical Formula 52>

-continued
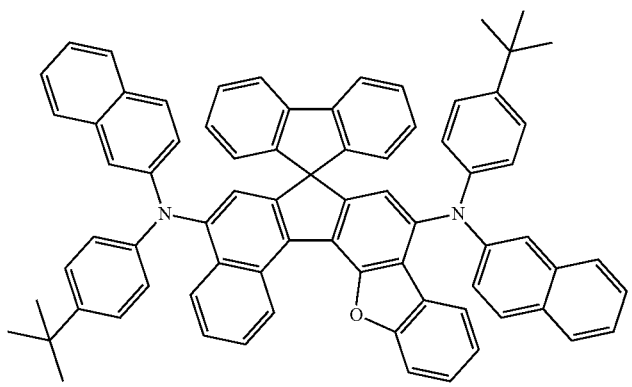
<Chemical Formula 53>
<Chemical Formula 54>
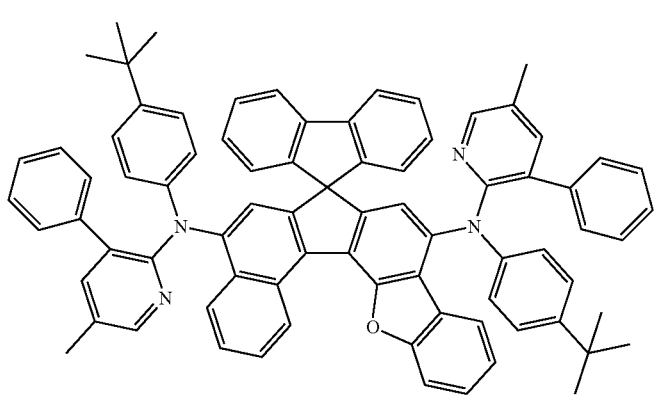
<Chemical Formula 55>
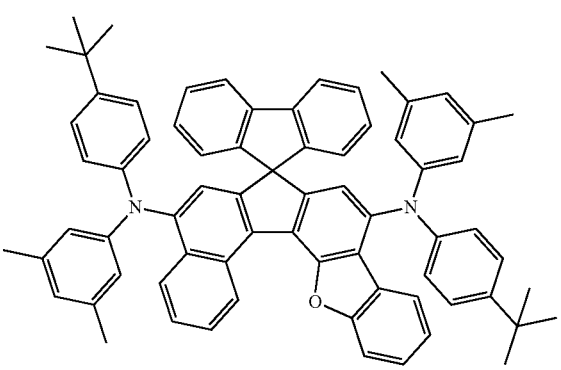
<Chemical Formula 56>
<Chemical Formula 57>
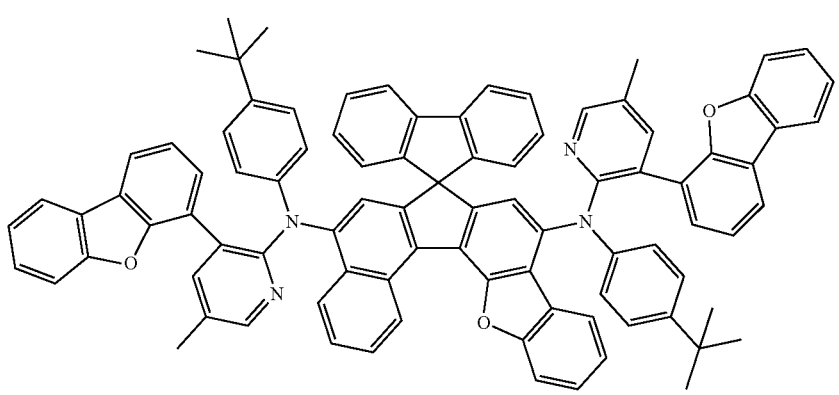

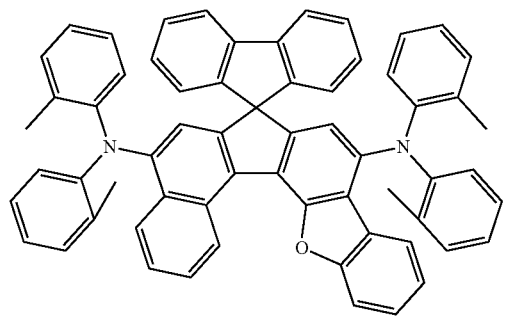
<Chemical Formula 58>
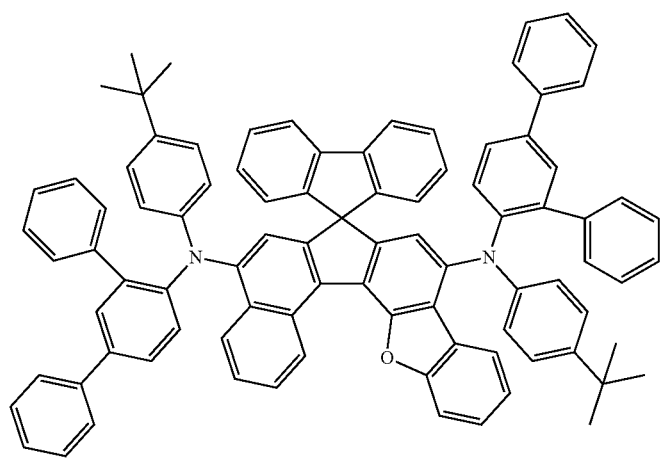
<Chemical Formula 59>
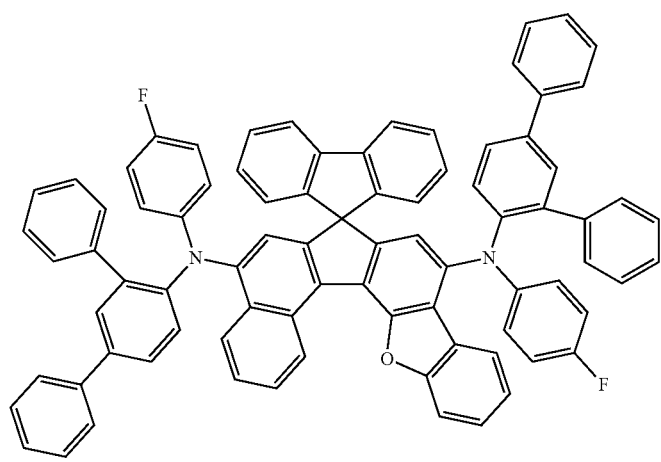
<Chemical Formula 60>

-continued
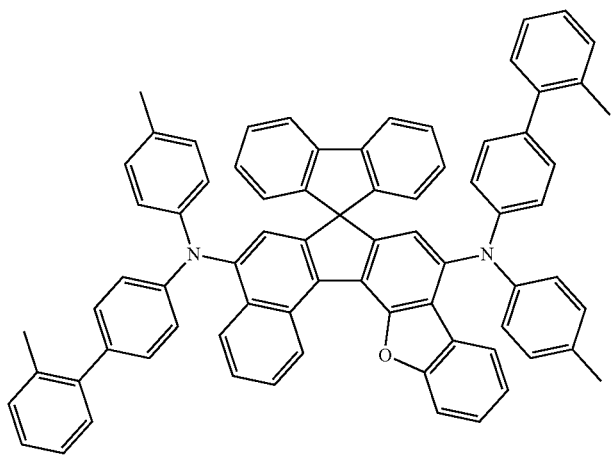
<Chemical Formula 61>
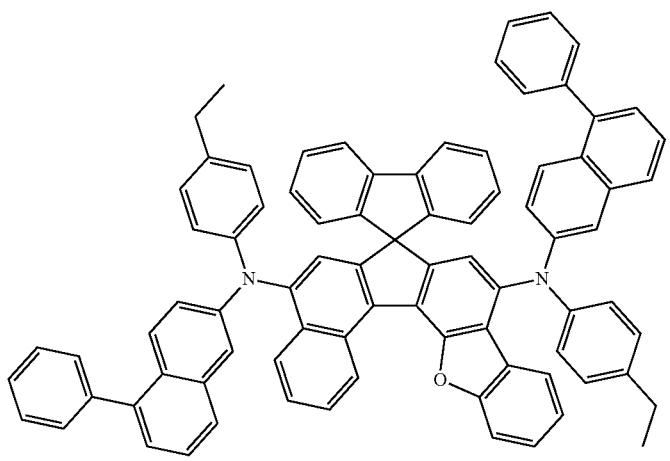
<Chemical Formula 62>
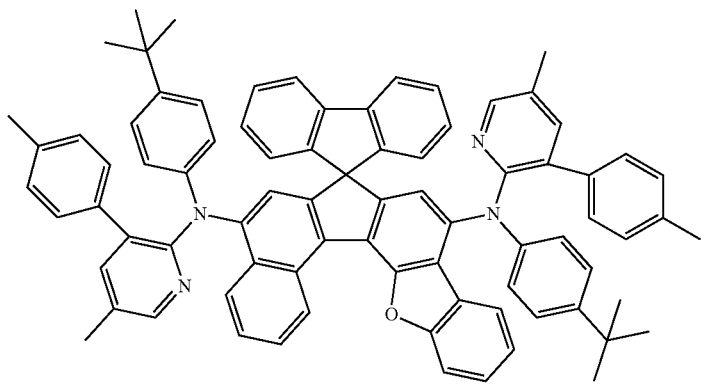
<Chemical Formula 63>

<Chemical Formula 64>
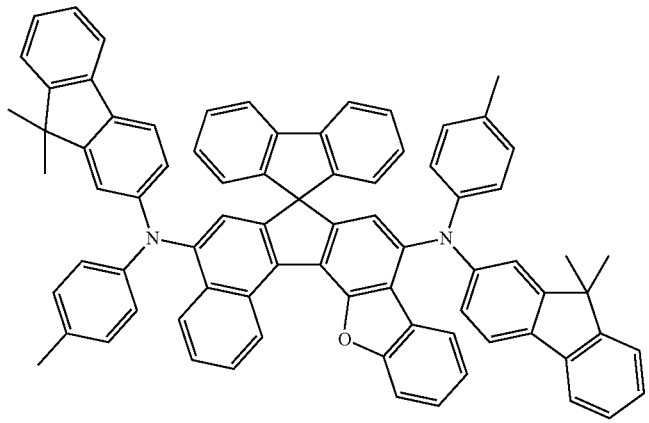
<Chemical Formula 65>
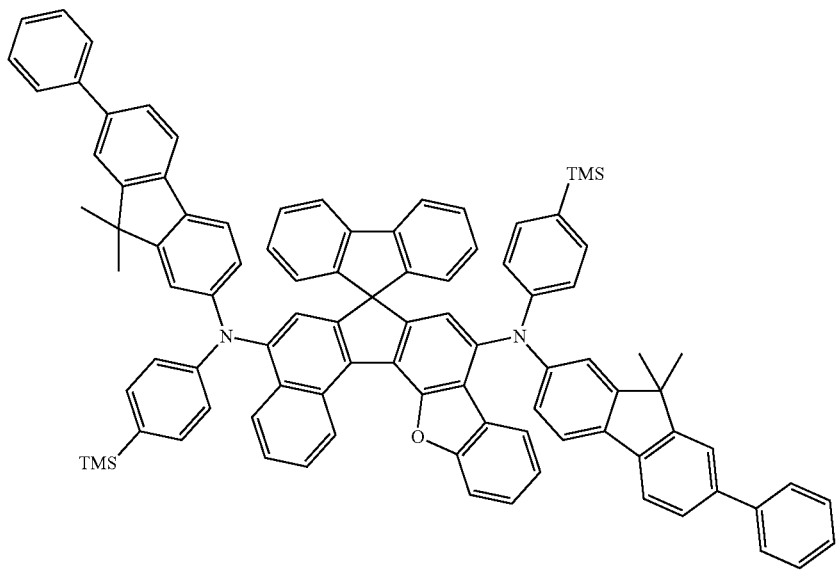
<Chemical Formula 66>
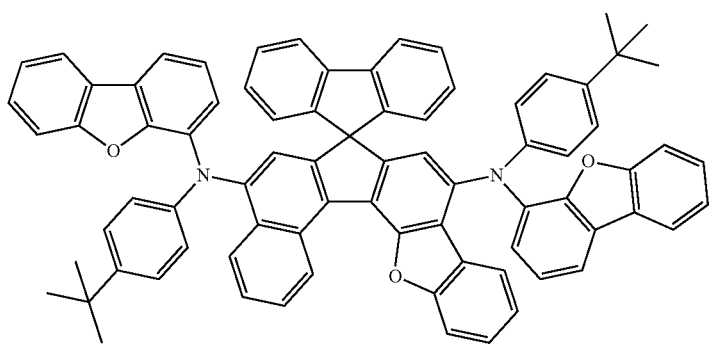

<Chemical Formula 67>
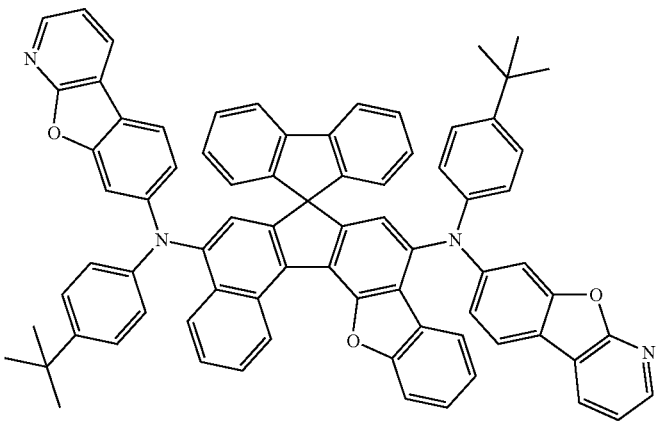
<Chemical Formula 68>
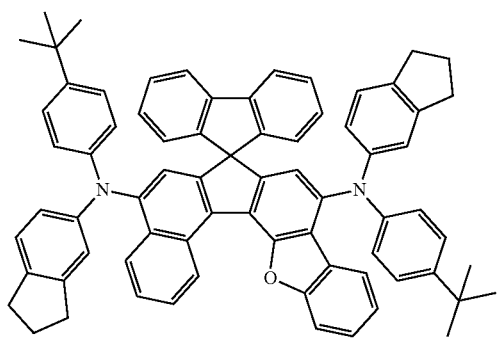
<Chemical Formula 69>
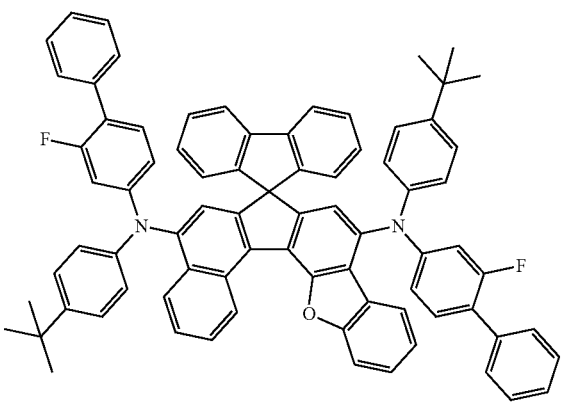
<Chemical Formula 70>
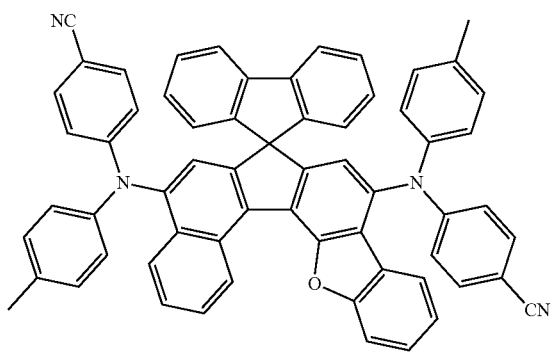
<Chemical Formula 71>
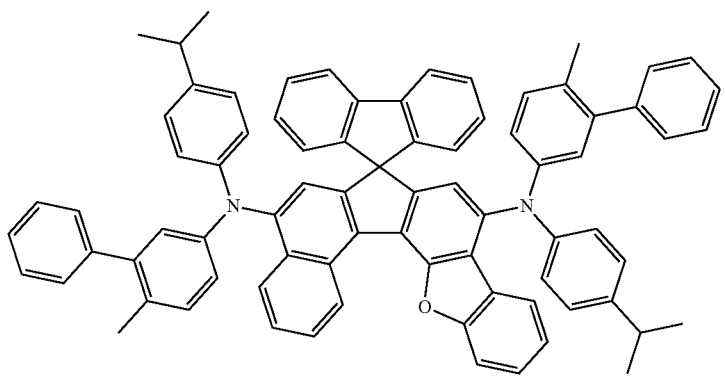

<Chemical Formula 72>
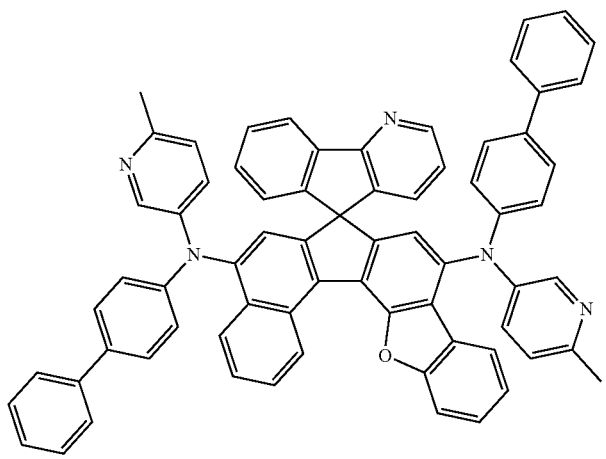
<Chemical Formula 73>
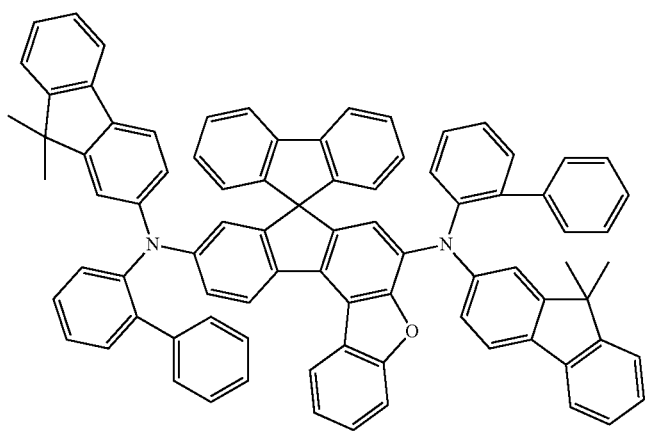
<Chemical Formula 74>
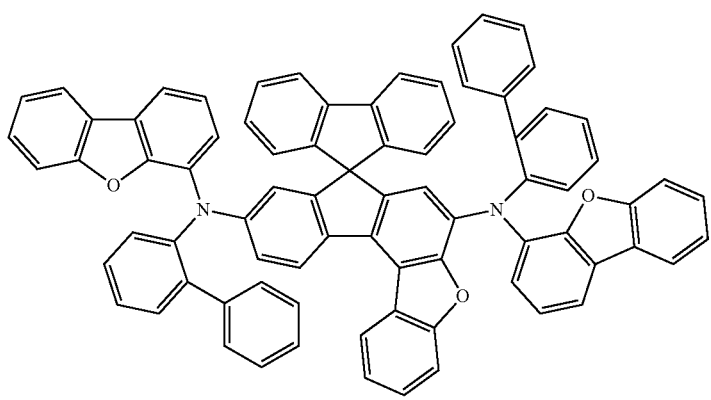

<Chemical Formula 75>
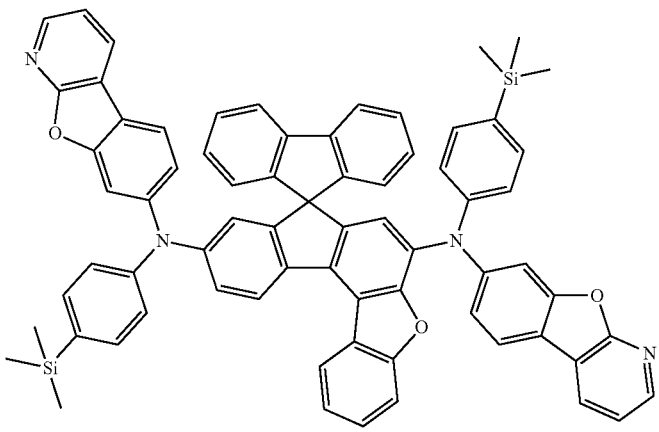
<Chemical Formula 76>
<Chemical Formula 77>
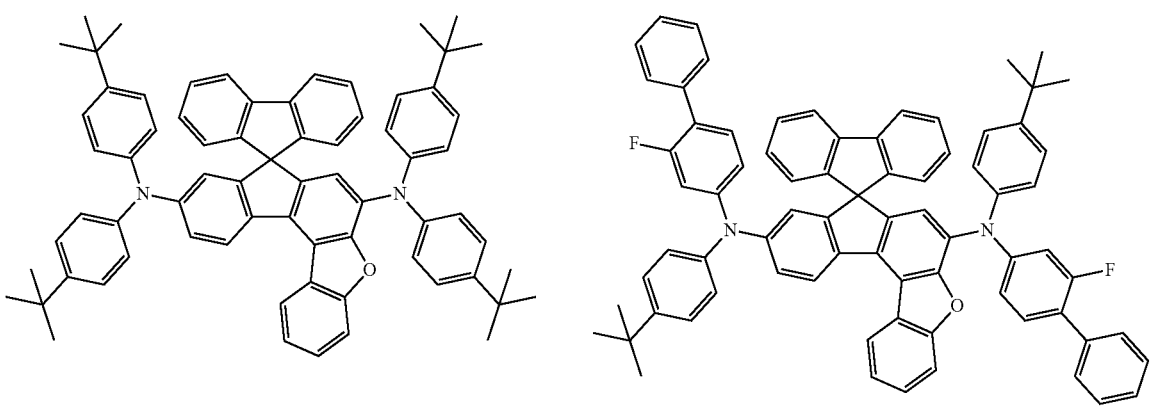
<Chemical Formula 78>
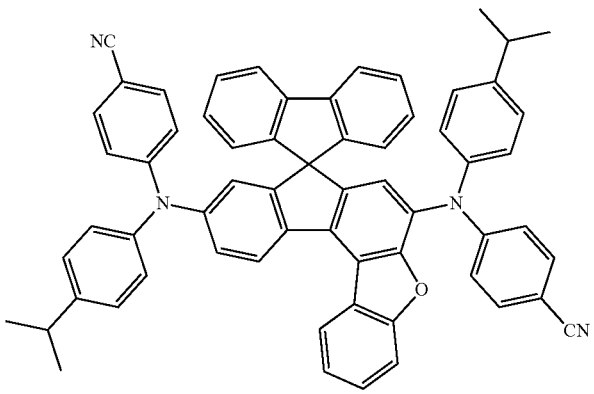

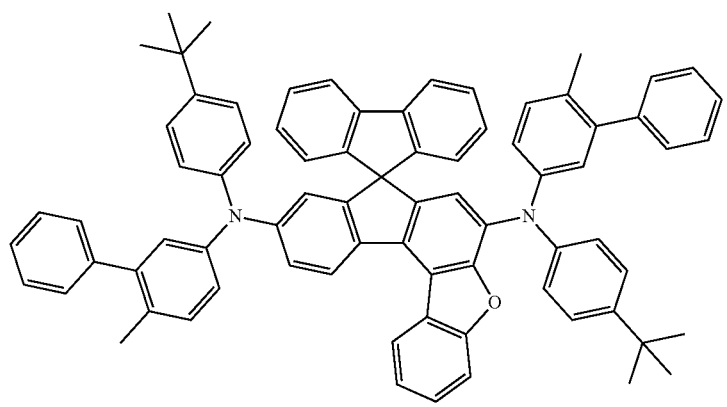
<Chemical Formula 79>
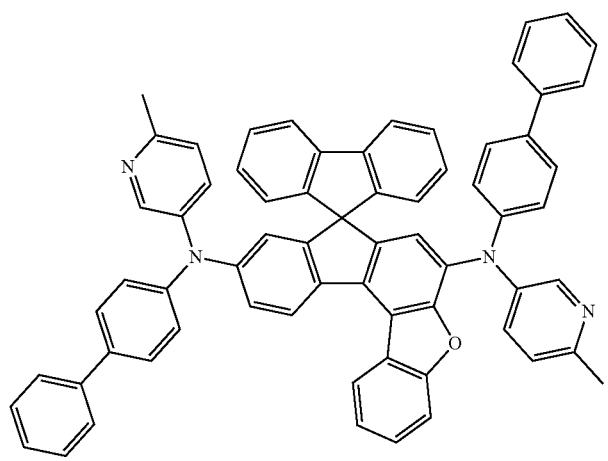
<Chemical Formula 80>
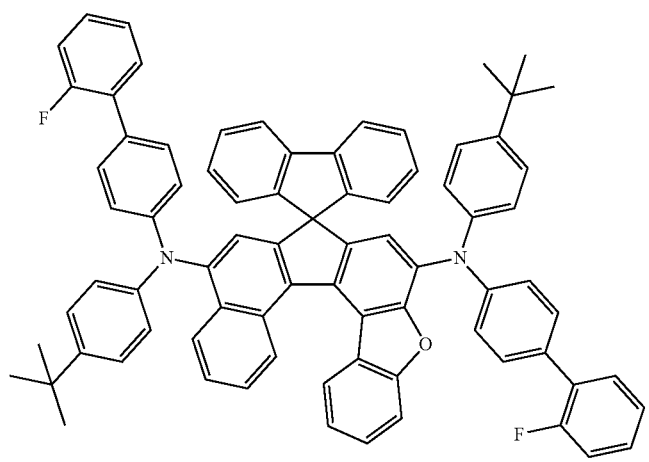
<Chemical Formula 81>

-continued
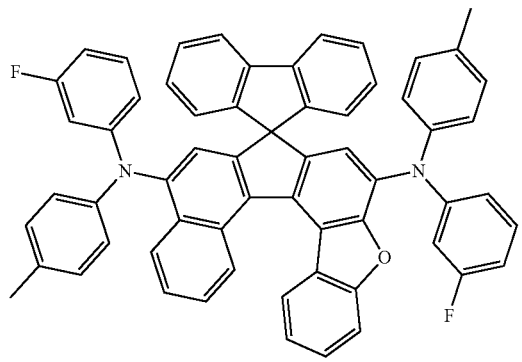
<Chemical Formula 82>
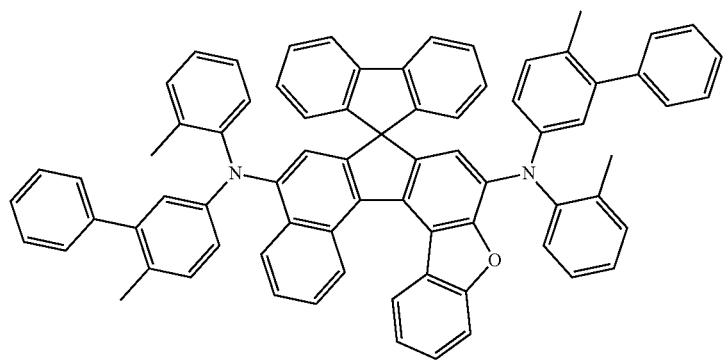
<Chemical Formula 83>
<Chemical Formula 84>
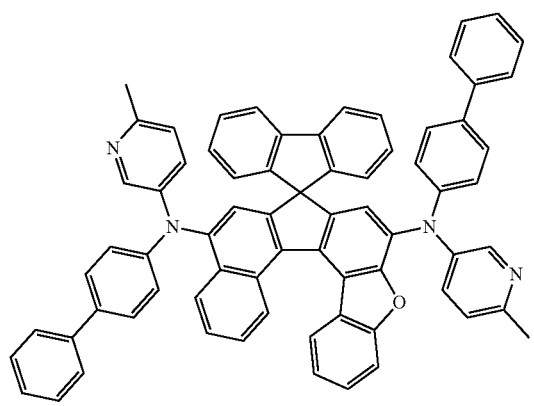
<Chemical Formula 85>
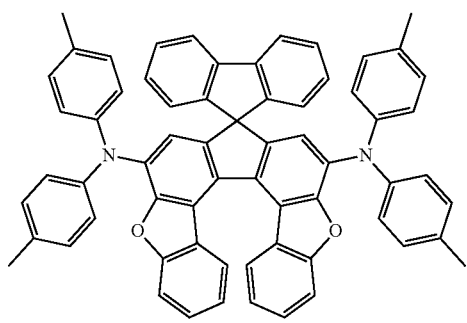
<Chemical Formula 86>
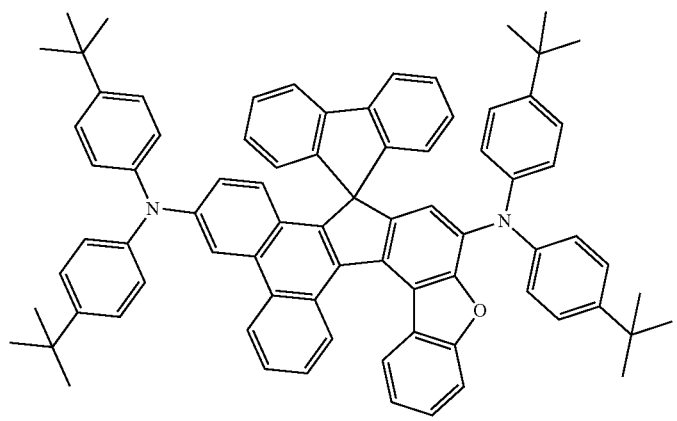

<Chemical Formula 87>
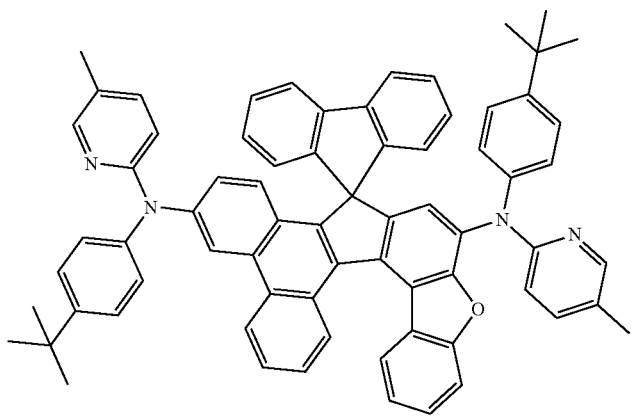
<Chemical Formula 88>
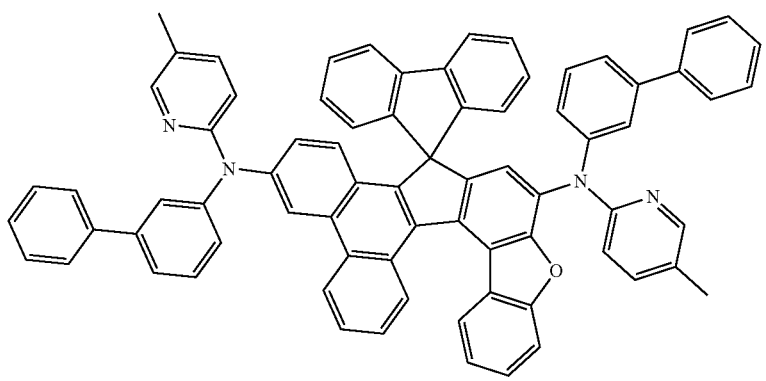
<Chemical Formula 89> <Chemical Formula 90>
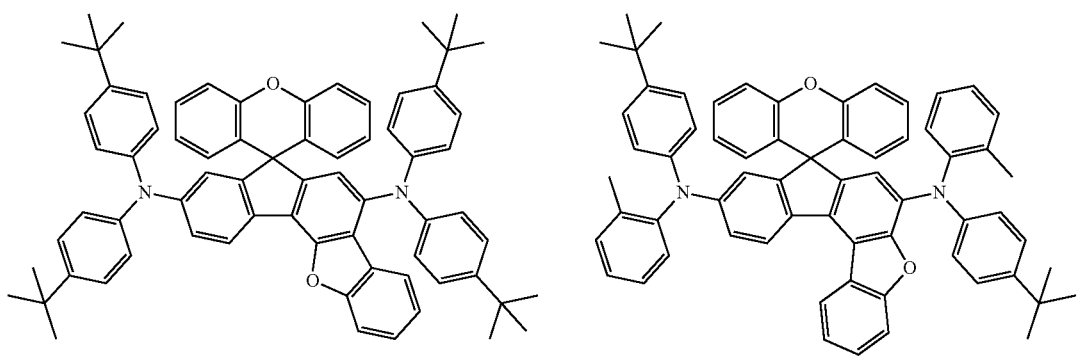
<Chemical Formula 91>
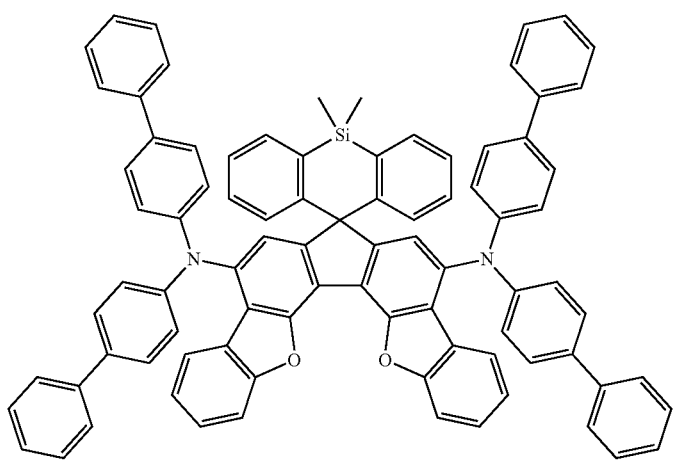

<Chemical Formula 92>
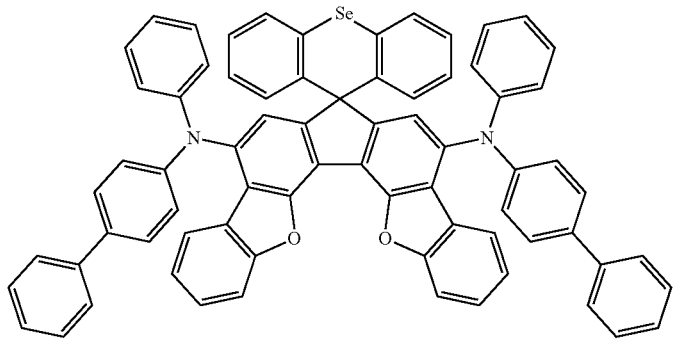
<Chemical Formula 93>
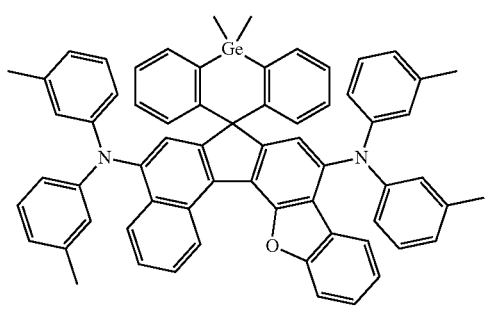
<Chemical Formula 94>
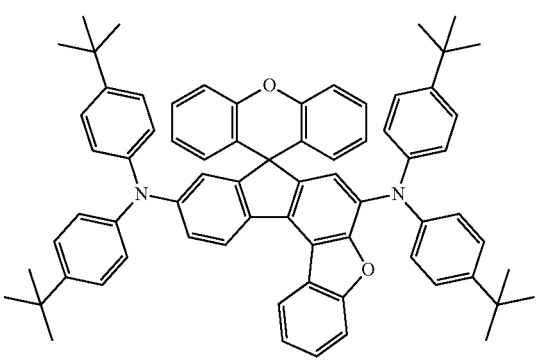
<Chemical Formula 95>
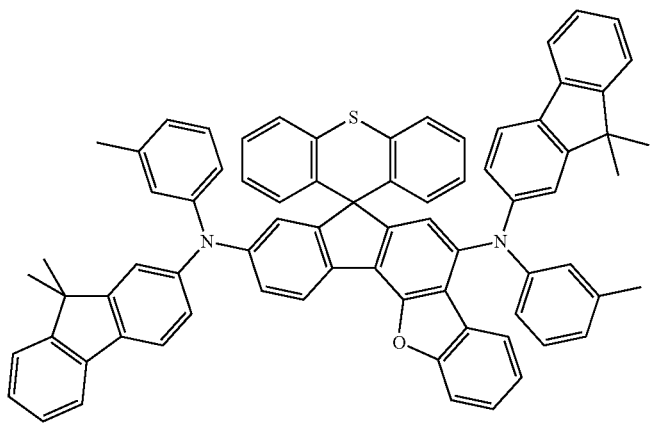
<Chemical Formula 96>
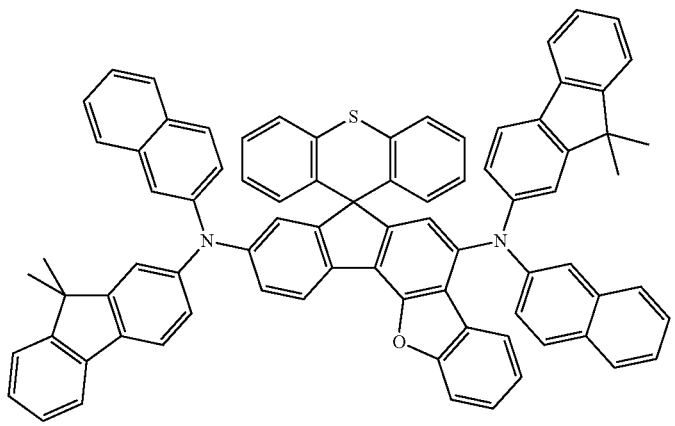

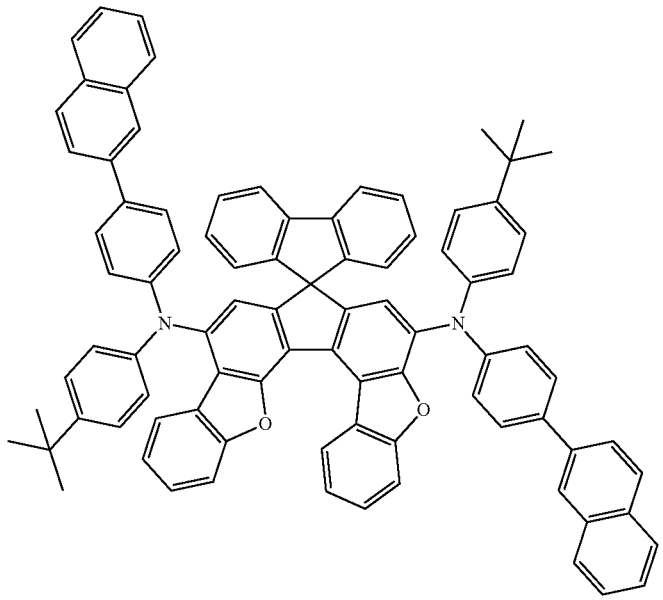
<Chemical Formula 97>
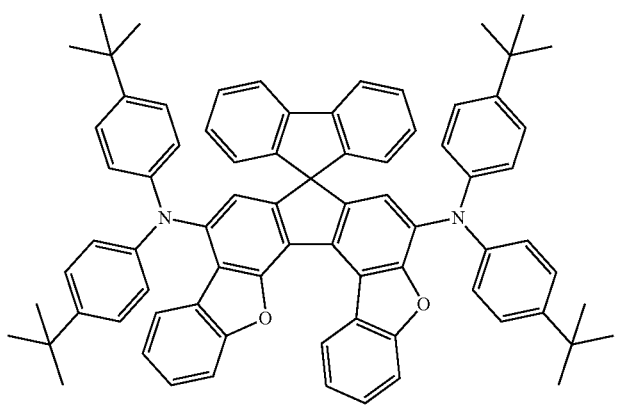
<Chemical Formula 98>
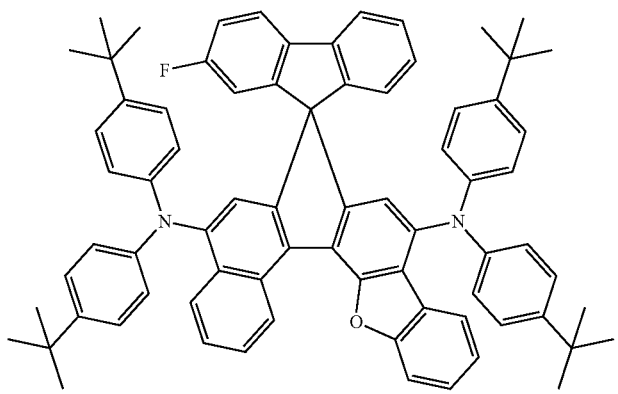
<Chemical Formula 99>

<Chemical Formula 100>
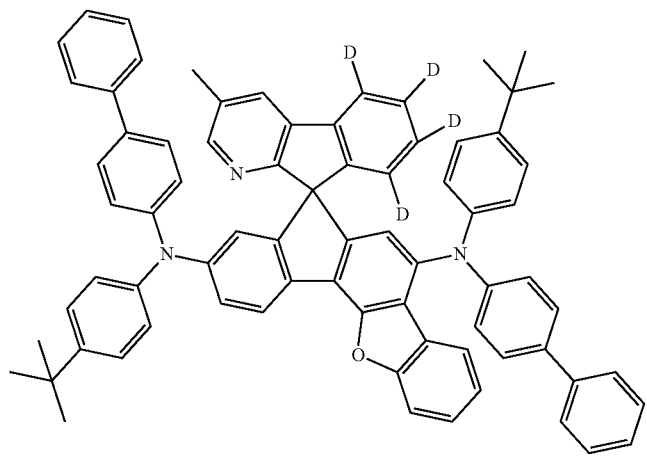
<Chemical Formula 101>
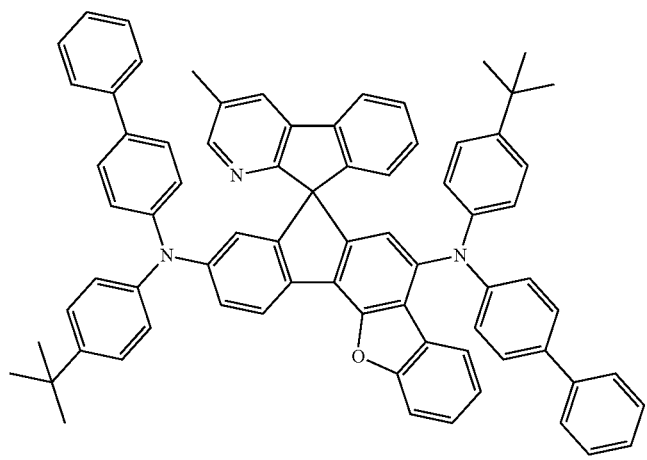
<Chemical Formula 102>
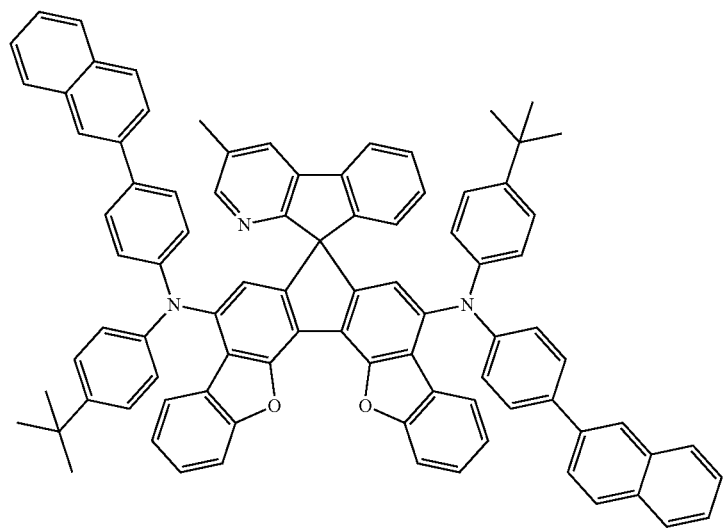

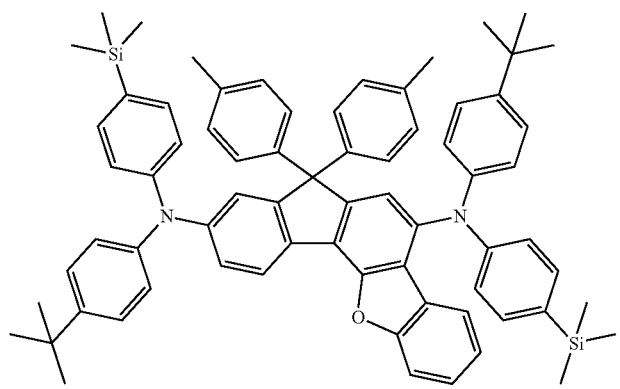
<Chemical Formula 103>
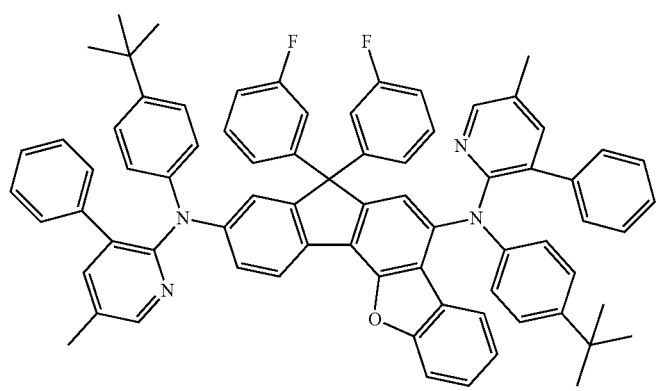
<Chemical Formula 104>
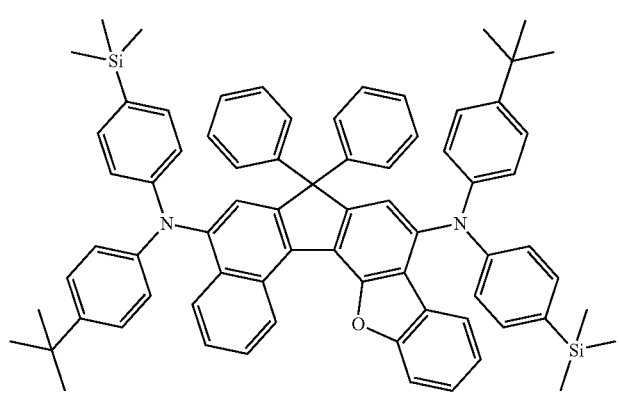
<Chemical Formula 105>
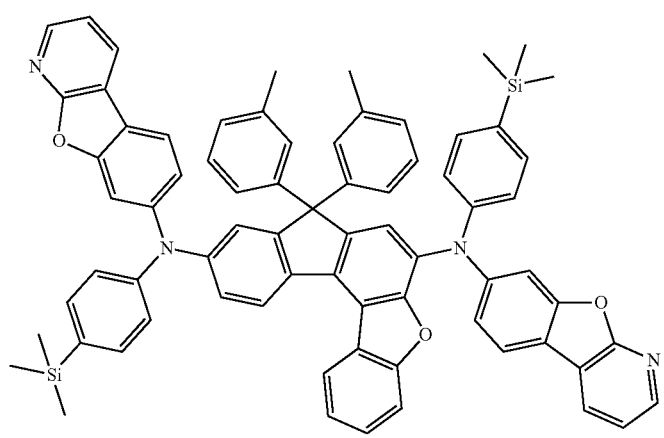
<Chemical Formula 106>

-continued
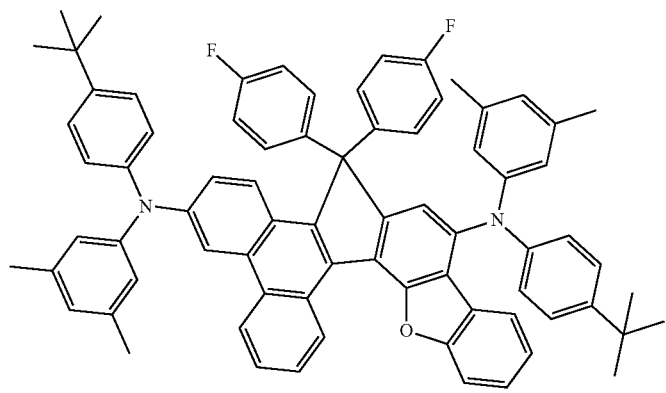
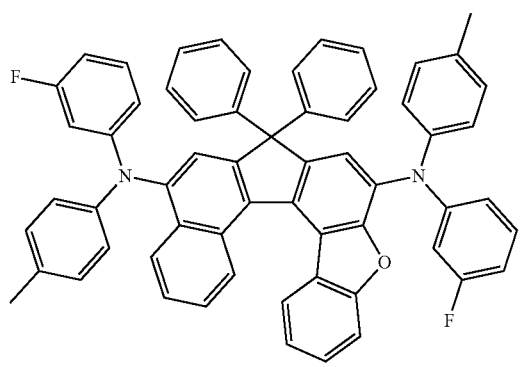
<Chemical Formula 107>
<Chemical Formula 108>
<Chemical Formula 109>
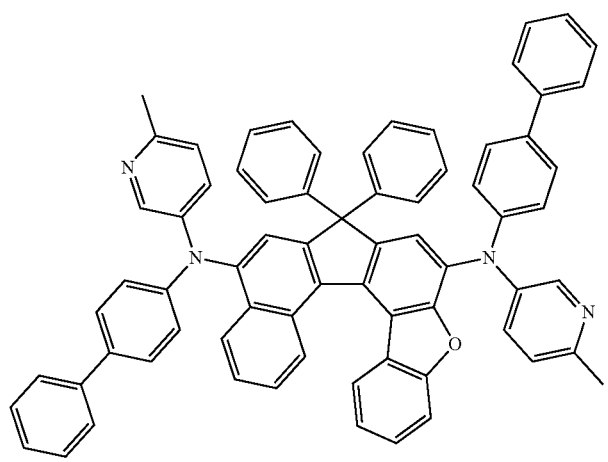

<Chemical Formula 110>
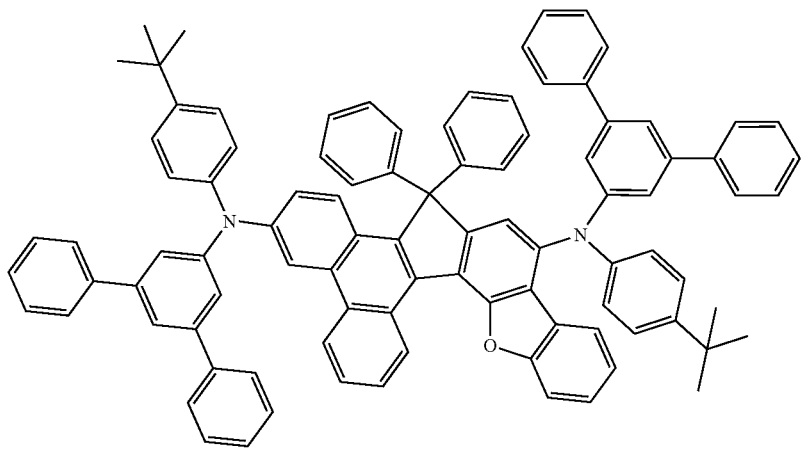
<Chemical Formula 111>
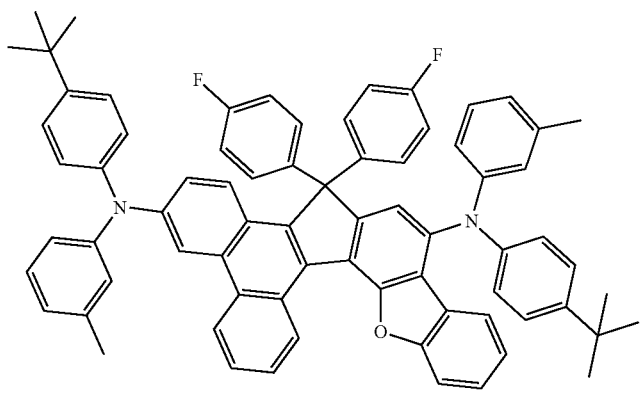
<Chemical Formula 112>
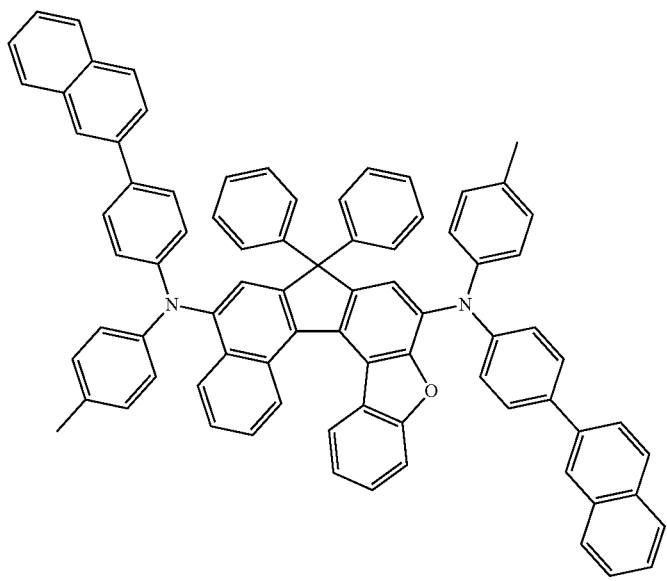

<Chemical Formula 113>
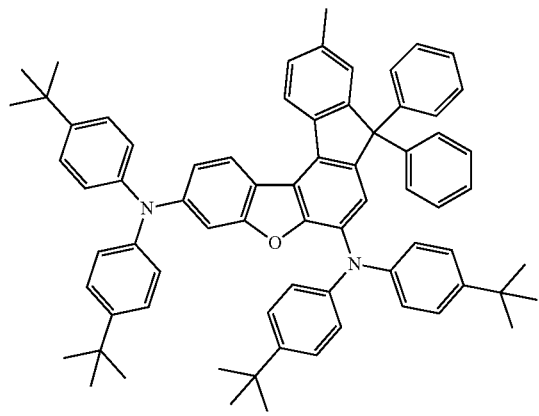
<Chemical Formula 114>
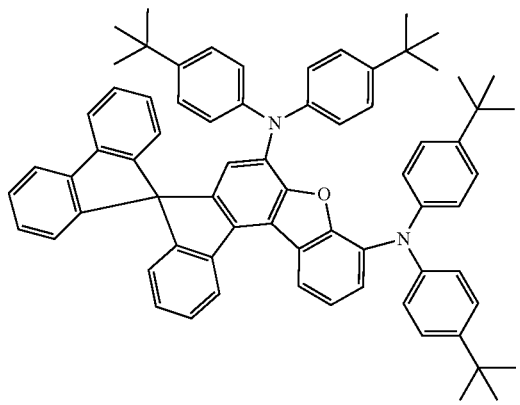
<Chemical Formula 115>
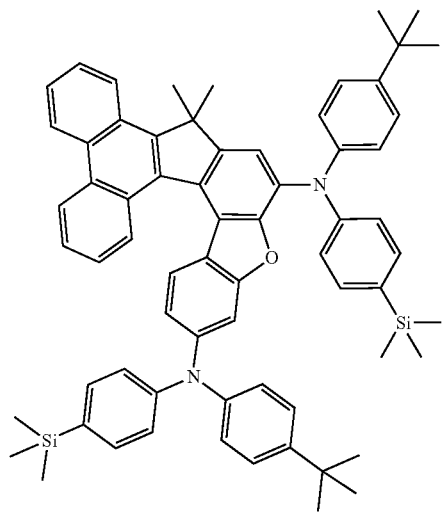
<Chemical Formula 116>
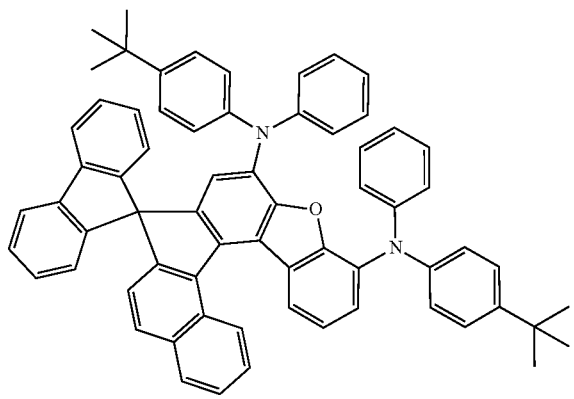
<Chemical Formula 117>
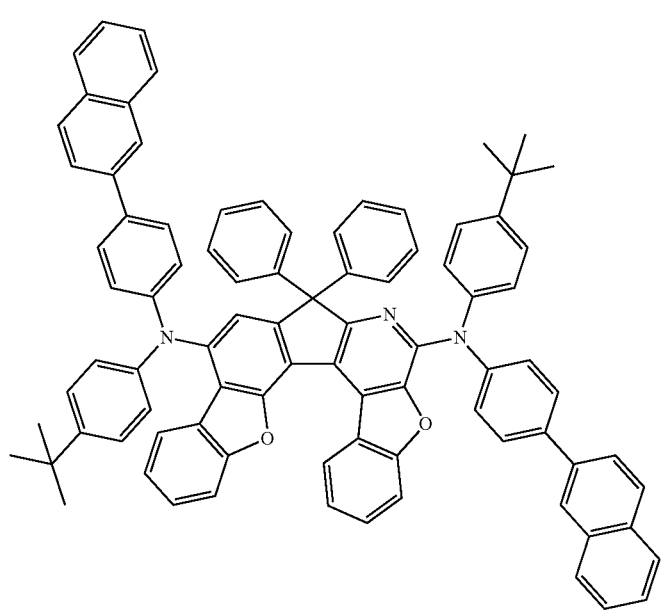

<Chemical Formula 118>
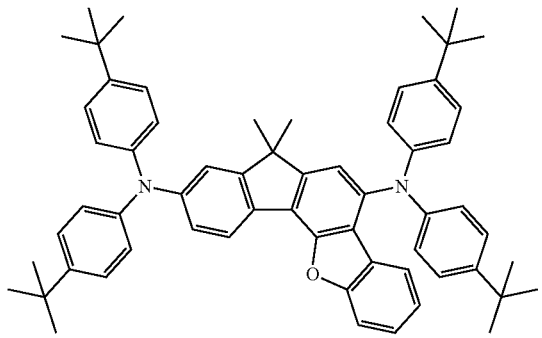
<Chemical Formula 119>
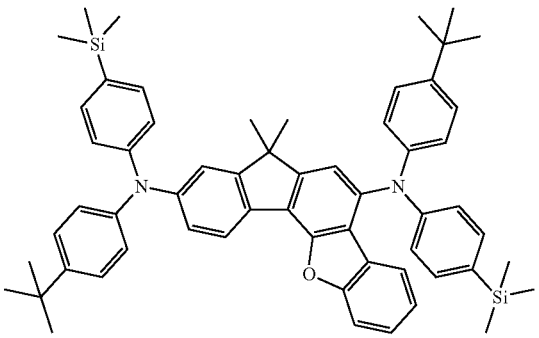
<Chemical Formula 120>
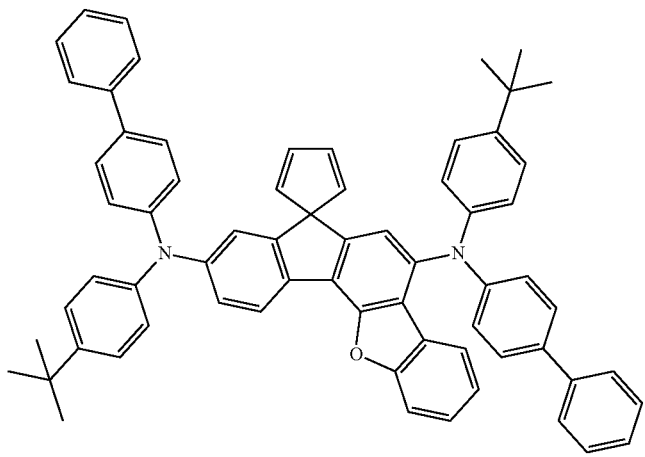
<Chemical Formula 121>
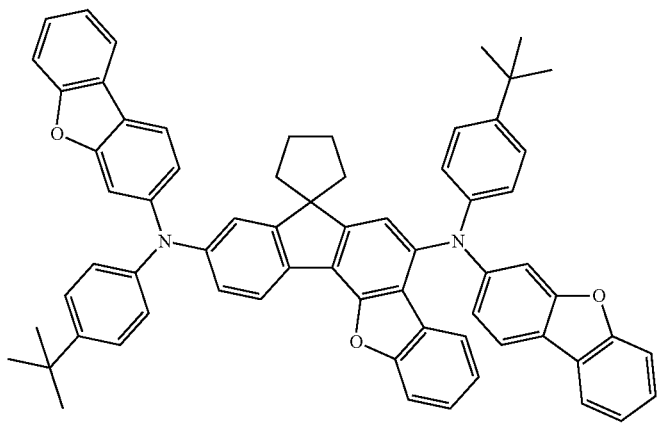
<Chemical Formula 122>
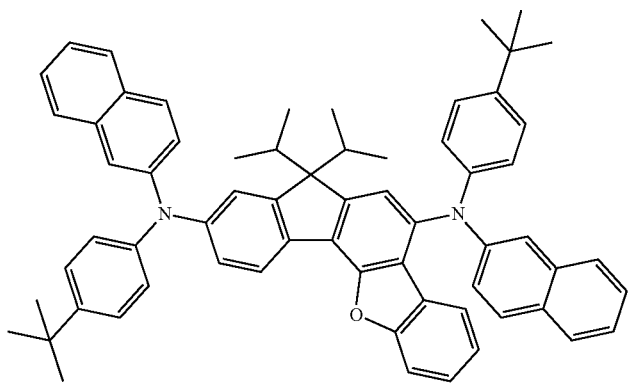

-continued
<Chemical Formula 123>
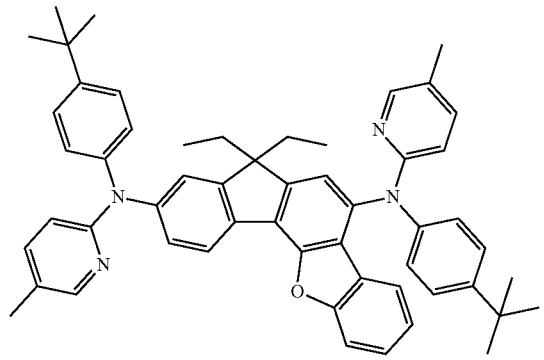
<Chemical Formula 124>
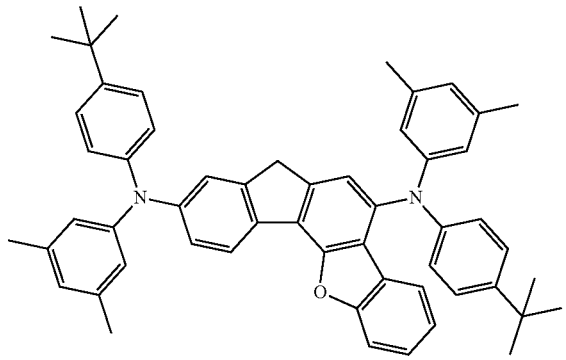
<Chemical Formula 125>
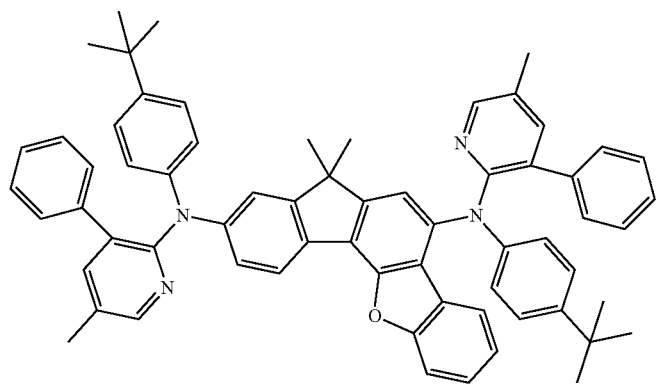
<Chemical Formula 126>
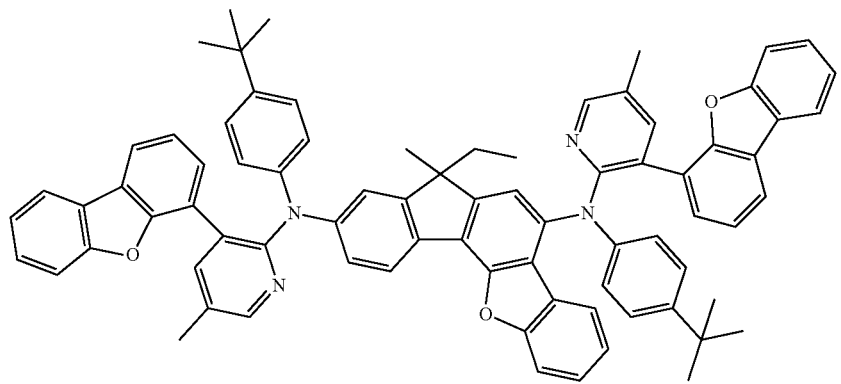
<Chemical Formula 127>
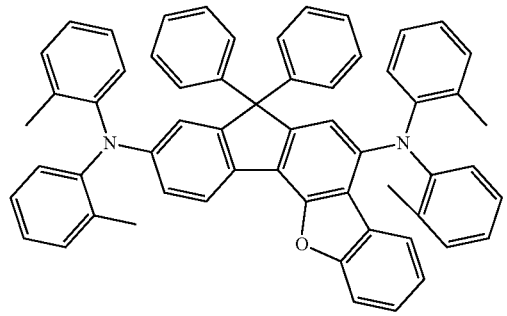

-continued
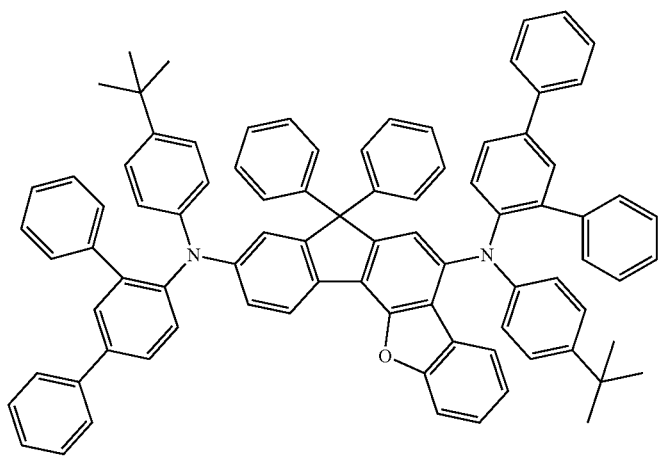
<Chemical Formula 128>
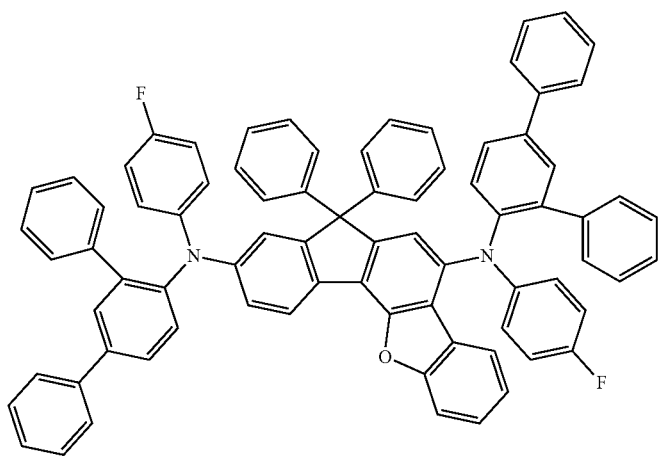
<Chemical Formula 129>
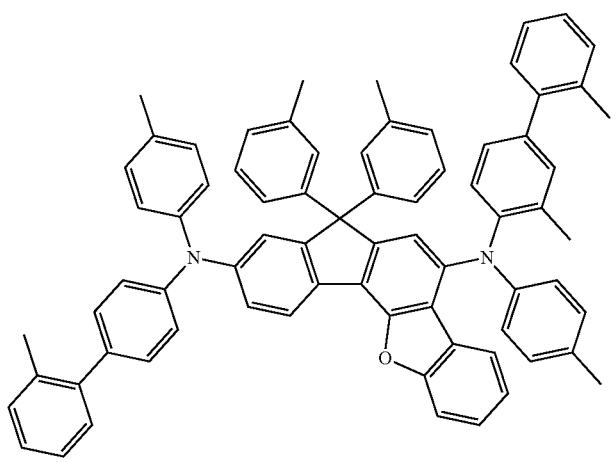
<Chemical Formula 130>

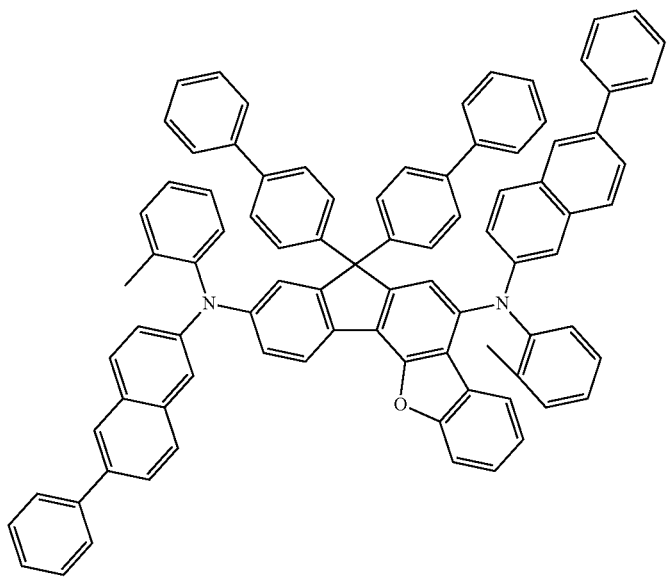
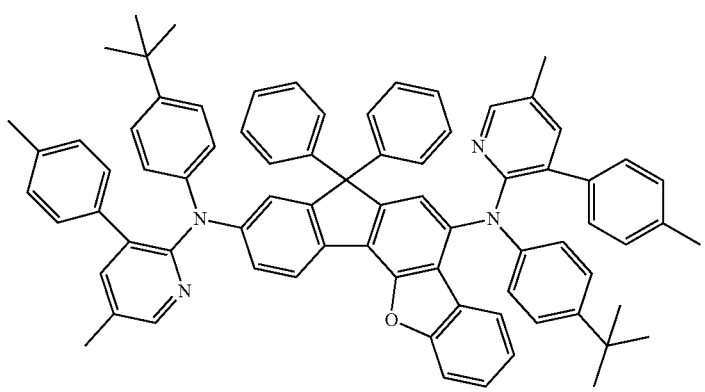
<Chemical Formula 131>
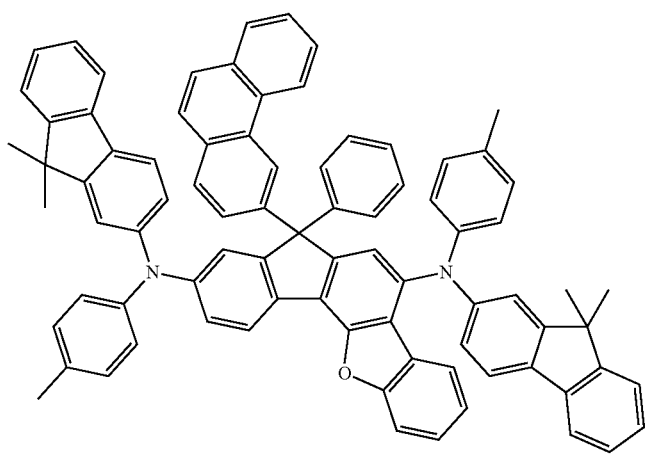
<Chemical Formula 132>
<Chemical Formula 133>

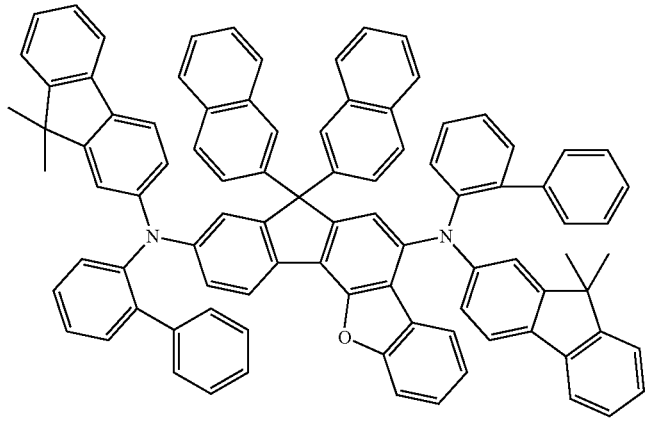
<Chemical Formula 134>
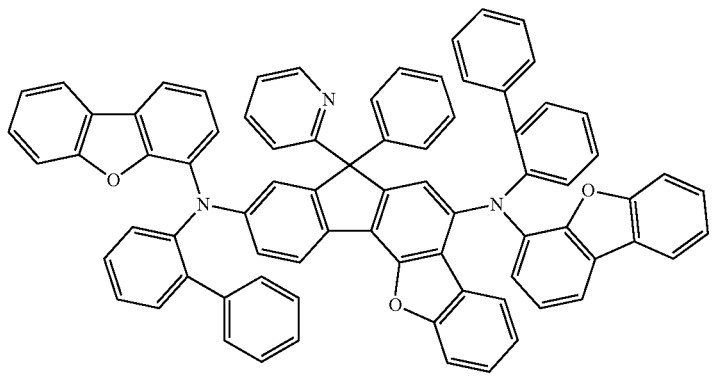
<Chemical Formula 135>
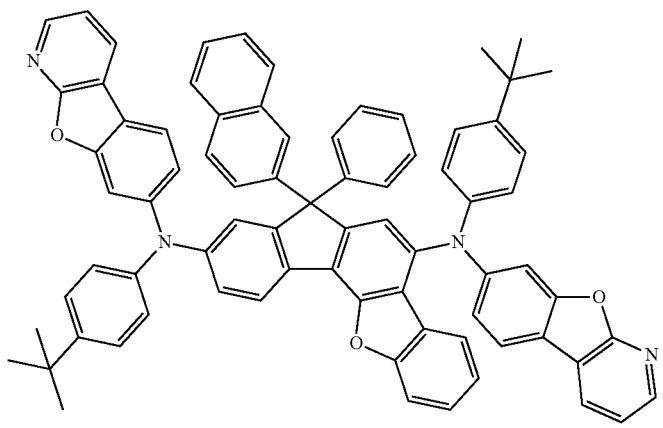
<Chemical Formula 136>
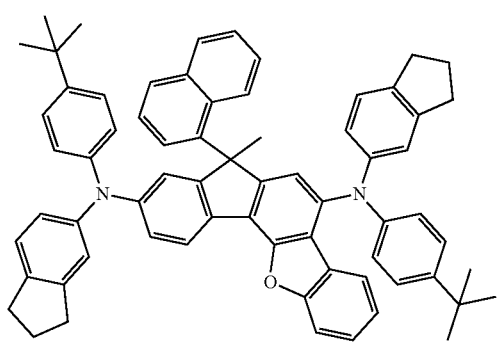
<Chemical Formula 137>
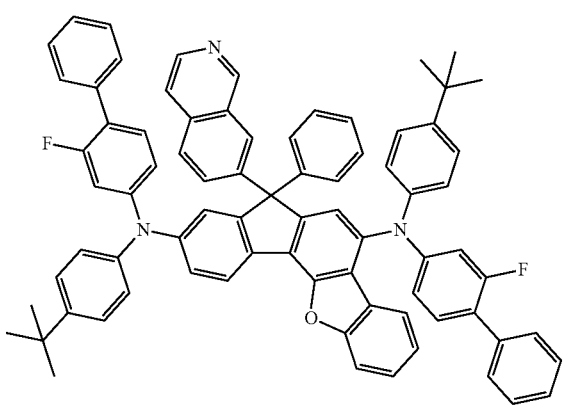
<Chemical Formula 138>

-continued
<Chemical Formula 139>
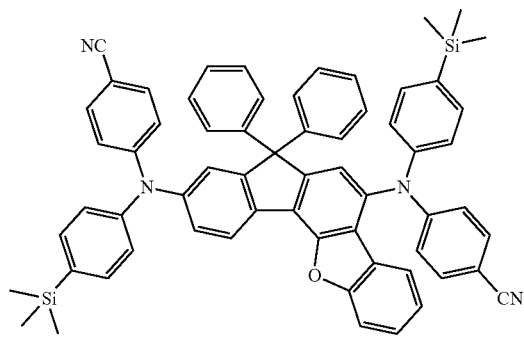
<Chemical Formula 140>
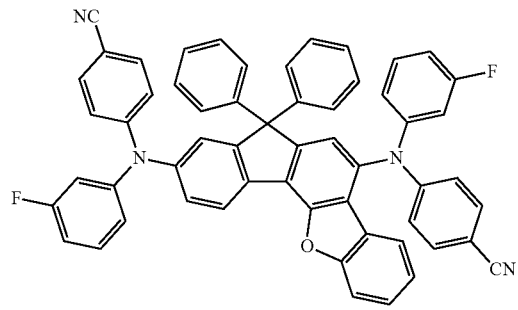
<Chemical Formula 141>
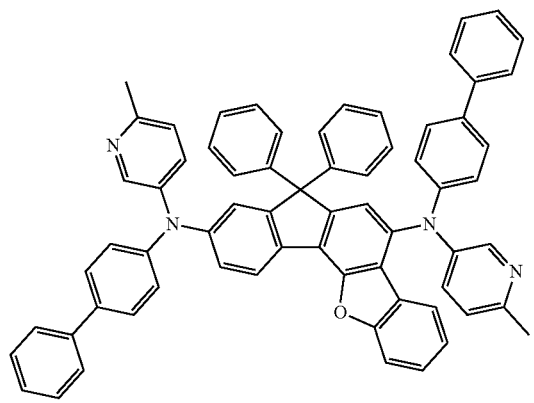
<Chemical Formula 142>
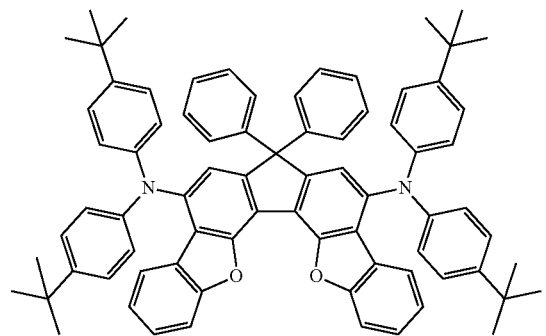
<Chemical Formula 143>
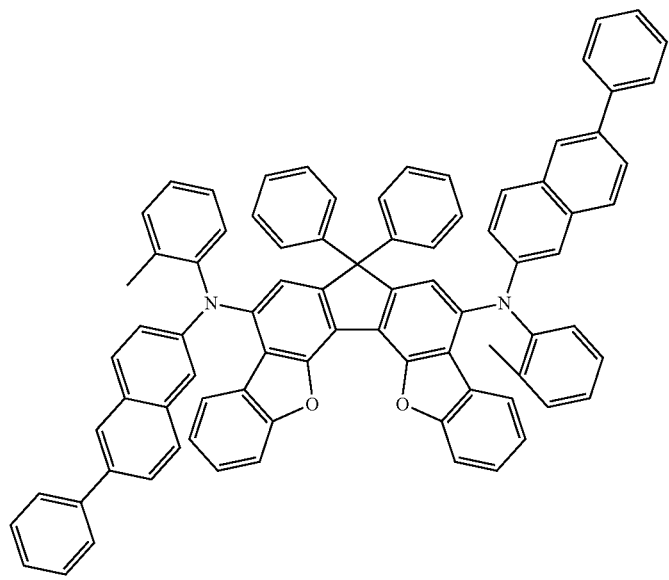

<Chemical Formula 144>
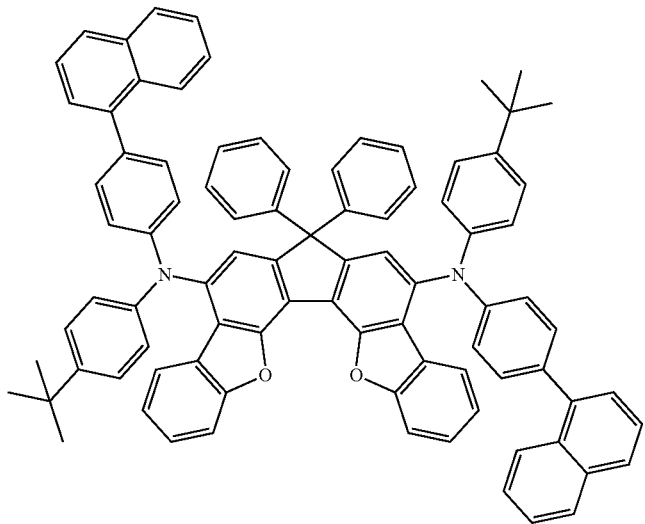
<Chemical Formula 145>
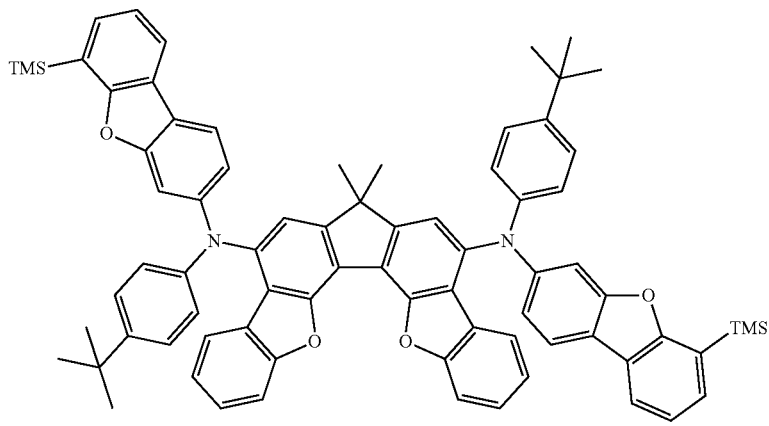
<Chemical Formula 146>
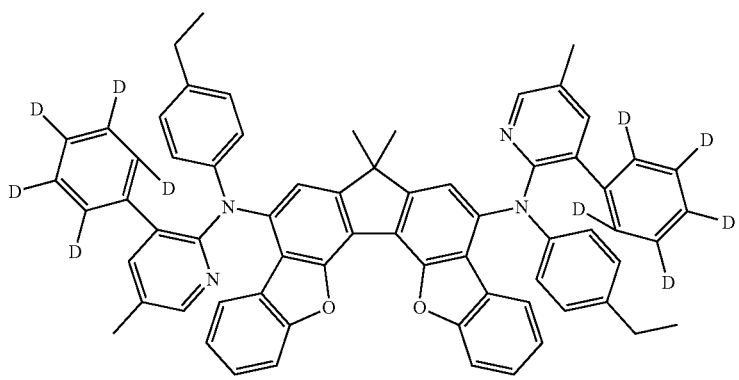

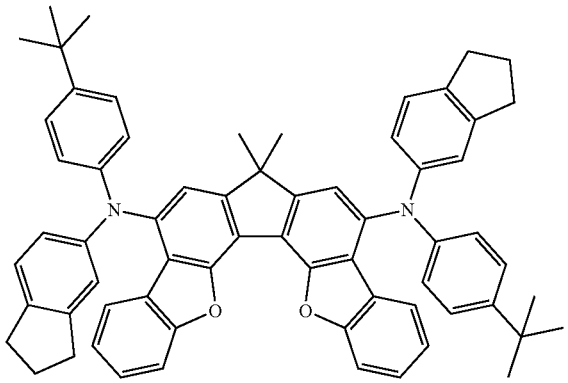
<Chemical Formula 147>
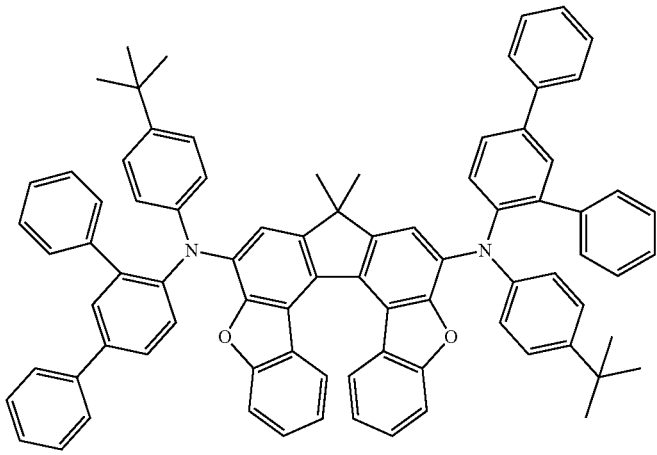
<Chemical Formula 148>
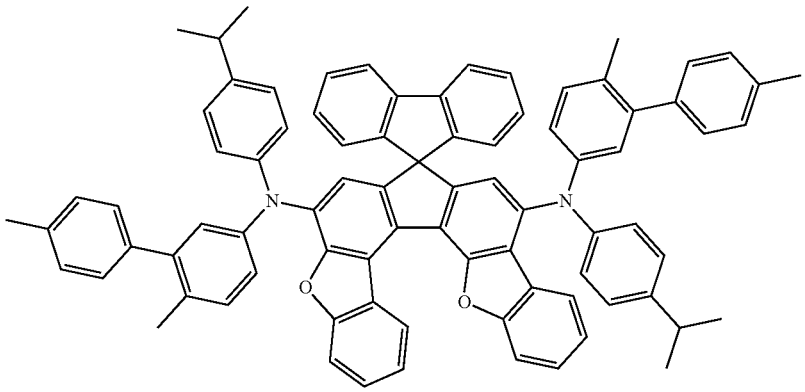
<Chemical Formula 149>
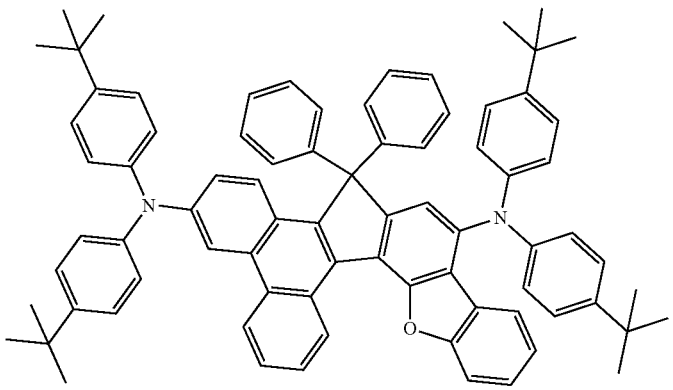
<Chemical Formula 150>

<Chemical Formula 151>
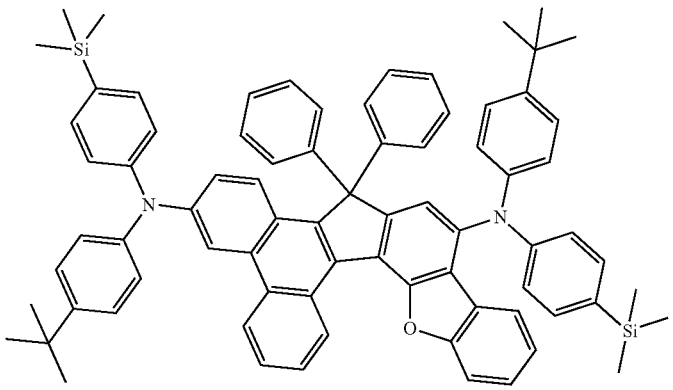
<Chemical Formula 152>
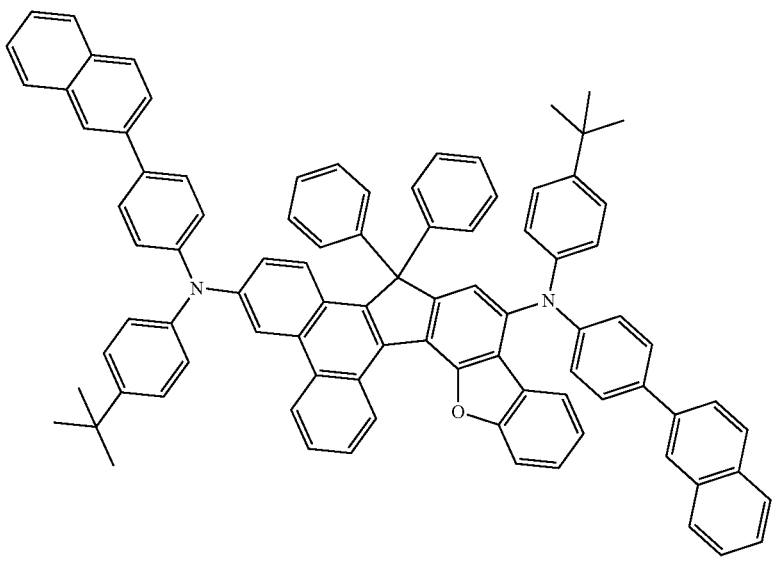
<Chemical Formula 153>
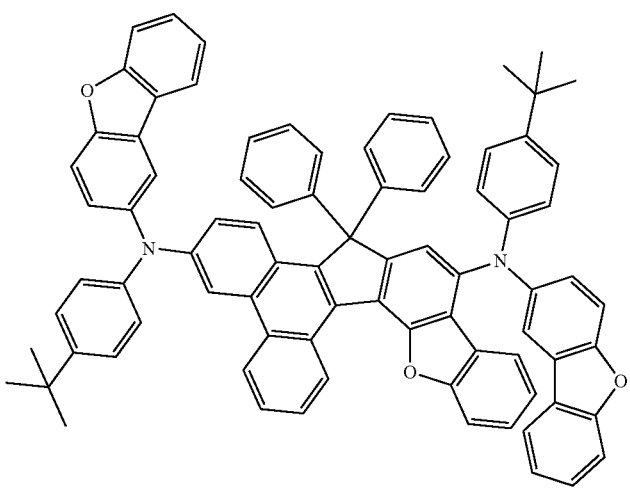

-continued
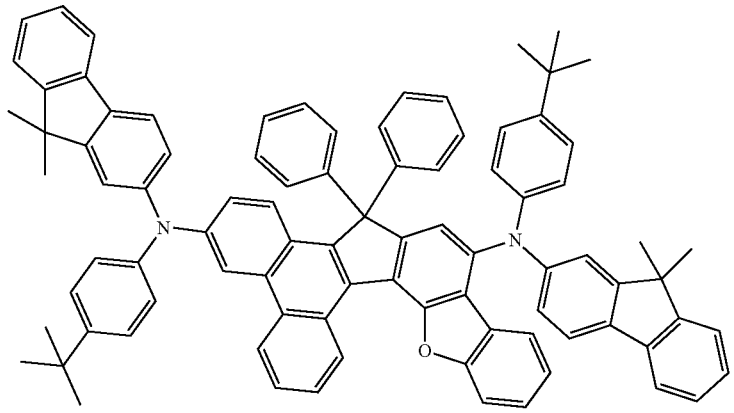
<Chemical Formula 154>
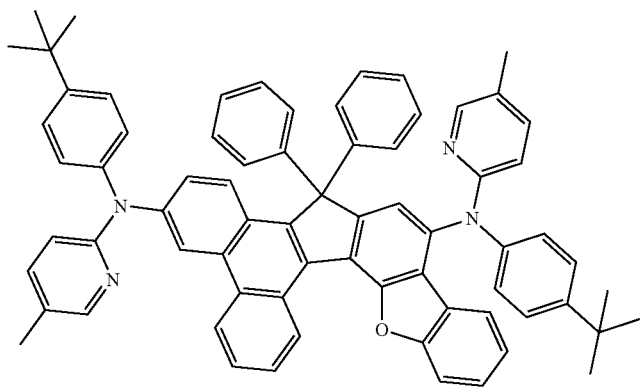
<Chemical Formula 155>
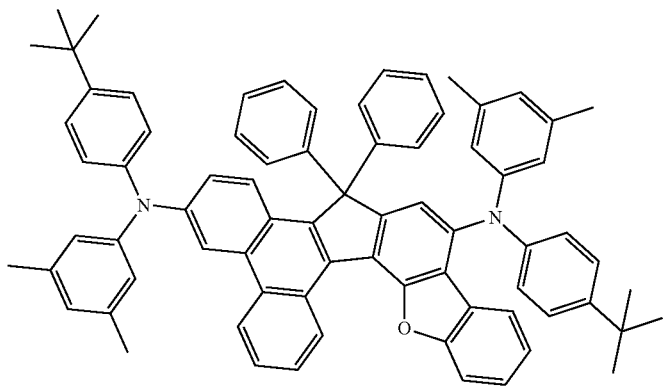
<Chemical Formula 156>
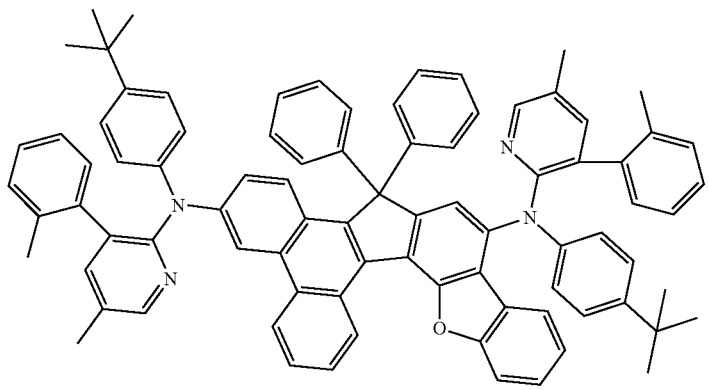
<Chemical Formula 157>

-continued
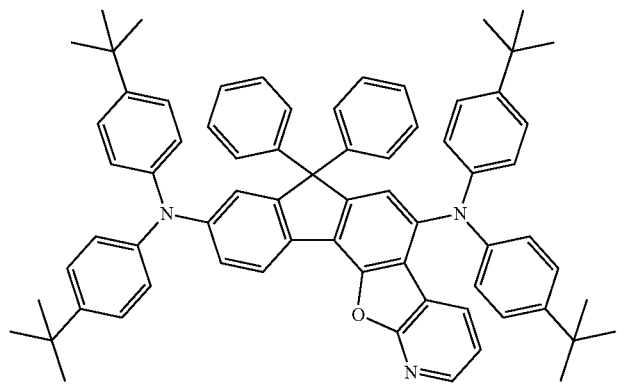
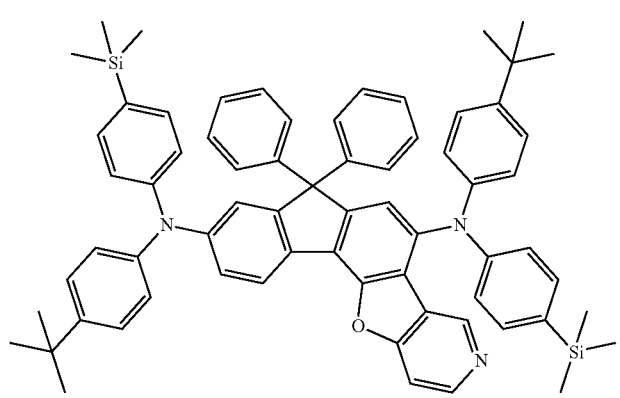
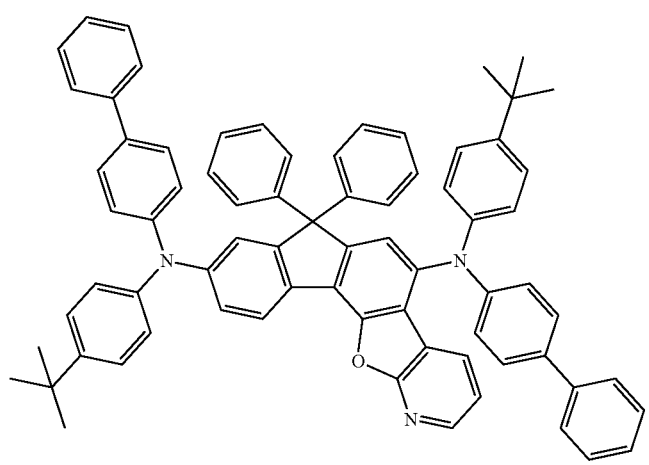
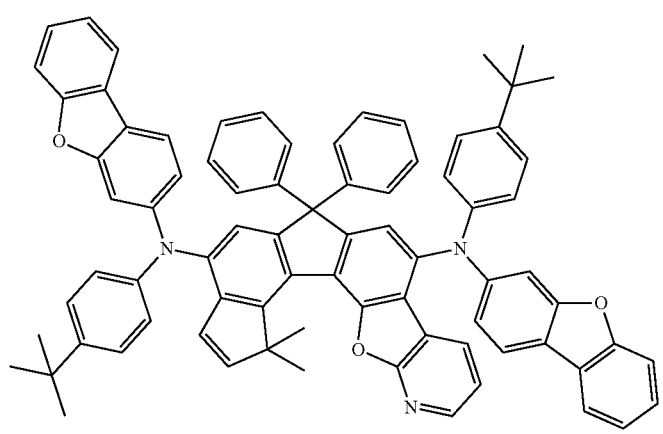
<Chemical Formula 158>
<Chemical Formula 159>
<Chemical Formula 160>
<Chemical Formula 161>

-continued
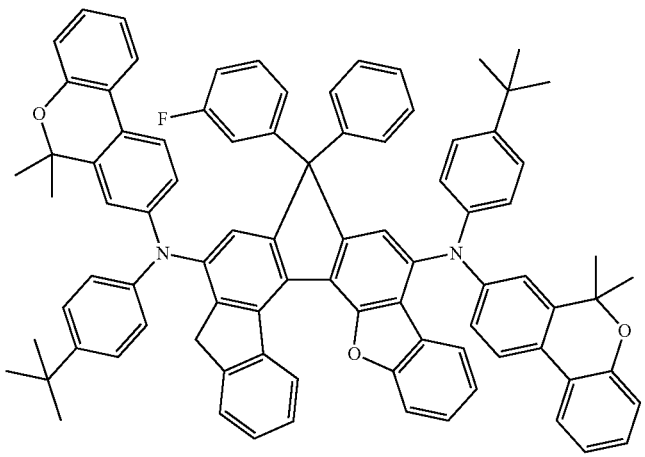
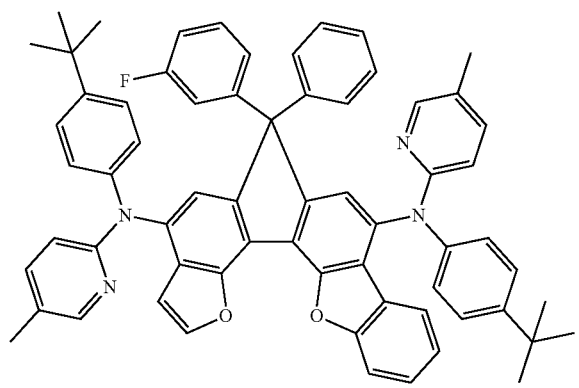
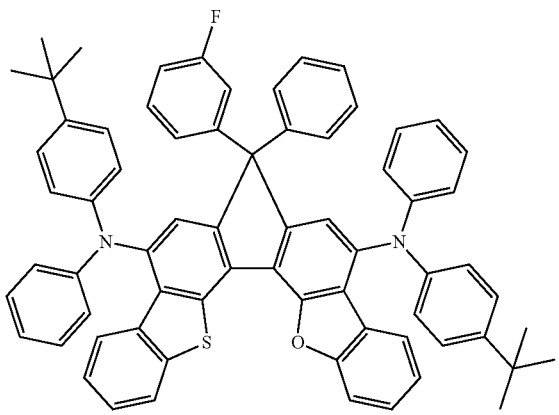
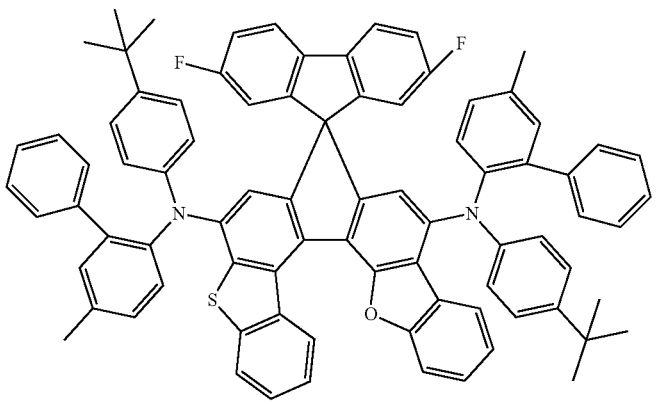
<Chemical Formula 162>
<Chemical Formula 163>
<Chemical Formula 164>
<Chemical Formula 165>

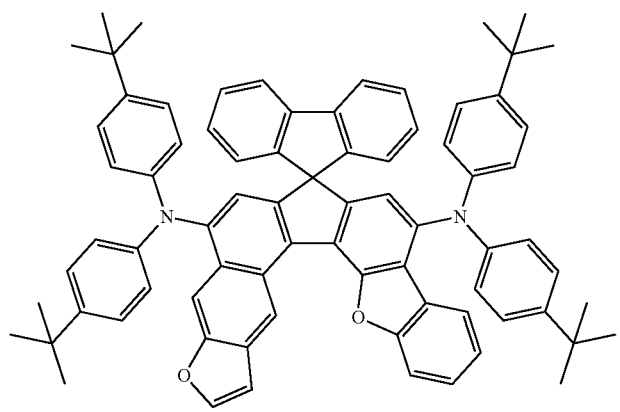
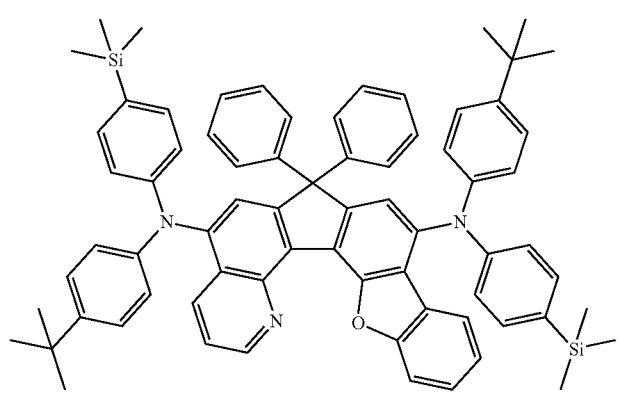
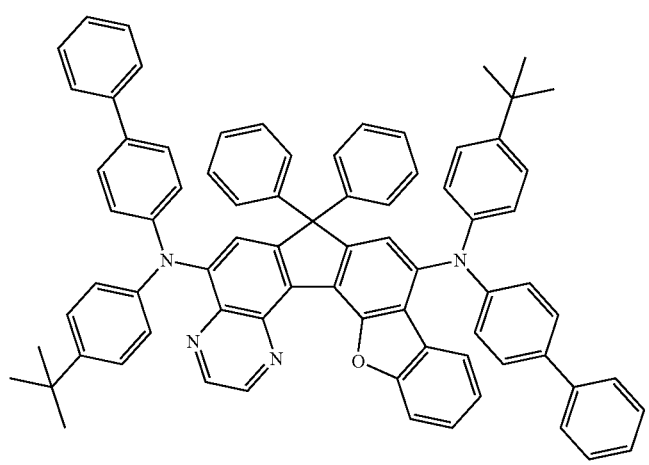
<Chemical Formula 166>
<Chemical Formula 167>
<Chemical Formula 168>

<Chemical Formula 169>
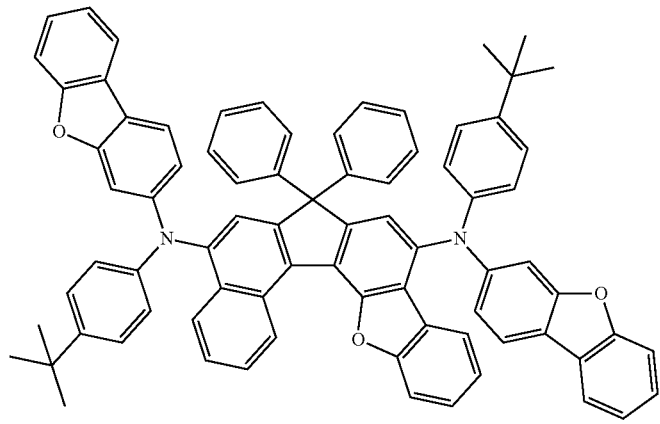
<Chemical Formula 170>
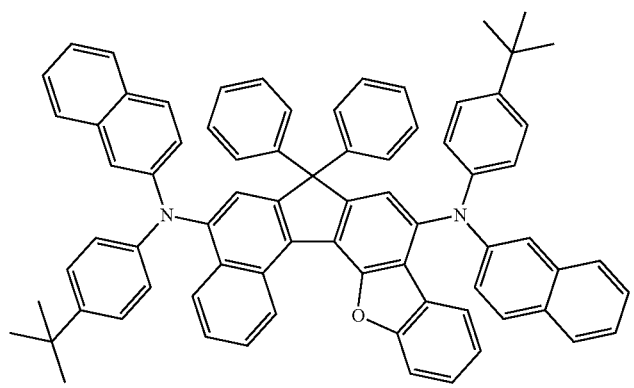
<Chemical Formula 171>
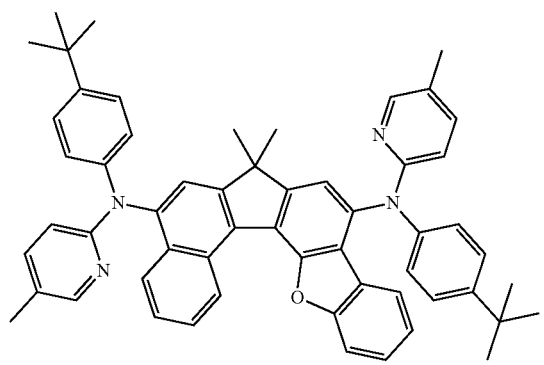
<Chemical Formula 172>
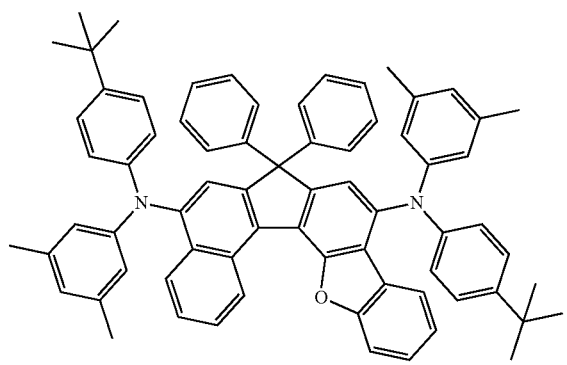
<Chemical Formula 173>
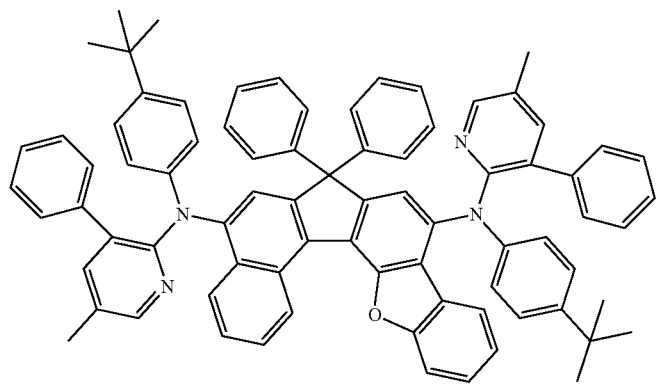

<Chemical Formula 174>
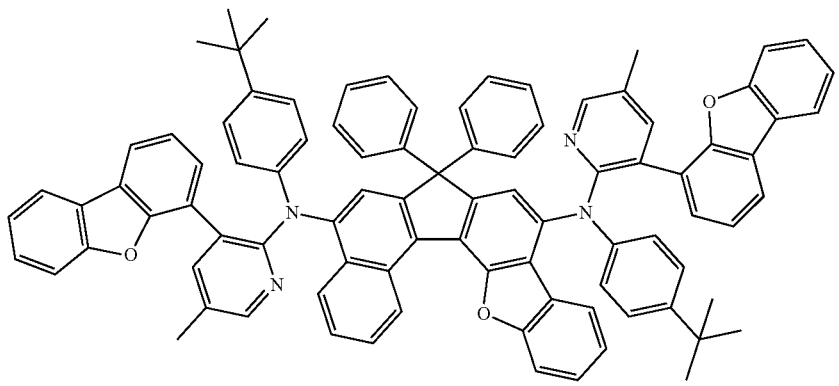
<Chemical Formula 175>
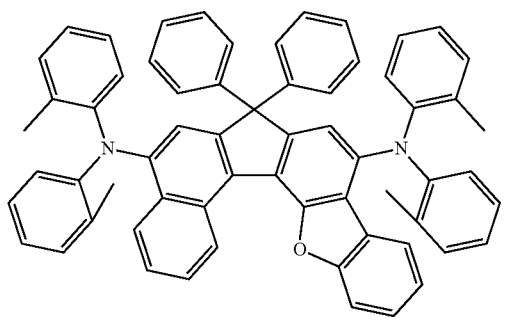
<Chemical Formula 176>
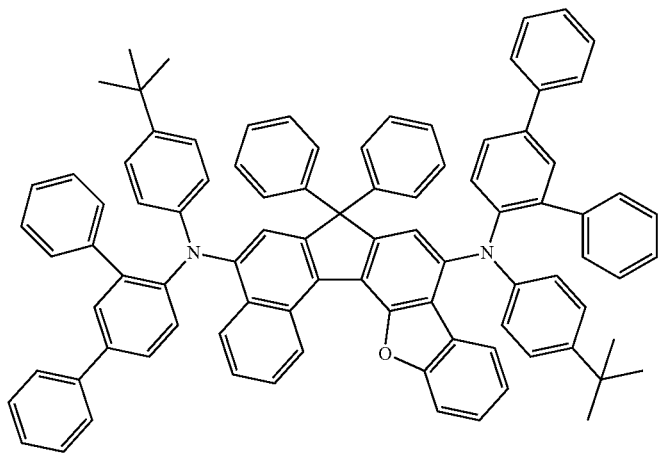
<Chemical Formula 177>
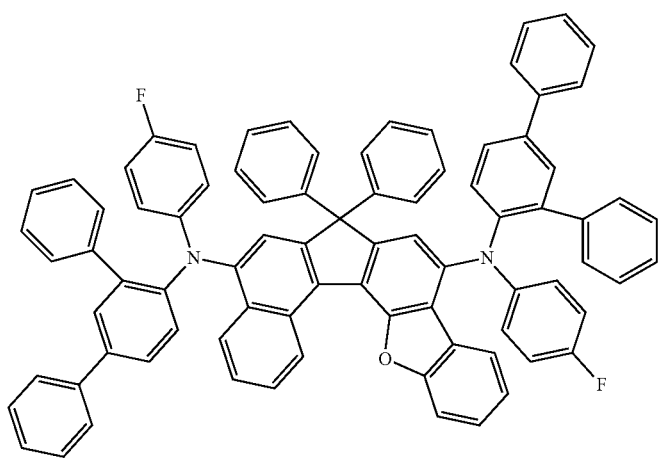

<Chemical Formula 178>
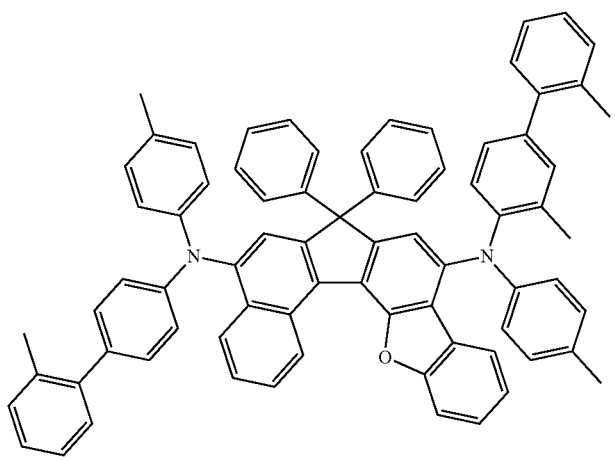
<Chemical Formula 179>
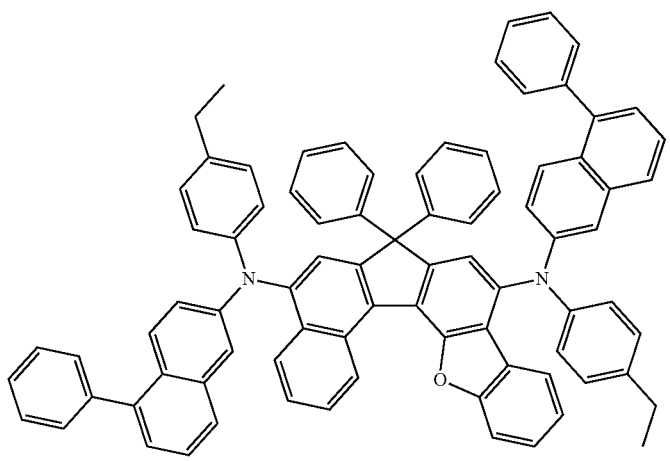
<Chemical Formula 180>
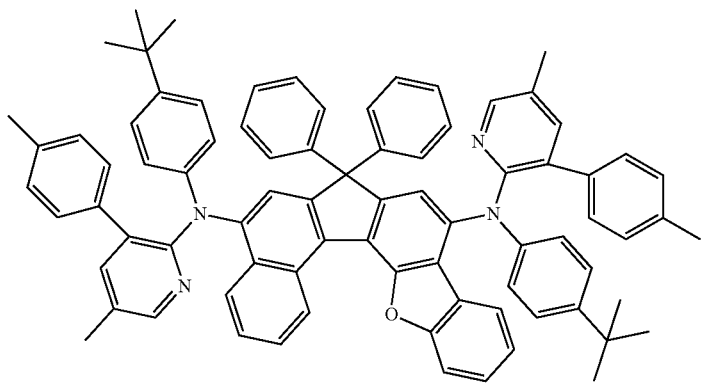

<Chemical Formula 181>
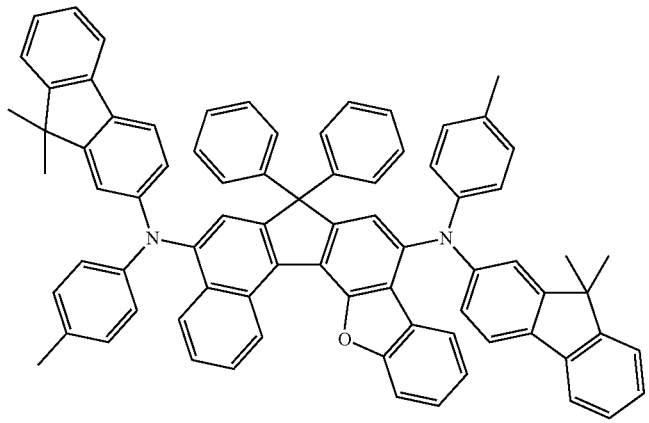
<Chemical Formula 182>
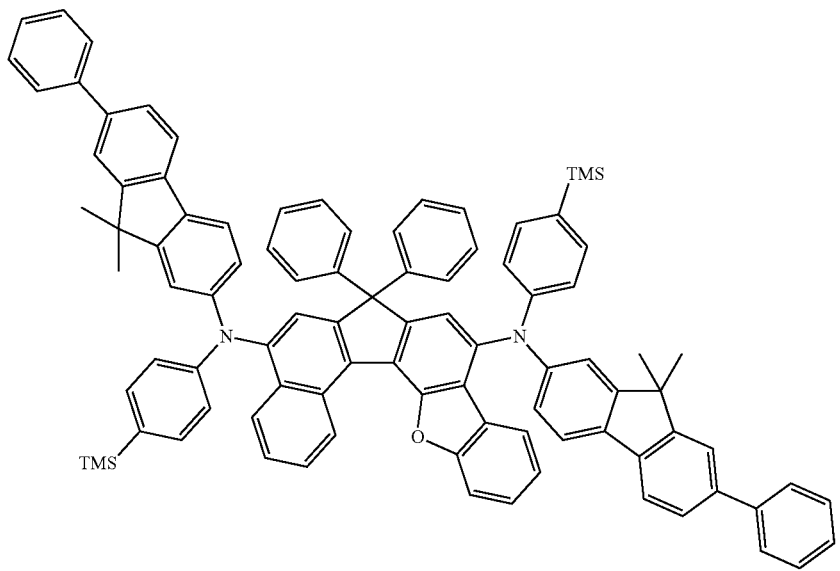
<Chemical Formula 183>
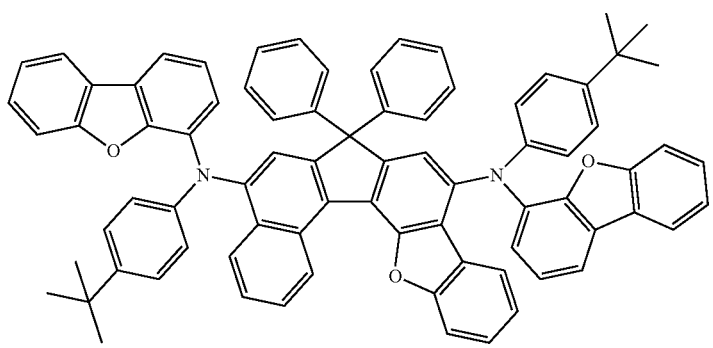

<Chemical Formula 184>
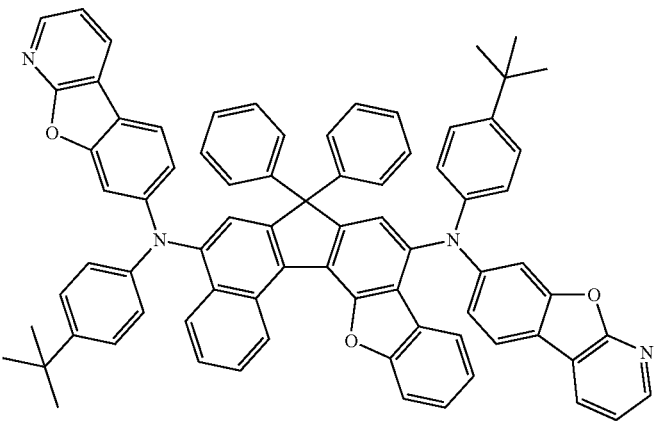
<Chemical Formula 185>
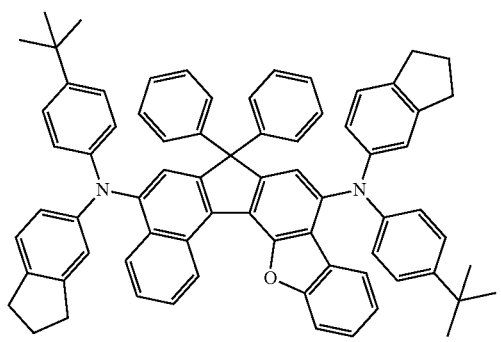
<Chemical Formula 186>
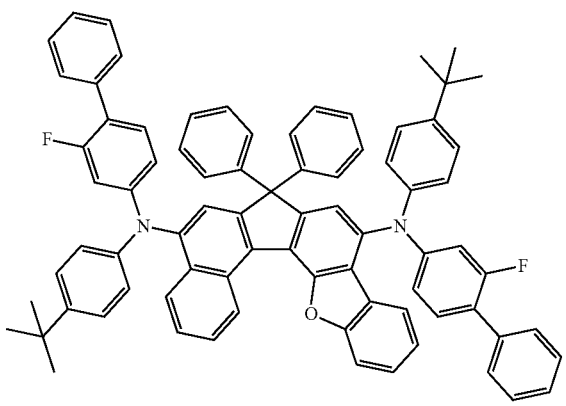
<Chemical Formula 187>
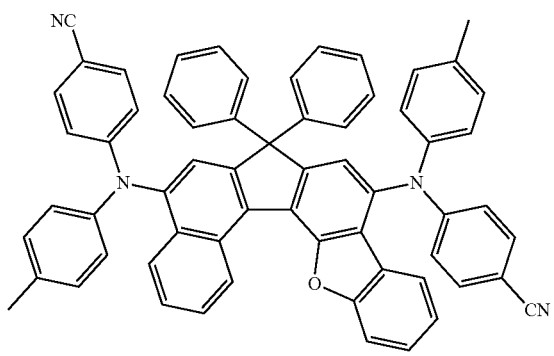
<Chemical Formula 188>
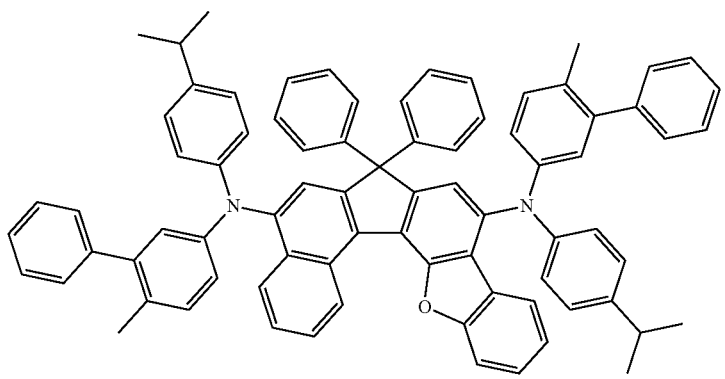

-continued
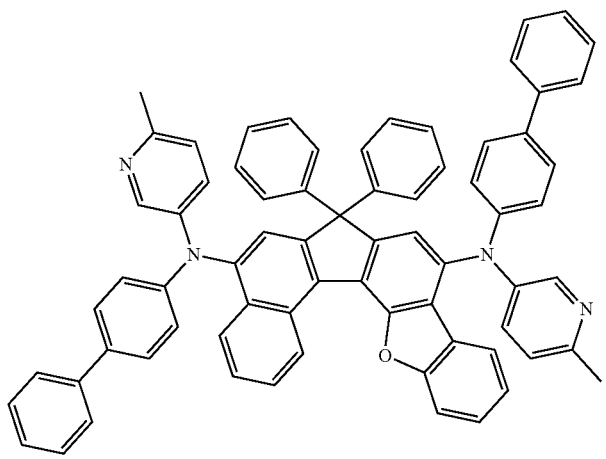
<Chemical Formula 189>
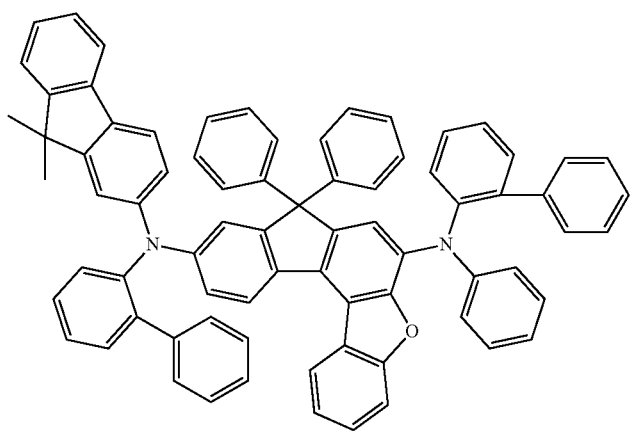
<Chemical Formula 190>
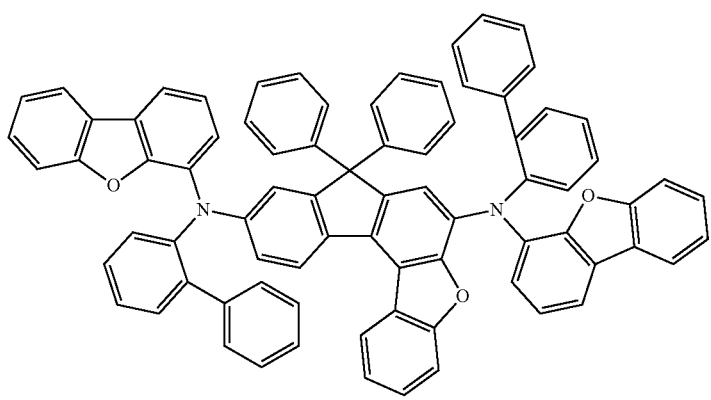
<Chemical Formula 191>

<Chemical Formula 192>
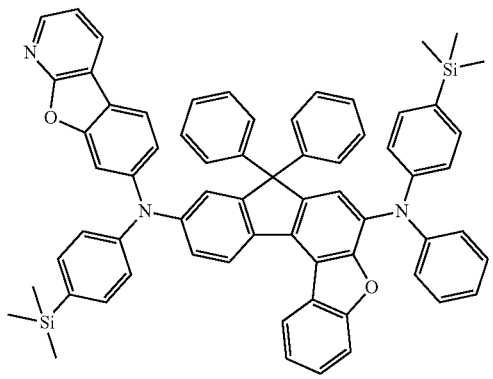
<Chemical Formula 193>
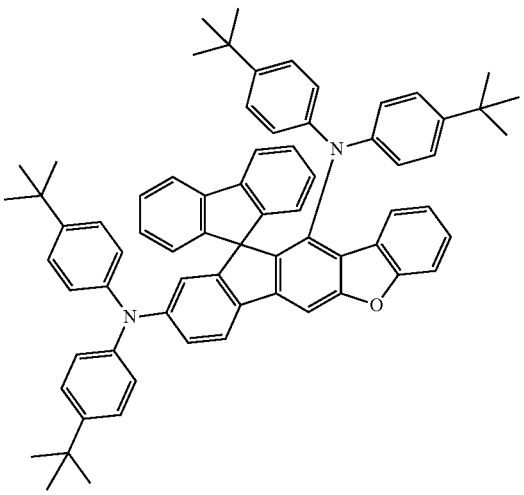
<Chemical Formula 194>
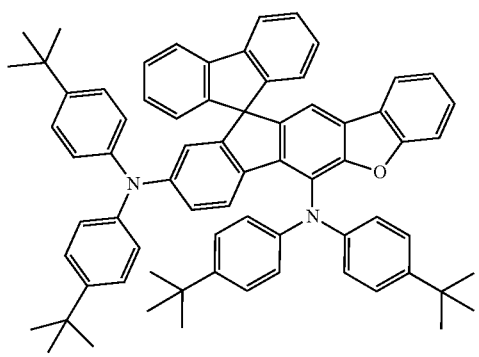
<Chemical Formula 195>
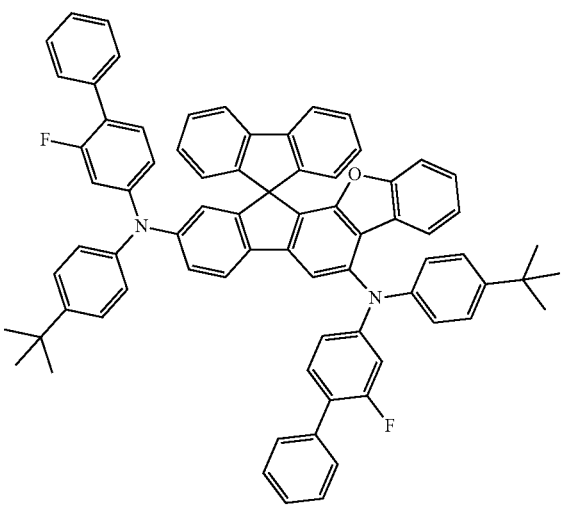
<Chemical Formula 196>
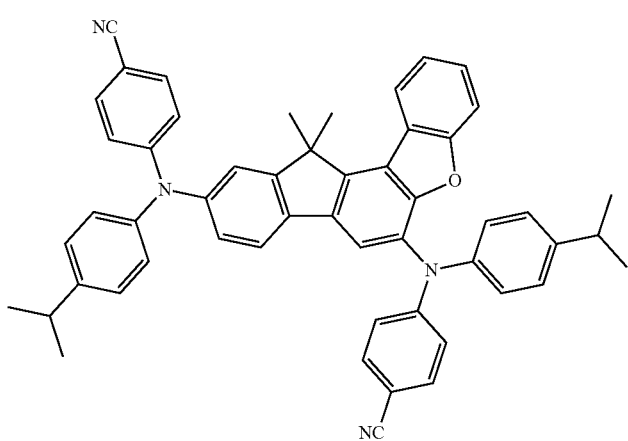

-continued
<Chemical Formula 197>
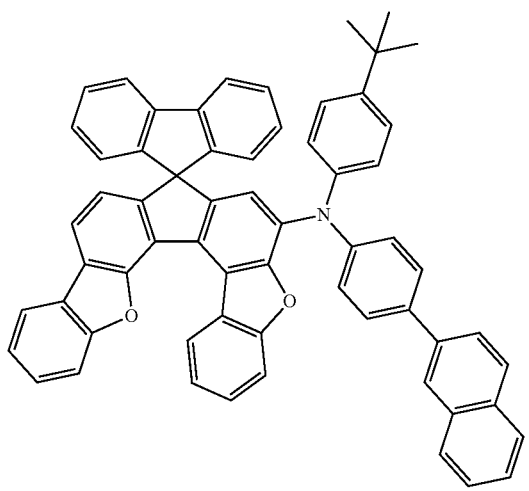
<Chemical Formula 198>
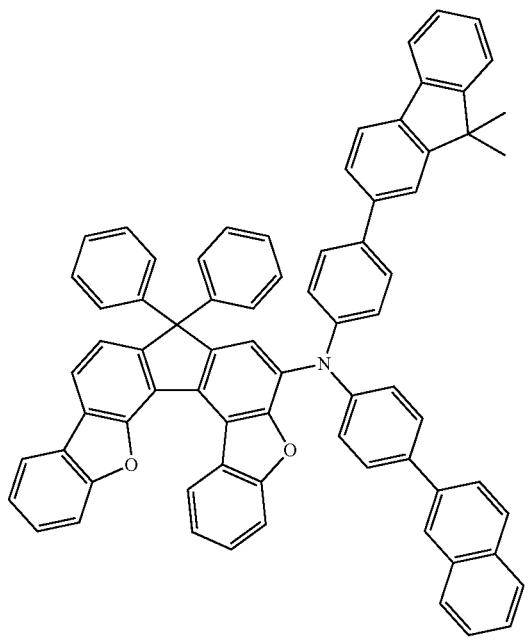
<Chemical Formula 199>
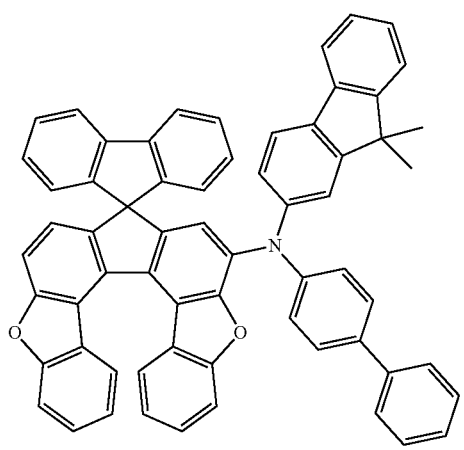
<Chemical Formula 200>
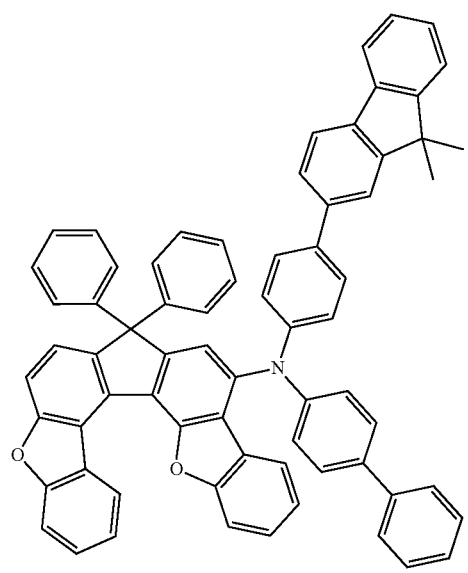

-continued
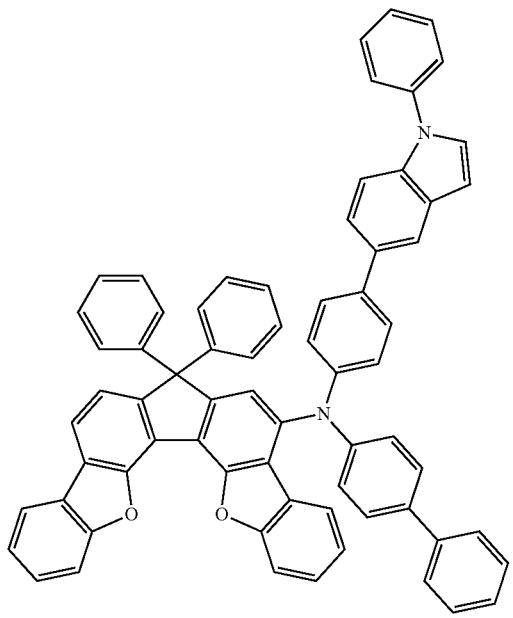
<Chemical Formula 201>
<Chemical Formula 202>
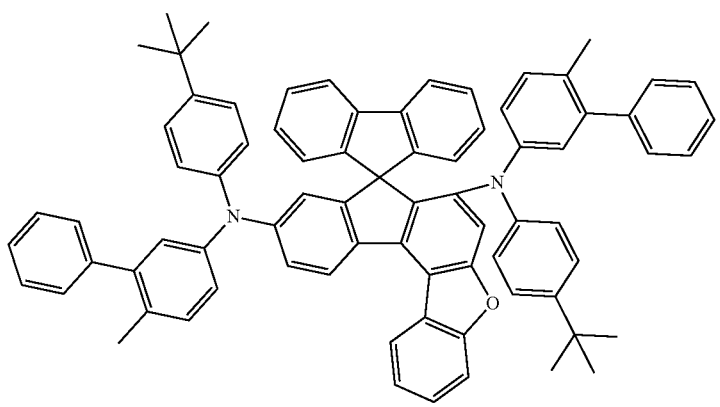

-continued
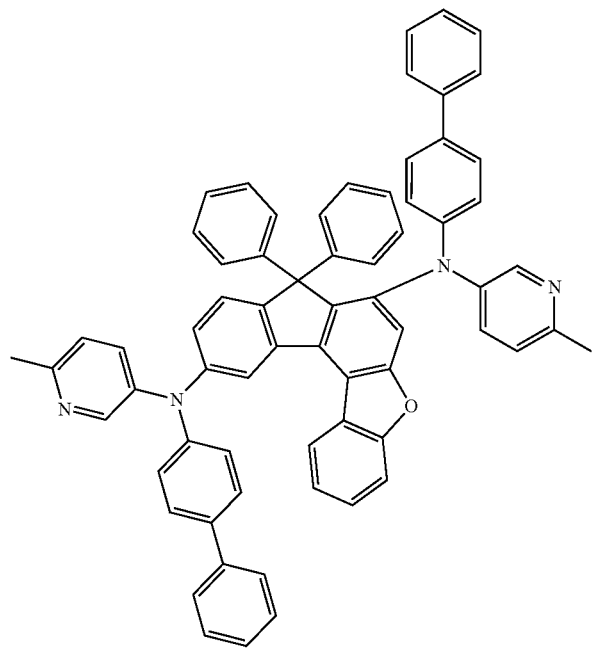
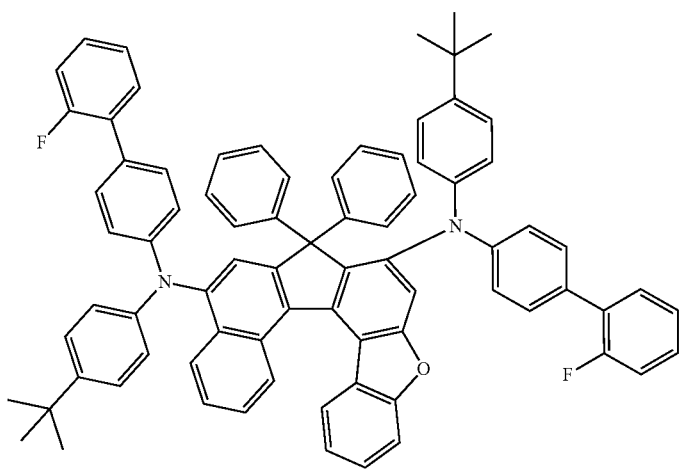
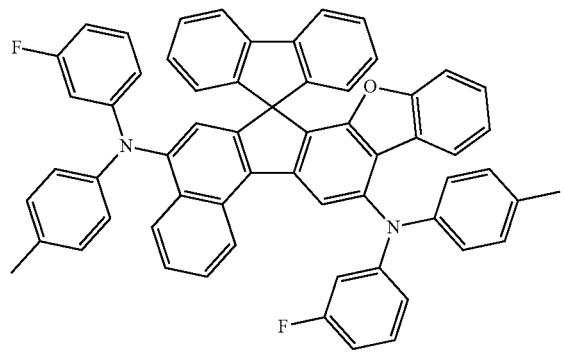
<Chemical Formula 203>
<Chemical Formula 204>
<Chemical Formula 205>

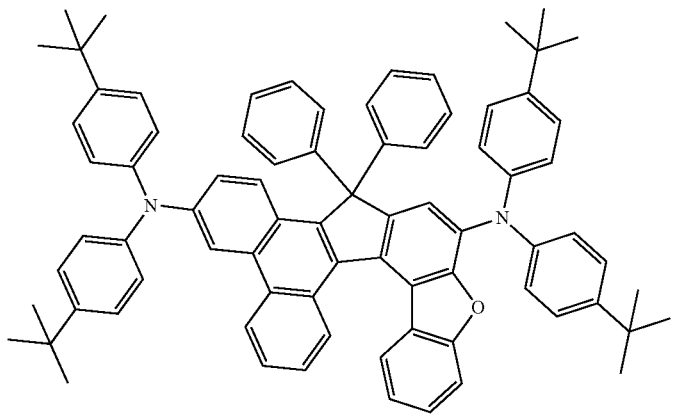
<Chemical Formula 206>
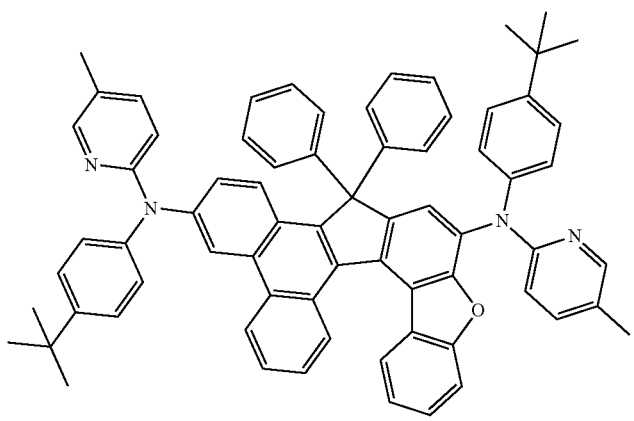
<Chemical Formula 207>
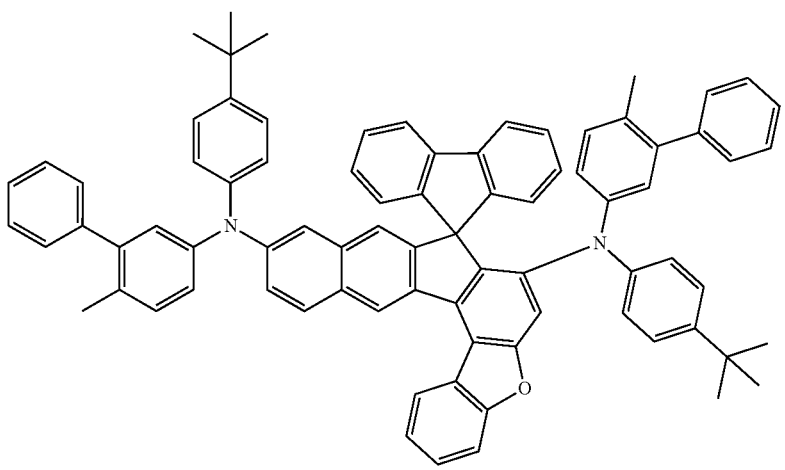
<Chemical Formula 208>

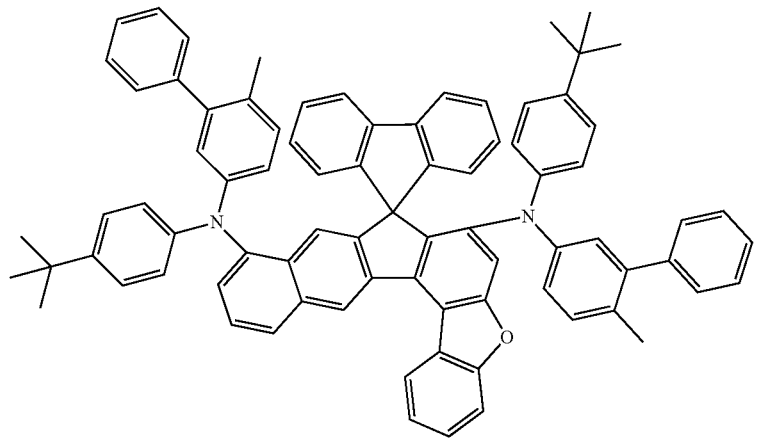
<Chemical Formula 209>
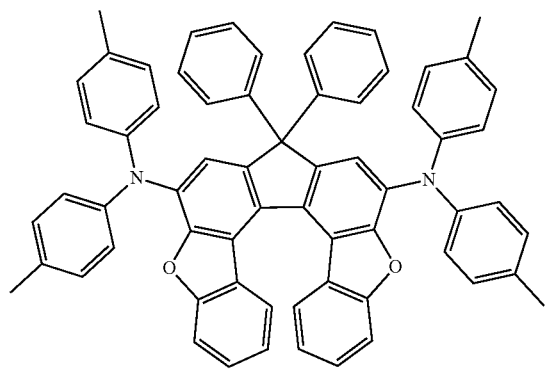
<Chemical Formula 210>
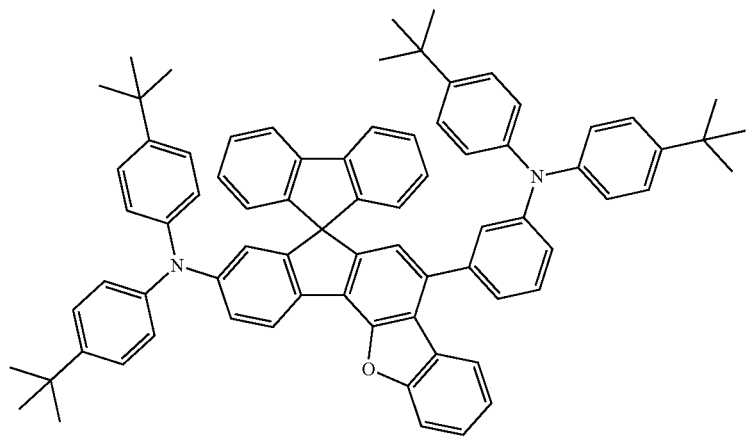
<Chemical Formula 211>

-continued
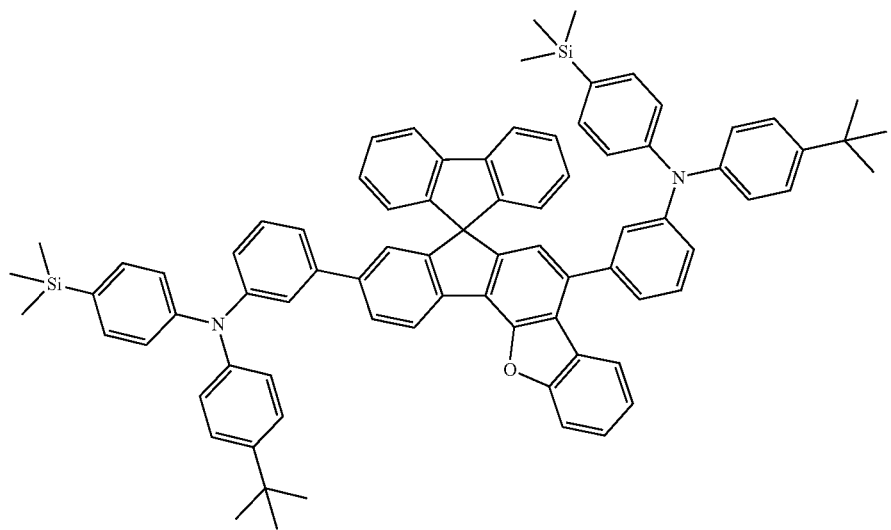
<Chemical Formula 212>
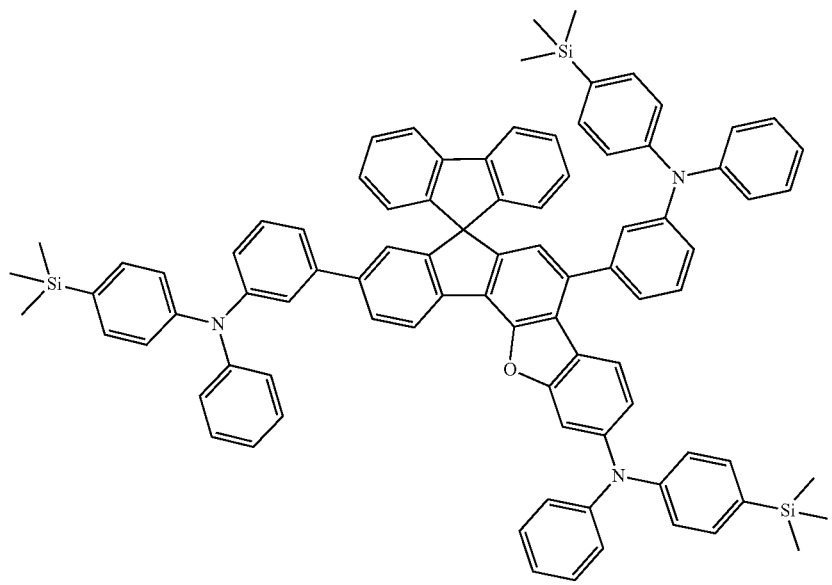
<Chemical Formula 213>
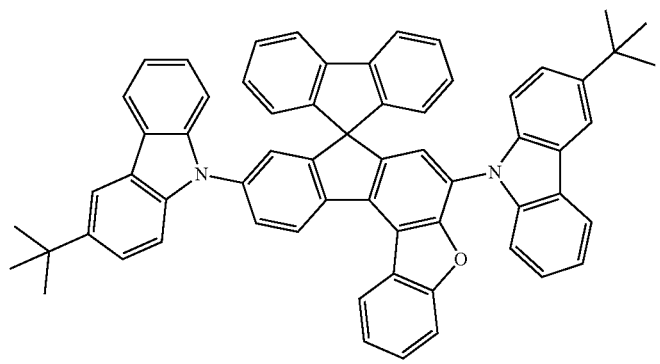
<Chemical Formula 214>

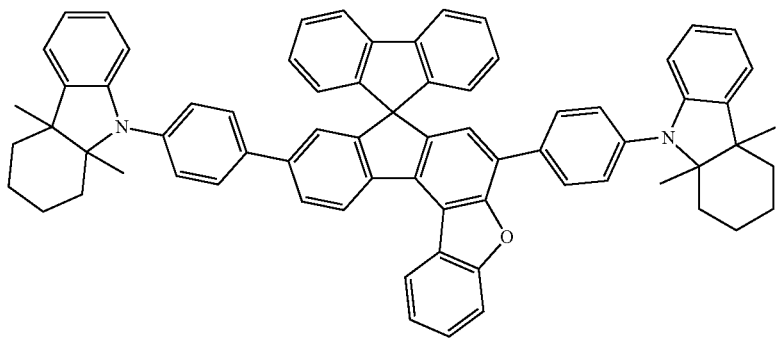
<Chemical Formula 215>
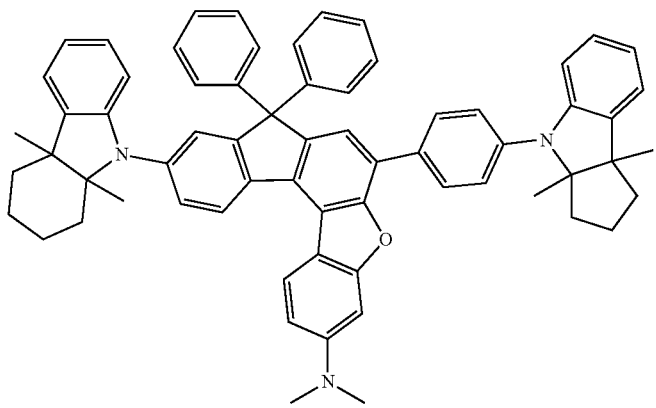
<Chemical Formula 216>
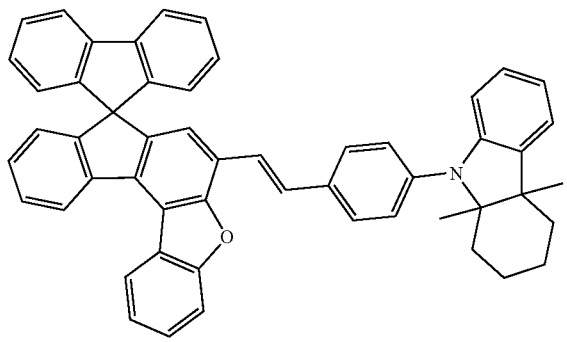
<Chemical Formula 217>
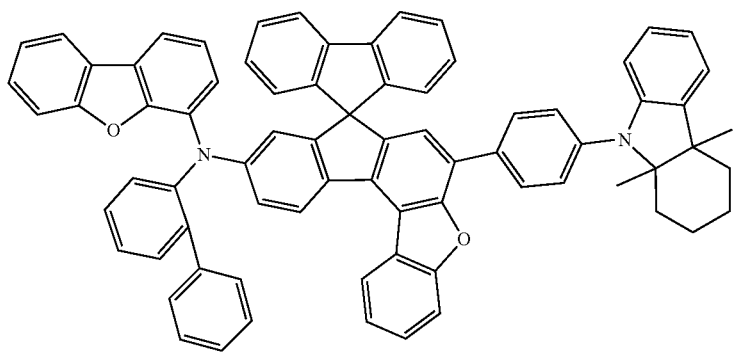
<Chemical Formula 218>

<Chemical Formula 219>
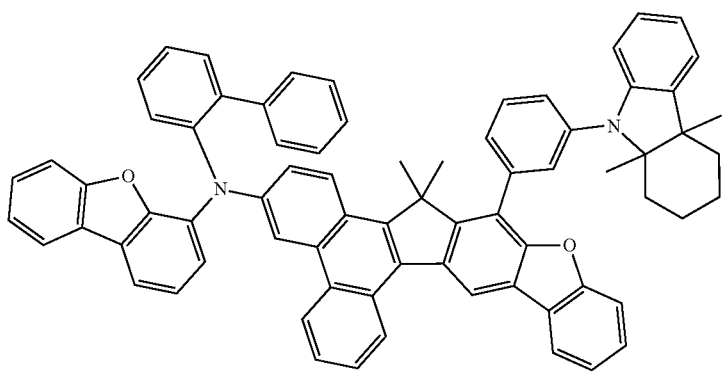
<Chemical Formula 220>
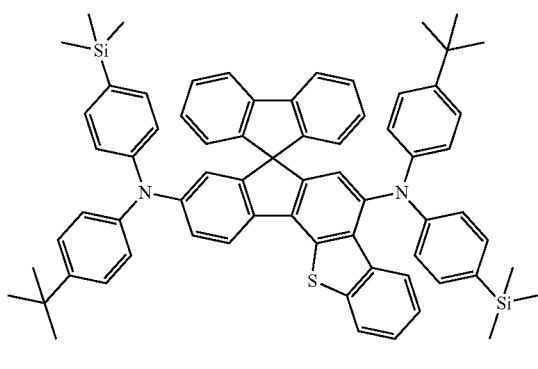
<Chemical Formula 221>
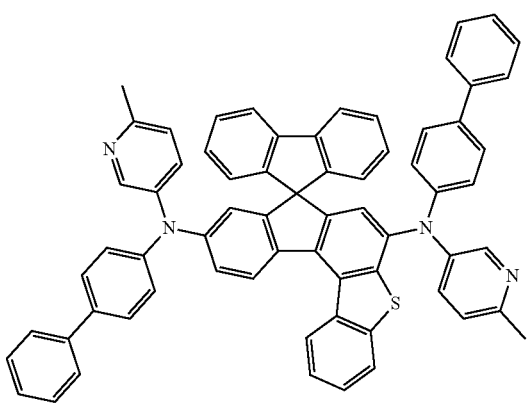
<Chemical Formula 222>
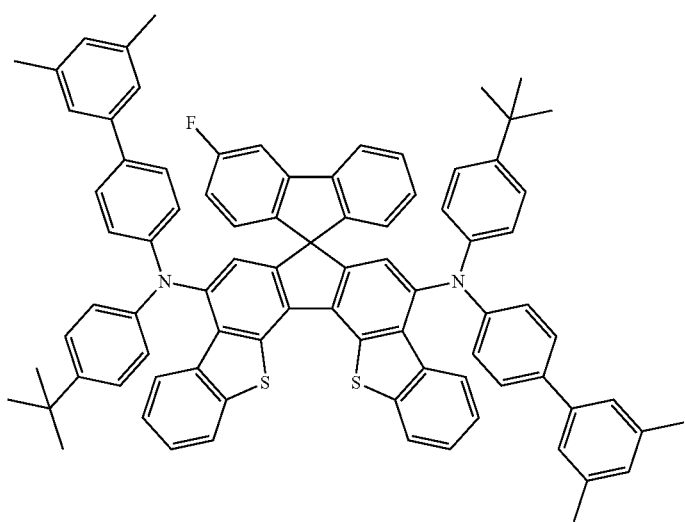

-continued
<Chemical Formula 223>
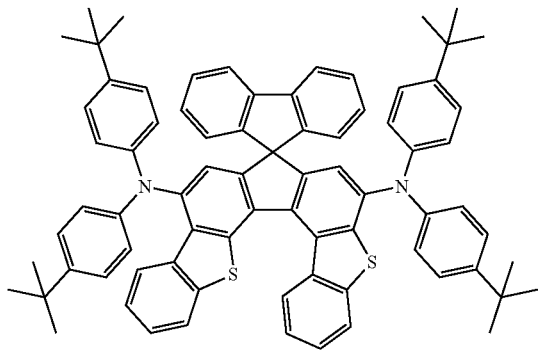
<Chemical Formula 224>
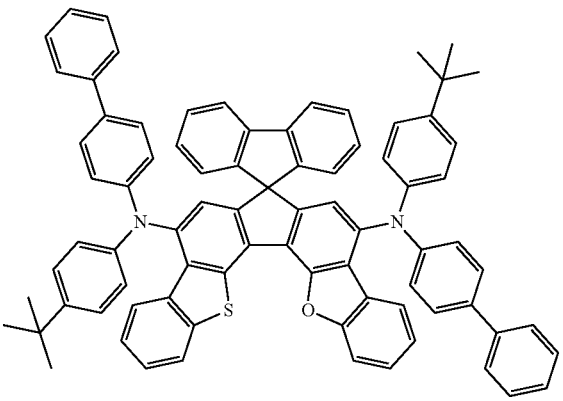
<Chemical Formula 225>
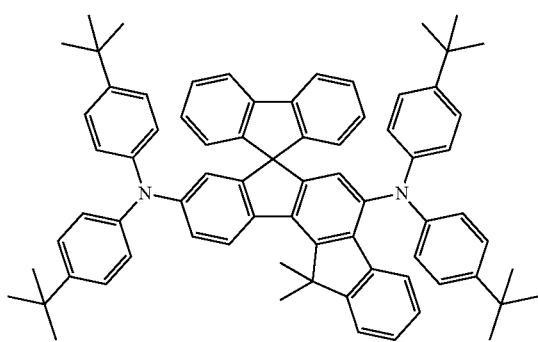
<Chemical Formula 226>
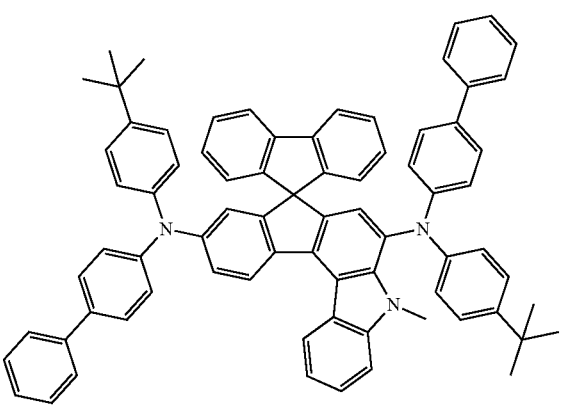
<Chemical Formula 227>
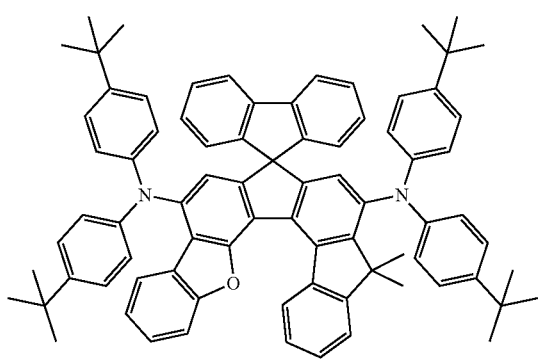
<Chemical Formula 228>
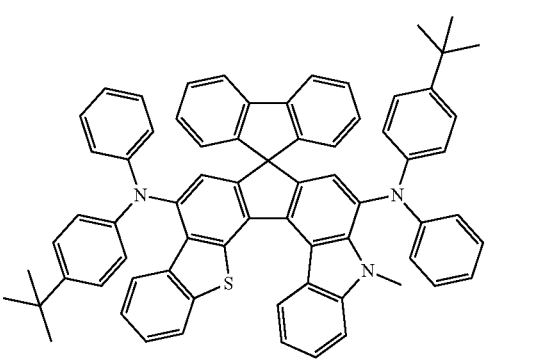
<Chemical Formula 229>
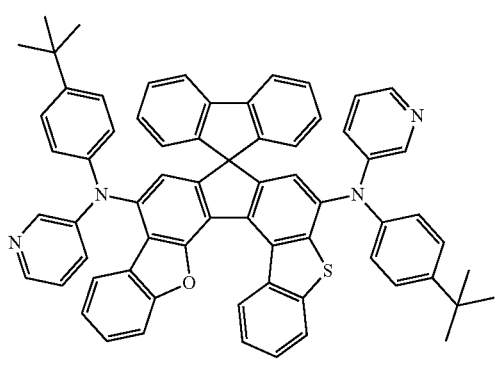
<Chemical Formula 230>
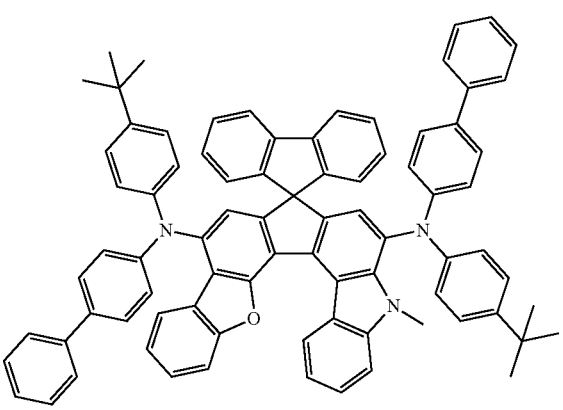

<Chemical Formula 231>
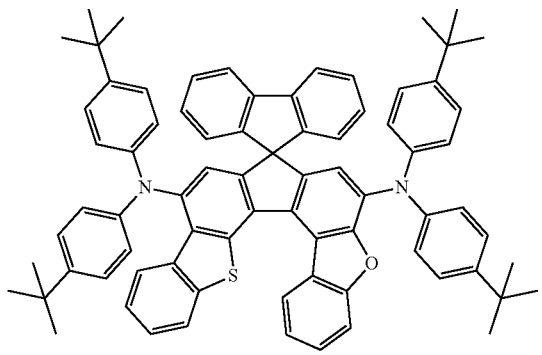
<Chemical Formula 232>
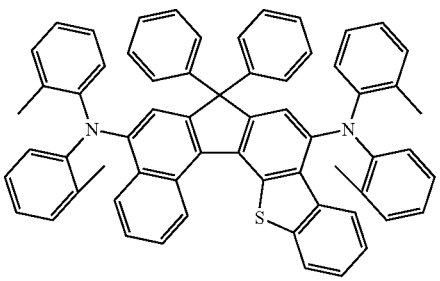
<Chemical Formula 233>
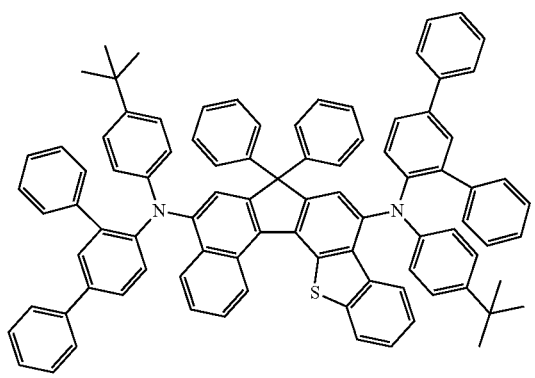
<Chemical Formula 234>
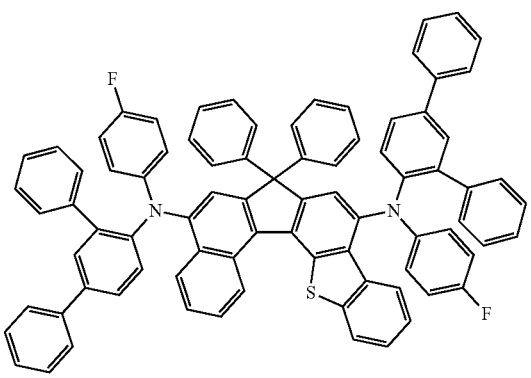
<Chemical Formula 235>
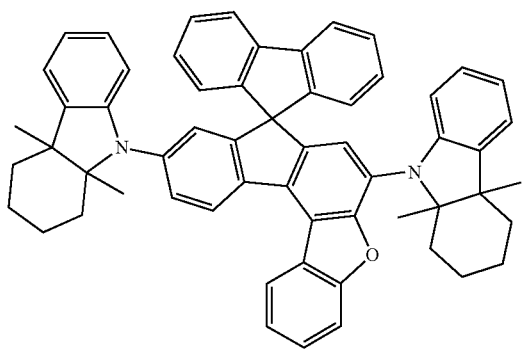
<Chemical Formula 236>
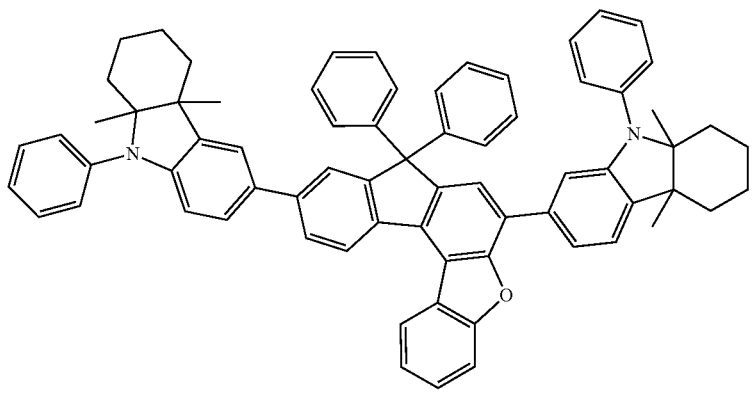

<Chemical Formula 237>
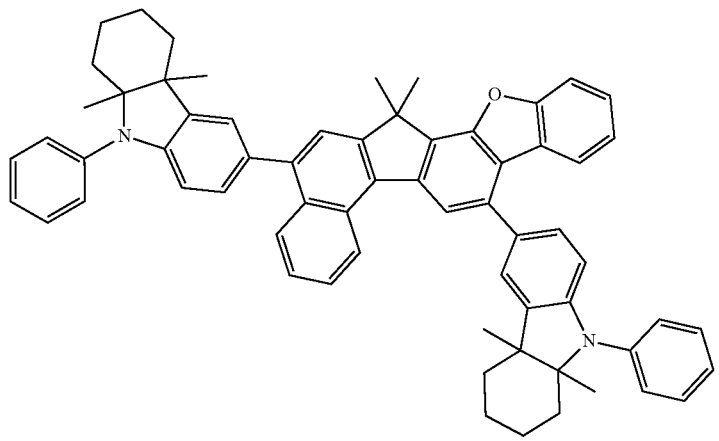
<Chemical Formual 238>
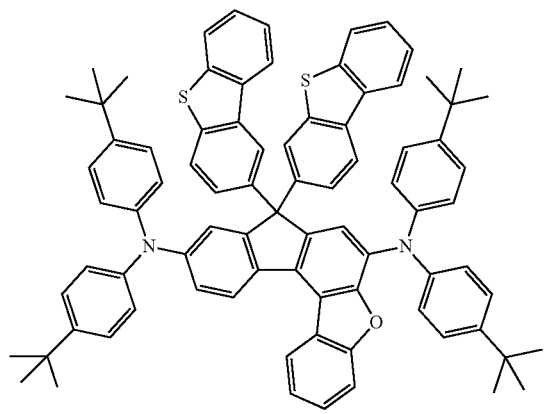
<Chemical Formula 239>
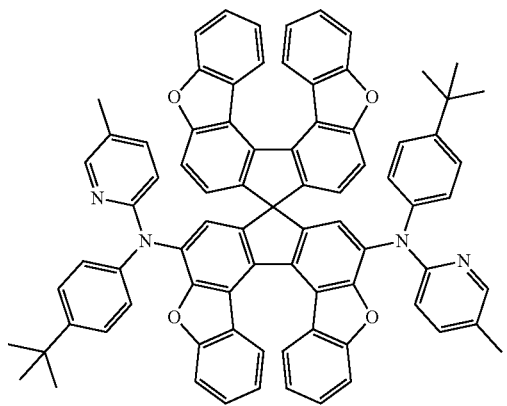

13. The organic light-emitting diode as set forth in claim 1, wherein the compound represented by Chemical Formula D is any one selected from the group consisting of the following Compounds 1 to 138:
<Compound 1>
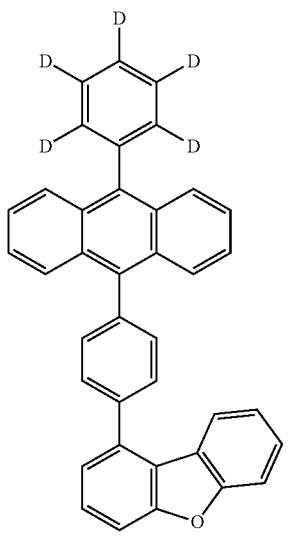
<Compound 2>
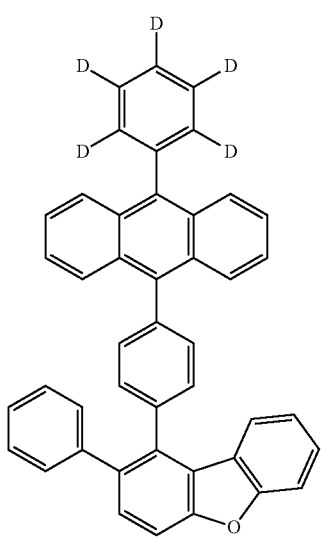
-continued
<Compound 3>
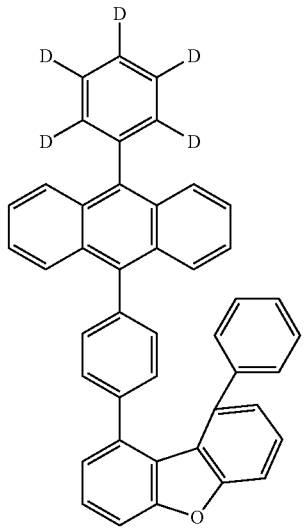
<Compound 4>
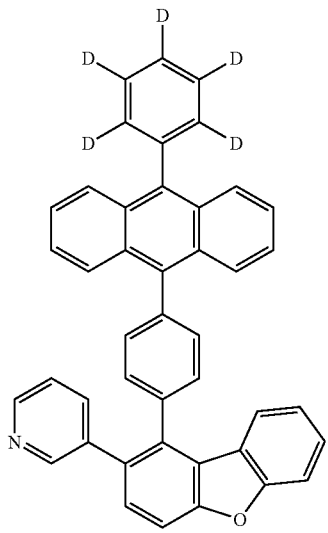
<Compound 5>
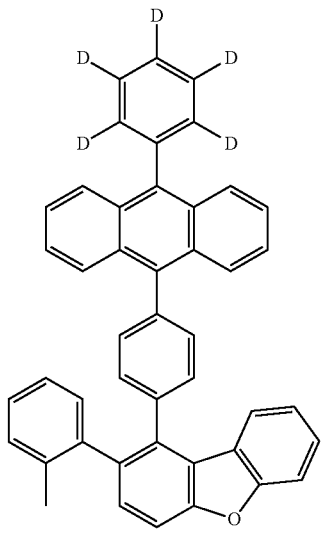

-continued
<Compound 6>
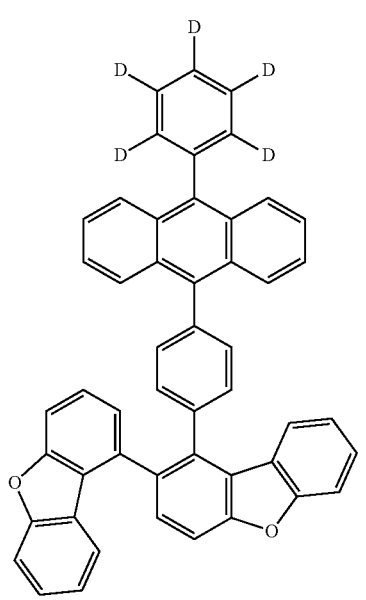
<Compound 7>
<Compound 9>
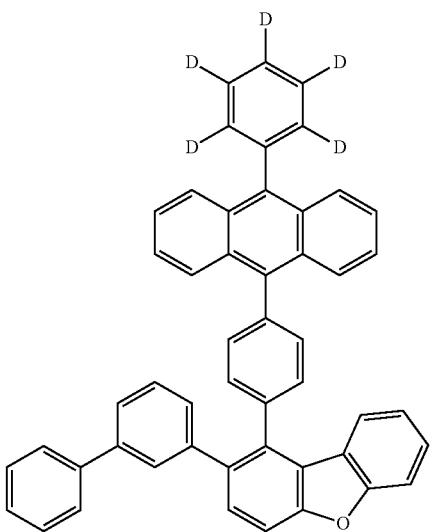
<Compound 10>
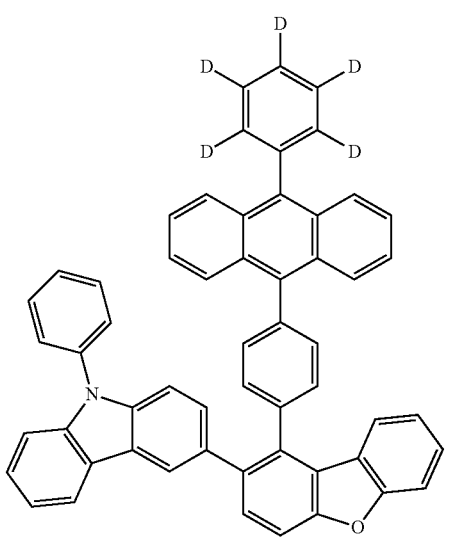
<Compound 8>
<Compound 11>
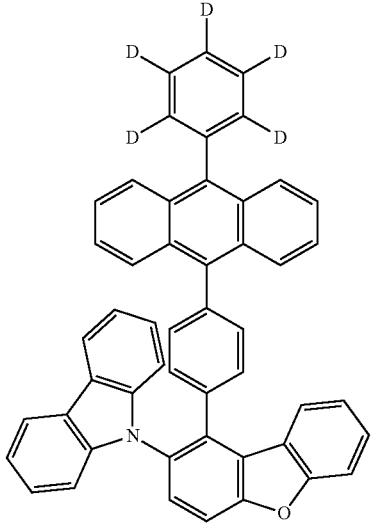

<Compound 12>
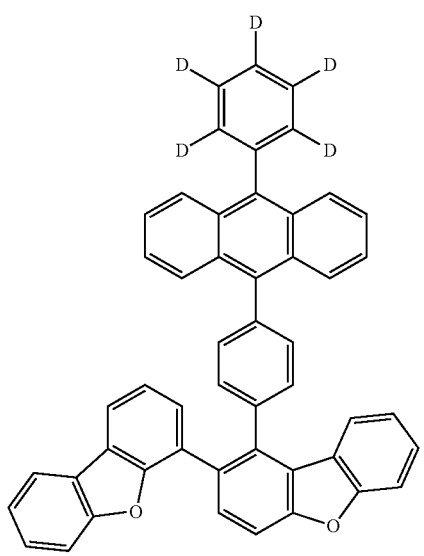
<Compound 14>
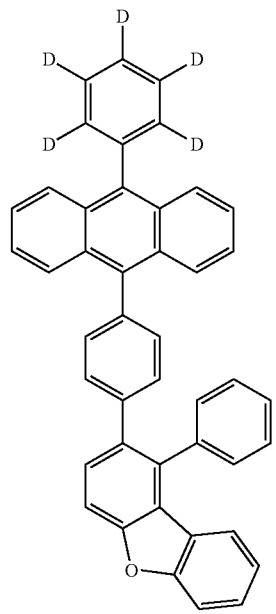
<Compound 13>
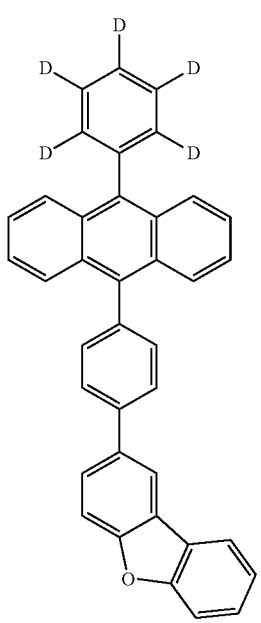
<Compound 15>
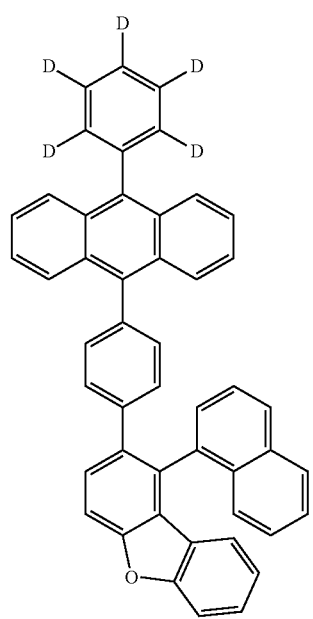

<Compound 16>
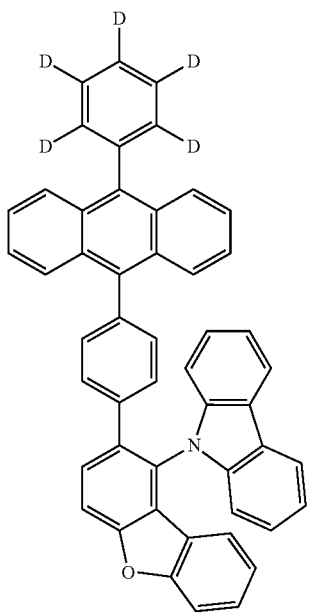
<Compound 18>
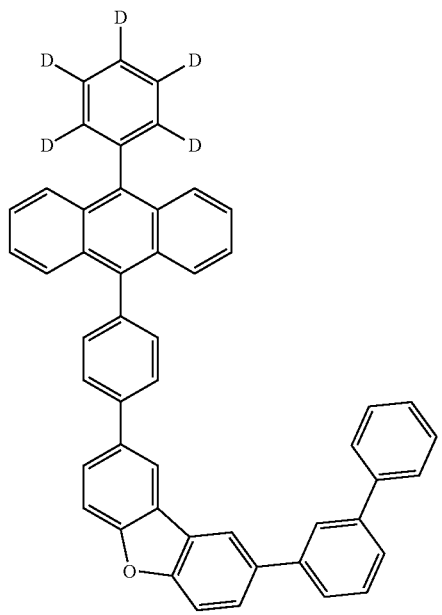
<Compound 17>
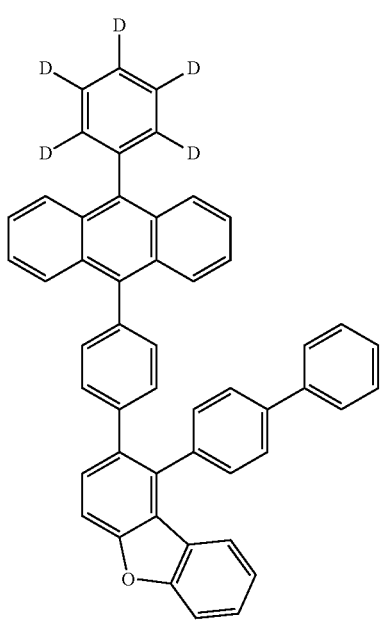
<Compound 19>
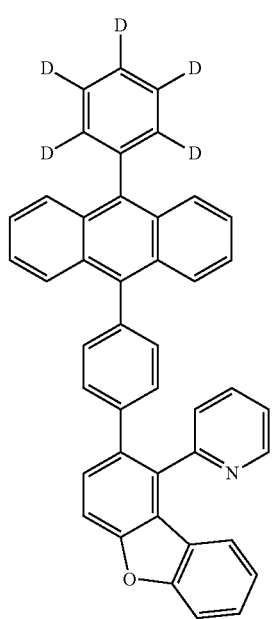

-continued
<Compound 20>
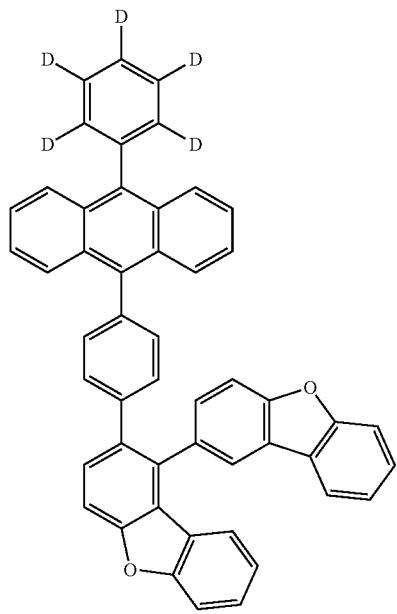
<Compound 21>
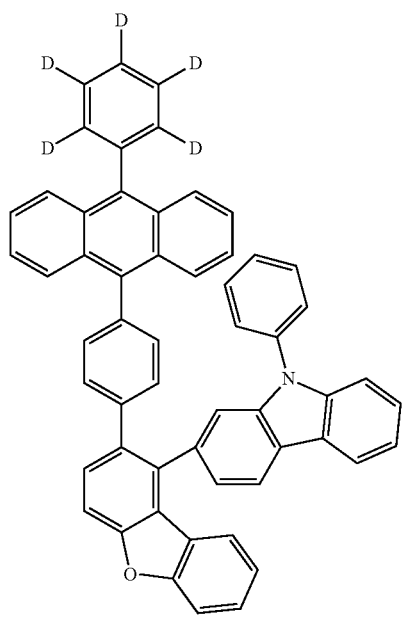
-continued
<Compound 22>
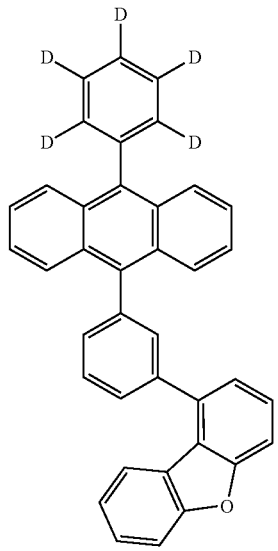
<Compound 23>
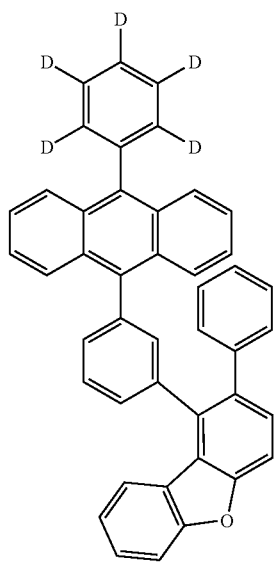

<Compound 24>
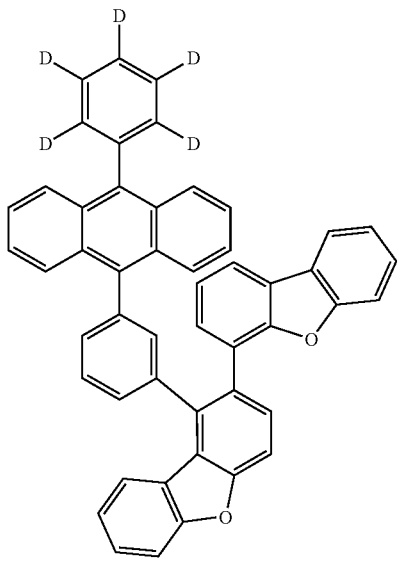
<Compound 25>
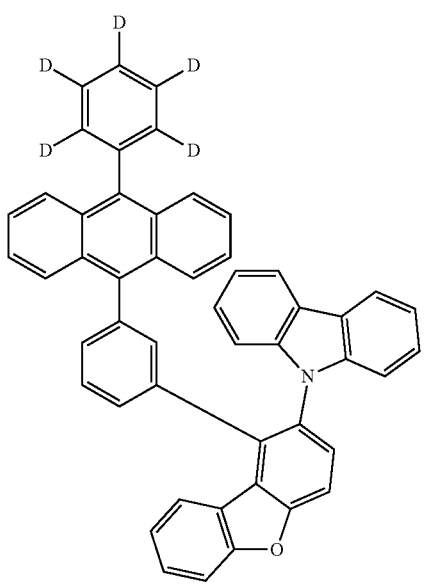
<Compound 26>
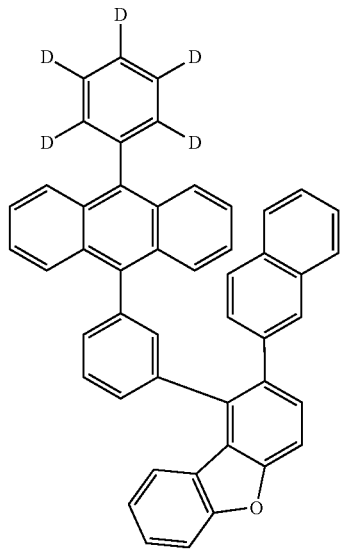
<Compound 27>
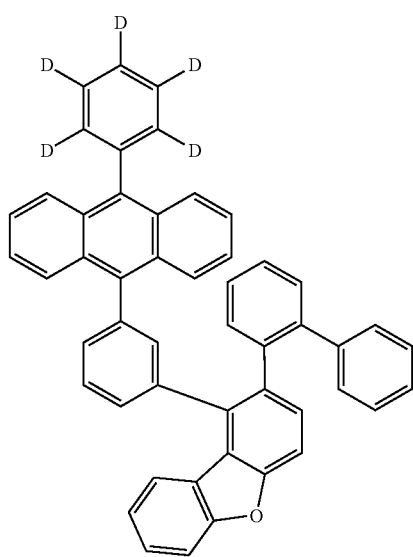
<Compound 28>

<Compound 29>
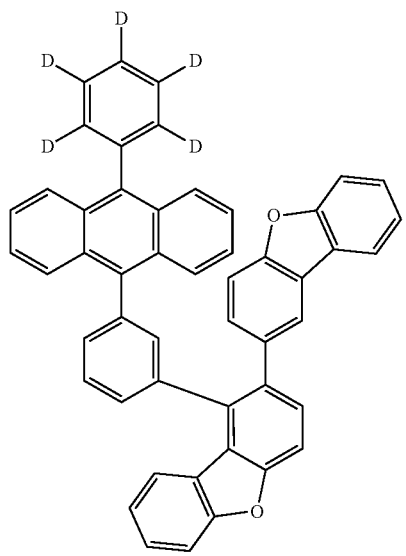
<Compound 31>
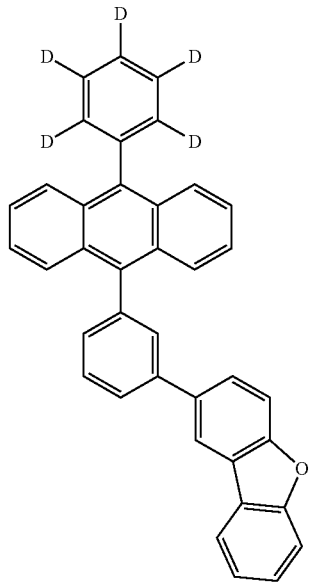
<Compound 30>
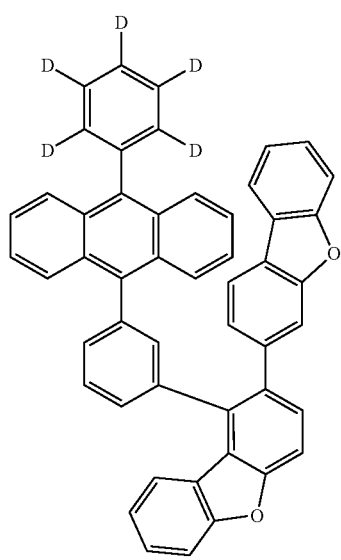
<Compound 32>
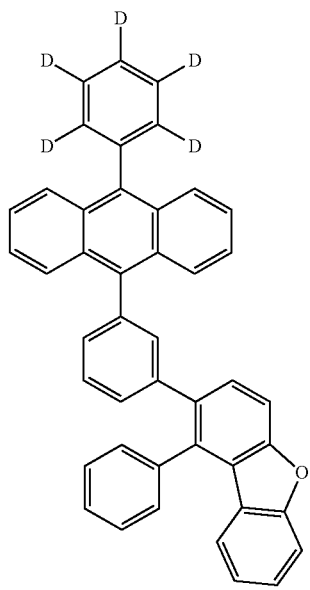

<Compound 33>
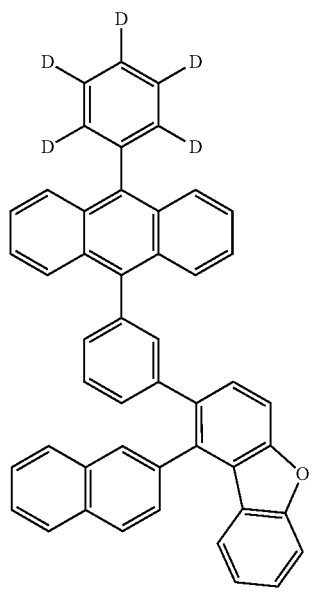
<Compound 35>
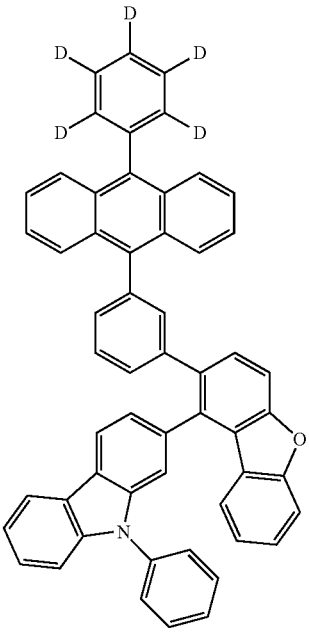
<Compound 34>
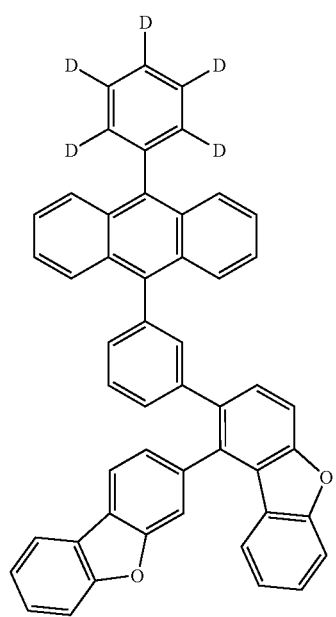
<Compound 36>
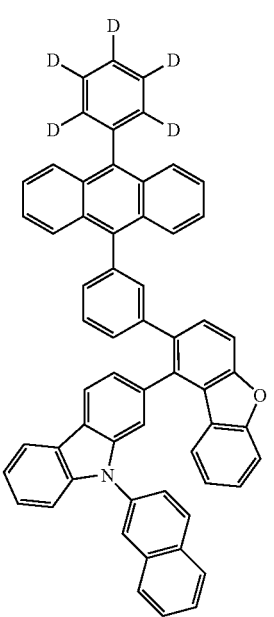

<Compound 37>
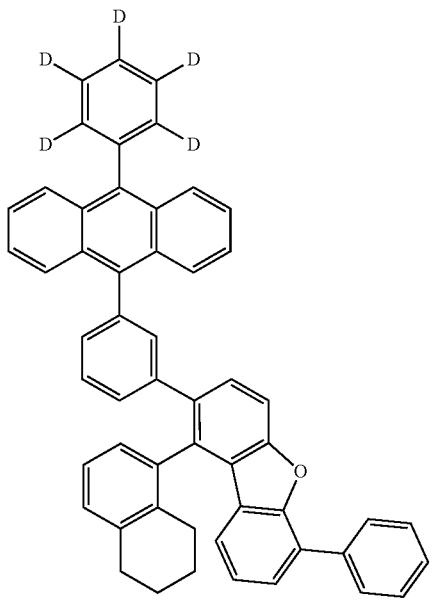
<Compound 39>
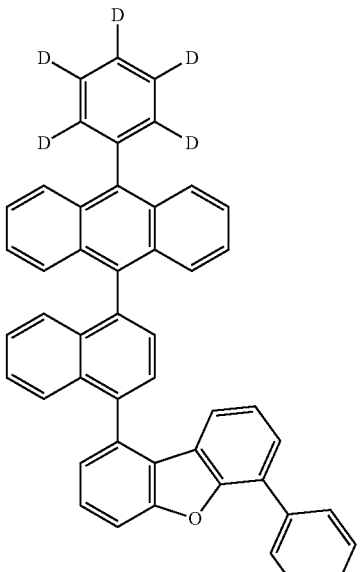
<Compound 38>
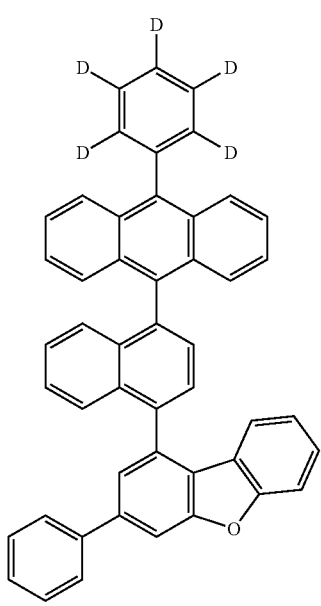
<Compound 40>
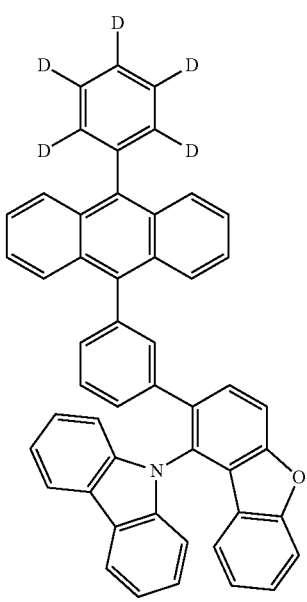

<Compound 41>
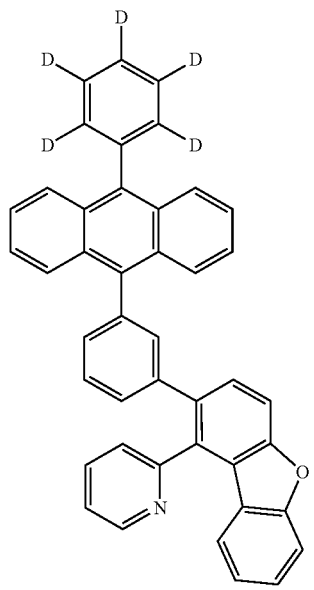
<Compound 43>
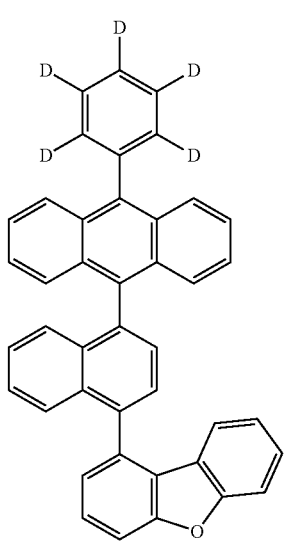
<Compound 42>
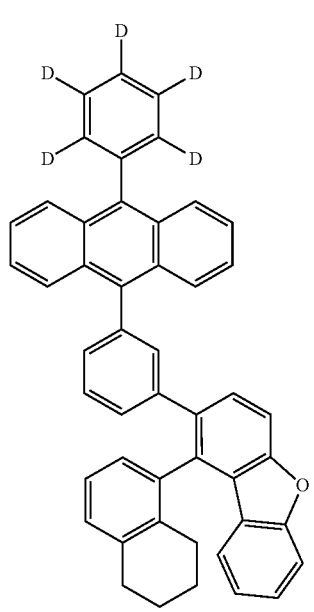
<Compound 44>
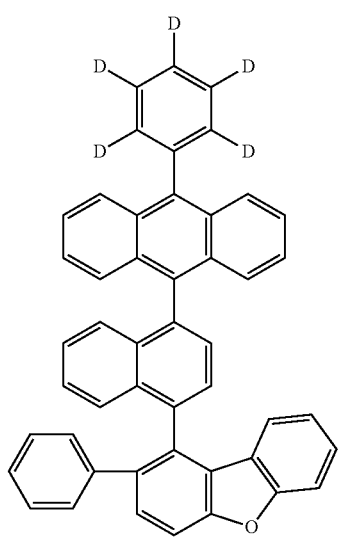

<Compound 45>
<Compound 47>
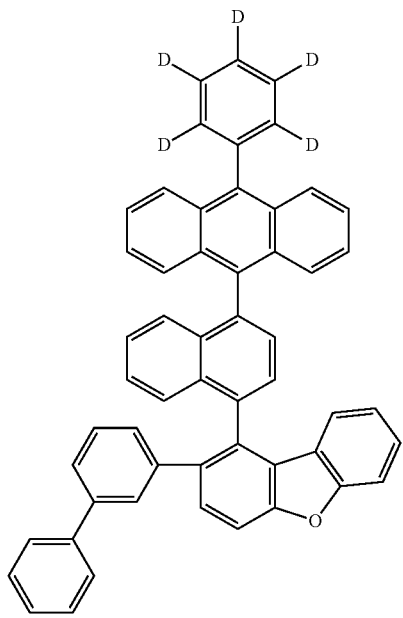
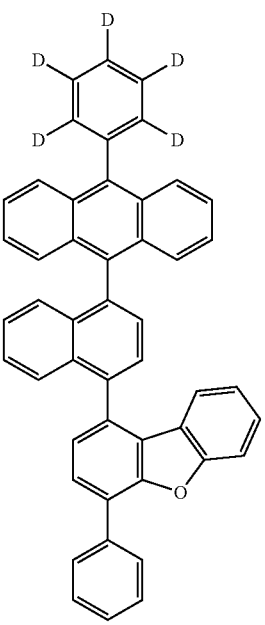
<Compound 46>
<Compound 48>
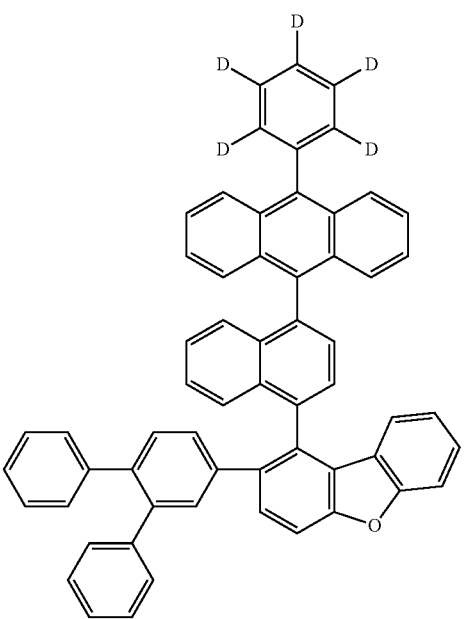

<Compound 49>
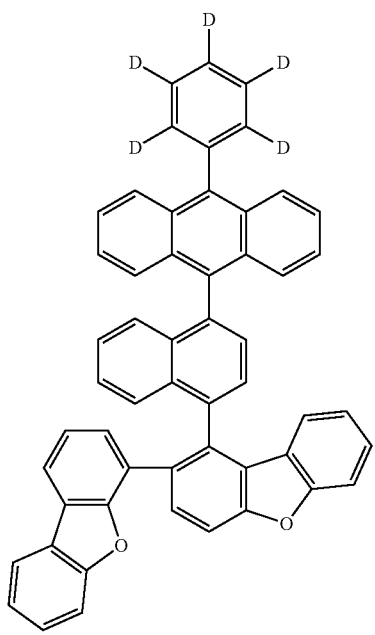
<Compound 50>
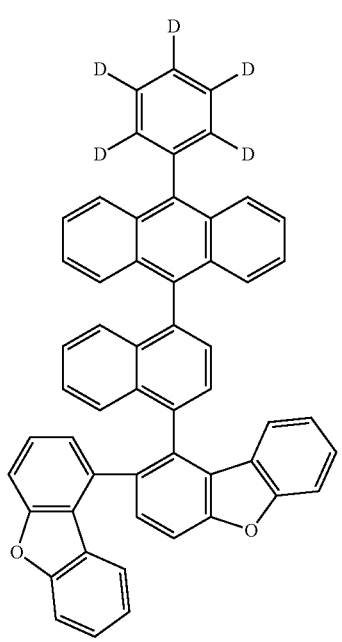
<Compound 51>
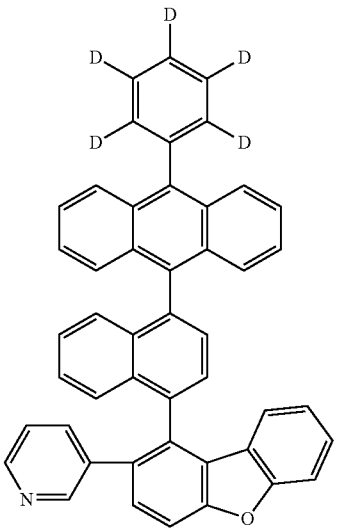
<Compound 52>
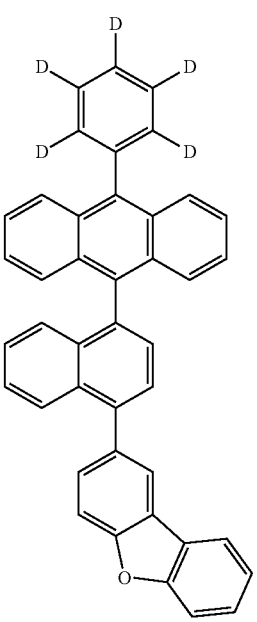

<Compound 53>
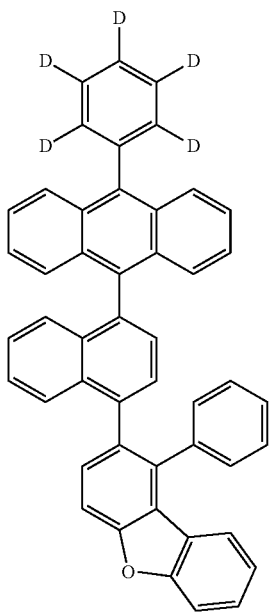
<Compound 55>
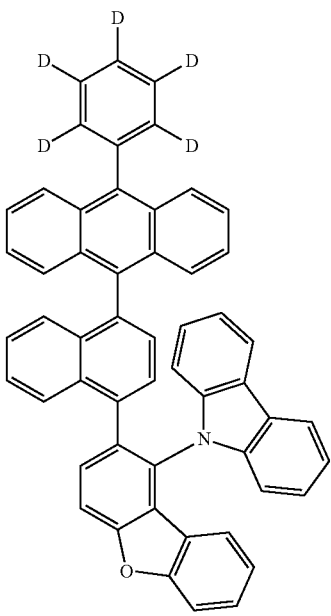
<Compound 54>
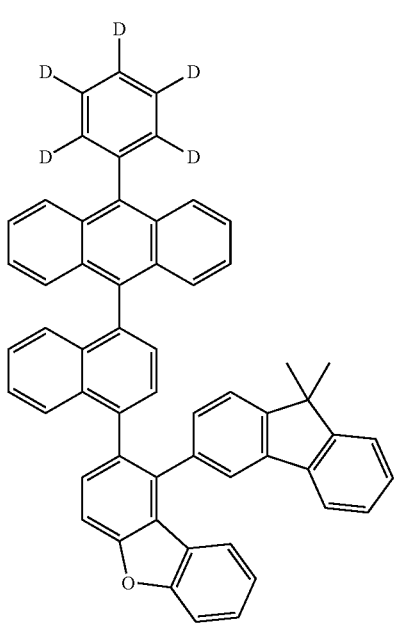
<Compound 56>
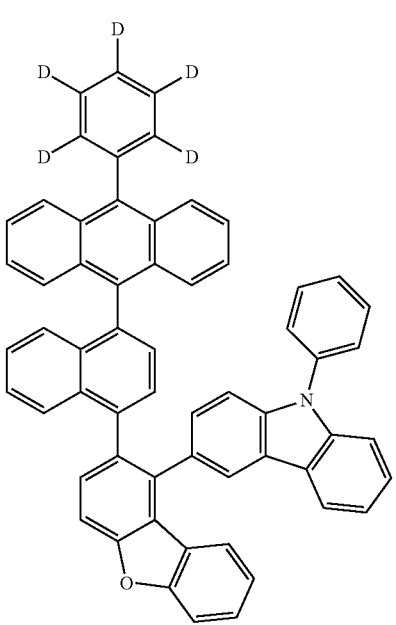

<Compound 57>
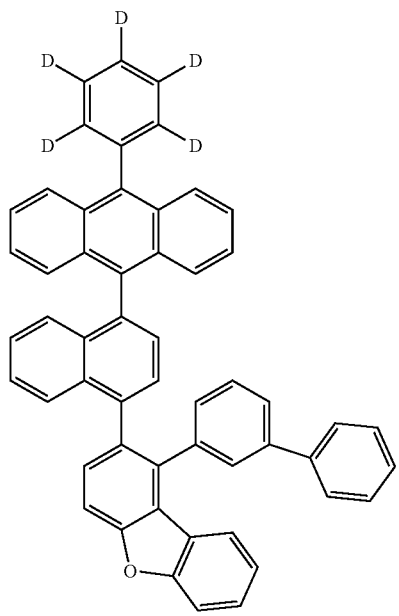
<Compound 59>
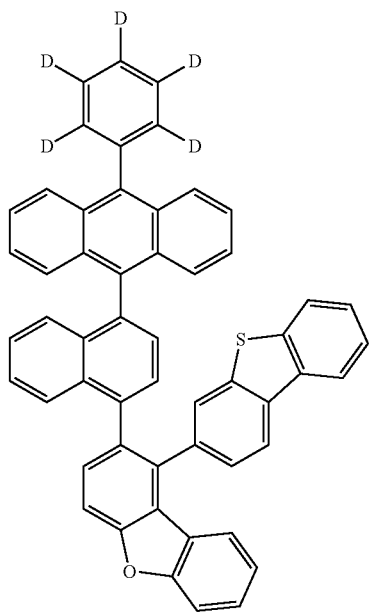
<Compound 58>
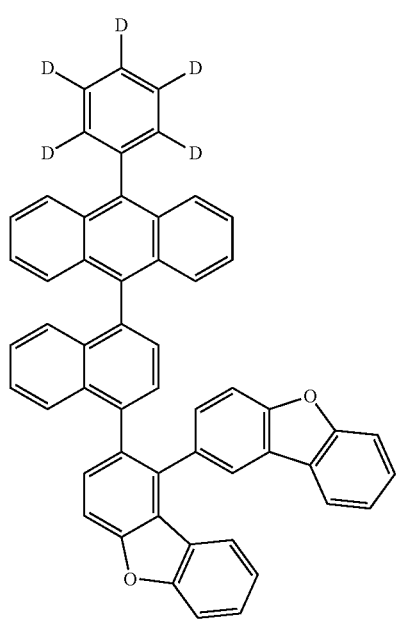
<Compound 60>
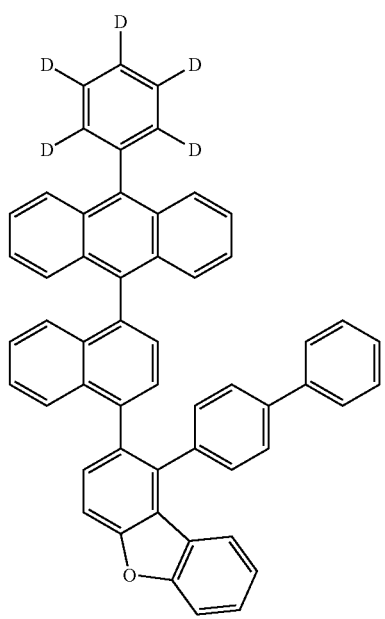

<Compound 61>
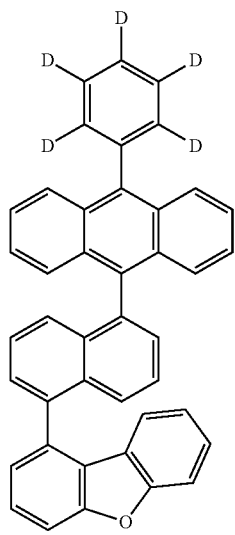
<Compound 62>
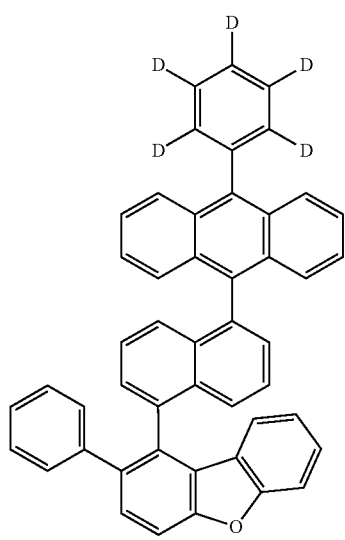
<Compound 63>
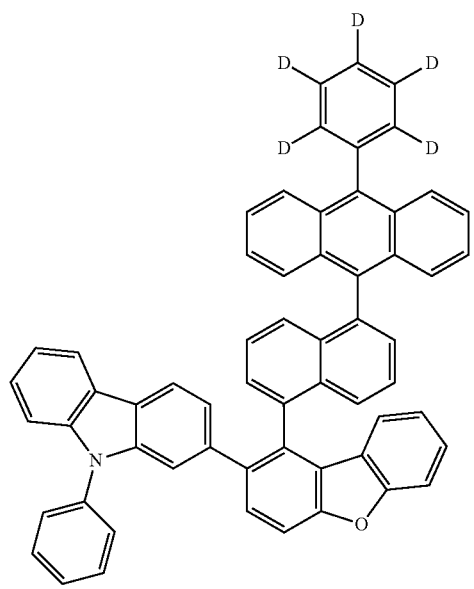
<Compound 64>
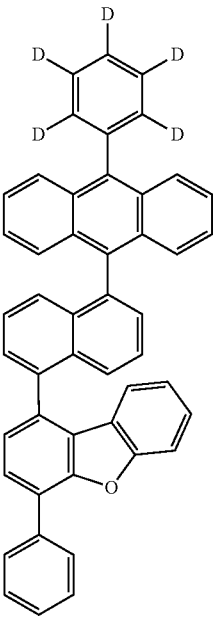
<Compound 65>
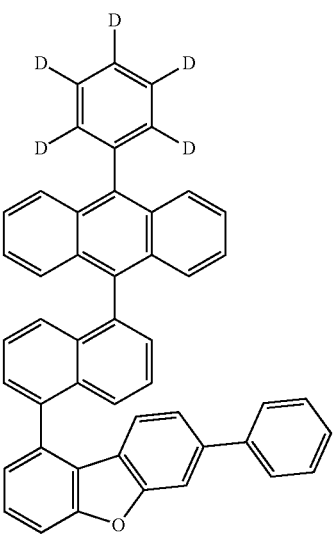

<Compound 66>
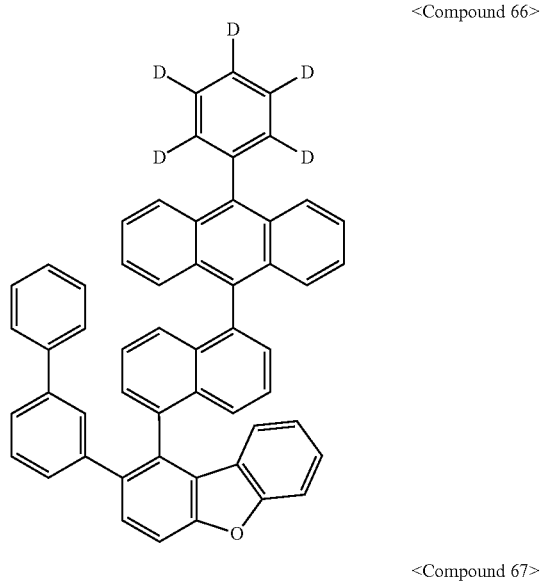
<Compound 67>
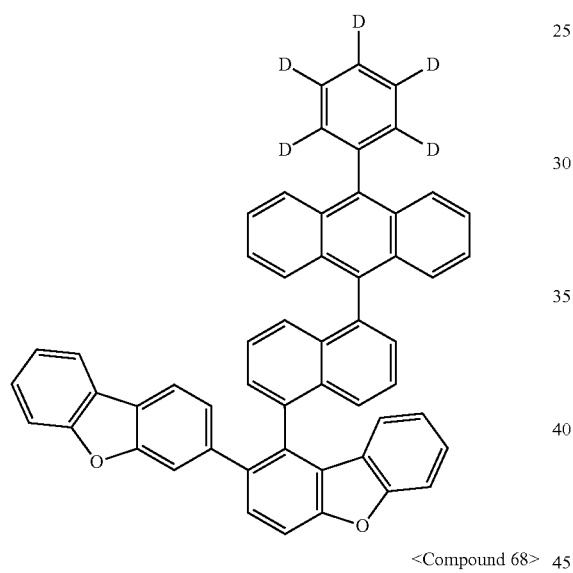
<Compound 68>
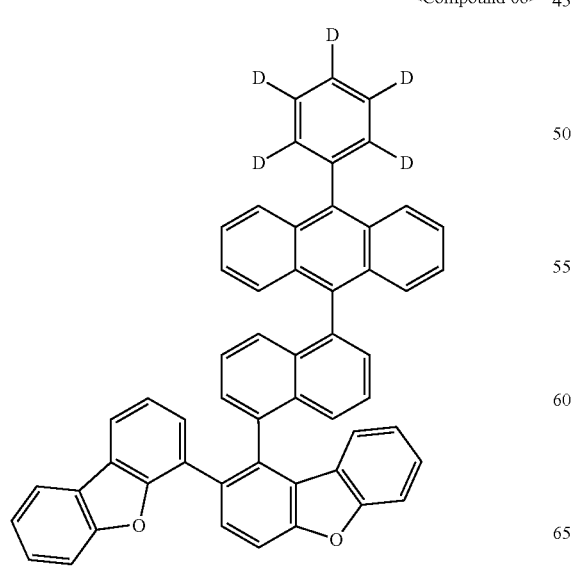
<Compound 69>
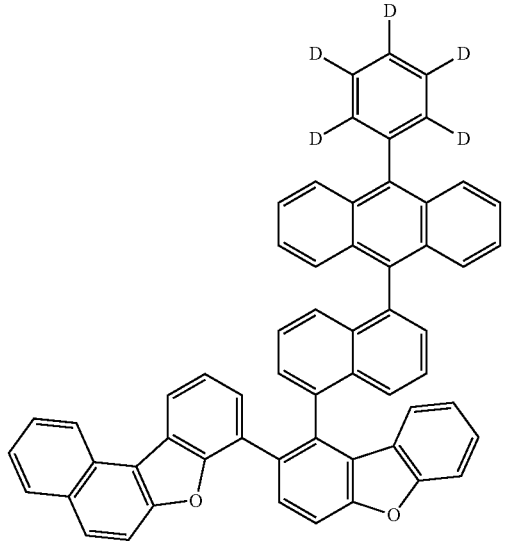
<Compound 70>
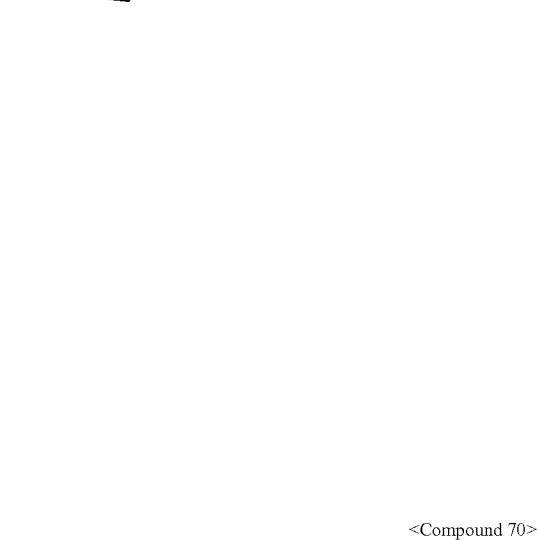

<Compound 71>
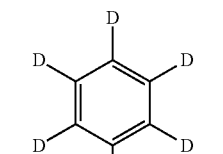
<Compound 73>
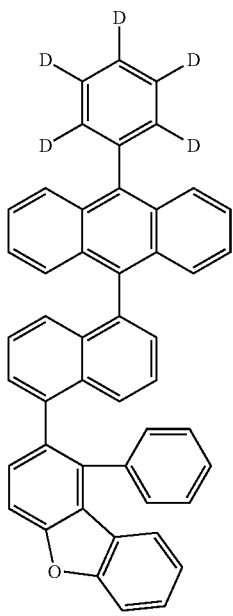
<Compound 72>
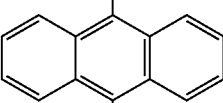
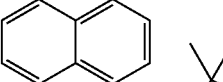
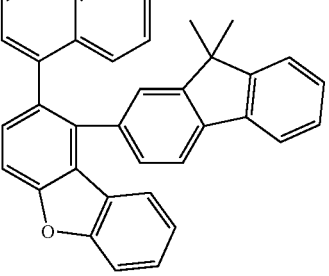
<Compound 74>
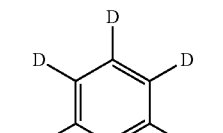
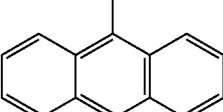
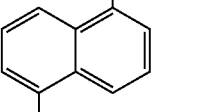
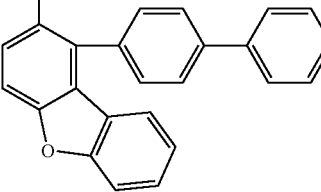

<Compound 75>
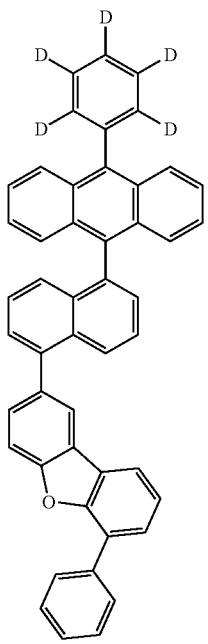
<Compound 76>
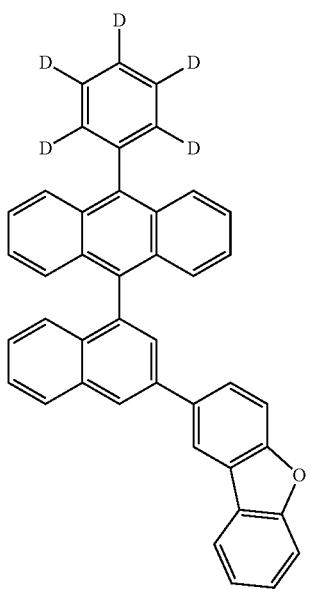
<Compound 77>
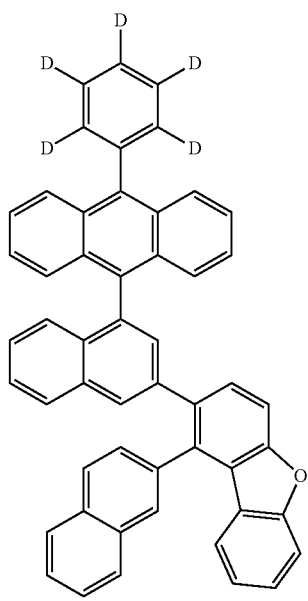
<Compound 78>
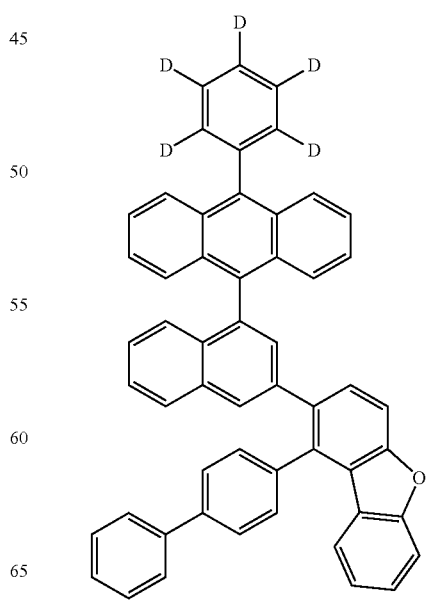

<Compound 79>
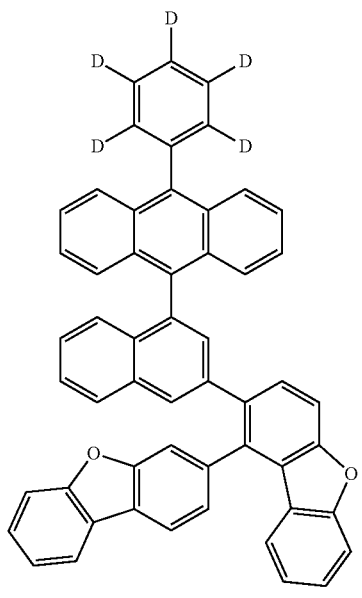
<Compound 81>
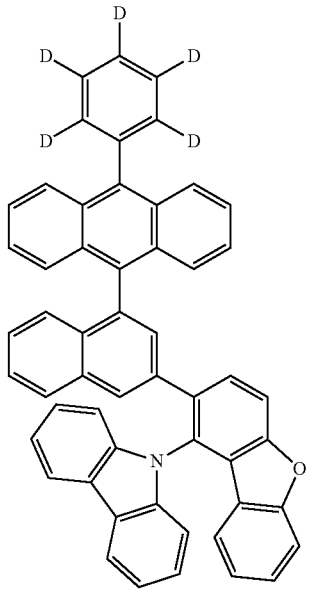
<Compound 80>
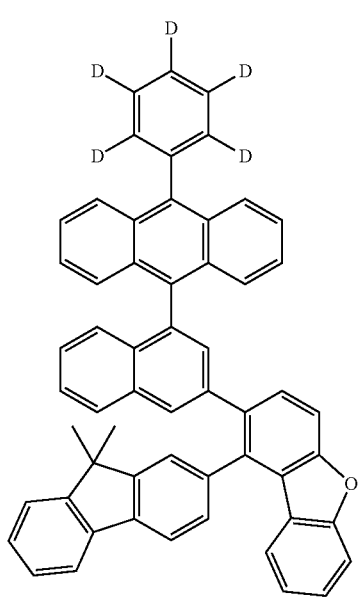
<Compound 82>
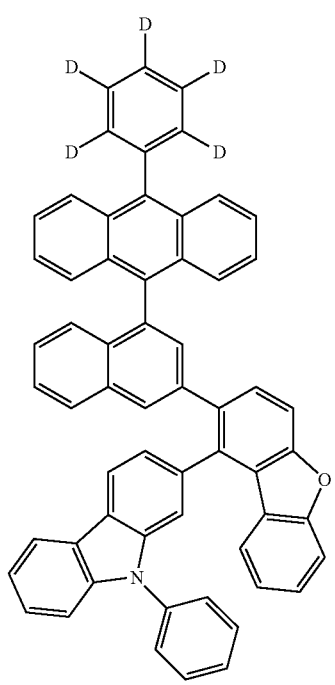

<Compound 83>
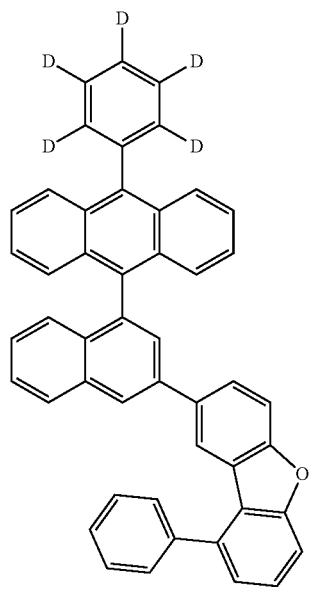
<Compound 84>
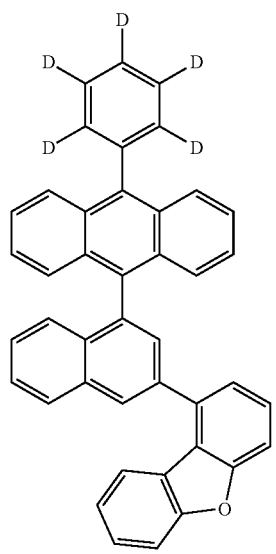
<Compound 85>
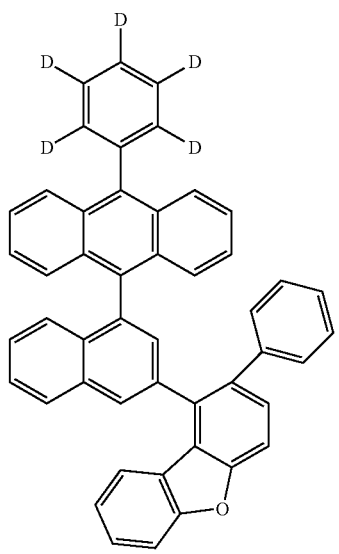
<Compound 86>
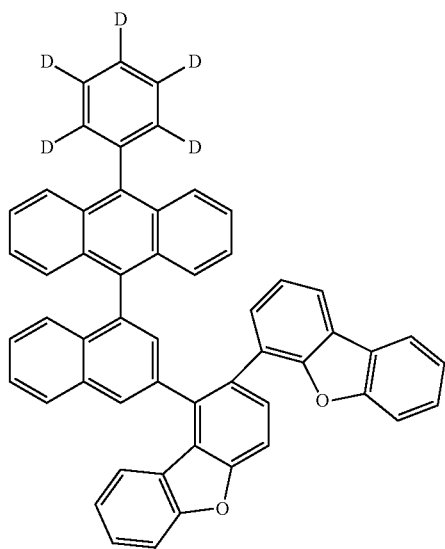

<Compound 87>
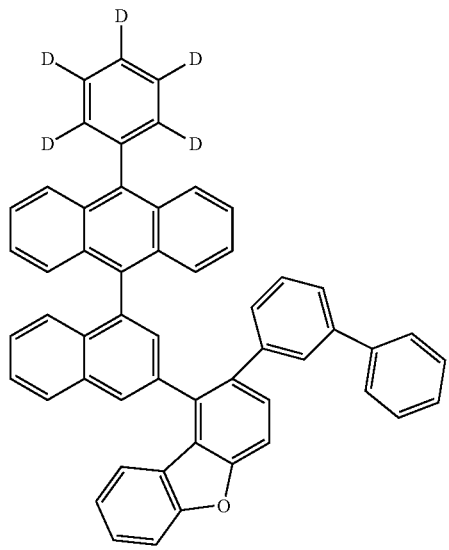
<Compound 88>
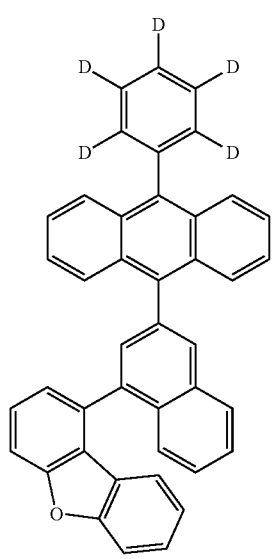
<Compound 89>
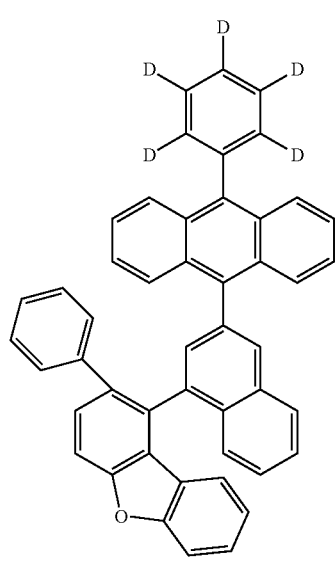
<Compound 90>
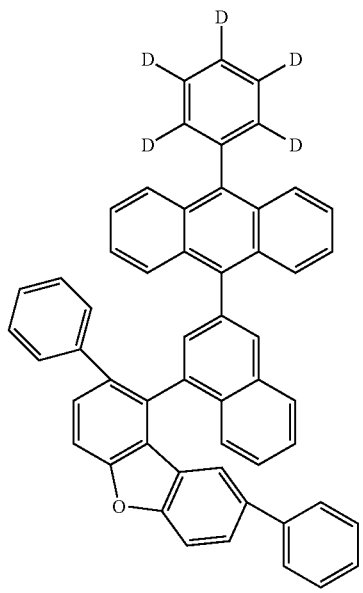
<Compound 91>
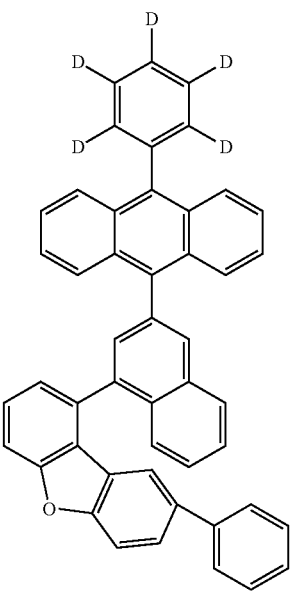

<Compound 92>
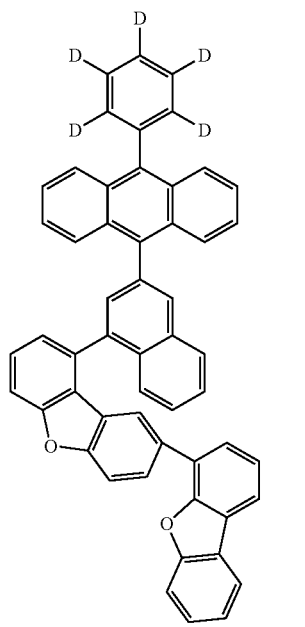
<Compound 93>
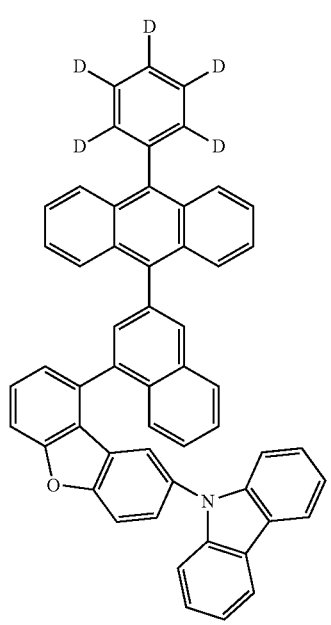
<Compound 94>
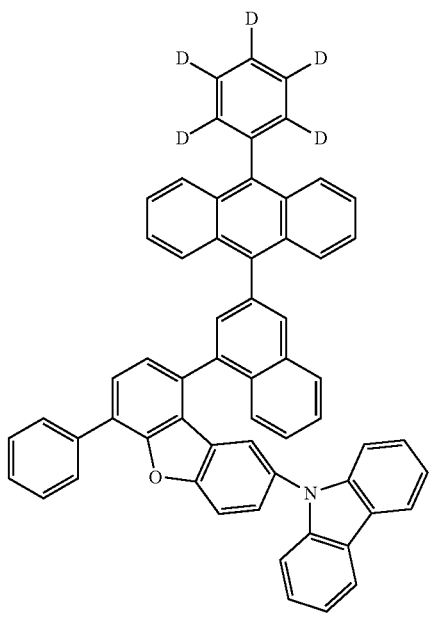
<Compound 95>
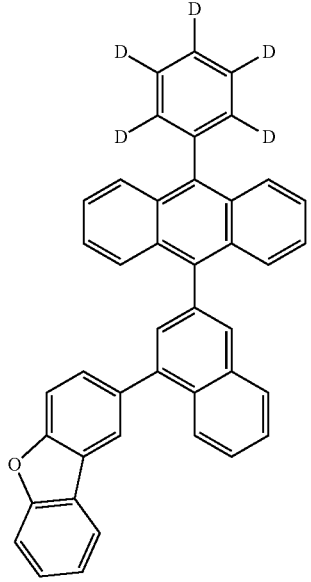

<Compound 96>
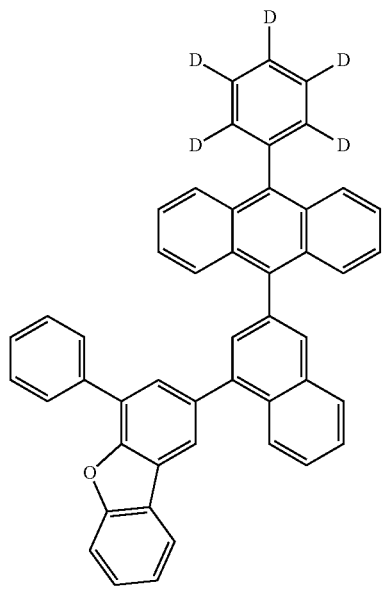
<Compound 97>
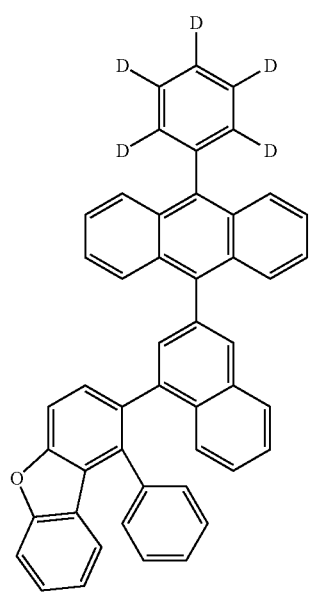
<Compound 98>
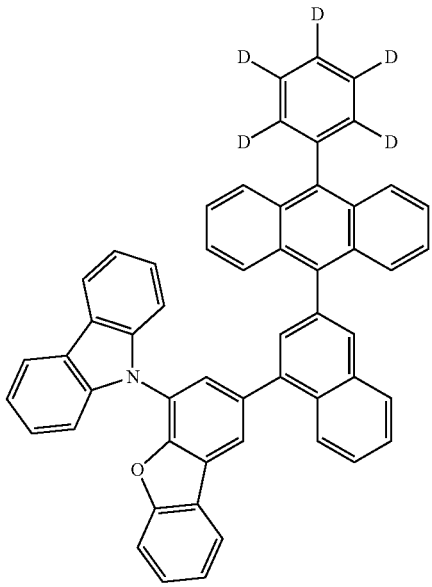
<Compound 99>
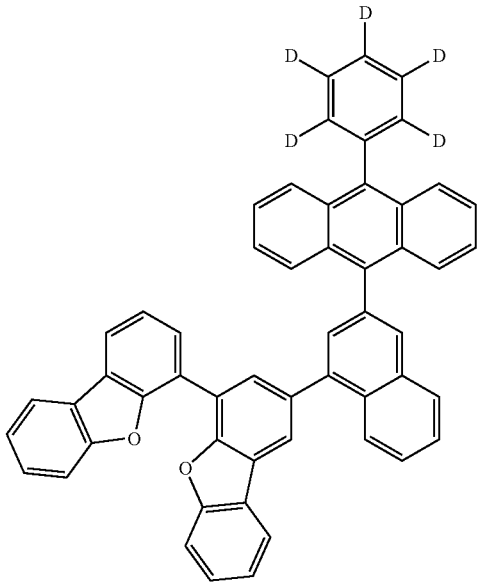

<Compound 100>
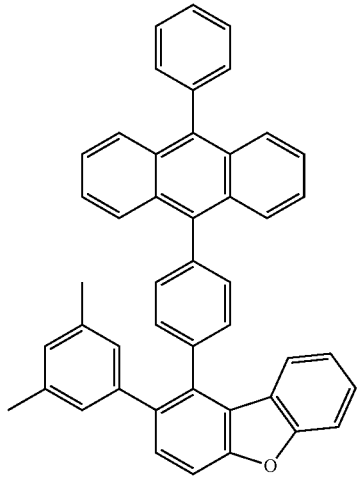
<Compound 101>
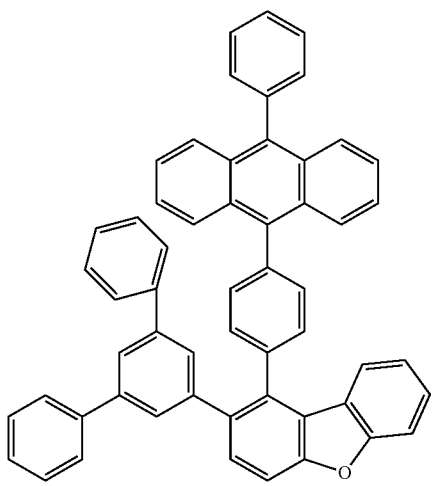
<Compound 102>
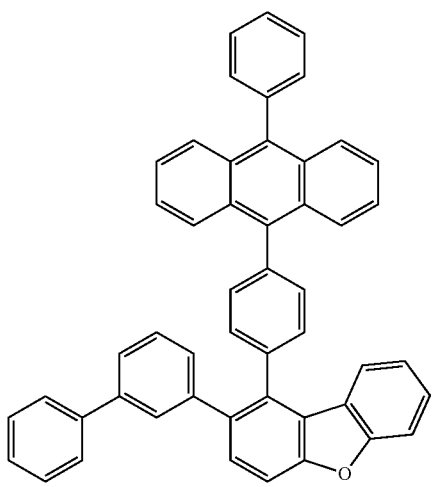
<Compound 103>
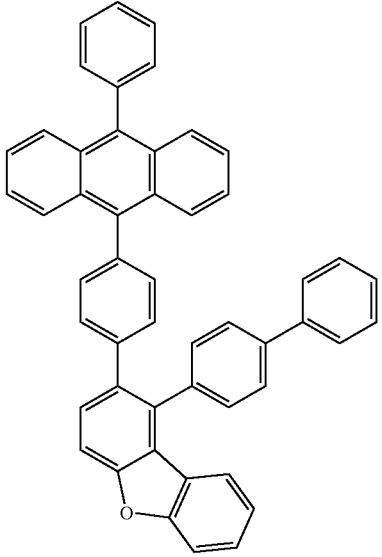
<Compound 104>
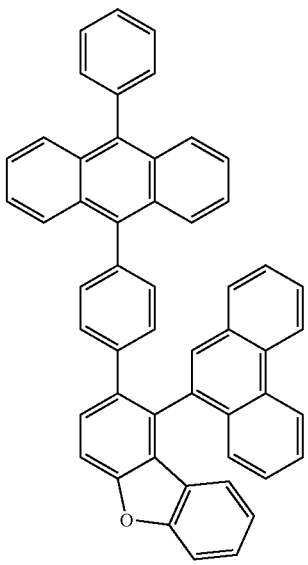

<Compound 105>
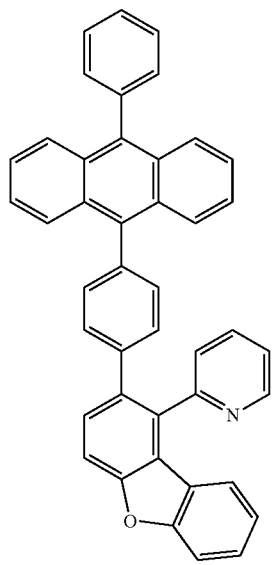
<Compound 106>
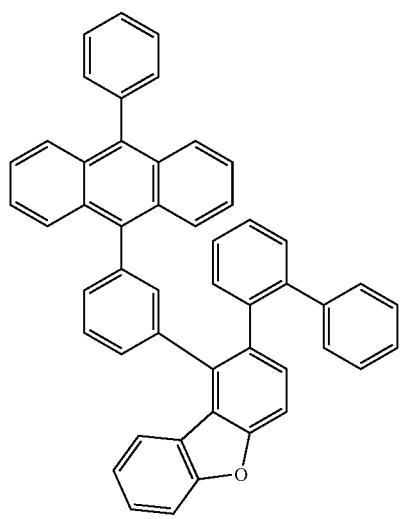
<Compound 107>
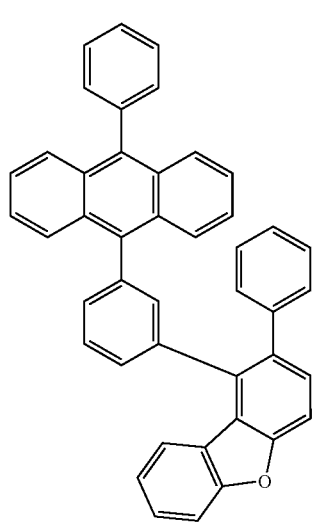
<Compound 108>
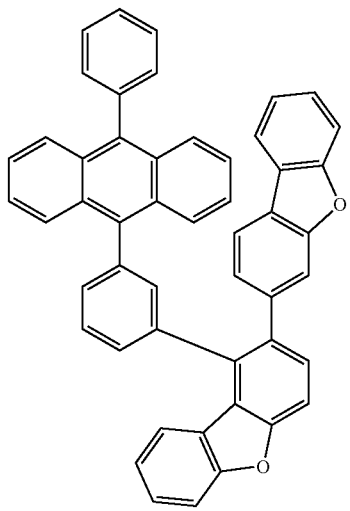
<Compound 109>
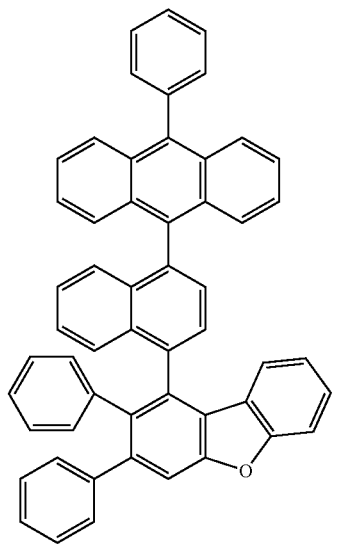
<Compound 110>
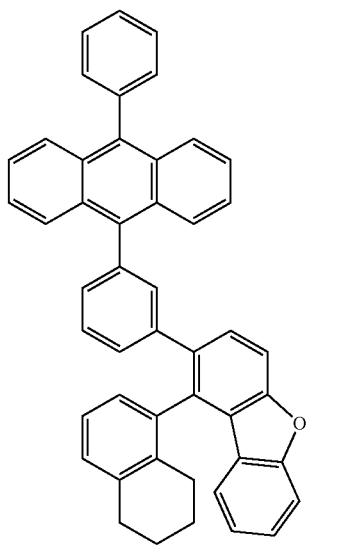

<Compound 111>
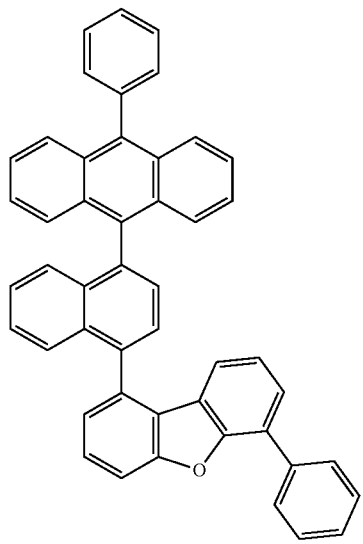
<Compound 112>
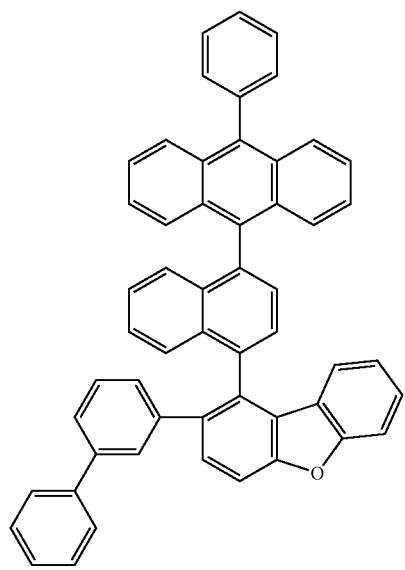
<Compound 113>
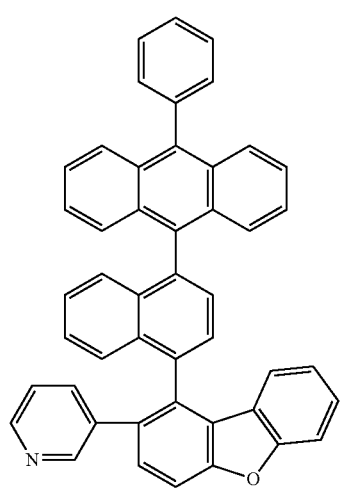
<Compound 114>
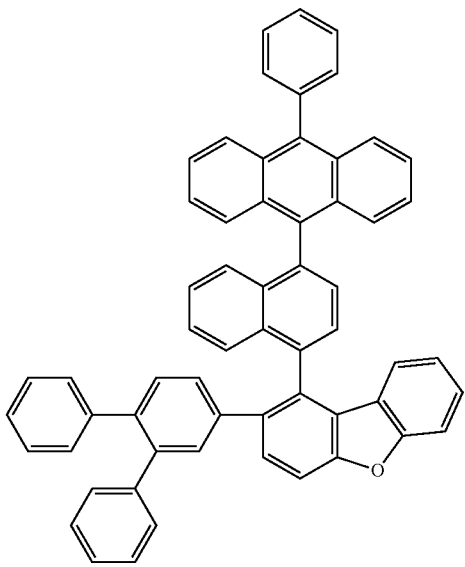
<Compound 115>
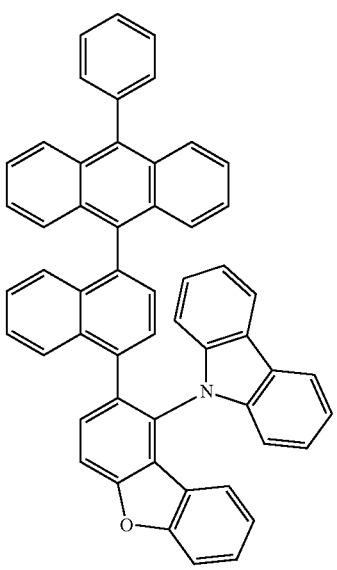

-continued
<Compound 116>
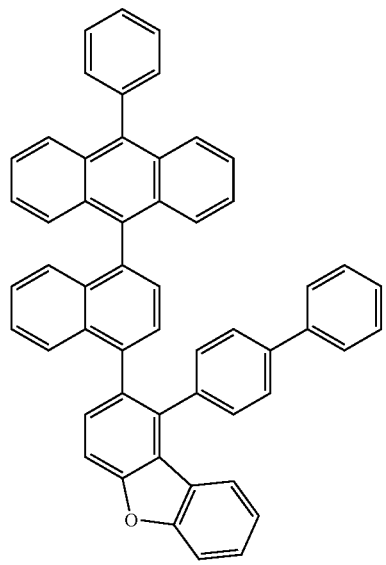
<Compound 117>
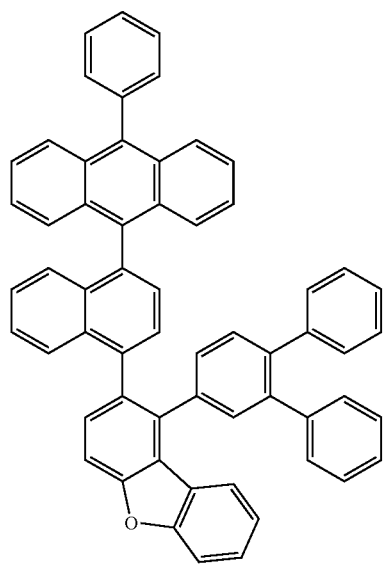
<Compound 118>
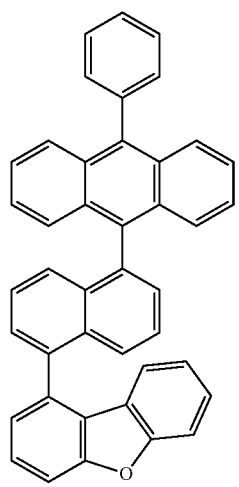
-continued
<Compound 119>
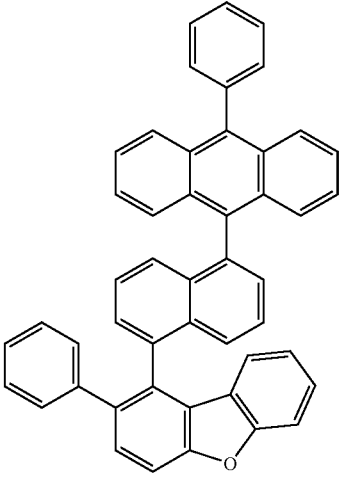
<Compound 120>
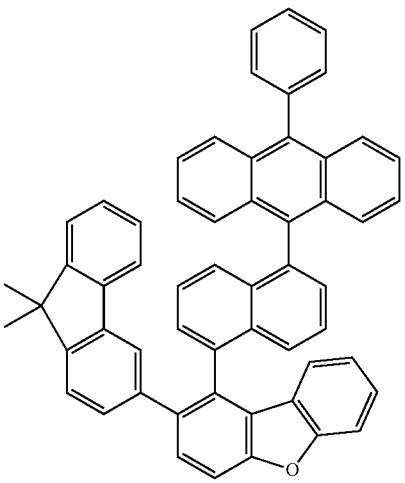
<Compound 121>
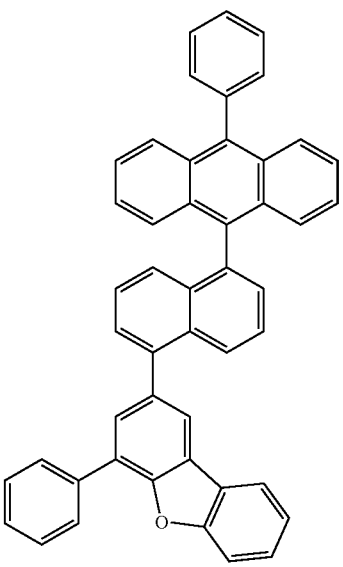

<Compound 122>
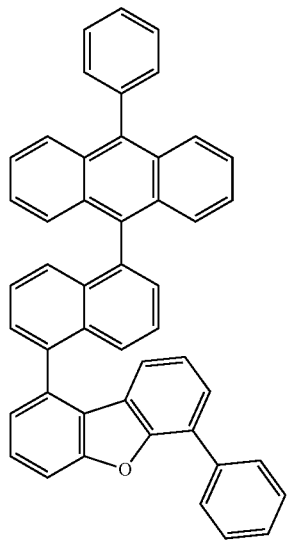
<Compound 123>
<Compound 124>
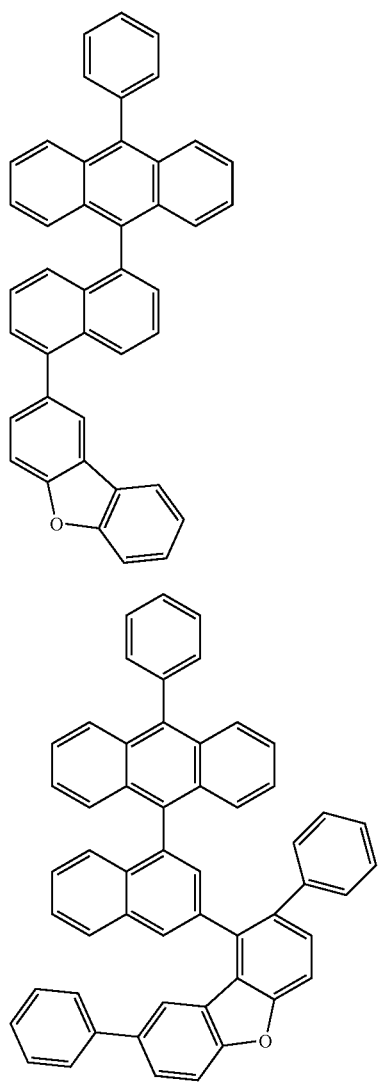
<Compound 125>
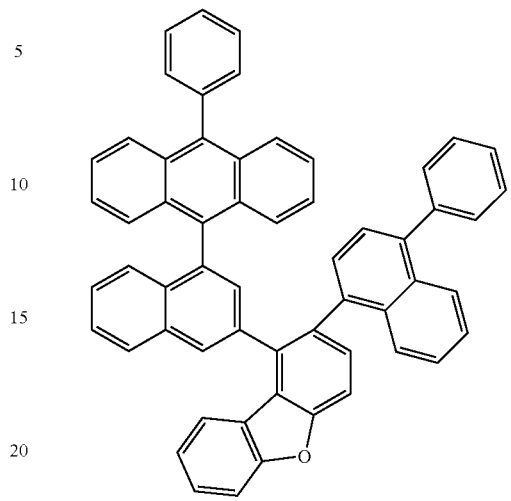
<Compound 126>
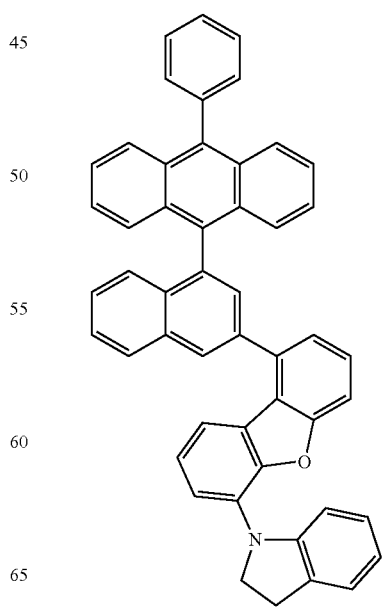

<Compound 127>
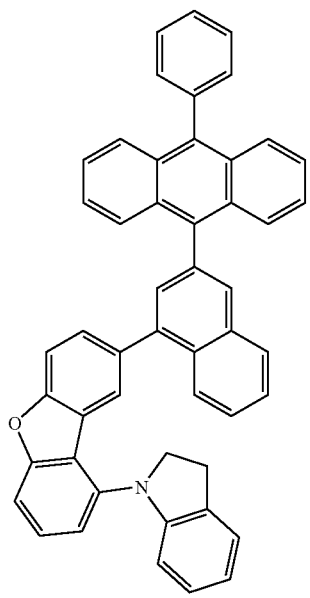
<Compound 128>
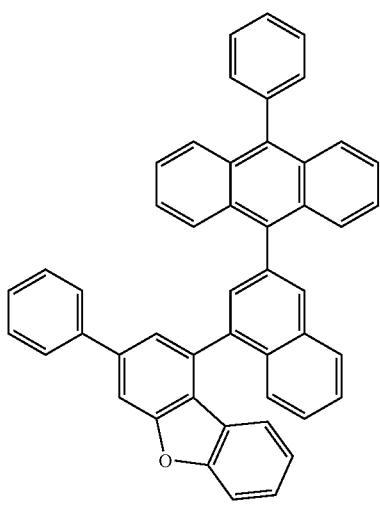
<Compound 129>
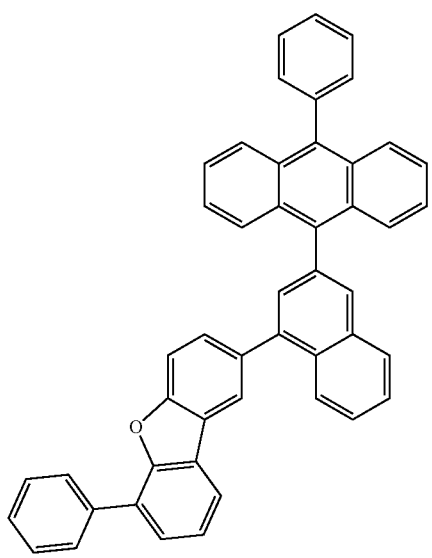
<Compound 130>
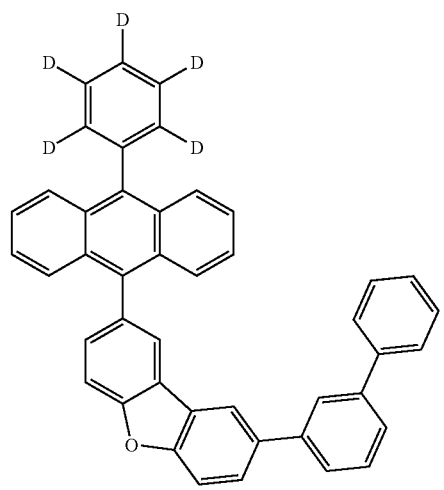
<Compound 131>
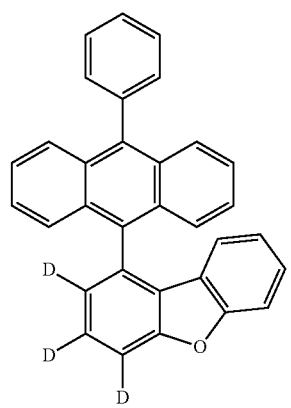
<Compound 132>

<Compound 133>
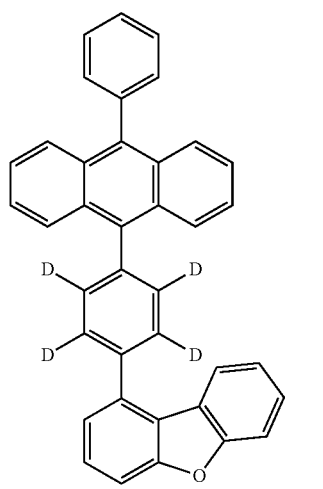
<Compound 134>
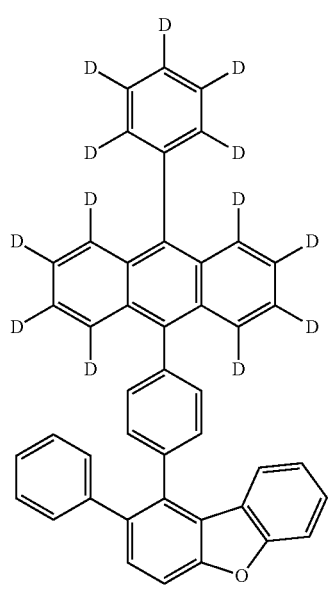
<Compound 135>
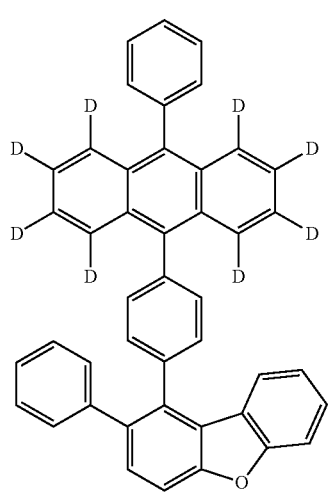
<Compound 136>
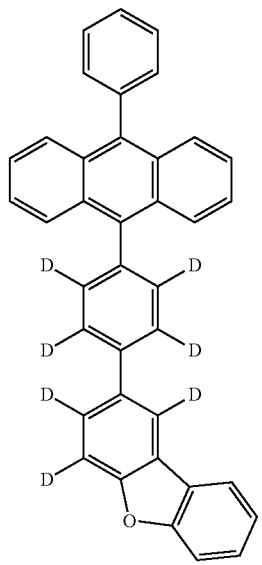
<Compound 137>
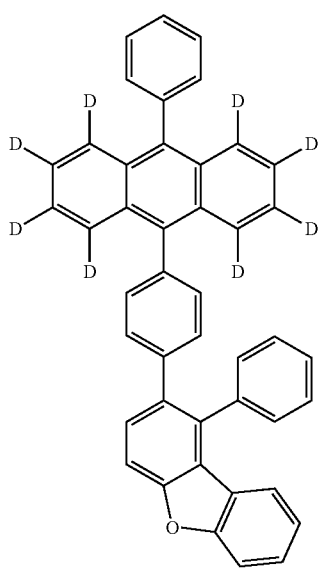

<Compound 138>

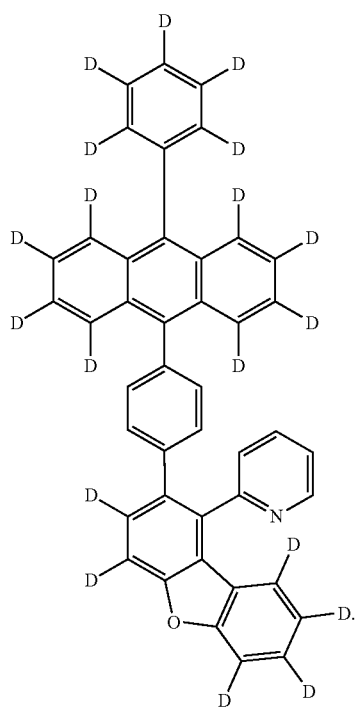

14. The organic light-emitting diode as set forth in claim 1, wherein the organic light-emitting diode comprises at least one of a hole injection layer, a hole transport layer, a functional layer capable of both hole injection and hole transport, an electron transport layer, and an electron injection layer, in addition to the light-emitting layer.

15. The organic light-emitting diode as set forth in claim 14, wherein at least one selected from among the layers is deposited using a deposition process or a solution process.

16. The organic light-emitting diode as set forth in claim 1, wherein the organic light-emitting diode is used for a device selected from among a flat display device, a flexible display device, a monochrome or grayscale flat illumination device, and a monochrome or grayscale flexible illumination device.

* * * * *